(12) United States Patent
Jiao et al.

(10) Patent No.: US 7,166,614 B2
(45) Date of Patent: Jan. 23, 2007

(54) TETRAHYDROPYRANYL CYCLOPENTYL TETRAHYDROISOQUINOLINE MODULATORS OF CHEMOKINE RECEPTOR ACTIVITY

(75) Inventors: Richard Jiao, Piscataway, NJ (US); Stephen D. Goble, Edison, NJ (US); Sander G. Mills, Scotch Plains, NJ (US); Gregori Morriello, Randolph, NJ (US); Alexander Pasternak, Princeton, NJ (US); Lihu Yang, Edison, NJ (US); Changyou Zhou, Plainsboro, NJ (US); Gabor Butora, Martinsville, NJ (US); Shankaran Kothandaraman, Kendall Park, NJ (US); Deodialsingh Guiadeen, Linden, NJ (US); Christopher Moyes, Hertford (GB)

(73) Assignees: Merck & Co., Inc., Rahway, NJ (US); Merck Sharp & Dohme Limited, Hertfordshire (GB)

( * ) Notice: Subject to any disclaimer, the term of this patent is extended or adjusted under 35 U.S.C. 154(b) by 0 days.

(21) Appl. No.: 10/512,925

(22) PCT Filed: Apr. 25, 2003

(86) PCT No.: PCT/US03/13121

§ 371 (c)(1),
(2), (4) Date: Aug. 5, 2005

(87) PCT Pub. No.: WO03/093231

PCT Pub. Date: Nov. 13, 2003

(65) Prior Publication Data

US 2006/0089379 A1    Apr. 27, 2006

Related U.S. Application Data

(60) Provisional application No. 60/376,407, filed on Apr. 29, 2002.

(51) Int. Cl.
C07D 217/02 (2006.01)
A61K 31/47 (2006.01)
(52) U.S. Cl. ...................................... 514/307; 546/146
(58) Field of Classification Search ................ 546/146; 514/307
See application file for complete search history.

(56) References Cited

U.S. PATENT DOCUMENTS 5,691,321 A    11/1997  Schaper et al.

OTHER PUBLICATIONS

Van Riper et al., "Characterization and Species Distribution of High Affinity GTP-couples Receptors for HumanRantes and Monocyte Chemoattractant Protein 1", J. Exp. Med., vol. 177, pp. 851-856 (1993).

Primary Examiner—Zinna N. Davis
(74) Attorney, Agent, or Firm—David A. Rubin; David L. Rose

(57) ABSTRACT

The present invention is directed to compounds of the formula I: I(wherein R1, R2, R3, R4, R5, R6, R7, R8, R9, R10, X, n and the dashed line are defined herein) which are useful as modulators of chemokine receptor activity. In particular, these compounds are useful as modulators of the chemokine receptor CCR-2

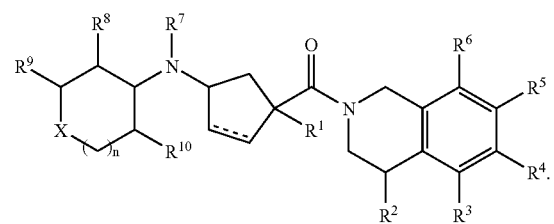

27 Claims, No Drawings

TETRAHYDROPYRANYL CYCLOPENTYL TETRAHYDROISOQUINOLINE MODULATORS OF CHEMOKINE RECEPTOR ACTIVITY

RELATED APPLICATION DATA

This is a National filing under 35 USC 371 of PCT/US03/13121, filed Apr. 25, 2003, which claims priority from U.S. Ser. No. 60/376,407, filed Apr. 29, 2002.

BACKGROUND OF THE INVENTION

The chemokines are a family of small (70–120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661–666 (1996)).

The chemokines are secreted by a wide variety of cell types and bind to specific G-protein coupled receptors (GPCRs) (reviewed in Horuk, *Trends Pharm. Sci.*, 15, 159–165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") Eotaxin, [Eotaxin 2, RANTES, MCP-2, MCP-3] (Rollins, et al., *Blood*, 90, 908–928 (1997)); CCR-4 (or "CKR-4" or "CC-CKR-4") [MIP-1α, RANTES, MCP-1] (Rollins, et al., *Blood*, 90, 908–928 (1997)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989–992 (1999)). A review of the role of eosinophils in allergic inflammation is provided by Kita, H., et al., *J. Exp. Med.* 183, 2421–2426 (1996). A general review of the role of chemokines in allergic inflammation is provided by Lustger, A. D., *New England J. Med.*, 338(7), 426–445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.*, 187, 601–608 (1998); Kurihara et al. *J. Exp. Med.*, 186, 1757–1762 (1997); Boring et al. *J. Clin. Invest.*, 100, 2552–2561 (1997); Kuziel et al. *Proc. Natl. Acad. Sci.*, 94, 12053–12058 (1997)). Furthermore, these animals show reduced monocyte infiltration into granulomatous lesions induced by the injection of schistosomal or mycobacterial antigens (Boring et al. *J. Clin. Invest.*, 100, 2552–2561 (1997); Warmington et al. *Am J. Path.*, 154, 1407–1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 –/– or CCR2 –/– mice backcrossed to APO-E –/–, LDL-R –/– or Apo B transgenic mice maintained on high fat diets (Boring et al. *Nature*, 394, 894–897 (1998); Gosling et al. *J. Clin. Invest.*, 103, 773–778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

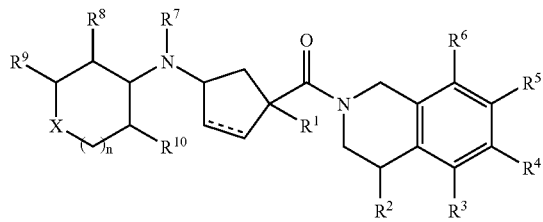

I wherein:
X is selected from the group consisting of:
—O—, —$NR^{20}$—, —S—, —SO—, —$SO_2$—, and —$CR^{21}R^{22}$—, —$NSO_2R^{20}$—,
—$NCOR^{20}$—, —$NCO_2R^{20}$—, —$CR^{21}CO_2R^{20}$—, —$CR^{21}OCOR^{20}$—, —CO—,
  where $R^{20}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl,
  where $R^{21}$ and $R^{22}$ are independently selected from: hydrogen, hydroxy, $C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl;
$R^1$ is selected from:
  —$C_{1-6}$alkyl, —$C_{0-6}$alkyl-O—$C_{1-6}$alkyl-, —$C_{0-6}$alkyl-S—$C_{1-6}$alkyl-,
  —($C_{0-6}$alkyl)-($C_{3-7}$cycloalkyl)-($C_{0-6}$alkyl), hydroxy, —$CO_2R^{20}$, heterocycle,
  —CN, —$NR^{20}R^{26}$, —$NSO_2R^{20}$—, —$NCOR^{20}$—, —$NCO_2R^{20}$—, —$NCOR^{20}$—,
  —$CR^{21}CO_2R^{20}$—, —$CR^{21}OCOR^{20}$—, phenyl and pyridyl,
  where $R^{26}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl
  where the alkyl and the cycloalkyl are unsubstituted or substituted with 1–7 substituents where the substituents are independently selected from:
  (a) halo,
  (b) hydroxy,
  (c) —O—$C_{1-3}$alkyl,
  (d) trifluoromethyl,
  (f) $C_{1-3}$alkyl,
  (g) —O—$C_{1-3}$alkyl,
  (h) —$CO_2R_{20}$,
  (i) —$SO_2R^{20}$,
  (j) —$NHCOCH_3$,
  (k) —$NHSO_2CH_3$,
  (l) -heterocycle,
  (m) =O,
  (n) —CN,
  and where the phenyl and pyridyl are unsubstituted or substituted with 1–3 substituents where the substituents are independently selected from: halo, hydroxy, $C_{1-3}$alkyl, $C_{1-3}$alkoxy and trifluoromethyl;
$R^2$ is selected from:
  (a) hydrogen,
  (b) hydroxy,
  (c) halo,
  (d) $C_{1-3}$alkyl, where the alkyl is unsubstituted or substituted with 1–6 substituents independently selected from: fluoro, and hydroxy,
  (e) —$NR^{20}R^{26}$,
  (f) —$CO_2R^{20}$,
  (g) —$CONR^{20}R^{26}$,
  (h) —$NR^{20}COR^{21}$,
  (i) —$OCONR^{20}R^{26}$,
  (j) —$NR^{20}CONR^{20}R^{26}$,
  (k) -heterocycle,
  (l) —CN,
  (m) —$NR^{20}$—$SO_2$—$NR^{20}R^{26}$,
  (n) —$NR^{20}$—$SO_2$—$R^{26}$,
  (o) —$SO_2$—$NR^{20}R^{26}$, and
  (p) =O, where $R^2$ is connected to the ring via a double bond;
$R^3$ is selected from:
  (a) hydrogen,
  (b) hydroxy,
  (c) halo,
  (d) $C_{1-6}$alkyl,
  (e) —O—$C_{1-6}$alkyl,
  (f) —$NR^{20}R^{21}$,
  (g) —$NR^{20}CO_2R^{21}$,
  (h) —$NR^{20}CONR^{20}R^{21}$,
  (i) —$NR^{20}$—$SO_2$—$NR^{20}R^{21}$,
  (j) —$NR^{20}$—$SO_2$—$R^{21}$,
  (k) heterocycle,
  (l) —CN,
  (m) —$CONR^{20}R^{21}$,
  (n) —$CO_2R_{20}$,
  (o) —$NO_2$,
  (p) —S—$R^{20}$,
  (q) —SO—$R^{20}$,
  (r) —$SO_2$—$R^{20}$, and
  (s) —$SO_2$—$NR^{20}R^{21}$;
$R^4$ is selected from:
  (a) hydrogen,
  (b) $C_{1-6}$alkyl,
  (c) trifluoromethyl, (d) trifluoromethoxy,
(e) chloro,
(f) fluoro,
(g) bromo, and
(h) phenyl;

$R^5$ is selected from:
(a) $C_{1-6}$alkyl, where alkyl may be unsubstituted or substituted with 1–6 fluoro and optionally substituted with hydroxyl,
(b) —O—$C_{1-6}$alkyl, where alkyl may be unsubstituted or substituted with 1–6 fluoro,
(c) —CO—$C_{1-6}$alkyl, where alkyl may be unsubstituted or substituted with 1–6 fluoro,
(d) —S—$C_{1-6}$alkyl, where alkyl may be unsubstituted or substituted with 1–6 fluoro,
(e) -pyridyl, which may be unsubstituted or substituted with one or more substituents selected from the group consisting of: halo, trifluoromethyl, $C_{1-4}$alkyl, and $CO_2R^{20}$,
(f) fluoro,
(g) chloro,
(h) bromo,
(i) —$C_{4-6}$cycloalkyl,
(j) —O—$C_{4-6}$cycloalkyl,
(k) phenyl, which may be unsubstituted or substituted with one or more substituents selected from the group consisting of: halo, trifluoromethyl, $C_{1-4}$alkyl, and $CO_2R^{20}$,
(l) —O-phenyl, which may be unsubstituted or substituted with one or more substituents selected from the group consisting of: halo, trifluoromethyl, $C_{1-4}$alkyl, and $CO_2R^{20}$,
(m) —$C_{3-6}$cycloalkyl, where alkyl may be unsubstituted or substituted with 1–6 fluoro,
(n) —O—$C_{3-6}$cycloalkyl, where alkyl may be unsubstituted or substituted with 1–6 fluoro,
(o) -heterocycle,
(p) —CN, and
(q) —$CO_2R^{20}$;

$R^6$ is selected from:
(a) hydrogen,
(b) $C_{1-6}$alkyl, and
(c) trifluoromethyl
(d) fluoro
(e) chloro, and
(f) bromo;

$R^7$ is selected from:
(a) hydrogen, and
(b) $C_{1-6}$alkyl, which is unsubstituted or substituted with 1–3 substituents where the substituents are independently selected from: halo, hydroxy, —$CO_2H$, —$CO_2C_{1-6}$alkyl, and —O—$C_{1-3}$alkyl;

$R^8$ is selected from:
(a) hydrogen,
(b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
(c) fluoro,
(d) —O—$C_{1-3}$alkyl, where alkyl may be unsubstituted or substituted with 1–3 fluoro, and
(e) $C_{3-6}$ cycloalkyl,
(f) —O—$C_{3-6}$cycloalkyl,
(g) hydroxy,
(h) —$CO_2R^{20}$,
(i) —$OCOR^{20}$, or $R^7$ and $R^8$ may be joined together via a $C_{2-4}$alkyl or a $C_{0-2}$alkyl-O—$C_{1-3}$alkyl chain to form a 5–7 membered ring;

$R^9$ is selected from:
(a) hydrogen,
(b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
(c) $CO_2R^{20}$,
(d) hydroxy, and
(e) —O—$C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$, or $R^8$ and $R^9$ may be joined together by a $C_{1-4}$alkyl chain or a $C_{0-3}$alkyl-O—$C_{0-3}$alkyl chain to form a 3–6 membered ring;

$R^{10}$ is selected from:
(a) hydrogen, and
(b) $C_{1-6}$alkyl, where alkyl may be unsubstituted or substituted with 1–6 fluoro,
(c) fluoro,
(d) —O—$C_{3-6}$cycloalkyl, and
(e) —O—$C_{1-3}$alkyl, where alkyl may be unsubstituted or substituted with 1–6 fluoro, or $R^8$ and $R^{10}$ may be joined together by a $C_{2-3}$alkyl chain to form a 5–6 membered ring, where the alkyl are unsubstituted or substituted with 1–3 substituents where the substituents are independently selected from: halo, hydroxy, —$CO_2R^{20}$, $C_{1-3}$alkyl, and $C_{1-3}$alkoxy, or $R^8$ and $R^{10}$ may be joined together by a $C_{1-2}$alkyl-O—$C_{1-2}$alkyl chain to form a 6–8 membered ring, where the alkyl are unsubstituted or substituted with 1–3 substituents where the substituents are independently selected from: halo, hydroxy, —$CO_2R^{20}$, $C_{1-3}$alkyl, and $C_{1-3}$alkoxy, or $R^8$ and $R^{10}$ may be joined together by a —O—$C_{1-2}$alkyl-O-chain to form a 6–7 membered ring, where the alkyl are unsubstituted or substituted with 1–3 substituents where the substituents are independently selected from: halo, hydroxy, —$CO_2R^{20}$, $C_{1-3}$alkyl, and $C_{1-3}$alkoxy;

n is selected from 0, 1 and 2;
the dashed line represents a single or a double bond;
and pharmaceutically acceptable salts thereof and individual diastereomers thereof.

Preferred compounds of the present invention include those of formula Ia:

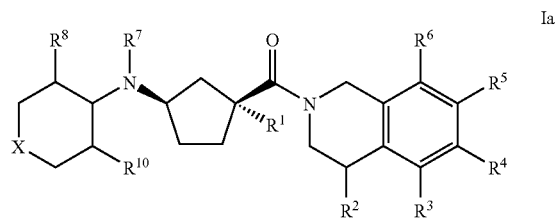

Ia wherein $R^1$, $R^2$, $R^3$, $R^4$, $R^5$, $R^6$, $R^7$, $R^8$, $R^{10}$ and X are defined herein; and pharmaceutically acceptable salts and individual diastereomers thereof.

More preferred compounds of the present invention also include those of formula Ic:

[Structure Ic]

wherein $R^1$, $R^2$, $R^3$, $R^5$ and $R^8$ are defined herein, and

More preferred compounds of the present invention also include those of formula Id:

[Structure Id]

wherein:
$R^1$ is selected from:
  (a) $C_{1-6}$alkyl,
  (b) $C_{1-6}$alkyl-hydroxy, and
  (c) $C_{1-6}$alkyl substituted with 1–6 fluoro;
$R^2$ is selected from:
  (a) hydrogen, and
  (b) hydroxy;
$R^3$ is selected from:
  (a) hydrogen,
  (b) —$NH_2$,
  (b) —$NO_2$,
  (c) —$NHSO_2$—$C_{1-6}$alkyl,
  (d) fluoro, and
  (g) heterocycle;
$R^5$ is selected from:
  (a) $C_{1-6}$alkyl substituted with 1–6 fluoro,
  (b) chloro,
  (c) bromo,
  (d) phenyl, and
  (e) —$OCF_3$;
$R^8$ is selected from:
  (a) hydrogen,
  (b) $C_{1-6}$alkyl,
  (c) $C_{1-6}$alkyl-hydroxy, and
  (d) $C_{1-6}$alkyl substituted with 1–6 fluoro, and
  (e) —O—$C_{1-3}$alkyl;

and pharmaceutically acceptable salts and individual diastereomers thereof.

In the present invention it is preferred that X is selected from the group consisting of:
—O—, —$CH_2$—, —S—, —SO—, and —$SO_2$—.

In the present invention it is more preferred that X is selected from the group consisting of: —O—, and —$CH_2$—.

In the present invention it is even more preferred that X is —O—.

In the present invention it is preferred that X is selected from the group consisting of:
—O—, —$CH_2$—, —S—, —SO—, and —$SO_2$—.

In the present invention it is more preferred that X is selected from the group consisting of: —O—, and —$CH_2$—.

In the present invention it is even more preferred that X is —O—.

In the present invention it is preferred that $R^1$ is selected from:
(1) —$C_{1-6}$alkyl, which is unsubstituted or substituted with 1–6 substituents where the substituents are independently selected from:
  (a) halo,
  (b) hydroxy,
  (c) —O—$C_{1-3}$alkyl, and
  (d) trifluoromethyl,
(2) —$C_{0-6}$alkyl-O—$C_{1-6}$alkyl-, which is unsubstituted or substituted with 1–6 substituents where the substituents are independently selected from:
  (a) halo, and
  (b) trifluoromethyl,
(3) —$C_{0-6}$alkyl-S—$C_{1-6}$alkyl-, which is unsubstituted or substituted with 1–6 substituents where the substituents are independently selected from:
  (a) halo, and
  (b) trifluoromethyl,
(4) —($C_{3-5}$cycloalkyl)-($C_{0-6}$alkyl), which is unsubstituted or substituted with 1–7 substituents where the substituents are independently selected from:
  (a) halo,
  (b) hydroxy,
  (c) —O—$C_{1-3}$alkyl, and
  (d) trifluoromethyl.

In the present invention it is more preferred that $R^1$ is $C_{1-6}$alkyl which is unsubstituted or substituted with 1–5 substituents where the substituents are independently selected from:
  (a) hydroxy, and
  (b) fluoro.

In the present invention it is even more preferred that $R^1$ is selected from:
  (a) isopropyl,
  (b) —CH(OH)$CH_3$, and
  (c) —$CH_2CF_3$.

In the present invention it is still more preferred that $R^1$ is isopropyl.

In the present invention it is preferred that $R^2$ is selected from:
  (a) hydrogen,
  (b) hydroxy,
  (c) —$NH_2$,
  (d) —$CO_2H$,
  (e) -triazolyl,
  (f) -tetrazolyl,
  (g) —$CO_2$—$C_{1-6}$alkyl,
  (h) —$CONH_2$,
  (i) —CONH—$C_{1-6}$alkyl,
  (j) —NHCO—$C_{1-6}$alkyl,
  (k) —$NHCONH_2$,
  (l) —NHCONH—$C_{1-6}$alkyl
  (m) —OCONH—$C_{1-6}$alkyl,
  (n) —NH—$SO_2$—$C_{1-6}$alkyl, and
  (o) —$SO_2$—NH—$C_{1-6}$alkyl.

In the present invention it is more preferred that $R^2$ is selected from:
  (a) hydrogen,
  (b) hydroxy, (c) —NH$_2$,
(d) —CO$_2$H,
(e) -triazolyl,
(f) -tetrazolyl,
(g) —NHCOCH$_3$,
(h) —NHCONH$_2$,
(i) —CONH$_2$,
(j) —NH—SO$_2$—CH$_3$, and
(k) —SO$_2$—NH—CH$_3$.

In the present invention it is even more preferred that R$^2$ is hydrogen.

In the present invention it is preferred that R$^3$ is selected from:
(a) hydrogen,
(b) hydroxy,
(c) fluoro,
(d) —O—C$_{1-6}$alkyl,
(e) —NO$_2$,
(f) —NH$_2$,
(g) —NHCO$_2$—C$_{1-6}$alkyl,
(h) —NHCONH—C$_{1-6}$alkyl,
(i) —NH—SO$_2$—NH—C$_{1-6}$alkyl,
(j) —NH—SO$_2$—C$_{1-6}$alkyl,
(k) -triazolyl,
(l) -tetrazolyl,
(m) —CN,
(n) —CO—NH$_2$,
(o) —CO$_2$H,
(p) —S—C$_{1-6}$alkyl,
(q) —SO—C$_{1-6}$alkyl,
(r) —SO$_2$—C$_{1-6}$alkyl, and
(s) —SO$_2$—NH—C$_{1-6}$alkyl.

In the present invention it is more preferred that R$^3$ is selected from:
(a) hydrogen,
(b) —NH$_2$,
(c) —NO$_2$,
(c) —NHSO$_2$—C$_{1-6}$alkyl,
(d) fluoro,
(e) -triazolyl, and
(f) -tetrazolyl.

In the present invention it is even more preferred that R$^3$ is selected from:
(a) hydrogen,
(b) —NH$_2$,
(b) —NO$_2$,
(c) —NHSO$_2$—CH$_3$, and
(d) fluoro.

In the present invention it is preferred that R$^4$ is selected from:
(a) hydrogen, and
(b) trifluoromethyl.

In the present invention it is more preferred that R$^4$ is hydrogen.

In the present invention it is preferred that R$^5$ is selected from:
(a) C$_{1-3}$alkyl substituted with 1–6 fluoro,
(b) chloro,
(c) bromo,
(d) —O-phenyl, which may be unsubstituted or substituted with one or more substituents selected from the group consisting of: halo and trifluoromethyl,
(e) phenyl, which may be unsubstituted or substituted with one or more substituents selected from the group consisting of: halo and trifluoromethyl, and
(f) —O—C$_{1-3}$alkyl substituted with 1–6 fluoro.

In the present invention it is more preferred that R$^5$ is selected from:
(a) trifluoromethyl,
(b) trifluoromethoxy,
(c) bromo, and
(d) chloro.

In the present invention it is most preferred that R$^5$ is trifluoromethyl.

In the present invention it is preferred that R$^6$ is hydrogen.

In the present invention it is preferred that R$^7$ is hydrogen or methyl.

In the present invention it is preferred that R$^8$ is selected from:
(a) hydrogen,
(b) C$_{1-3}$alkyl, which is unsubstituted or substituted with 1–6 fluoro,
(c) —O—C$_{1-3}$alkyl, and
(d) fluoro, and
(e) hydroxy.

In the present invention it is more preferred that R$^8$ is selected from:
(a) hydrogen,
(d) trifluoromethyl,
(c) methyl,
(d) methoxy,
(e) ethoxy,
(f) ethyl,
(g) fluoro, and
(h) hydroxy.

In the present invention it is preferred that R$^9$ is hydrogen.

In the present invention it is preferred that R$^{10}$ is selected from:
(a) hydrogen,
(b) methyl, and
(c) methoxy.

In the present invention it is preferred that R$^{10}$ is hydrogen.

In the present invention it is also preferred that R$^8$ and R$^{10}$ are joined together by a —CH$_2$CH$_2$— chain or a —CH$_2$CH$_2$CH$_2$— chain to form a cyclopentyl ring or a cyclohexyl ring.

Representative compounds of the present invention include those of the formula:

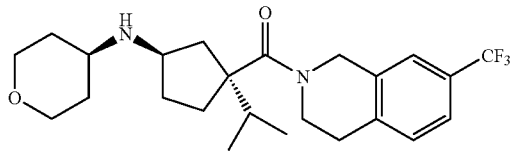

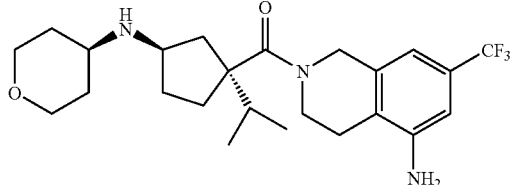

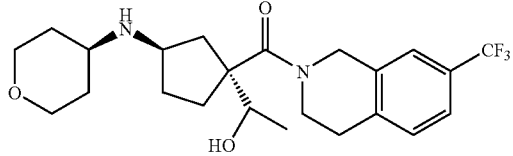

-continued

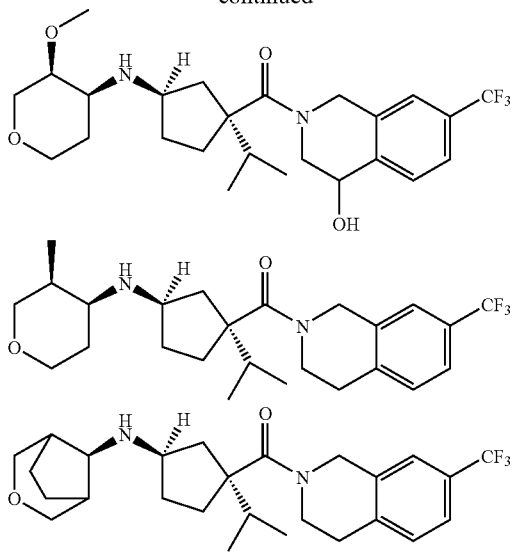

and pharmaceutically acceptable salts and individual diastereomers thereof.

The compounds of the instant invention have at least two asymmetric centers at the 1- and 3-positions of the cyclopentyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of the more preferred compounds of this orientation where the substituents on the cyclopentyl ring (amide and amine units) are cis, as depicted:

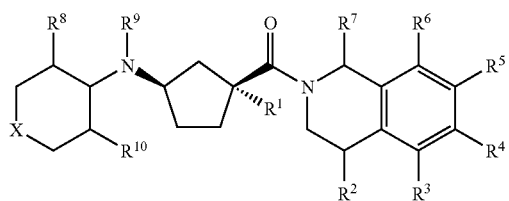

The absolute configurations of the most preferred compounds of this invention are those of the orientation as depicted:

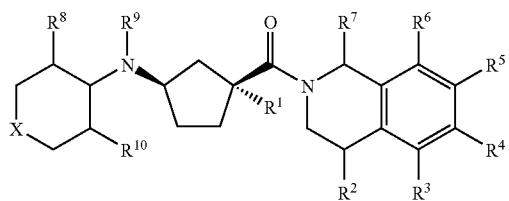

wherein the carbon bearing the amine substituent is designated as being of the (R) absolute configuration and the carbon bearing the amide subunit can be designated as being of either the (S) or (R) absolute configuration depending on the priority for $R^1$. For example if R is isopropyl then the absolute stereochemistry at the carbon bearing the amide subunit would be (S) since the amide and amine units are preferred to have the cis arrangement on the cyclopentyl ring.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2,5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 µM Calcien-AM (Molecular Probes), for 30 min at 37° C. Labeled cells were washed twice and suspended at $5\times10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis,* Hookworm, *Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in the prevention and treatment of a wide variety of inflammatory and immunoregulatory disorders and diseases, allergic conditions, atopic conditions, as well as autoimmune pathologies. In a specific embodiment, the present invention is directed to the use of the subject compounds for the prevention or treatment of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in the prevention or treatment of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, preferably 2.0 to 500, more preferably 3.0 to 200, particularly 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

One of the principal routes used for preparation of compounds within the scope of the instant invention which bear a 1,1,3-trisubstituted cyclopentane framework 1–9 is depicted in Scheme 1A.

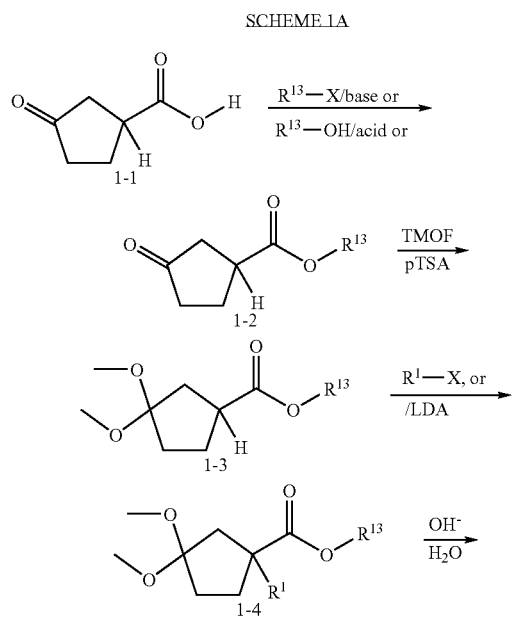

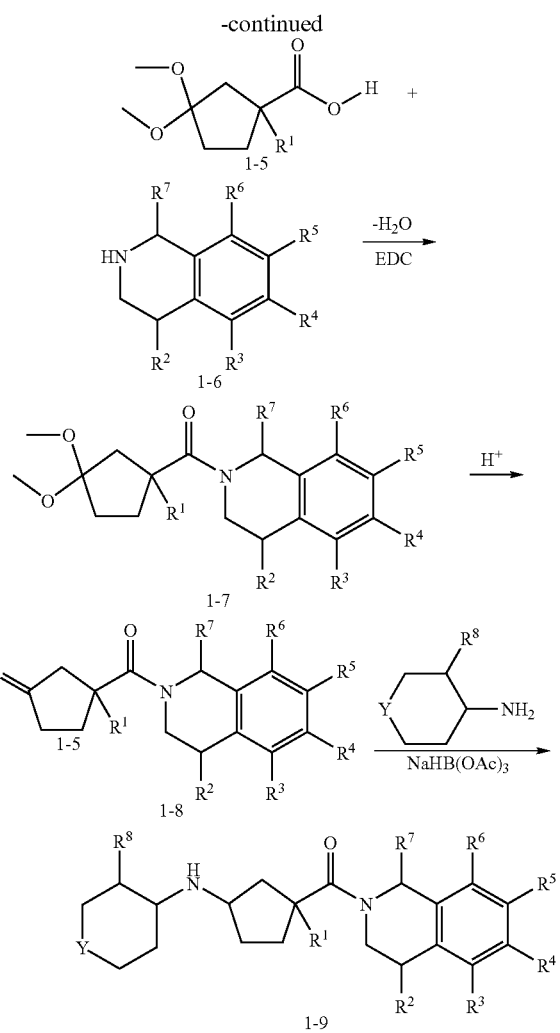

According to this route, 3-oxocyclopentanecarboxylic acid (1-1) which was synthesized following a known procedure (Stetter, H., Kuhlman, H., *Liebigs Ann. Chim.*, 1979, 944) is esterified under standard conditions. In the case of $R^{13}$ being a benzyl group the acid is reacted with benzyl chloride in the presence of sodium carbonate in an appropriate solvent, e.g. dimethyl formamide. When $R^{13}$ represents a tert-Butyl group, the respective ester 1-2 can be prepared by reacting the appropriate alcohol in this case tert-Butanol with acid 1-1 in the presence of sulfuric acid. Protection of the oxo-group in 1-2 can be achieved by a number of ways (Greene, T., Wuts, P. G. M., *Protective Groups in Organic Chemistry*, John Wiley & Sons, Inc., New York, N.Y. 1991). The particularly suitable dimethyl acetal protecting group can be introduced using trimethyl orthoformate as a reagent in a suitable solvent such as dichloromethane and methyl alcohol in the presence of an acidic catalyst. Alternatively, in the case of $R^{13}$ being a methyl group, the acid 1-1 can be converted to 1-3 directly by using trimethyl orthoformate and an acidic catalyst, such as para-Toluenesulfonic acid. An alkylation of esters 1-3 with an alkylating agent such as alkyl chloride, bromide or iodide in the presence of an appropriate base such as lithium diisopropylamide, produces intermediates 1-4. The ester protecting group present in 1-4 can be removed by a number of ways, depending on the nature of the ester. Benzyl esters ($R^{13}$=benzyl) can be easily removed by catalytic hydrogenation, methyl esters ($R^{13}$=methyl) can be hydrolyzed in the presence of an acid or base at ambient or elevated temperatures, whereas tert-Butyl esters ($R^{13}$=tert-Butyl) can be easily cleaved under acidic conditions. The amides 1-7 are then prepared by reaction of acids 1–5 with tetrahydroisoquinolines 1-6 in the presence of a suitable coupling agent, such as 1-[3-(dimethylamino)propyl]-3-ethylcarbodiimide or other agents described in the literature. The acetal protecting group is in general removed under acidic conditions and the final chemokine receptor modulators 1-9 can be then prepared by reaction of ketones 1-8 with appropriate cycloalkylamines in a presence of a reducing agent such as sodium triacetoxyborohydride or sodium cyanoborohydride.

The enolate generated from ester 1-3 ($R^{13}$ being a benzyl or tert-Butyl group) in the presence of a strong base such as lithium diisopropylamide can be reacted with aldehydes ($R^{1a}$CHO) or ketones ($R^{1a}R^{2a}$CO) to produce the appropriate hydroxyalkyl substituted intermediates 1-4a as indicated in Scheme 1B. Once again the ester protecting group is removed under conditions suitable for the particular protecting group: the cleavage of the benzyl esters can be achieved hydrogenolytically, and the acids can be converted to the final products 1-9a as described in Scheme 1, or, in the case of the tert-Butyl esters, under acidic conditions. The latter induces usually cleavage of the acetal protecting group as well, and the keto acids 1–10 can be prepared this way in an one-pot procedure. Their conversion to the final modulators of chemokine activity 1-9a can be achieved as described previously.

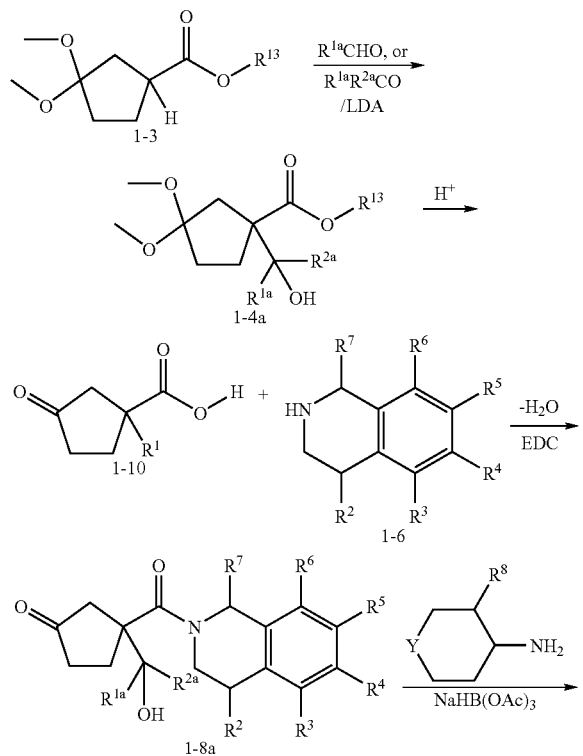

SCHEME 1B

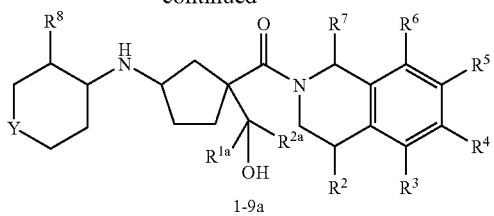

-continued 1-9a

The compounds, which can be synthesized according to the chemistry described in Schemes 1A and 1B represent diastereoisomeric mixtures (Eliel, E. E., Wilen, S. H., *Stereochemistry of Organic Compounds,* John Wiley & Sons, Inc., New York), and these can be separated into their components by chromatography using normal phase, reverse phase or chiral columns, depending on the nature of the separation. The chiral chromatographic separations are particularly suitable to obtain single isomers.

An alternative route for preparation of compounds 1-9 and 1-9a is detailed in Schemes 2A, 2B and 2C.

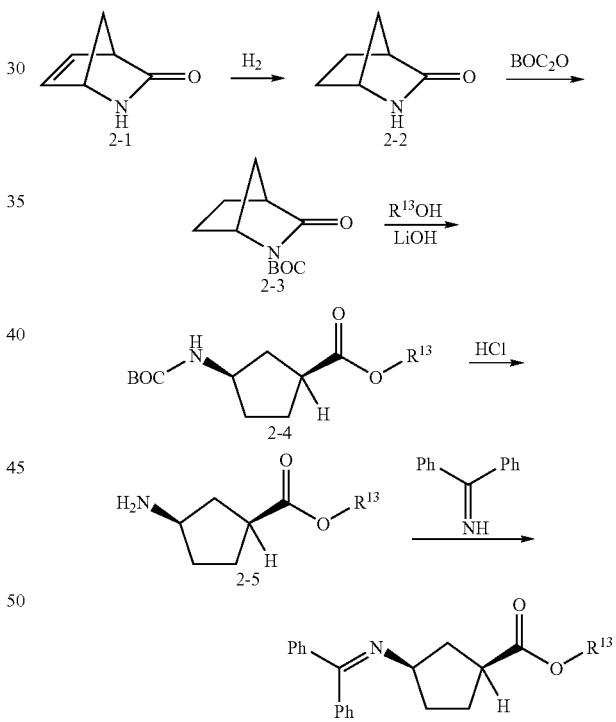

SCHEME 2A

According to this, the commercially available homochiral lactam 2-1 is hydrogenated and the saturated 2-2 is treated with $BOC_2O$ in the presence of a suitable catalyst, e.g. N,N-dimethylamino pyridine. A base catalyzed cleavage of the amide bond in the presence of a suitable alcohol $R^{13}$—OH provides then the respective ester 2-4. The BOC-protecting group is removed, preferably with an acid such as HCl in a aprotic solvent, such as dioxane, to yield the amine 2-5 in a form of a salt. When this amine is mixed with benzophenone imine, the respective Schiff base 2-6 is formed, which can be obtained in pure form by simple filtration to remove ammonium chloride.

The enolate formed from ester 2-6 with a strong base, such as LDA can be reacted with alkyl halides $R^1$—X, as well as aldehydes $R^{1a}$CHO or ketones $R^{1a}R^{2a}$CO to obtain intermediates 2-7a, 2-7b and 2-8a, 2-8b respectively, Scheme 2B These reactions produce a mixture of the respective cis-(2-7a and 2-8a) and trans-(2-7b and 2-8b) diastereoisomers, which can be separated by a suitable chromatography. In most cases, normal phase flash chromatography on deactivated silica gel can be applied with success.

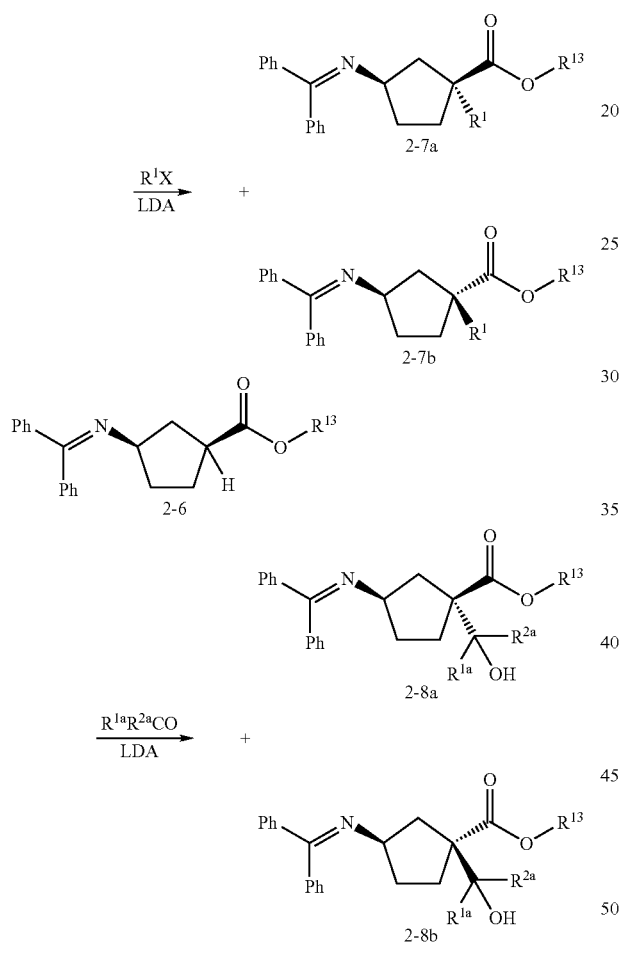

The desired cis diastereoisomers 2-7a and 2-8a are then treated with an acid such as HCl to aid hydrolysis of the imine group and the resulting amino group is suitably protected e.g. in a form of a tert-butoxycarbonyl amide (Scheme 2C). The ester group present in intermediates 2-10a is then cleaved. The applied procedure depends on the nature of the ester: e.g. a benzyl ester can be cleaved by hydrogenolysis, an tert-Butyl ester under aprotic acidic conditions and an alkyl ester can be hydrolyzed under either acidic or basic conditions. The formed acids are then coupled with suitable amines as described before and the BOC protecting group is removed with an acid. A reductive alkylation of amines 2-13a with suitable cycloketones.

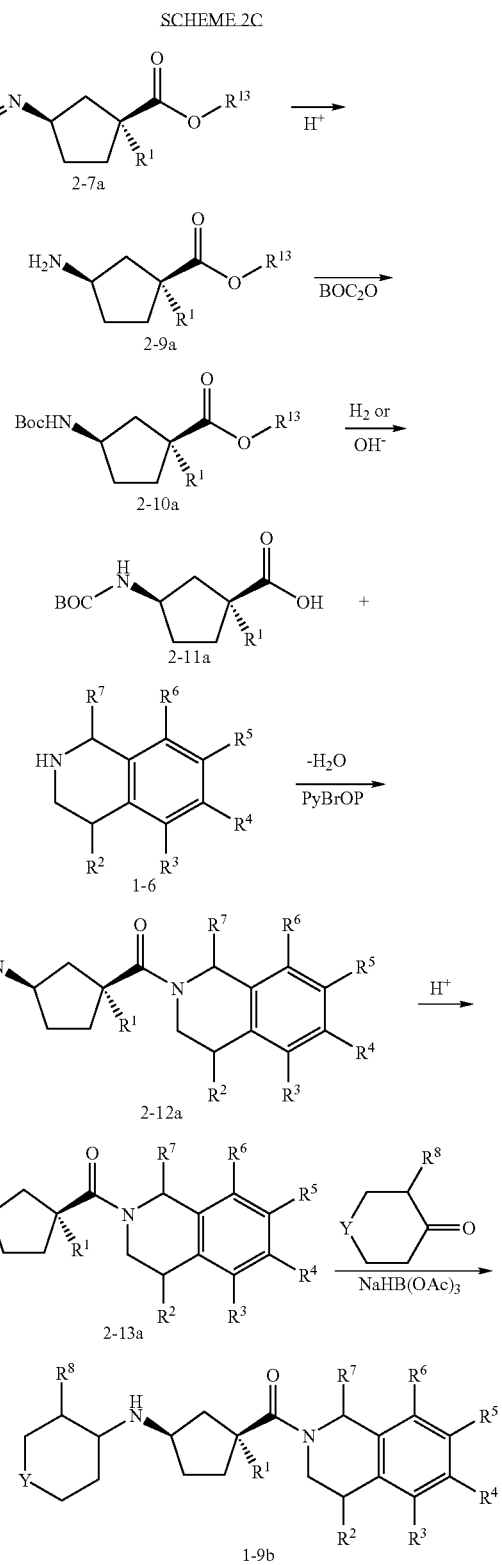

If necessary, a second reductive alkylation to introduce the $R^{9a}$ substituent is then performed to yield the final modulators of chemokine activity 1-9c. Further modification of $R^{9b}$ gives the new modulators of chemokine activity 1-9d.

SCHEME 2D

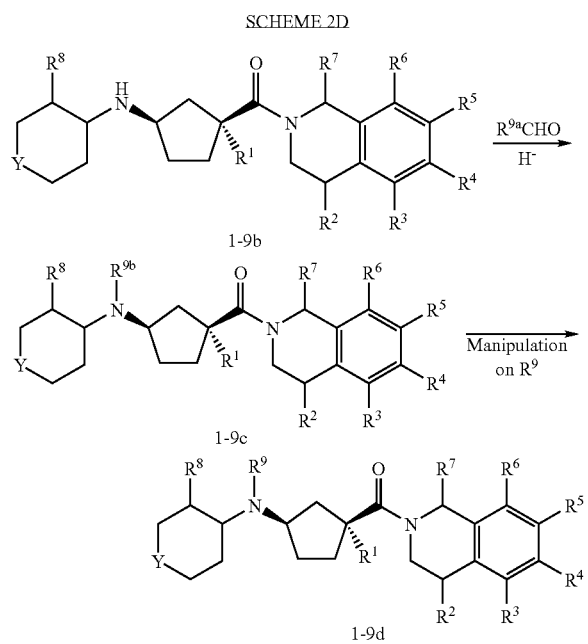

The bicyclic chemokine modulators 1-9e is also prepared via direct reductive alkylation of the amine 2-13a with the keto aldehydes.

SCHEME 2E

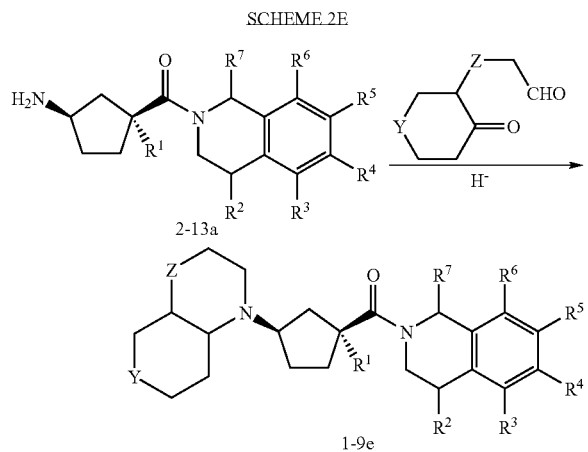

In the cases of bicyclic ketones, the bridged chemokine modulators 1-9f is prepared by standard reductive amination conditions.

SCHEME 2F

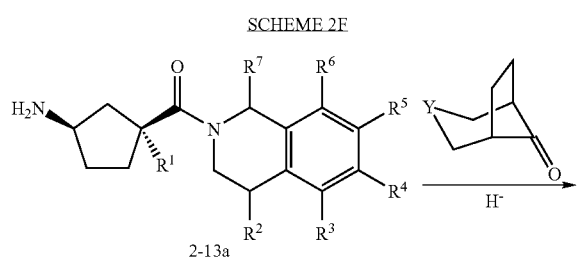

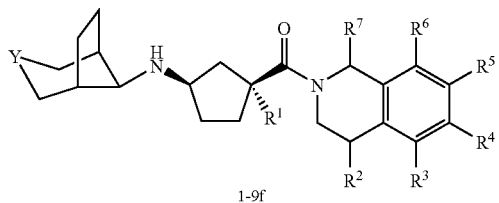

Intermediates 2-8a can be transformed into final products 1-8a in a sequence of steps (Scheme 2G) analogous to those described in Scheme 2C except that a base catalyzed hydrolysis of the ester group was found not to be suitable for the desired transformation.

The chemistry described in Schemes 2A-G offers a considerable advantage in that following these transformations products 1-9 are obtained in a homochiral form, rendering the separation step described in Scheme 1 unnecessary.

SCHEME 2G

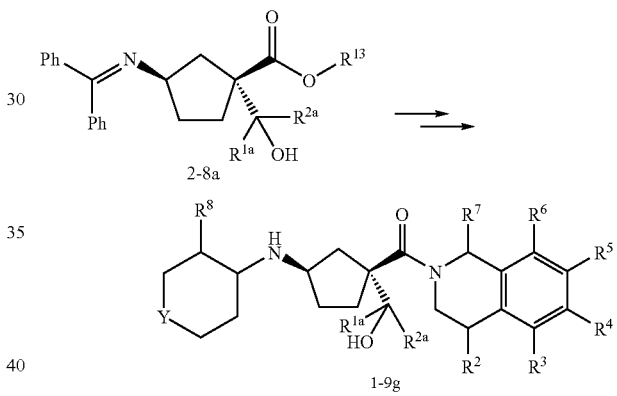

The third principal route to synthesize compounds within the scope of the instant invention is detailed in Scheme 3A and 3B.

SCHEME 3A

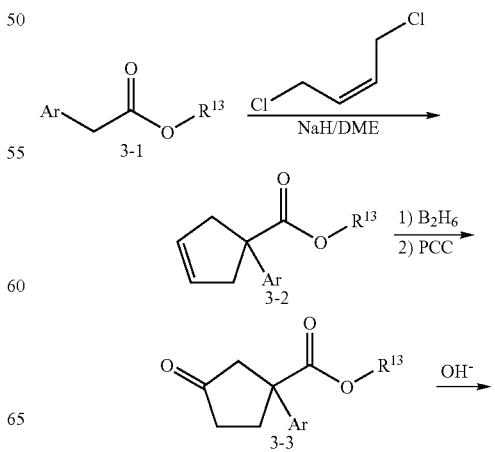

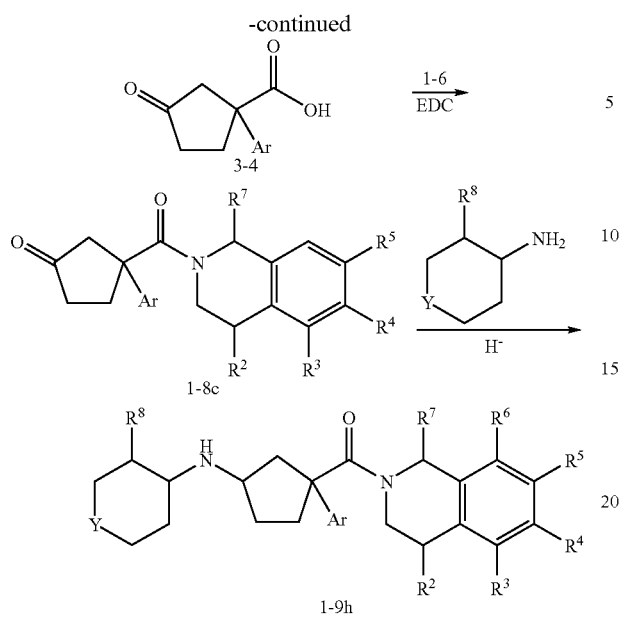

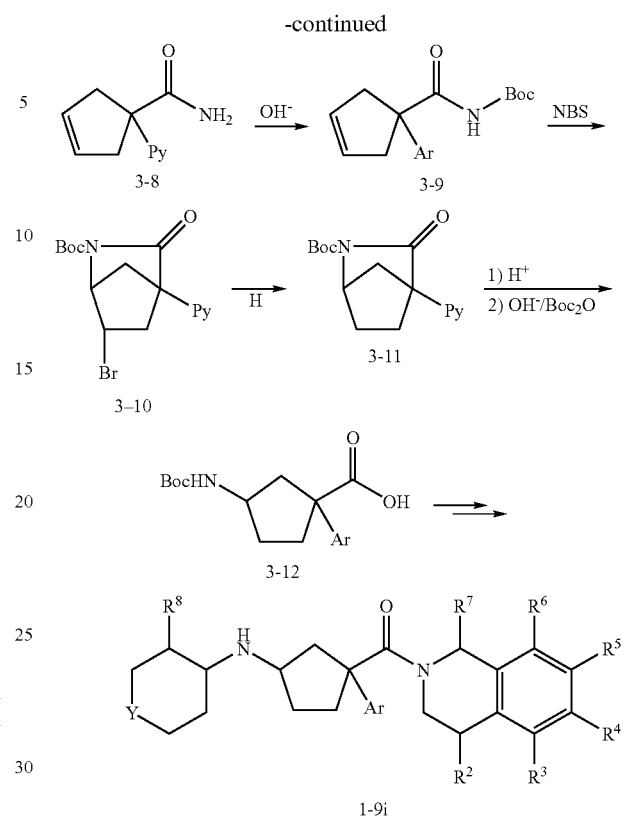

According to this, the enolate, generated from ester 3-1 with a strong base, e.g. sodium hydride is then double alkylated with 1,4-dichloro-2-butene in a suitable solvent, such as dimethoxyethane preferably in the presence of an additional co-solvent (e.g. DMPU) to suppress undesired side-reactions. Addition of borane to the double bond (see March, J. *Advanced Organic Chemistry*, 4$^{th}$ edition, John Wiley & Sons Inc., New York, p. 702–707) is followed by a direct pyridinium chlorochromate mediated oxidation of the formed adduct to produce ketones 3-3 directly, in fair yield. The ester group present in intermediates 3-3 is then removed by a base catalyzed hydrolysis, and the acids 3-4 are coupled to tetrahydroisoquinolines as discussed previously. The last step in preparation of final compounds 1-9h is a reductive amination of ketones 1-8c with cyclic amines as detailed above. Similarly to the case described in Scheme 1A and 1B this synthetic sequence produces mixtures of diastereoisomers, and their separation can be accomplished using chromatography on normal-, reverse-, or chiral phases.

The previously described synthetic sequence can be used to obtain other modulators of chemokine activity, which carry an aromatic and other groups which can not be introduced by direct alkylation (e.g. cyano).

In the cases of pyridyl substitution, a modified procedure (Scheme 3B) is used to prepare the key acid intermediates.

SCHEME 3B

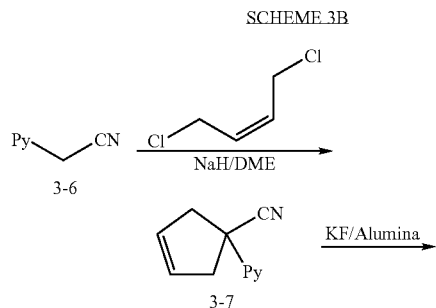

According to this, a pyridylacetonitrile 3-6 is reacted with 1,4-dichloro-2-butene, the resultant nitrile 3-7 is hydrolyzed to yield the amide 3-8 which is further converted into the Boc amide 3-9. NBS-induced cyclization is followed by radical reduction yield bicyclic amide 3-11. A acid catalyzed hydrolysis is followed by Boc protection to yield the acid 3-12 (cis racemate), and the final amines 1-9i are then prepared in a sequence of steps(Scheme 3B) analogous to those described in Scheme 2C.

In the cases discussed so far, the formation of the amide bond always preceded the reductive amination step. In some instances, however, it was advantageous to reverse this order (Scheme 4A).

SCHEME 4A

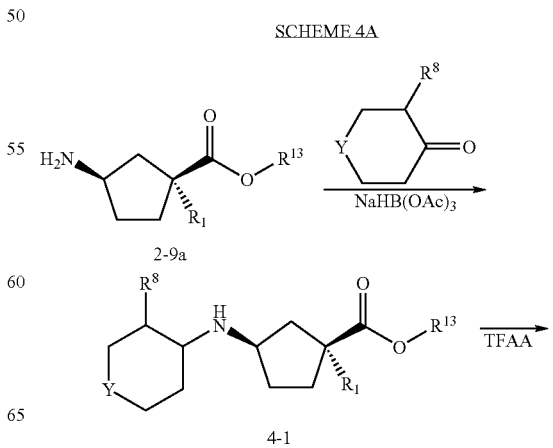

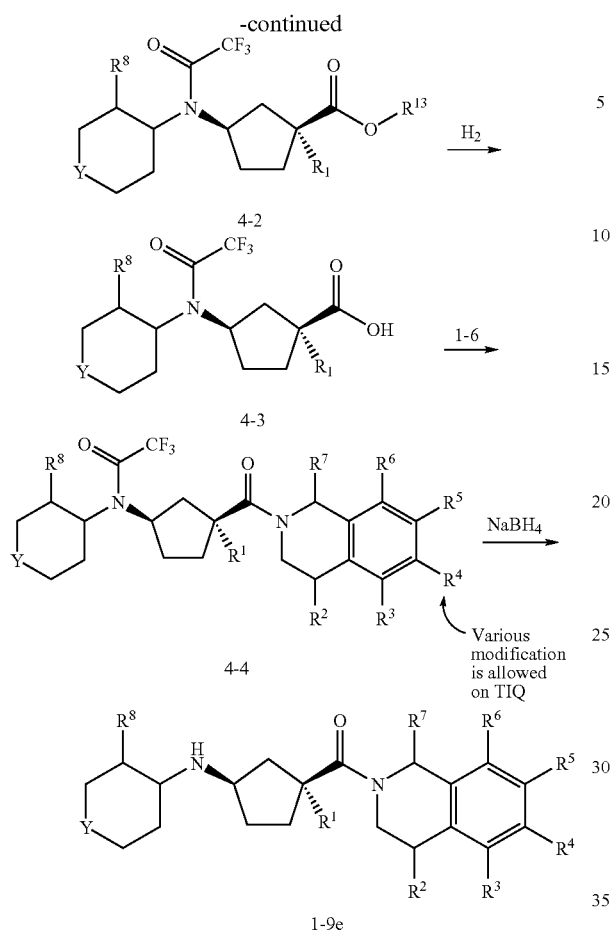

4-2

4-3

4-4

1-9e

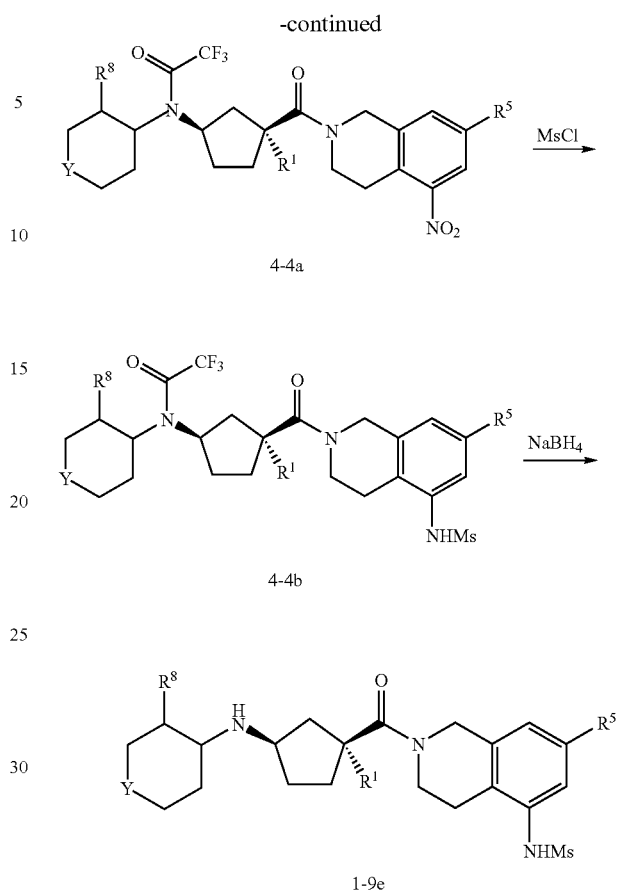

4-4a 4-4b 1-9e

According to this, the amine intermediate 2-9a is reductively alkylated with an appropriate ketone and the resultant secondary amine is protected e.g., as a trifluroacetamide. The ester group is now cleaved (hydrogenolysis if $R^{13}$ is a benzyl group) and the amide is attached as described above. A reductive or base catalyzed removal of the trifluoroacetyl protecting group then affords the desired modulators of chemokine activity 1-9e. Instead, the functional groups ($R^2$, $R^3$, $R^4$, $R^5$, $R^6$, $R^7$) on the tetrahydroisoquinoline rings can be modified before the final cleavage of the TFA amide to provide various new type of chemokine modulators. One example is given in Scheme 4B. The nitro compound 4-4 is reduced into the aniline 4-5 which can be further converted into sulfonamide 1-9e.

Another example of such a conversion is illustrated in Scheme 4C. The ketone 4-4 is reduced to the alcohol 4-4c. A variety of new derivatives are prepared based on this alcohol by a synthetic manipulation sequence as detailed in Scheme 4C.

SCHEME 4C

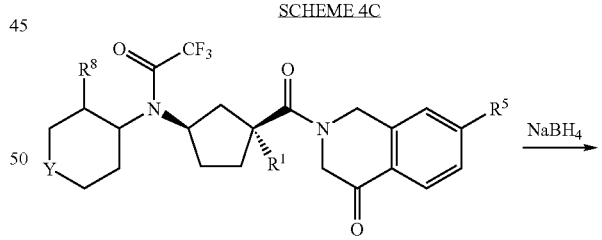

4-4

SCHEME 4B

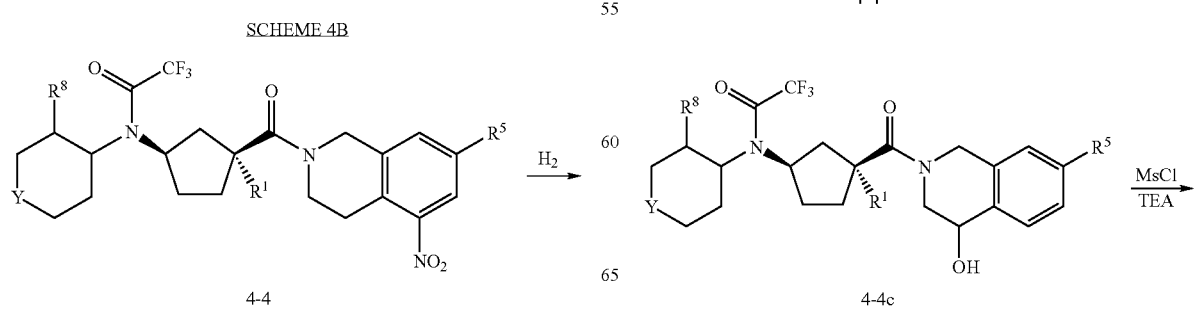

4-4

4-4c

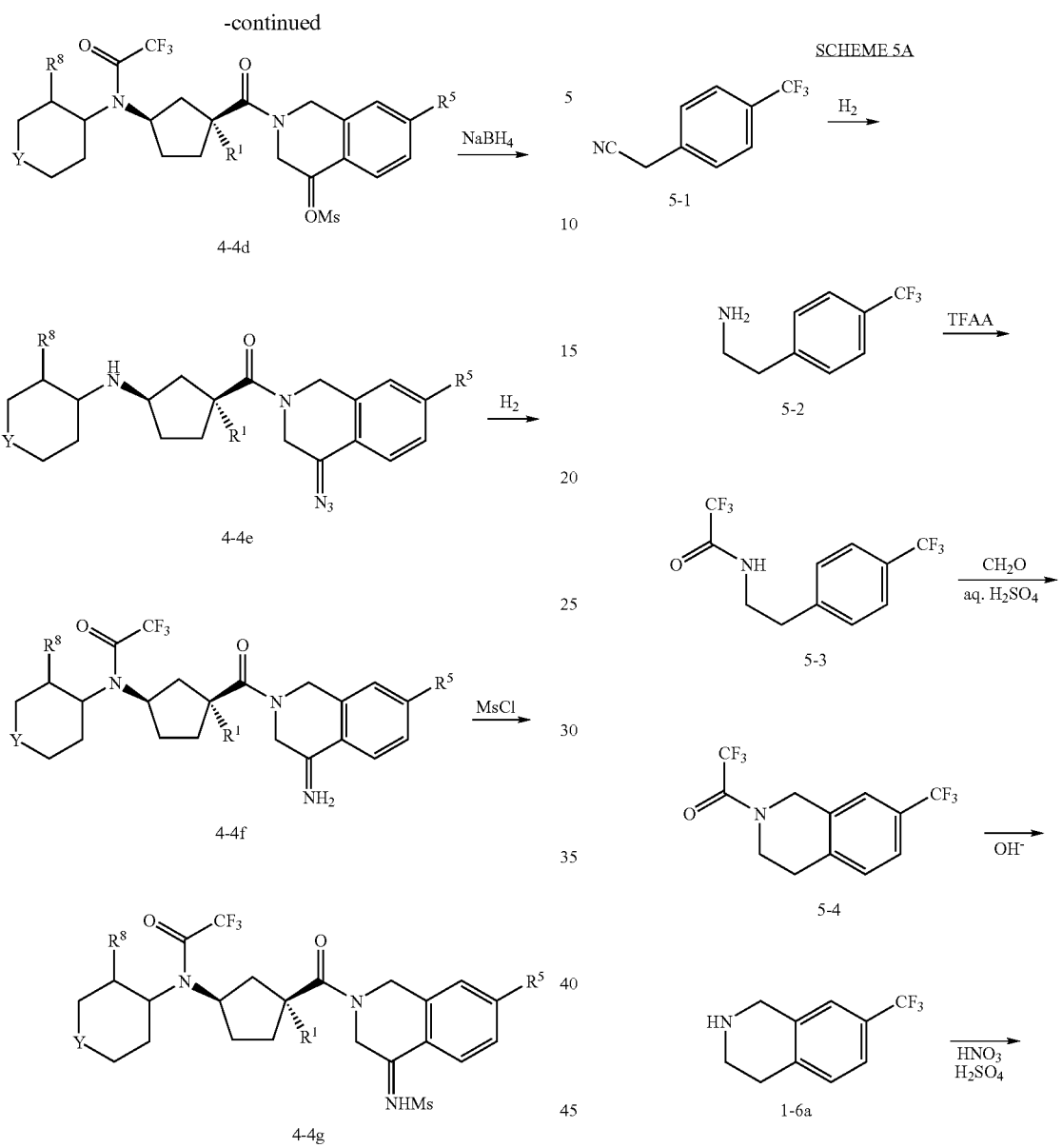

The tetrahydroisoquinolines 1-6 incorporated into the amide portion of 1-9 often contain one or two substituted groups on various positions (Scheme 5). Most of these are not available commercially, however, can be obtained through synthesis, Schemes 5A, 5B.

An example of such a synthesis is depicted in Scheme 5A. According to this, the commercially available 4-trifluoromethyl phenylacetonitrile (5-1) is converted to the corresponding amine (5-2) using hydrogenation in the presence of Ra—Ni, and trifluoroacetic anhydride is then used to cap the amine. The resultant amide (5-3) is treated with formaldehyde in the presence of sulfuric acid to give the cyclic compound (5-4) which is further converted into tetrahydroisoquinoline (1-6a). Further nitration on 5-position undergoes smoothly under standard nitration condition to yield a viable intermediate 1-6b.

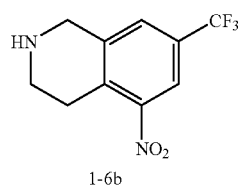

Many 5-substituted amines can also be prepared based on 5-4 (Scheme 5B). Iodolization on 5-posotion yield a viable intermediate 5-6. After conversion to cyano compound 5-7 under palladium (0) catalyzed reaction, the amide 5-7 is cleaved into the amine 1-6c which can be converted into amino ester 1-6d in high yield by a two step sequence. The iodo compound 5-6 can also be converted into sulfide 5-8. The sulfone 1-6e and sulfonamide 1-6f are prepared by oxidation with either mCPBA or chlorine.

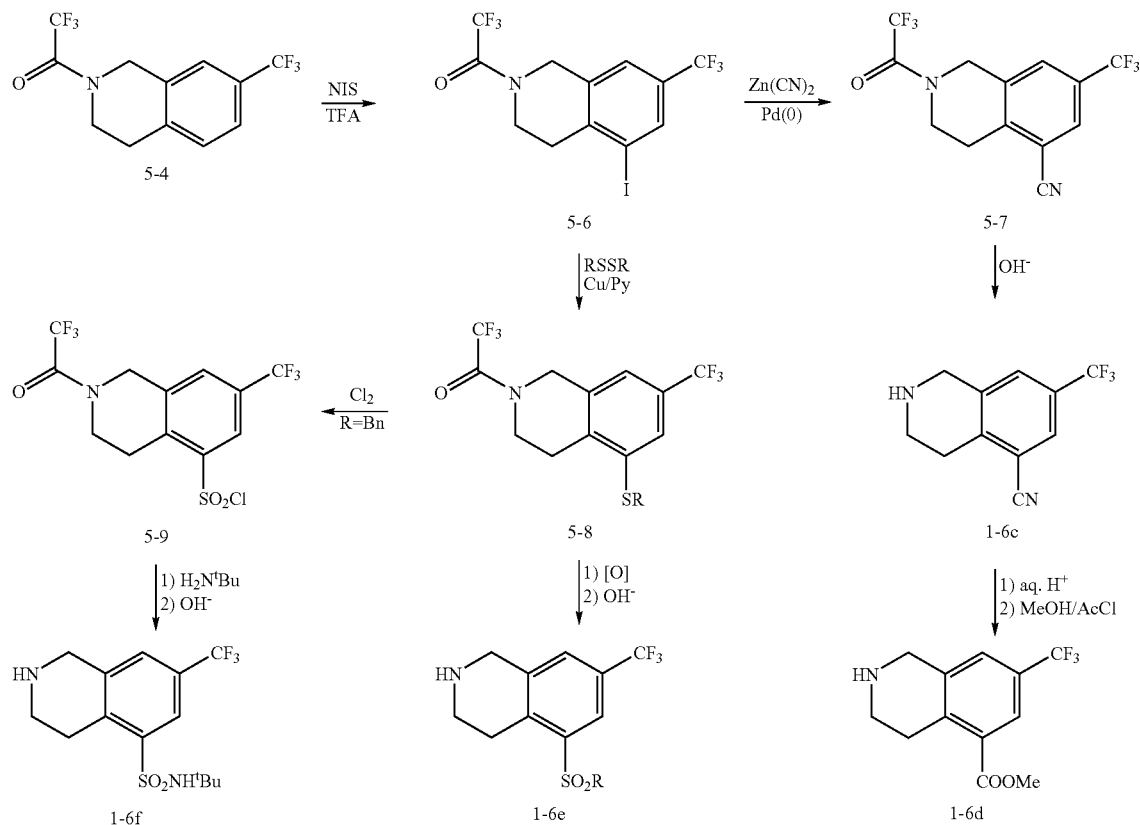

Another example, which describes a synthesis of 5-substituted tetrahydroisoquinoline 1-6g is detailed in Scheme 6. According to this, the commercially available 3-trifluoromethyl-toluene (6-1) is iodolated in trifluoromethane sulfonic acid and the aromatic iodide is converted to the respective acid 6-3 by Grignard reaction and quench with carbon dioxide. Esterification of the corresponding acid yields the required ester (6-4) and then NBS is used to produce the respective benzyl bromide. The replacement of the bromide with N-benzyl glycinate is followed by treatment with sodium hydride to yield 6-7 which is further decarboxylated to produce 6-8. Debenzylation can be accomplished with catalytic hydrogenation, preferably with palladium on charcoal.

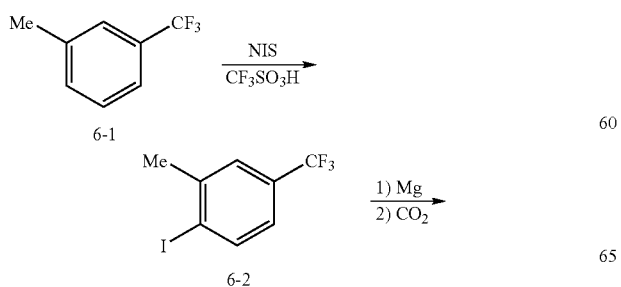

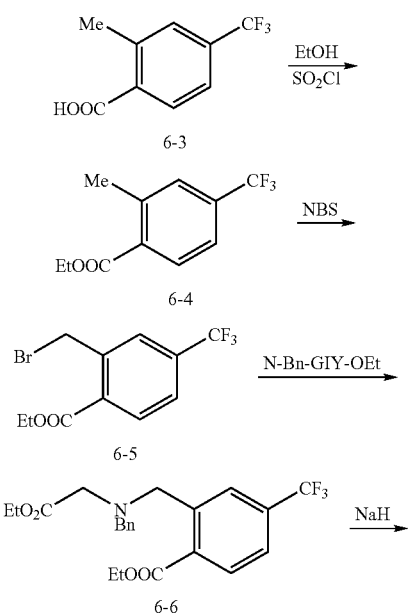

5,6-dihydro-4-methoxy-2H-pyran (8-1) is treated with m-chloroperbenzoic acid to affect epoxidation of the double bond. This in turn reacts with the formed chlorobenzoic acid and the epoxide ring opening furnishes the ketone 8-2. Its protection in the form of an acetal is followed by removal of the ester. An alkylation of the secondary alcohol with an appropriate alkyl halide $R^{10}X$ in a presence of a base affords the ether 8-5. Deprotection of the acetal under acidic conditions affords the desired ketones 8-6. In this manner, besides the 3-hydroxy-tetrahydropyran-4-one, a number of 3-alkoxyderivatives can be synthesized. Further details, as well as examples are described in the Experimental section.

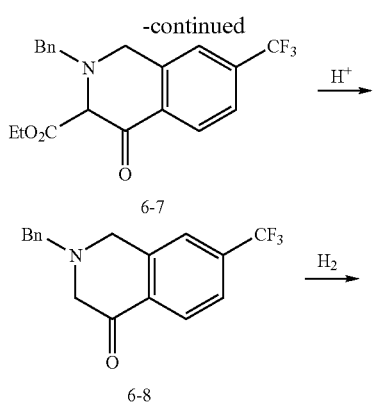

Additional examples of tetrhydroisoquinolines incorporated into the amide portion of compounds within the scope of the instant invention, as well as their syntheses are further described in the Experimental section.

The amine portion of the target compounds 1-9 can be, as detailed above, prepared either from reductive alkylation of amines 2-9a and 2-13a with the corresponding ketones 7-1 or by a reductive amination of the corresponding ketones 1-8, 1-8a and 1-8c with appropriate cyclic amines 7-3. The amines 7-3 can be easily prepared by a two step sequence detailed in Scheme 7. The ketones 7-2 typically represent cyclic structures, some of which, e.g. tetrahydropyran-4-one and a number of lower cyclic ketones, can be obtained commercially, others have to be synthesized either by known or newly developed procedures.

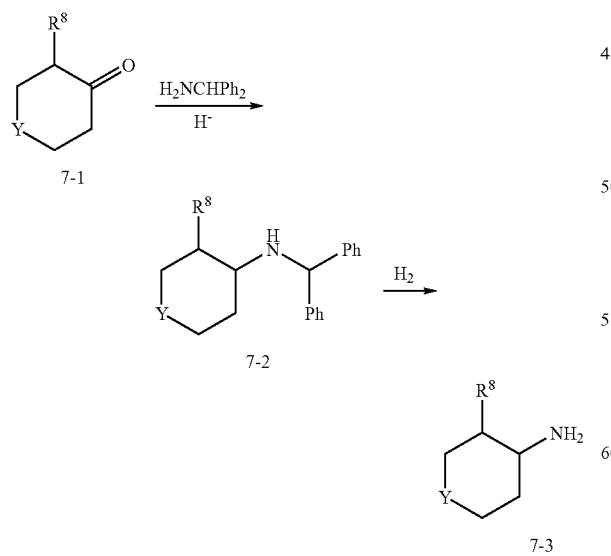

A synthesis of some of the ketones 7-1 is detailed in Scheme 8. According to this, a commercially available

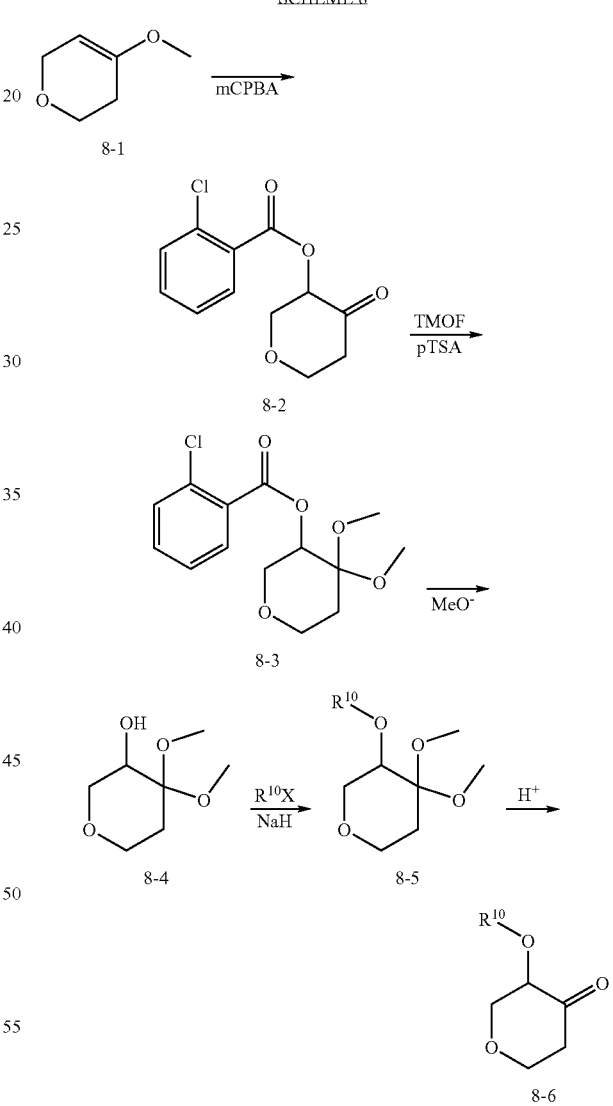

An example of preparation of keto aldehyde 9-3 is detailed in Scheme 9. According to this, 3-allyl tetrahydropyran-4-one, which can be synthesized from tetrahydropyran-4-one following a previously published procedure (*J. Am. Chem. Soc.*, 1991, 113, 2079–2089) is reacted with ozone and then treated with triphenyl phosphine to 9-3 in fair yield.

SCHEME 9

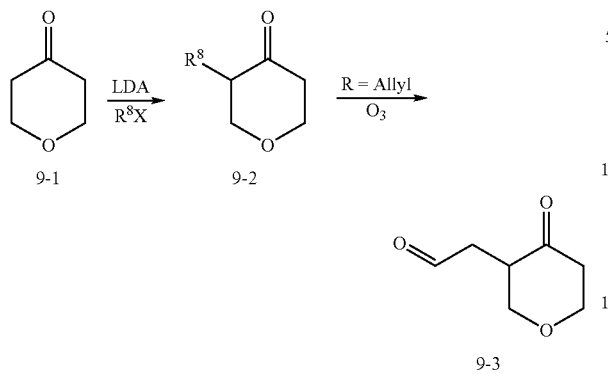

Additional details as well as examples of preparation of analogs of ketone 9-2 and keto aldehyde 9-3 can be found in the Experimental section.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230–400 mesh). MPLC refers to medium pressure liquid chromatography and was carried out on a silica gel stationary phase unless otherwise noted. NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

INTERMEDIATE 1

Step A

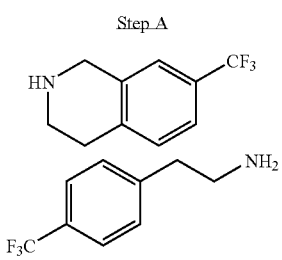

To a solution of 4-trifluoromethyl phenylacetonitrile (40 g, 215 mmol) in 2N NH3/MeOH (400 mL) was added Raney Ni (~4.0 g). The reaction mixture was placed in a par-shaker and shook under 50 Lb pressure overnight. The solution was filtered through celite and concentrated in vacuo to yield the desired amine (38 g, 95%). ESI-MS calc. For C9H10F3N: 189; Found: 190 (M+H).

Step B

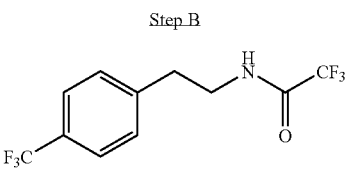

The above amine (Step A, Intermediate 1) (38 g, 200 mmol) and DIEA (52 mL, 300 mmol) were dissolved in DCM (300 mL). The solution was cooled to 0° C. before TFAA (36 mL, 250 mmol) was added slowly. The reaction mixture was stirred in the ice bath for another 10 minutes before warmed up to room temperature. The reaction was completed in 30 minutes and dumped in water and extracted with DCM (2×). The organic layer was washed with 1N HCl and saturated NaCl solution, dried over MgSO$_4$, and concentrated in vacuo to yield the desired amide (56 g, 98%). ESI-MS calc. For C11H9F6NO: 285; Found: 286 (M+H).

Step C

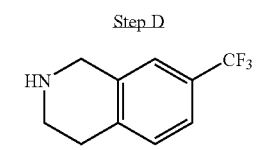

To a mixture of the amide (Step B, Intermediate 1) (73 g, 256 mmol) and paraformaldehyde (11.5 g, 385 mmol) was added 200 mL of acetic acid. The reaction mixture was stirred at room temperature for 5 min before concentrated sulfuric acid (200 mL). An exothermic reaction was observed. After 30 min, TLC showed a complete conversion. The mixture was cooled to RT before poured onto ice water (2000 mL) and extracted with EtOAc (3×500 mL). Combined organic layers were washed with water (2×), saturated NaHCO$_3$, and brine, dried over MgSO$_4$, filtered, evaporated and dried in vacuum. The desired amide (72.7 g, 96%) was obtained as a light-yellow solid. 1H NMR (400 MHz, CDCl$_3$) δ 7.22 (q, J=11.67 Hz, 8.46 Hz, 1H), 7.11 (t, J=10.53 Hz, 1H), 7.03 (d, J=11.67 Hz, 1H), 4.79 (d, J=23.57 Hz, 2H), 3.91 (t, J=6.18 Hz, 1H), 3.87 (t, J=5.72 Hz, 1H), 2.97 (m, 2H).

ESI-MS calc. For C12H9F6NO: 297; Found: 298 (M+H).

Step D

The amide (Step C, Intermediate 1) (50 g, 168 mmol) was dissolved in EtOH (200 mL) before solid K$_2$CO$_3$ (50 g, 360 mmol) and H$_2$O (50 mL) were added. The reaction mixture was refluxed for 15 hours before concentrated in vacuo. The concentrate was diluted with H$_2$O (100 mL) and extracted with DCM (5×). Combined organic layers were dried over MgSO$_4$, filtered, concentrated and purified on FC (10% [aq. NH4OH/MeOH 1/9]/DCM) to yield the amine (Step D, Intermediate 1)(30 g, 89%). 1HNMR (400 Mz, CDCl$_3$) δ 7.11 (d, J=8.4 Hz, 1H), 7.01 (bd, J=8.4 Hz, 1H), 6.89 (s, 1H), 4.03 (s, 2H), 3.15 (t, J=6.1 Hz, 2H), 2.80 (t, J=5.6 Hz, 2H), 1.80 (s, 1H). ESI-MS calc. For C10H10F3N: 201; Found: 202 (M+H).

INTERMEDIATE 2

Step A

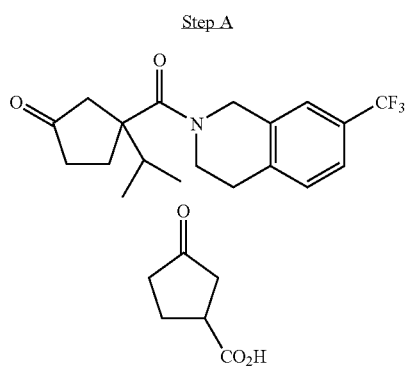

This compound was prepared according to the literature procedure) Stetter, H., Kuhlman, H. *Liebigs Ann. Chim.*, 1979, 944).

Step B

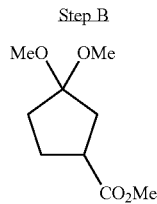

The keto acid (Step A, Intermediate 2) (20 g, 156 mmol) was dissolved in MeOH first before TMOF (85 mL, 781 mmol) was added. TsOH (3 g, 15.6 mmol) was added last. The reaction mixture was stirred at room temperature for 4 hours before concentrated under house vacuum, diluted with ether, quenched with saturated NaHCO$_3$, washed with brine, and dried over anhydrous MgSO$_4$. The crude product was purified by flash chromatography (25/75, ether/pentane) to yield the ketal ester (21.52 g, 73.2%). 1H NMR (500 MHz, CDCl3) δ 3.68 (s, 3H), 3.21 (d, J=9.9 Hz, 6H), 2.89 (p, J=8.5 Hz, 1H), 2.14–2.05 (m, 2H), 2.02–1.80 (m, 4H).

Step C

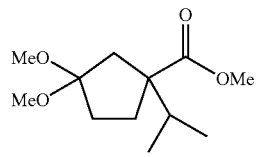

To a flame-dried 500 mL round-bottomed flask, was added dry THF (150 mL). The solution was cooled to −78° C. before iPr$_2$NH (19.2 mL, 137.3 mmol), 2.5 M nBuLi (55 mL, 137.3 mmol), and neat ketal ester (Step B, Intermediate 2) (21.52 g, 114.4 mmol), were added sequentially. The reaction mixture was stirred at −78° C. for 30 minutes before 2-iodopropane (34.3 mL, 343.2 mmol) was added. After the reaction was stirred for another 20 minutes at −78° C., the mixture was placed in the refrigerator (0° C.) overnight. The mixture was quenched with 10% citric acid and extracted with ether (3×). Combined organic layer was washed with H$_2$O and brine, dried over anhydrous MgSO$_4$, and concentrated. The crude product was purified by flash chromatography (20/80 ether/pentane) to yield the alkylated ester (16.74 g, 63.6%). 1H NMR (400 Mz, CDCl3) δ 3.69 (s, 3H), 3.18 (d, J=20.5 Hz, 6H), 2.57 (d, J=13.9 Hz, 1H), 2.29 (m, 1H), 1.90 (p, J=6.8 Hz, 1H), 1.81 (m, 2H), 1.65 (m, 2H), 0.89 (q, J=11.9 Hz, 6.8 Hz, 6H).

Step D

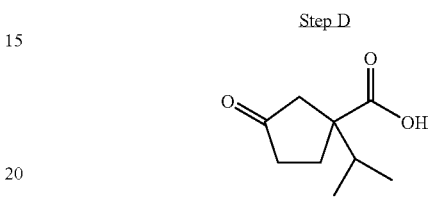

The alkylated ester (Step C, Intermediate 2) (16.74 g, 72.7 mmol) was dissolved in EtOH (30 mL) before a solution of NaOH (11 g, 275 mmol) in H$_2$O (30 mL) was added. The reaction mixture was refluxed for 3 days before cooled to room temperature and acidified with concentrated HCl. The organic solvent was evaporated under vacuum and the aqueous layer was extracted with DCM (5×). Combined organic layer was dried over anhydrous MgSO$_4$ and concentrated in vacuo to yield the desired keto acid (11.07 g, 89.5%). %). 1H NMR (500 MHz, CDCl3) δ 2.70 (d, J=18.1 Hz, 1H), 2.44–2.39 (m, 1H), 2.30–2.15 (m, 2H), 2.14 (dd, J=18.1 Hz, 1.0 Hz, 1H), 2.06 (p, J=6.9 Hz, 1H), 1.98 (m, 1H), 0.98 (dd, J=11.4 Hz, 6.9 Hz, 6H).

Step E

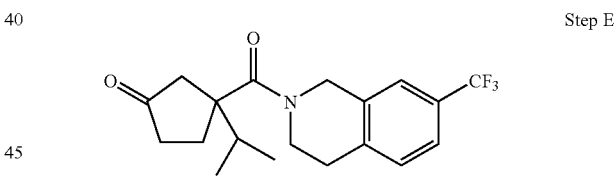

To a solution of the keto acid (Step D, Intermediate 2) (2 g, 11.76 mmol) in DCM (50 mL) was added oxalyl chloride (1.54 mL, 17.64 mmol) followed by 2 drops of DMF. The mixture was stirred at room temperature for 80 minutes before concentrated in vacuo. The concentrate was dissolved in DCM and added slowly to a solution of Intermediate 1 (2.36 g, 11.76 mmol) and Et$_3$N (2.13 mL, 15.29 mmol) in DCM. The resulting mixture was stirred at room temperature for 18 hours before washed with H$_2$O, 1N HCl, saturated NaHCO$_3$, and brine, dried over anhydrous MgSO$_4$, and concentrated in vacuo. The crude product was purified by MPLC (60/40, EtOAc/Hexanes) to yield 2-E (3.18 g, 76.6%). 1H NMR (500 MHz, CDCl3) δ 7.46 (d, J=7.3 Hz, 1H), 7.39 (s, 1H), 7.29 (d, J=7.7 Hz, 1H), 4.81 (ABq, 2H), 3.93 (m, 1H), 3.82 (m, 1H), 2.94 (m, 3H), 2.54 (m, 1H), 2.43 (d, J=8.5 Hz, 1H), 2.32 (m, 2 H), 2.26 (p, J=6.6 Hz, 1H), 2.16 (m, 1H), 0.93 (dd, J=19.7 Hz, 6.8 Hz, 6H). LC-MS for C$_{19}$H$_{23}$F$_3$NO$_2$ [M$^+$H$^+$] calculated 354.16, found 354.25.

INTERMEDIATE 3

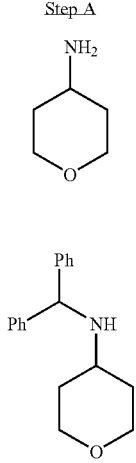

To a solution of tetrahydro-4H-pyran-4-one (5 g, 50 mmol) and benzhydryl amine (8.41 mL, 50 mmol) in DCM (250 mL) was added molecular sieves (4A, powder) followed by NaBH(OAc)₃ (32 g, 150 mmol). The reaction mixture was stirred at room temperature overnight before filtered through celite, washed with saturated NaHCO₃ (4×), dried over MgSO₄, filtered, and concentrated in vacuo to yield a crude product of the amine which was used on next step (13.25 g, 99.9%). 1H NMR (400 MHz, CDCl3) δ 7.42 (bd, J=7.0 Hz, 4H), 7.32 (bt, J=7.2 Hz, 4H), 7.24 (bt, J=7.3 Hz, 2H), 5.07 (s, 1H), 3.96 (dt, J=11.1 Hz, 3.5 Hz, 2H), 3.33 (td, J=11.5 Hz, 2.1 Hz, 2H), 2.66 (m, 1H), 1.93 (m, 2H), 1.54 (bs, 1H), 1.44 (m, 2H).

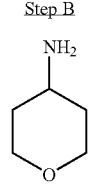

A mixture of the amine (Step A, Intermediate 3) (13.2 g, 49.4 mmol), 4N HCl/dioxane (12.5 mL, 49.4 mmol), Pd/C 10% (1.1 g), dioxane (30 mL), and EtOH (120 mL) was placed under par-shaker and shook at 35 Lb pressure overnight. The reaction mixture was filtered through celite and concentrated to dryness. The concentrate was stirred in DCM. The precipitate was filtered and dried to yield Intermediate 3 (4.91 g, 72.2%). 1H NMR (400 MHz, CD3OD) δ 3.99 (dd, J=12.1 Hz, 5.1 Hz, 2H), 1.89 (td, J=11.9 Hz, 2.1 Hz, 2H), 3.38–3.32 (m, 1H), 1.96–1.92 (m, 2H), 1.70–1.59 (m, 2H).

INTERMEDIATE 4

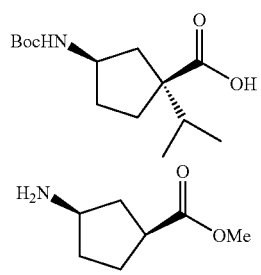

A mixture of (1S)-(+)-2-azabicyclo[2.2.1]hept-5-ene-3-one (10.3 g, 94.4 mmol) in EtOAc (200 mL) and 10% Pd/C (0.5 g) was hydrogenated at RT. After 24 h the reaction mixture was filtered and evaporated leaving behind 10.4 g (100%) of the product that was taken in 250 ml methanol and HCl (12M, 6 ml). The resultant mixture was stirred at RT, until the reaction was complete (72 h). Evaporation of methanol followed by drying under high vacuo, yielded the title compound as an off white solid (16.0 g, 96%). ¹H NMR (D₂O, 500 MHz): 3.70 (s, 3H), 3.01 (m, 1H), 2.38 (m, 1H), 2.16–1.73 (m, 6H).

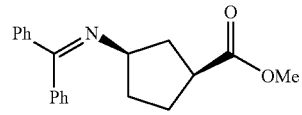

To a suspension of the Intermediate (Step A, Intermediate 4) (10.2 g, 56.8 mmol) in dry dichloromethane (200 mL) was added benzophenone imine (10.2 g, 56.8 mmol) at RT and resultant mixture was stirred for 24 h. The reaction mixture was filtered and the filtrate was evaporated, leaving behind yellow oil that was triturated with ether (100 mL), filtered and evaporated. This operation was repeated twice to ensure that the product was free of ammonium chloride impurities. The resultant oil was thoroughly dried under vacuo to yield the title compound (18.03 g, >100%) and required no further purification. ¹H NMR (CDCl₃, 500 MHz): 7.5–7.18 (m, 10 H), 3.75 (m, 1H), 3.7 (s, 3H), 2.78 (m, 1H), 2.26–1.71 (m, 6H).

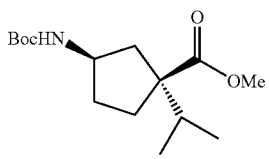

To a solution of LDA (prepared from diisopropylamine (7.7 g, 76.1 mmol) and n-BuLi (30.4 ml, 2.5 M in hexane, 76.1 mmol) in THF (120 mL) at −78° C. and the ester (Step B, Intermediate 4) was slowly added (18.0 g, 58.6 mmol). The resultant burgundy colored solution was stirred for 20 min. after which it was quenched with 2-iodopropane (14.9 g, 88 mmol). The reaction mixture was gradually warmed over 3 h to 0° C. and this temperature was maintained for additional 3 h. reaction was quenched with water and extracted with EtOAc. The organic layer was washed with water, brine, dried (anhydrous magnesium sulfate) and concentrated to yield an oil. To the solution of the crude Schiff base (20.0 g) in THF (100 mL) was added HCl (5.0 mL, 12 M) and was allowed to stir at RT for 3 h. After removal of all volatiles, the hydrochloride salt was taken up in dichloromethane (250 mL), saturated solution of sodium bicarbonate (250 mL) and Boc2O (26.0 g, 1.4 eq.) was added. The resultant mixture was vigorously stirred overnight at RT. The organic layer was separated and washed with water, brine, dried (anhydrous magnesium sulfate) and concentrated to yield an oil. Purification by flash column chromatography (eluent:hexane:EtOAc 19:1) gave the desired product (4.91 g, 30%). $^1$H NMR (CDCl$_3$, 500 MHz): 4.79 (br, 1H), 4.01 (m, 1H), 3.72 (s, 3H), 2.18–1.60 (m, 6H), 1.44 (s, 9H), 0.87 (d, J=6.9 Hz, 3H), 0.86 (d, J=6.9 Hz, 3H).

Step D

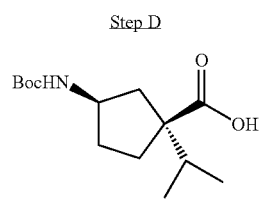

To a solution of the ester (Step C, Intermediate 4) (4.91 g, 17.2 mmol) in MeOH (100 mL) was added a solution of LiOH (3.6 g, 85 mmol) in water (20 mL) and THF (10 mL). The resultant mixture was heated at 80° C. until the reaction was complete (18 h). Methanol was removed in vacuo and the crude product was taken up with water/EtOAc (200 mL, 1:4) and cooled to 0° C. The acidity of the mixture was adjusted to pH 6. The EtOAc layer was separated, washed with water, brine, dried (anhydrous magnesium sulfate) and concentrated to yield an oil. Purification by flash column chromatography (eluent:hexane:EtOAc 1:1+2% AcOH) gave the title acid (39 g, 84%). $^1$H NMR (CDCl$_3$, 500 MHz): 11.36 (br, 1H), 6.49 (br, 1H), 4.83 (m, 1H), 3.71 (s, 3H), 2.30–1.55 (m, 6H), 1.46 (s, 9H), 0.94 (d, J=6.9 Hz, 3H), 0.933 (d, J=6.9 Hz, 3H).

INTERMEDIATE 5

Procedure A
Step A

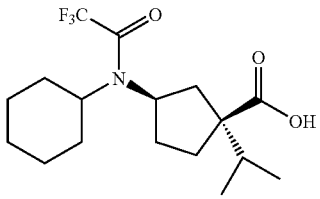

-continued

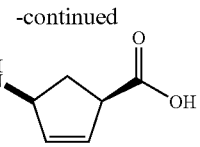

A mixture of (1R,4S)-4-amino-cyclopen-2-ene carboxylic acid (127 g, 1.0 mol), water (250 mL), sodium bicarbonate (168 g, 2.0 mol) and THF (750 mL) was stirred for 30 min, then solid Boc2O (230 g, 1.05 mol) was added. The mixture was stirred overweekend, filtered to remove insoluble material, evaporated to remove THF, cooled at 0° C. To the residue was added 2N aq. HCl (~500 mL) until pH=3.0. The resulting precipitate was collected by filtration and washed with water, dried in vacuum overnight. The desired acid was obtained as a white solid (227 g, 100%).

$^1$H NMR (400 MHz, CD$_3$OD): 5.95 (m, 1H), 5.79 (m, 1H), 4.80 (br s, 1H), 3.45 (m, 1H), 2.50 (m, 1H), 1.79 (m, 1H), 1.44 (s, 9H).

Step B

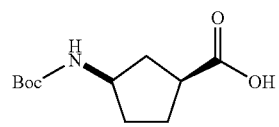

The acid (Step A, Procedure A, Intermediate 5) (227 g, 1.0 mol) and 10% Pd/C (5.0 g) in 500 mL of methanol on a Parr shaker was hydrogenated under 50 lb of hydrogen for one hour. The catalyst was removed by filtration and the filtrate was evaporated. The residue was dissolved in dichloromethane and dried over anhydrous sodium sulfate. After filtered, the filtrate was evaporated and dried in vacuum. The title compound was obtained as a light yellow solid (226.0 g, 99%). LC-MS for C11H19NO4 [M$^+$H$^+$] calculated 230, found 230.

Step C

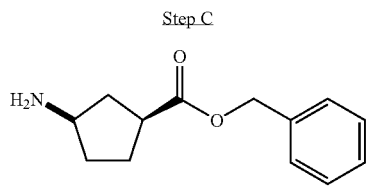

To a mechanically stirred solution of the acid (Step B, Procedure A, Intermediate 5) (226.0 g, 1.0 mol) in 500 mL of DMF was added solid potassium carbonate (210 g, 1.5 mol). The resulting mixture was stirred for 20 minutes, a neat benzyl bromide (118 mL, 1.0 mol) was added in one portion. An exothermic reaction was observed. After stirred for 3 h at RT, the entire mixture was dumped into ice-water mixture (1000 mL) was added. The crude product was extracted out with ether (2×800 mL). The combined ether layers were washed with water, dried over sodium sulfate, filtered and evaporated to offer a yellow solid. This solid was mixed with 4N HCl/dioxane (400 mL), stirred overnight and condensed. The resulting solid was collected by filtration, washed with ether and dried in vacuum. The title product was obtained as HCl salt (140 g, 55%). $^1$H NMR (400 MHz, CD$_3$OD): 5.15 (s, 2H), 3.65 (m, 1H), 3.02 (q, J=8 Hz, 1H), 2.50 (m, 1H), 2.15 (m, 1H), 2.05 (m, 2H), 1.90 (m, 1H), 1.75 (m, 1H).

Step D

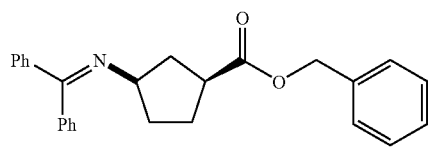

The amino benzyl ester HCl salt (Step C, Procedure A, Intermediate 5) (127 g, 0.5 mol) was suspended in 500 mL of dichloromethane. Benzophenone imine (91 g, 0.5 mol) was added. The resulting mixture was stirred overnight, filtered to remove the inorganic salt. The filtrate was washed with water and brine, dried over sodium sulfate, evaporated. The residue was dissolved in 200 mL of toluene, evaporated. This procedure was repeated once a time. The title compound (178 g) was obtained as an brown oil which was used in next step without further purification. $^1$H NMR (400 MHz, CDCl$_3$): 1.80 (m, 1H), 1.95 (m, 2H), 2.15 (m, 2H), 2.50 (m, 1H), 2.89 (m, 1H), 3.61 (m, 1H), 5.20 (s, 2H), 7.18 (d, 2H), 7.38 (m, 8H), 7.47 (m, 3H), 7.64 (d, 2H).

Step E

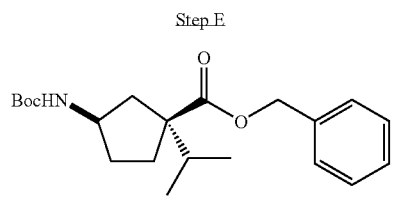

The starting Schiff base benzyl ester (Step D, Procedure A, Intermediate 5) (76.6 g, 200 mmol) in 300 mL of THF was cooled at −78° C. under nitrogen protection. While stirring, a solution of LDA (2.0 M, 110 mL, 220 mmol) in heptane was added over 20 minutes. The mixture was stirred for 30 minutes at −78° C., then a solution of 68 mL of isopropyl iodide (440 mmol) in 50 mL of THF was added, continued to stir for 30 min. The reaction temperature was raised to 0° C. by removing cooling bath. After stirred for 2 h, the entire mixture evaporated to remove THF. The residue was dissolved in ether (1000 mL), washed with water and brine, dried over sodium sulfate, evaporated. The crude product was dissolved in 500 mL of THF, mixed with 400 mL of 1N HCl, stirred for one hour, evaporated to remove THF at 50° C. The aq. solution was extracted with hexane (3×), basified with sat. aq. sodium carbonate (pH>9), mixed and stirred with a solution of Boc2O (53 g) in 500 mL of dichloromethane for 30 min. The organic phase was separated and the aq. phase was extracted with dichloromethane (3×). The combined organic phases were dried over sodium sulfate and evaporated. The residue was purified on FC (10% EtOAc/hexane) to yield a mixture of the title compound as a mixture of cis and trans isomers (~1:1, 24 g). Further purification on MPLC (5% EtOAc/Hexane) afforded single cis isomer (fast-eluted, 5.0 g) and trans isomer (slow-eluted, 4.3 g). ESI-MS calc. for C21H31NO4: 361; Found: 362 (M+H).

Step F

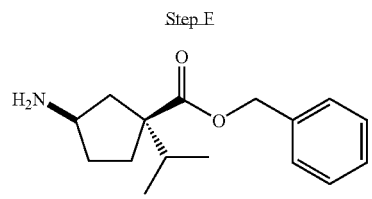

The above cis-Boc amino ester (1.25 g, 3.45 mmol) was stirred with 20 mL of 4N HCl/dioxane for one hour, evaporated and dried in high vacuum to yield the title product (1.05 g, 100%). ESI-MS calc. for C16H23NO2: 261; Found: 262 (M+H).

Step G

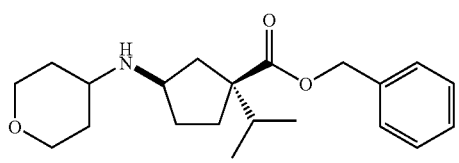

A mixture of the above amino ester (HCl salt, 1.05 g, 3.45 mmol), tetrahydro-4H-pyran-4-one (1.0 g, 10 mmol), molecular sieves (4 Å, 1.0 g), DIEA (0.78 g, 6 mmol) and sodium triacetoxyborihydride (1.33 g, 6 mmol) in 30 mL of dichloromethane was stirred overnight. The reaction was quenched with sat. aq. sodium carbonate, filtered to remove insoluble material. The crude product was extracted into dichloromethane, dried over anhydrous sodium sulfate, evaporated and dried in high vacuum. The crude product was used in next step without further purification.

Step H

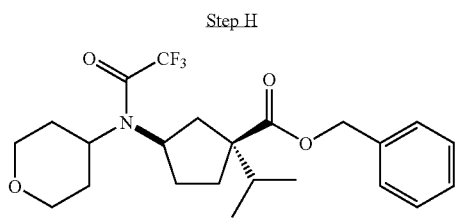

To a mixture of the crude amino ester (Step G, Procedure A, Intermediate 5) (6.85 g, 19.84 mmol), Et$_3$N (5.6 mL, 39.68 mmol), and DCM (50 mL), was slowly added TFAA (6.91 mL, 49.6 mmol). The reaction was stirred at room temperature for 1 hour before washed with 1N HCl and brine, dried over anhydrous MgSO$_4$, and concentrated in vacuo. The crude product was purified by MPLC (20/80, EtOAc/Hexanes) to yield the title compound (3.7 g, 42.2%). LC-MS for C$_{23}$H$_{31}$F$_3$NO$_4$ [M$^+$H$^+$] calculated 442.21, found 442.3.

Step I

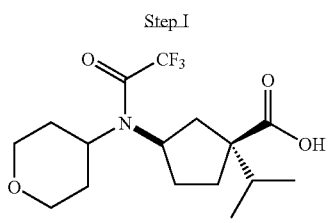

A mixture of the amide (Step H, Procedure A, Intermediate 5) (4.7 g, 10.7 mmol), 10% Pd/C (500 mg), and MeOH (50 mL) was stirred under a hydrogen balloon for 2 hours before filtered through celite and concentrated in vacuo to yield 14-C (3.92 g, 99+%). LC-MS for $C_{16}H_{25}F_3NO_4$ [M+H+] calculated 352.17, found 352.15.

Procedure B
Step A

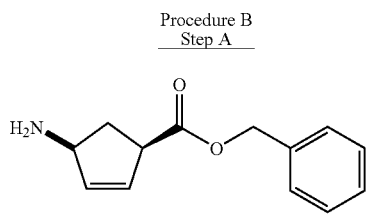

To a magnetically stirred solution of the Boc-amino acid (Step A, Procedure A, Intermediate 5) (159 g, 0.7 mol) in 500 mL of DMF was added solid potassium carbonate (138 g, 1.0 mol). The resulting mixture was stirred for 20 minutes, a neat benzyl bromide (84 mL, 0.7 mol) was added in one portion. An exothermic reaction was observed. After stirred overnight at RT, the entire mixture was dumped into ice-water mixture (1000 mL) was added. The crude product was extracted out with ethyl acetate (2×800 mL). The combined organic layers were washed with water, dried over sodium sulfate, filtered and evaporated to offer a brown oil. This material was mixed with 4N HCl/dioxane (350 mL) and stirred until no bubble evolved. 500 mL of ether was added, the precipitate was collected by filtration and washed with ether and hexane. The desired product was obtained as HCl salt (164 g, 93%). $^1$H NMR (400 MHz, CD$_3$OD): 7.38 (m, 5H), 6.25 (m, 1H), 5.94 (m, 1H), 5.20 (s, 2H), 4.32 (br s, 1H), 3.80 (br s, 1H), 2.67 (m, 1H), 2.14 (m, 1H).

Step B

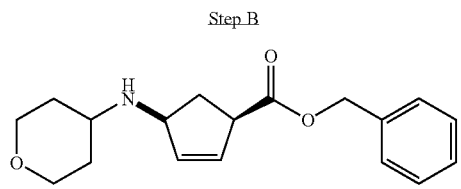

To a mixture of the amino ester HCl salt (Step A, Procedure B, Intermediate 5) (38 g, 150 mmol), tetrahydro-4-H-pyran-4-one (15 g, 150 mmol), DIEA (20.6 g, 160 mmol) and molecular sieves (4 Å, 20 g) in 200 mL of dichloromethane was added sodium triacetoxy borohydride (42.4 g, 200 mmol) in multiple portions. After complete addition, the mixture was stirred at RT overnight, quenched with sat. aq. sodium carbonate, filtered through celite. The crude product was extracted into dichloromethane (3×), dried over sodium sulfate and evaporated. The residue was purified on FC (10%[aq. NH4OH/MeOH 1/9]/DCM0. The desired fractions were combined and evaporated. The residue was mixed with THF and evaporated, redissolved in toluene and evaporated, dried in vacuum to yield a light brown oil (38 g, 84%). $^1$H NMR (400 MHz, CDCl$_3$): 7.38 (m, 5H), 5.98 (m, 1H), 5.85 (m, 1H), 3.98 (m, 3H), 3.54 (m, 1H), 3.40 (m, 2H), 2.82 (m, 1H), 2.44 (m, 1H), 1.90 (m, 1H), 1.79 (m, 2H), 1.70 (m, 1H), 1.44 (m, 2H).

Step C

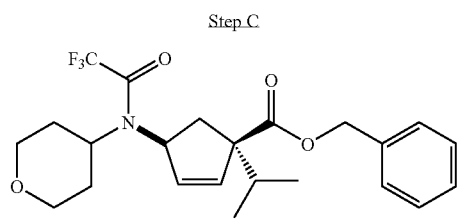

To a round flask containing solid potassium bis-(trimethylsilyl)amide (30 g, 151 mmol) under nitrogen was added 500 mL of anhydrous THF, cooled at −78° C. A solution of the amino ester (Step B, Procedure B, Intermediate 5) (38 g, 126 mmol) in 100 mL of THF was added in 20 minutes. The dry ice-acetone bath was changed into a dry ice-water (~−15° C.). The mixture was stirred at −15° C. for one hour, recooled at −78° C. A neat solution of isopropyl iodide (65 mL, 378 mmol) was added. The flask was placed into −15° C. bath again. After a few minutes, a large amount of white precipitate formed. The reaction mixture was stirred for additional one hour, poured into a mixture of ice and water, extracted with ether (3×). The ether layers were anti-washed with water and brine, dried over sodium sulfate and evaporated. The residue was dissolved in dichloromethane, dried over sodium sulfate again and evaporated. The residue was dried in vacuum, mixed with dichloromethane (200 mL) and cooled at 0° C. under nitrogen. To the solution was added pyridine (33 mL, 400 mmol) and trifluoroacetic anhydride (27 mL, 190 mmol) dropwise. After one hour, the reaction was quenched with water. The organic phase was separated and washed with 2N aq. HCl, water and brine. After dried over sodium sulfate and evaporated, the residue was purified on FC (20% EtOAc/hexane) to yield an light brown oil (41 g, 74%). 1H-NMR showed a 5:1 mixture of cis/trans isomers. %). $^1$H NMR (400 MHz, CDCl$_3$): CH=CH:Cis: 6.06 (m, 1H), 5.68 (m, 1H), trans: 5.92 (m, 0.2 H), 5.79 (m, 0.2H). LC-MS for C23H28F3NO4 [M+H+] calculated 440, found 440.

Step D

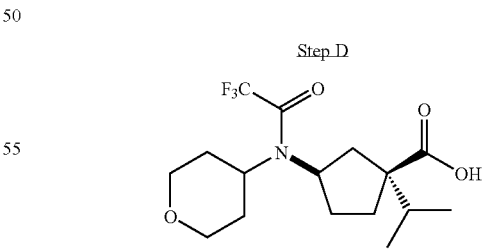

The unsaturated benzyl ester (Step C, Procedure B, Intermediate 5) (41 g) and 10% Pd/C (2.0 g) in ethyl acetate (100 mL) was hydrogenated on a Parr shaker under 50 lb of hydrogen overnight. The catalyst was removed by filtration through a pad of celite. The filtrate was evaporated and dissolved in dichloromethane, evaporated and dried in vacuum overnight. The desired acid was obtained as a gummy white solid (32.5 g, 100%). LC-MS for C16H24F3NO4 [M+H+] calculated 352, found 352.

INTERMEDIATE 6

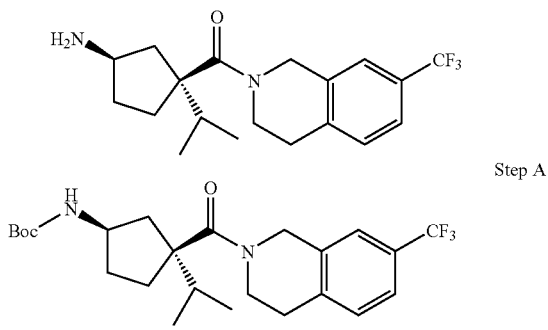

To a flask was added Boc-amino acid (Intermediate 4, 1.10 g, 4 mmol), isoquinoline hydrochloride (Intermediate 1, 0.944 g, 4 mmol), PyBrOP (1.85 g, 4 mmol), DMAP (0.29 g, 2.4 mmol), DIEA (2.77 mL, 16 mmol) and DCM (20 mL). The resulting mixture was stirred for 36 h under nitrogen. The entire material was dumped onto a silica gel column and eluted with 20% EtOAc/Hexane. The desired Boc-amide was obtained as a gummy solid (1.5 g, 82%). ESI-MS calc. for C24H33F3N2O3: 454; Found: 455 (M+H).

Step B

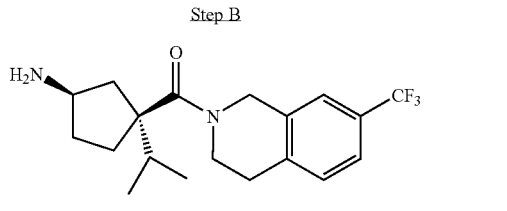

The Boc amino amide (Step A, Intermediate 6) was treated with 10 mL of 4N HCl/Dioxane for 1 h, evaporated, dried in vacuum. The intermediate 6 was obtained as a yellow solid (1.2 g). ESI-MS calc. for C19H25F3N2O: 354; Found: 355 (M+H).

EXAMPLE 1

Procedure A

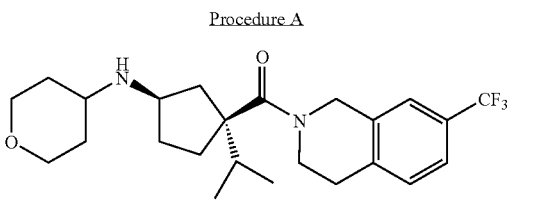

A solution of Intermediate 6 (1.00 g, 2.56 mmol), tetrahydro-4H-pyran-4-one (512 mg, 5.12 mmol), diisopropylethylamine (446 µL, 2.56 mmol) and crushed molecular sieves (4 A, 500 mg) in dichloromethane (35 mL) was treated with sodium triacetoxyborohydride (2.72 g, 12.80 mmol) and stirred at room temperature overnight. The reaction was quenched with saturated sodium bicarbonate solution (50 mL) and diluted with an additional 35 mL of DCM. The organic layer was separated and the aqueous washed with dichloromethane (2×25 mL). The organics were combined, dried over anhydrous sodium sulfate, filtered and evaporated under reduced pressure. The crude product was purified by preparative TLC (8 plates) to yield the final product (Example 1, 942 mg, 84%) as the single desired isomer. LC-MS for $C_{24}H_{33}F_3N_2O_2$ calculated 438.26, found [M+H]$^+$439.3.

Procedure B

A solution of Intermediate 2 (435 mg, 1.22 mmol), Intermediate 3 (250 mg, 1.83 mmol), diisopropylethylamine (309 µL, 1.83 mmol) and crushed molecular sieves (4A, 300 mg) in dichloromethane (30 mL) was treated with sodium triacetoxyborohydride (1.30 g, 6.10 mmol) and stirred at room temperature overnight. The reaction was quenched with saturated sodium bicarbonate solution (30 mL) and diluted with an additional 20 mL of DCM. The organic layer was separated and the aqueous washed with dichloromethane (2×20 mL). The organics were combined, dried over anhydrous sodium sulfate, filtered and evaporated under reduced pressure. The residue was purified by preparative TLC (eluant: 0.5% NH4OH: 5% MeOH:94.5% CH2Cl2) to yield 413 mg (77%) of the final product as a mixture of four diastereomers. The single isomers were obtained by using a Gilson HPLC equipped with a Preparatory ChiralPak AD column eluting with 20% ethanol and 80% hexane with a flow rate of 9 mL/min. LC-MS for $C_{24}H_{33}F_3N_2O_2$ calculated 438.25, found [M+H]$^+$439.2 for all 4 isomer.

EXAMPLE 2

Step A

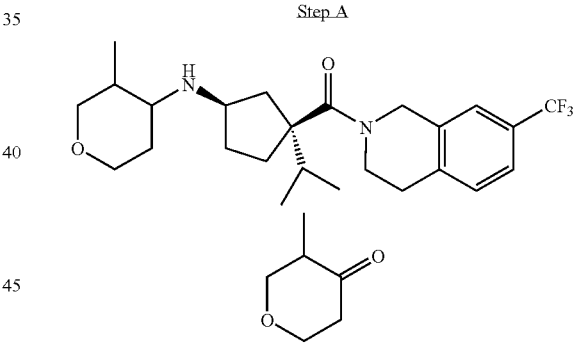

This compound was prepared according to the procedure described in *J. Am. Chem. Soc.,* 1991, 113, 2079.

Step B

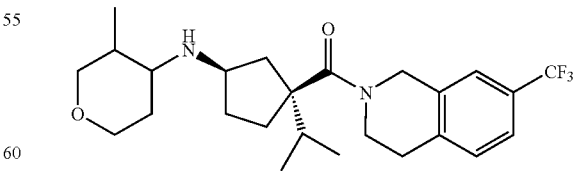

This product was prepared in an analogous fashion to that of Example 1, Procedure A, except tetrahydro-4H-pyran-4-one was replaced with 3-methyl-tetrahydro-4H-pyran-4-one. Purification by preparative TLC (eluant: 0.5% NH4OH: 5% MeOH: 94.5% CH2Cl2) afforded 310 mg (87%) of the product as a mixture of four diastereomers. The pure single diastereoisomers were obtained by separation on chiral HPLC (first by ChiralPak AD, 5% ethyl alcohol in hexanes, 9.0 mL/min, to remove and separated the trans isomers, and then to separate the cis isomers by ChiralCel OD, 7% ethyl alcohol in hexanes, 9.0 mL/min). LC-MS for $C_{25}H_{35}F_3N_2O_2$ calculated 452.27, found [M+H]$^+$453.3.

EXAMPLE 3

Step A

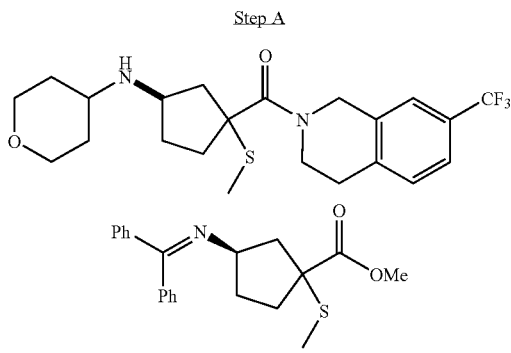

To a flame-dried 500 mL round-bottomed flask, was added dry THF (50 mL). The solution was cooled to −78° C. before iPr$_2$N (2.63 mL, 18.8 mmol), 2.5 M nBuLi (7.5 mL, 18.8 mmol), and a solution of the Schiff base (Step B, Intermediate 4) (5 g, 16.3 mmol) in THF (20 mL), were added sequentially. The reaction mixture was stirred at −78° C. for 30 minutes before methyl disulfide (4.4 mL, 48.9 mmol) was added. After the reaction was stirred for another hour, the mixture was quenched with saturated NH$_4$Cl, extracted with ether, dried over MgSO4, and concentrated. The crude product was purified by MPLC (10/90 EtOAc/Hexanes) to yield the title compound (3.98 g, 69.0%). LC-MS for $C_{21}H_{24}NO_2S$ [M$^+$H$^+$] calculated 354.14, found 354.25.

Step B

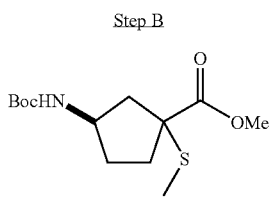

The alkylated Schiff base (Step A, Example 3) (3.98 g, 11.3 mmol) was dissolved in THF (35 mL) before 2N HCl (35 mL) was added. The reaction mixture was stirred and monitored by TLC. After completion of reaction, the mixture was concentrated in vacuo to remove THF. The aqueous layer was basified to pH 9.0 with saturated Na$_2$CO$_3$ solution and extracted with DCM. The organic layer was dried over MgSO$_4$ and Boc-anhydride (3.3 g, 15 mmol) was added. The reaction was stirred at room temperature overnight before extracted with DCM, dried over MgSO$_4$, and concentrated in vacuo. The crude product was purified by MPLC (35/65, EtOAc/Hexanes) to yield the title compound (2.10 g, 64.4%). LC-MS for $C_{13}H_{24}NO_4S$ [M$^+$H$^+$] calculated 290.13, found 190.1 (-Boc).

Step D

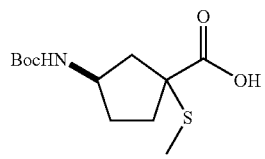

The ester (Step B, Example 3) (2.10 g, 7.27 mmol) was dissolved in MeOH (10 mL) and THF (10 mL) before a solution of LiOH (1.5 g, 36.3 mmol) in H$_2$O (10 mL) was added. The mixture was heated at 60° C. overnight before concentrated in vacuo to get rid of organic solvents. The aqueous layer was washed with hexanes, acidified to pH 7-4, and extracted with DCM (3×). Combined organic layer was dried over anhydrous MgSO$_4$ and concentrated to dryness. The crude product was used on next step.

Step D

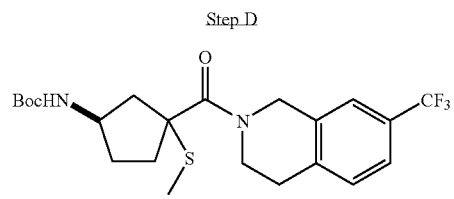

The acid (Step C, Example 3) (500 mg, 1.82 mmol), Intermediate 1 (366 mg, 1.82 mmol), and HOAT (250 mg, 1.82 mmol) were dissolved in DCM (20 mL) before EDC (525 mg, 2.73 mmol) was added. The resulting mixture was stirred overnight before washed with saturated NaHCO$_3$, H$_2$O (2×), and brine, dried over MgSO$_4$, and concentrated in vacuo. The crude product was purified by preparation plate (30/70, EtOAc/Hexanes) to yield the title compound (742 mg, 89.2%). LC-MS for $C_{22}H_{30}F_3N_2O_3S$ [M$^+$H$^+$] calculated 459.19, found 403.15 (-tert-butyl group).

Step E

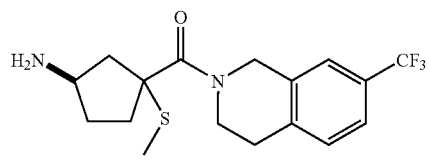

This compound was prepared as detailed in Intermediate 6-step B. LC-MS for $C_{17}H_{22}F_3N_2OS$ [M$^+$H$^+$] calculated 359.3, found 359.2.

Step F

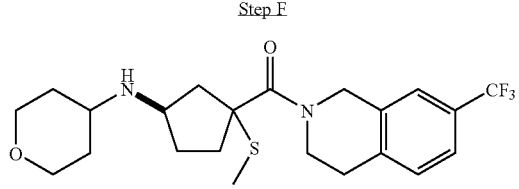

This compound was prepared starting from the amino amide (Step E, Example 3) and tetrahydro-4H-pyran-4-one as detailed in Example 1-Procedure A. Cis and trans isomers were resolved on preparation plate (4/95.6/0.4, MeOH/DCM/NH₄OH) with cis being the desired and more active isomer. LC-MS for $C_{22}H_{30}F_3N_2O_2S$ [M⁺H⁺] calculated 443.19, found 443.2.

EXAMPLE 4

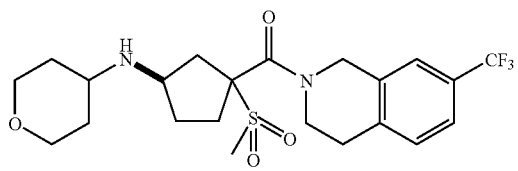

Step A

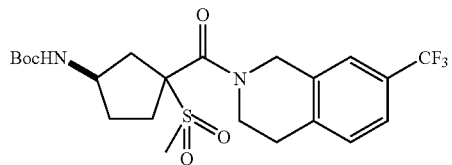

Intermediate (Step D, Example 3) (200 mg, 0.44 mmol) was dissolved in iPrOH (5 mL) before a solution of oxone (540 mg, 0.88 mmol) in H₂O (5 mL) was added. The mixture was stirred at room temperature for 2 hours before concentrated to dryness. The concentrate was diluted with ether, washed with H₂O (3×), dried over anhydrous MgSO₄, and concentrated in vacuo to yield the title compound (212 mg, 99.1%). LC-MS for $C_{22}H_{30}F_3N_2O_5S$ [M⁺H⁺] calculated 491.17, found 391.15 (-Boc group).

Step B

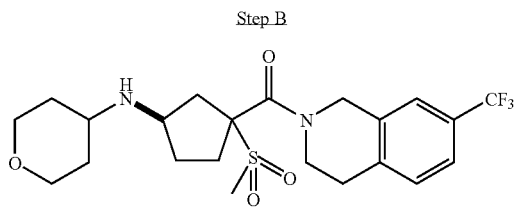

This compound was prepared as detailed in Example 3-Step E & F. The two isomers were resolved on the preparation plates (4/95.6/0.4, MeOH/DCM/NH₄OH). LC-MS for $C_{22}H_{30}F_3N_2O_4S$ [M⁺H⁺] calculated 475.18, found 475.15.

INTERMEDIATE 7

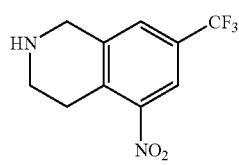

Step A

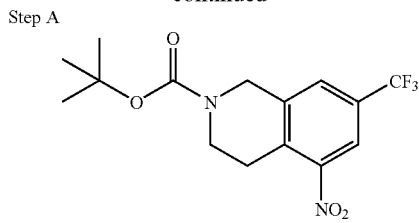

To a flask containing INTERMEDIATE 1 (10.0 g, 50 mmol) was added 30 mL of 70% nitric acid. The mixture was cooled at 0° C., 30 mL of concentrated sulfuric acid was added in 30 min. The resulting solution was stirred at RT overnight, poured into an ice-water mixture, treated to pH>10 with solid LiOH.H2O at 0° C. Under vigorous stirring, a solution of di-tert-butyl carbonate (21.8 g, 100 mmol) in 500 mL of DCM was added. The mixture was stirred for 30 min, the organic layer was separated, the aqueous layer was extracted with DCM (2×200 mL). The combined extracts were washed with water (500 mL), dried over Na2SO4, evaporated. The crude product was purified on FC (Silica gel, 20% EtOAc/Hexane) to afford the title compound as a white solid (17.0 g, 98%). 1H NMR (400 MHz, CDCl3) δ 8.05 (s, 1H), 7.62 (s, 1H), 4.72 (s, 2H), 3.67 (t, J=6.0 Hz, 2H), 3.13 (t, J=6.0 Hz, 2H), 1.49 (s, 9H).

Step B

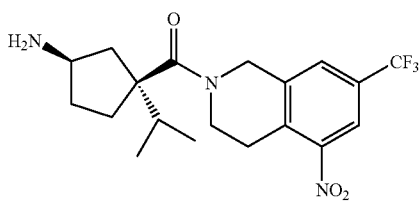

The above intermediate (Step A, Intermediate 7) (17.0 g) was dissolved in 100 mL of 4N HCl/dioxane and stirred for one hour, evaporated and dried in vacuum. The intermediate 1-B was obtained as white solid. 1H NMR (400 MHz, CD3OD) δ 8.75 (s, 1H), 8.00(s, 1H), 2.58 (s, 2H), 3.57 (t, J=6.0 Hz, 2H), 3.42 (t, J=6.0 Hz, 2H).

INTERMEDIATE 8

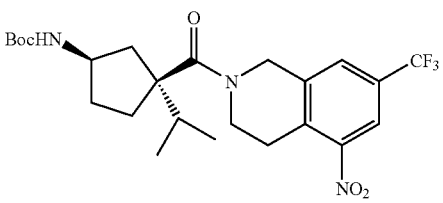

Step A

To a flask was added Boc-amino acid (Intermediate 4, 1.10 g, 4 mmol), isoquinoline hydrochloride (Intermediate 1, 1.15 g, 4 mmol), PyBrOP (1.85 g, 4 mmol), DMAP (0.29 g, 2.4 mmol), DIEA (2.77 mL, 16 mmol) and DCM (20 mL). The resulting mixture was stirred for 36 h under nitrogen. The entire material was dumped onto a silica gel column and eluted with 20% EtOAc/Hexane to yield the title compound as a gummy solid (1.5 g, 75%). ESI-MS calc. for C24H32F3N3O5: 499; Found: 500 (M+H).

Step B

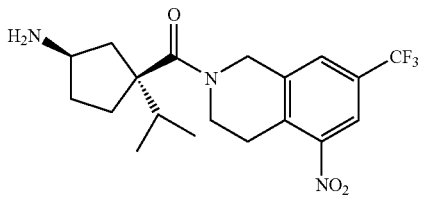

The coupling product (1.5 g) was treated with 10 mL of 4N HCl/Dioxane for 1 h, evaporated and dried under high vacuo to yield the title compound as a yellow solid (1.2 g). 1H NMR (400 MHz, CD3OD) δ 8.20 (s, 1H), 7.95(wide, 1H), 4.98 (s, 2H), 4.00 (dd, 2H), 3.90 (t, 2H), 3.68 (m, 1H), 3.45 (m, 3H), 3.20 (s, 2H), 2.15–2.50 (m, 3H), 1.80–2.10 (m, 2H), 1.80 (m, 2H), 0.90 (m, 6H). ESI-MS calc. for C19H24F3N3O3: 399; Found: 400 (M+H).

EXAMPLE 5

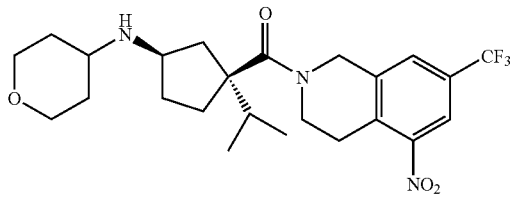

A mixture of the INTERMEDIATE 8 (130 mg, 0.3 mmol), tetrahydro-4H-pyran-4-one (100 mg, 1.0 mmol), molecular sieve (4 Å, 250 mg), DIEA (52 mg, 0.4 mmol) in DCM (10 mL) was stirred for 5 min. Then sodium triacetoxy borihydride (85 mg, 0.4 mmol) was added. The resulting mixture was stirred overnight, quenched with sat. aq. Na2CO3, filtered, washed with DCM. The filtrates were separated, the aq. solution was extracted with DCM. The combined DCM layers were dried over Na2SO4, evaporated. The residue was purified on preparative LC (1000 micron) (developed by 10% [aq. NH4OH/MeOH 1/9]/DCM) to yield the final product of the title compound as a free base. Its HCl salt (78 mg) was formed by treatment with 4N HCl/dioxane. H NMR (CDCl3, 400 MHz): δ 8.20 (s, 1H), 7.90 (s, 1H), 4.98 (s, 2H), 3.90 (s, 1H), 3.65 (s, 4H), 58 (m, 1H), 3.30 (s, 4H), 3.20 (s, 1H), 2.50 (m, 5H), 2.10 (m, 1H), 1.98 (m, 1H), 1.56 (m, 1H), 0.92 (m, 6H). ESI-MS calc. for C24H32F3N3O4: 483; Found: 484 (M+H).

EXAMPLE 6

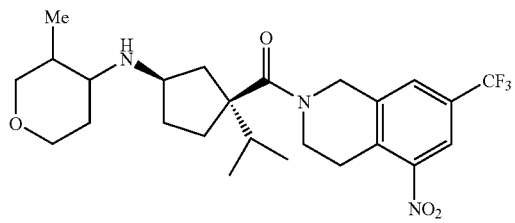

A mixture of the INTERMEDIATE 8 (218 mg, 0.5 mmol), 2-methyl-tetrahydro-4H-pyran-4-one (114 mg, 1.0 mmol), molecular sieve (4 Å, 350 mg), DIEA (78 mg, 0.6 mmol) in DCM (10 mL) was stirred for 5 min. Then sodium triacetoxy borihydride (130 mg, 0.6 mmol) was added. The resulting mixture was stirred overnight, quenched with sat. aq. Na2CO3, filtered, washed with DCM. The filtrates were separated, the aq. solution was extracted with DCM. The combined DCM layers were dried over Na2SO4, evaporated. The residue was purified on preparative TLC (1000 micron) (developed by 10% [aq. NH4OH/MeOH 1/9]/DCM) to yield the final product of the title compound as a mixture of 4 diastereoisomers (150 mg). ESI-MS calc. for C25H34F3N3O4: 497; Found: 498 (M+H). The diastereoisomers were separated into two major single isomers on chiral HPLC (OD column, 15% EtOHtHexane). First major isomer: ESI-MS calc. for C25H34F3N3O4: 497; Found: 498 (M+H). Second major isomer: ESI-MS calc. for C25H34F3N3O4: 497; Found: 498 (M+H).

INTERMEDIATE 9

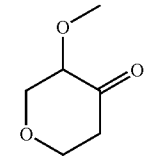

Step A

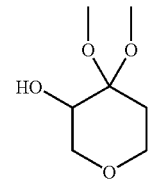

To a mixture of 5,6-dihydro-4-methoxy-2H-pyran (10.0 g, 87.5 mmol) in methanol (200 mL) at 0° C. was added dropwise a solution of m-CPBA (30.2 g, 175.06 mmol) in methanol (50 mL) via addition funnel. The resulting solution was stirred for 5 hours allowing to warm to room temperature. The methanol was removed under reduced pressure affording a white solid. The material was dissolved in 500 mL of dichloromethane and cooled to 0° C. To the mixture, while stirring vigorously, was added in portions an excess of solid calcium hydroxide (50–60 g). After stirring an additional 30 minutes, the mixture was filtered through a plug of celite and the filtrate evaporated under reduced pressure to afford 11.62 g (82%) of the desired product as a clear oil.

1H-NMR (500 MHz, CDCl3) δ 3.88–3.80 (m, 2H), 3.54–3.48 (m, 1H), 3.28 (s, 3H), 3.27 (s, 3H), 2.00–1.93 (m, 1H), 1.82–1.77 (m, 1H).

Step B

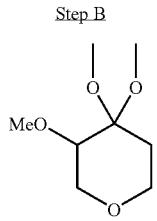

To a solution of product from Step A, Intermediate 9 (9.40 g, 58.0 mmol) in THF (200 mL) under nitrogen cooled to 0° C. was slowly added NaH (2.32 g, 58.0 mmol) and the resulting slurry stirred for 1 hour at 0° C. Iodomethane (7.22 mL, 116.0 mmol) was then added via syringe to the slurry and the resulting mixture was stirred overnight allowing to warm to room temperature. The reaction was quenched with a saturated solution of ammonium chloride (200 mL) and the organic layer was then removed using a separatory funnel. The aqueous was extracted with ether (3×150 mL) and all the organics were combined, dried over anhydrous sodium sulfate, filtered, and evaporated in vacuo. Purification was done by flash column using a stepwise gradient eluant of 10–60% ether/hexane to afford 8.46 g (83%) of the desired product as a clear oil. 1H-NMR (500 MHz, CDCl3) δ 3.98 (dd, J=2.5, 11.7 Hz, 1H), 3.77 (ddd, J=3.5,7.1,10.8 Hz, 1H), 3.57 (dd, J=1.4, 12.4 Hz, 1H), 3.50 (dd, J=2.5, 11.7 Hz, 1H), 3.46 (s, 3H), 3.25 (s, 3H), 3.22 (s, 3H), 3.22–3.20 (m, 1H), 1.96 (ddd, J=4.7, 11.8, 16.5 Hz, 1H), 1.75 (br dd, J=1.7, 14.2 Hz, 1H).

Step C

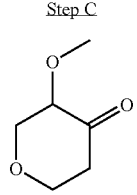

A solution of the product from Step B, Intermediate 9 (3.0 g, 17.04 mmol) in THF/water (60 mL/10 mL) was treated with concentrated hydrochloric acid (6 mL) and the resulting solution stirred at room temperature for 1 hour. The mixture was concentrated in vacuo to remove the THF and the aqueous layer then extracted with ether (6×50 mL). The organics were combined, dried over anhydrous sodium sulfate, filtered, and evaporated under reduced pressure to afford the title compound (1.75 g, 79%) as a clear oil. 1H-NMR (500 MHz, CDCl3) δ 4.23 (ddd, J=1.2, 11.4, 12.4 Hz, 1H), 4.15–4.09 (m, 1H), 3.82 (dd, J=5.95, 8.7 Hz, 1H), 3.74 (ddd, J=5.5, 8.5, 13.6 Hz, 1H), 3.56 (dd, J=8.8, 11.3 Hz, 1H), 3.50 (s, 3H), 2.61 (app dd, J=5.0, 8.9 Hz, 2H).

EXAMPLE 7

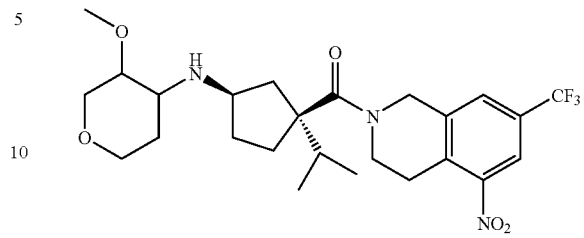

A mixture of the INTERMEDIATE 8 (218 mg, 0.5 mmol), 2-methoxy-tetrahydro-4H-pyran-4-one (INTERMEDIATE 9) (130 mg, 1.0 mmol), molecular sieve (4 Å, 350 mg), DIEA (78 mg, 0.6 mmol) in DCM (10 mL) was stirred for 5 min. Then sodium triacetoxy boride (130 mg, 0.6 mmol) was added. The resulting mixture was stirred overnight, quenched with sat. aq. Na2CO3, filtered, washed with DCM. The filtrates were separated, the aq. solution was extracted with DCM. The combined DCM layers were dried over Na2SO4, evaporated. The residue was purified on preparative TLC (1000 micron) (developed by 10% [aq. NH4OH/MeOH 1/9]/DCM) to yield the final product of the title compound as a mixture of 4 diastereoisomers (180 mg). ESI-MS calc. for C25H34F3N3O5: 513; Found: 514 (M+H). The diastereoisomers were separated into two major single isomers on chiral HPLC (OD column, 15% EtOH/Hexane). First major isomer: ESI-MS calc. for C25EL34F3N3O5: 513; Found: 514 (M+H). Second major isomer: ESI-MS calc. for C25H34F3N3O5: 513; Found: 514 (M+H).

INTERMEDIATE 10

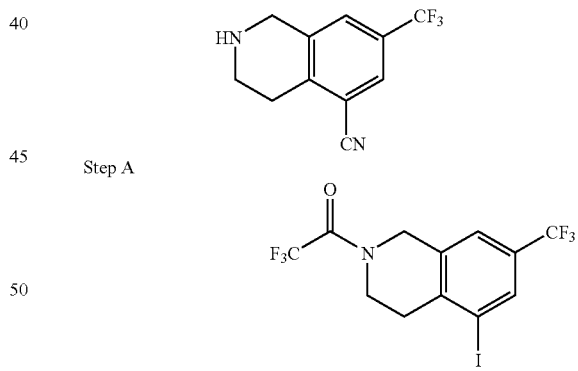

Step A

To a stirring mixture of N-trifluoroacetyl-7-trifluoromethyl-1,2,3,4-tetrahydroisoquinoline (Step C, Intermediate 1) (6.0 g, 20 mmol), NIS (6.9 g, 30 mmol) and TFA (15 mL) was added dropwise concentrated sulfuric acid (1.5 mL). A large amount of solid was formed. The mixture was stirred overnight at RT, poured into an ice-water mixture, extracted with ethyl acetate (3×). The combined organic phases were washed with water and brine, dried over Na2SO4, evaporated. The residue was purified on silica gel (eluted with 10% EtOAc/Hexane). The combined elutes were washed with sat. NaHSO3, dried over Na2SO4, evaporated and dried in vacuum to afford the title compound as a white solid (5.0 g). 1H NMR (400 MHz, CDCl3) δ 8.02 (d, J=2.5 Hz, 1H), 7.42 (d, j=3.0 Hz, 1H), 4.85, 4.79 (ss, 2H), 3.95, 3.90 (tt, J=1.5, 1.5 Hz, 2H), 2.97 (m, 2H). ESI-MS calc. For C12H8F6INO: 423; Found: 424 (M+H).

Step B

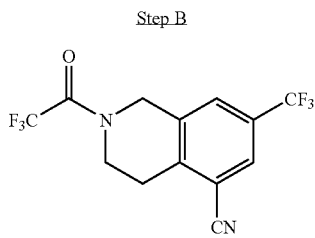

A mixture of the iodo compound (Step A, Intermediate 10) (4.23 g, 10 mmol), zinc cyanide (2.34 g, 20 mmol) and tetrakis-triphenyl phosphene palladium (0) complex (0.4 g) in 50 mL of DMF was purged with nitrogen several times, then heated at 85° C. overnight under nitrogen. LC-MS showed an complete conversion. The insoluble material was removed by filtration. The filtrate was diluted with water and extracted with ethyl acetate (3×). The ethyl acetate layers were combined and filtered through celite again, then washed with water, dried over Na2SO4, evaporated. The residue was purified on silica gel (eluted with 10% EtOAc/ Hex) to yield the title compound as a white solid (2.5 g). 1H NMR (400 MHz, CDCl3) δ 7.85 (d, J=2.1 Hz, 1H), 7.65 (d, J=2.6 Hz, 1H), 4.91, 4.86 (ss, 2H), 4.00 (m, 2H), 3.25 (m, 2H). ESI-MS calc. For C13H8F6N2O: 323; Found: 323 (M+H).

Step C

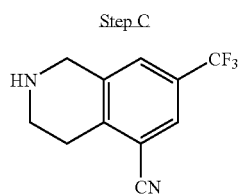

A mixture of the amide (Step B, Intermediate 10) (0.5 g, 1.55 mmol), potassium carbonate (1.5 g), ethanol (20 mL) and water (0.5 mL) was heated at 80° C. until TLC showed a complete cleavage, evaporated, diluted with water, extracted with DCM (3×), dried over Na2SO4, evaporated, dried in vacuum. The title product was obtained as a white solid (0.41 g). ESI-MS calc. For C11H9F3N2: 226; Found: 227 (M+H).

EXAMPLE 8

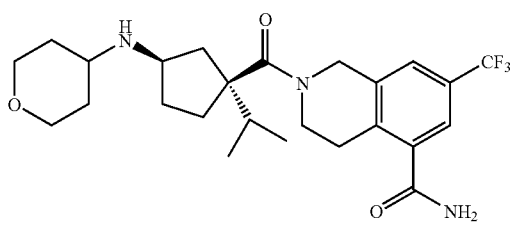

Step A

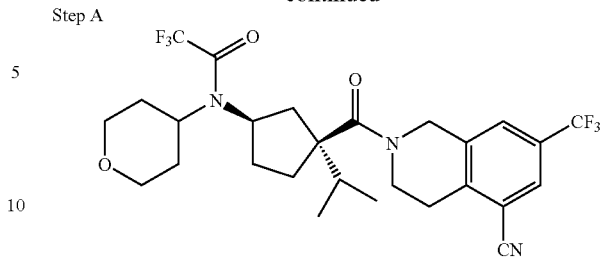

The INTERMEDIATE 5 (735 mg, 2.1 mmol) in 25 mL of DCM was stirred with a solution of oxalyl chloride (2.0 M, 1.25 mL, 2.5 mmol) under N2 for 5 min, then a trace amount of DMF was added. The mixture was stirred for one hour, evaporated, dried in vacuum. The residue was dissolved in 5 mL of DCM and then added into a stirring mixture of the INTERMEDIATE 10 (0.41 g, 1.77 mmol) and DIEA (0.36 g, 3.0 mmol) in 5 mL of DCM. The resulting mixture was stirred at RT for 2 h, dumped on a silica gel column and eluted with 10% methanol/DCM. The title compound was obtained as a white solid (1.10 g). ESI-MS calc. For C27H31F6N3O3: 559; Found: 560 (M+H).

Step B

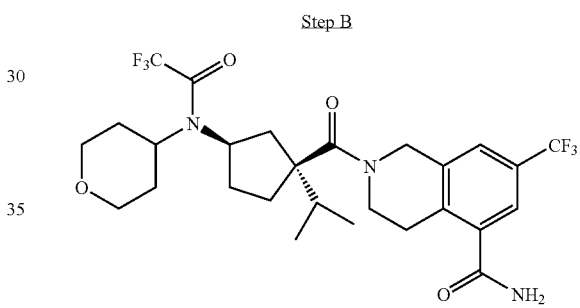

The product from Example 8 Step A (110 mg, 0.20 mmol) was combined with potassium carbonate (32 mg, 0.20 mmol) and hydrogen peroxide (30% Aqueous solution, 90 μL) in DMSO (2 mL) and stirred at room temperature. After 5 days the reaction was diluted with DCM and washed with water and brine. The organic layer was dried over MgSO4, filtered and concentrated under reduced pressure to give 115 mg of the desired product.

ESI-MS calc. for C27H33F6N3O4: 577; found 578 (M+H).

Step C

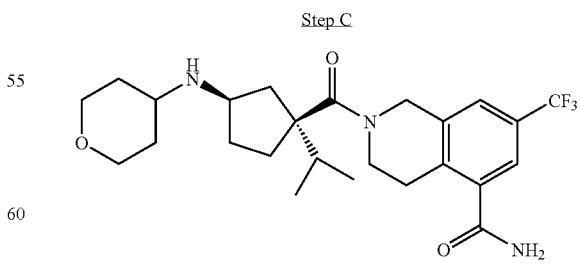

The intermediate 5 (26 mg) was stirred with sodium boron hydride (20 mg) in 1 mL of ethanol overnight. The entire mixture was loaded on preparative TLC (1000 micron) and developed with 10% [aq. NH4OH/MeOH 1/9]/DCM. The title product was obtained as a gummy solid (9 mg). ESI-MS calc. For C25H34F3N3O3: 481; Found: 482 (M+H).

EXAMPLE 9

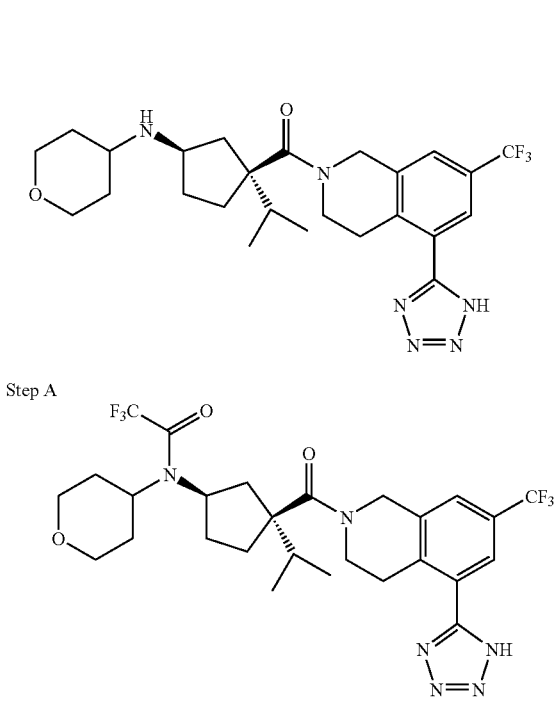

Step A

A mixture of the cyano compound (Step A, Example 8) (110 g, 0.2 mmol) and azidotrimethyltin (124 mg, 0.6 mmol) in 2 mL of toluene was heated at 100° C. over weekend, quenched with methanol, evaporated, purified on preparative TLC (10% MeOH/DCM) to yield the title compound as a yellow solid (110 mg). ESI-MS calc. For C27H32F6N6O3: 602; Found: 603 (M+H).

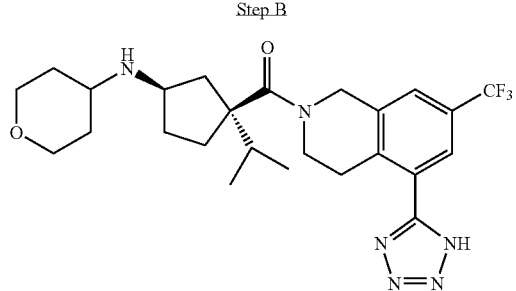

The tetrazole (Step A, Example 9) (110 mg, 0.18 mmol) was stirred with sodium boron hydride (80 mg) in 5 mL of ethanol for 3 days, quenched with methanol and 4N HCl/dioxane, evaporated, dissolved in methanol, filtered to remove insoluble solid, evaporated, purified on preparative TLC (developed with 20% methanol/DCM). The title product was obtained as a white solid (24 mg). ESI-MS calc. For C25H33F3N6O2: 506; Found: 507 (M+H).

EXAMPLE 10

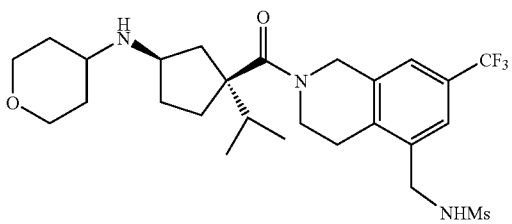

Step A

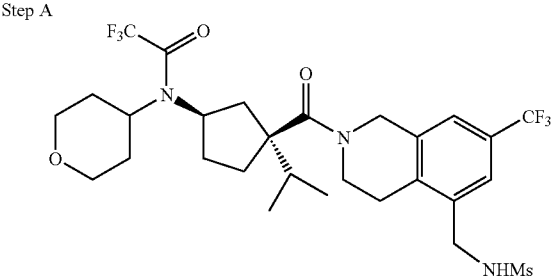

The cyano compound (Step A, Example 8) (230 mg, 0.5 mmol) was shaken with Ra—Ni (0.2 g) in 2N NH3/MeOH (50 mL) under 50 lbs hydrogen on a Parr shaker overnight. The catalyst cake was removed by filtration and wash with methanol. The filtrates were evaporated and dried in vacuum. The resulting solid (LC-MS: 564) was dissolved in 5 mL of DCM, triethyl amine (202 mg, 2.0 mmol) was added followed by methanesulfonyl chloride (115 mg, 1.0 mmol). After 30 min, LC-MS showed a complete conversion. The mixture was diluted with DCM (20 mL), washed with 1N aq. HCl and water, dried over Na2SO4, evaporated, purified on preparative TLC (5% MeOH/DCM) to yield the title product as a white solid (140 mg). ESI-MS calc. For C28H37F6N3O5S: 641; Found: 642 (M+H).

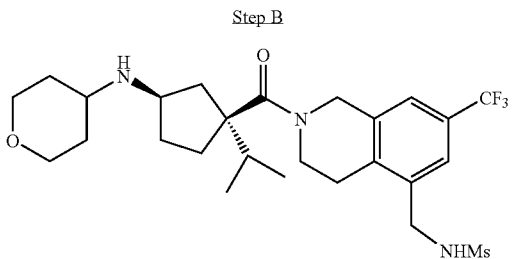

The amide (Step A, Example 10) (140 mg, 0.218 mmol) was stirred with sodium boron hydride (57 mg) in 5 mL of ethanol for 15 h, quenched with methanol and 4N HCl/dioxane, evaporated, dissolved in methanol, filtered to remove insoluble solid, evaporated, purified on preparative TLC (developed with 10% [aq. NH4OH/MeOH 1/9]/DCM). The title product was obtained as a white solid (90 mg). ESI-MS calc. For C26H38F3N3O4S: 545; Found: 546 (M+H).

EXAMPLE 11

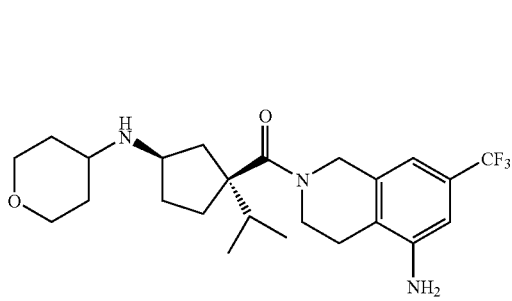

Step A

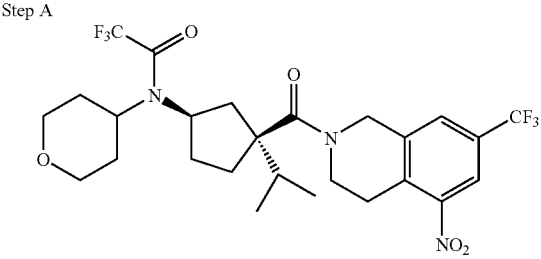

The INTERMEDIATE 5 (0.228 g, 0.8 mmol) in 2 mL of DCM was stirred with a solution of oxalyl chloride (2.0 M, 0.5 mL, 1 mmol) under N2 for 5 min, then a trace amount of DMF was added. The mixture was stirred for one hour, evaporated, dried in vacuum. The residue was dissolved in 2 mL of DCM and then added into a stirring mixture of the intermediate 1 (0.2 g, 0.71 mmol) and DIEA (0.26 g, 2.0 mmol) in 5 mL of DCM. The resulting mixture was stirred at RT for 2 h, dumped on a silica gel column and eluted with 10% methanol/DCM. The title compound was obtained as a white solid (0.3 g). ESI-MS calc. For $C_{26}H_{31}F_6N_3O_5$: 579; Found: 580 (M+H).

Step B

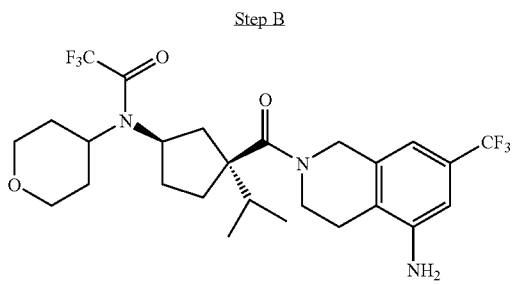

The nitro compound (Step A, Example 11) (0.25 g, 0.432 mmol) was shaken with 10% Pd/C (0.1 g) in MeOH (20 mL) under 50 lbs hydrogen on a Parr shaker for one hour. The catalyst cake was removed by filtration and wash with methanol. The filtrates were evaporated and dried in vacuum. The title compound was obtained as a white solid (230 mg). ESI-MS calc. For $C_{26}H_{33}F_6N_3O_3$: 549; Found: 550 (M+H).

Step C

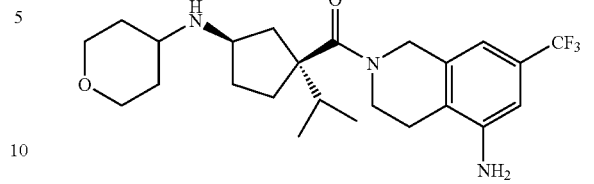

The aniline (Step B, Example 11) (0.055 g, 0.1 mmol) was stirred with sodium boron hydride (37 mg) in 5 mL of ethanol for 15 h, quenched with methanol and 4N HCl/dioxane, evaporated, dissolved in methanol, filtered to remove insoluble solid, evaporated, purified on preparative TLC (developed with 10% [aq. NH4OH/MeOH 1/9]/DCM). The title product was obtained as a light yellow solid (42 mg). ESI-MS calc. For $C_{24}H_{34}F_3N_3O_2$: 454; Found: 455 (M+H).

INTERMEDIATE 11

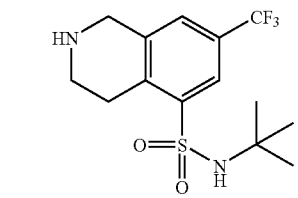

Step A

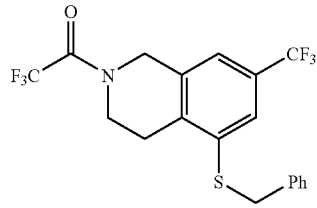

A mixture of the iodo compound (Step A, Intermediate 10) (4.23 g, 10 mmol), Copper powder (2.48 g, 40 mmol), benzyl disulfide (6.5 g, 26.5 mmol) and pyridine (50 mL) was heated at 100° C. for 2 days, cooled at RT and diluted with DCM (200 mL), cooled at 0° C., then added trifluoro acetic acid anhydride (10 mL) to convert the free tetrahydroisoquinolines (from partial decomposition of amide) into trifluoro acetamides. The reaction mixture was washed with water, 2N aq. HCl. The precipitate formed was removed by filtration. The two layers were separated. The organic layer was dried over Na2SO4, evaporated and purified on silica gel (5% ethyl acetate/hexane) to yield the title product as a white solid (2.0 g). 1H NMR (400 MHz, CD3OD) δ 7.47 (d, J=5.0 Hz, 1H), 7.30 (m, 6H), 4.81, 4.76 (ss, 2H), 4.14 (s, 2H), 3.85, 3.78 (tt, J=6, 4 Hz, 2H), 2.87 (t, J=15 Hz, 1H). ESI-MS calc. for $C_{19}H_{15}F_6NOS$: 419; Found: 420 (M+H).

Step B

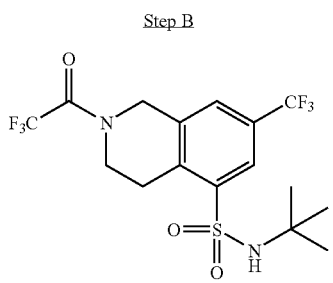

To a suspension of the thio ether (Step A, Intermediate 11) (2.0 g, 4.77 mmol) in 15 mL of acetic acid and water (7:1 v/v) was bubbled chlorine gas until a large amount of yellow solid formed (~30 min). The mixture was diluted with DCM, washed with ice-water (3×), dried over Na2SO4, slowly poured into a mixture of tert-butyl amine (20 mL) in 100 mL of DCM at 0° C. The resulting solution was stirred at 0° C. for another 30 min, washed with water, 2N aq. HCl and brine, dried over Na2SO4. FC on silica gel (20% ethyl acetate/hexane) gave the title product as a white solid (1.40 g).

ESI-MS calc. for C16H18F6N2O3S: 432; Found: 433 (M+H).

Step C

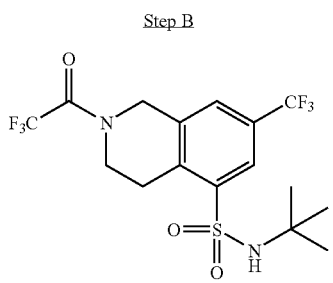

The sulfonamide (Step B, Intermediate 11) (1.40 g, 3.0 mmol) was heated at 80° C. with potassium carbonate (2.8 g, 20 mmol) in 20 mL of ethanol until the starting material disappeared. The solid was removed by filtration. The filtrates were condensed and purified on FC (Silica Gel, 10% [aq. NH4OH/MeOH 1/9]/DCM) to yield the title product as a white solid (0.80 g). 1H NMR (400 M, CDCl3) δ 8.18 (s, 1H), 7.46 (s, 1H), 4.70 (s, 1H), 4.16 (s, 2H), 3.20 (m, 4 H), 1.87 (s, 2H), 1.26 (s, 9H). ESI-MS calc. for C14H19F3N2O2S: 336; Found: 337 (M+H).

EXAMPLE 12

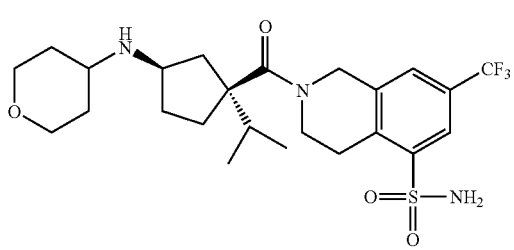

-continued

Step A

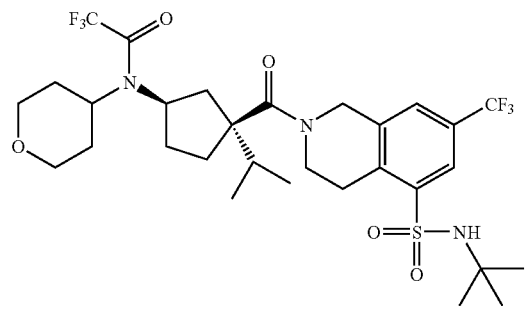

INTERMEDIATE 4 (0.351 1.0 mmol) in 2 mL of DCM was stirred with a solution of oxalyl chloride (2.0 M, 0.6 mL, 1.2 mmol) under N2 for 5 min, then a trace amount of DMF was added. The mixture was stirred for one hour, evaporated, dried in vacuum. The residue was dissolved in 2 mL of DCM and then added into a stirring mixture of the intermediate 10 (0.336 g, 1.1 mmol) and DIEA (0.26 g, 2.0 mmol) in 5 mL of DCM. The resulting mixture was stirred at RT for 2 h, dumped on a silica gel column and eluted with 10% methanol/DCM. The title compound was obtained as a white solid (0.62 g). ESI-MS calc. For C30H41F6N3O5S: 669; Found: 670 (M+H).

Step B

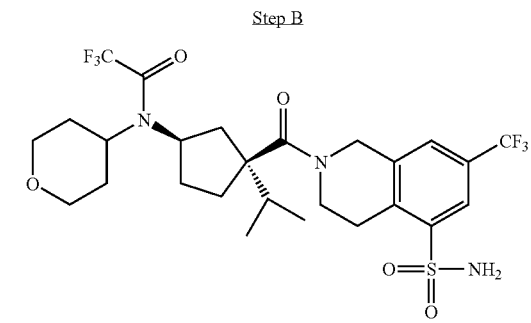

To a mixture of the sulfonamide (Step A, Example 12) (0.62 g, 0.92 mmol) in 5 mL of TFA was added 1.0 mL of concentrated sulfuric acid. The resulting mixture was stirred for one hour, poured into ice-water, extracted with DCM (2×), dried over Na2SO4, evaporated and purified on FC (10% MeOH/DCM) to yield the title product as a white solid (500 mg). ESI-MS calc. For C26H33F6N3O5S: 613; Found: 614 (M+H).

Step C

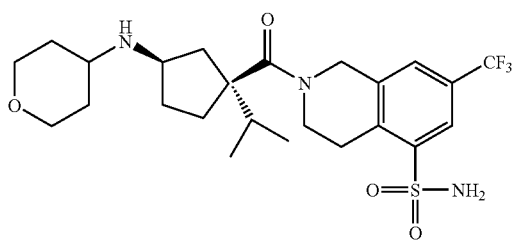

The amide (Step B, Example 12) (0.5 g, 0.82 mmol) was stirred with sodium boron hydride (100 mg) in 5 mL of ethanol for 15 h, quenched with methanol and 4N HCl/dioxane, evaporated, dissolved in methanol, filtered to remove insoluble solid, evaporated, purified on preparative TLC (developed with 10% [aq. NH4OH/MeOH 1/9]/DCM). The title product was obtained as a white solid (250 mg). ESI-MS calc. For C24H34F3N3O4S: 517; Found: 518 (M+H).

EXAMPLE 13

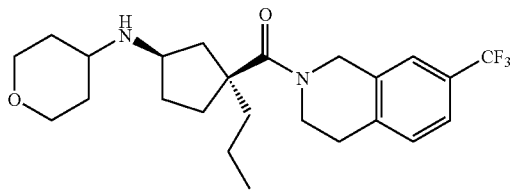

Step A

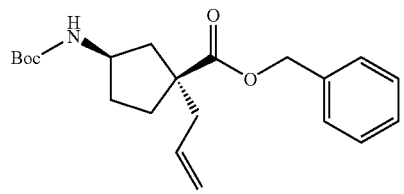

To a stirred, −78° C. solution of the Schiff base (Step D, Intermediate 6) (38.4 g, 100 mmol) in 200 mL of THF was added a solution of LDA (2M, 55 mL, 110 mmol) in THF. The mixture was stirred for 30 min at −78° C., then a solution of allyl bromide (20 mL, 200 mmol) in HMPA (18 mL, 100 mmol) was added dropwise. The resulting red solution was stirred at −78° C. for one hour, warmed to RT by removing cooling bath, diluted with water, extracted with ether. Ether layer was anti-washed with water and brine, dried over Na2SO4, evaporated. The residue was dissolved in 300 mL of THF. To this solution was added 150 mL of 2N aq. HCl, stirred for one hour, evaporated to remove THF, extracted with hexane (3×). The aqueous solution was basified to pH>9 with sat. aq. sodium carbonate, immediately was mixed and stirred with a solution of di-tert-butyl dicarbonate (42 g, 200 mmol) in 200 mL of dichloromethane. After 30 min, the organic phase was separated and the aqueous layer was extracted with dichloromethane (2×). The combined organic phases were washed with water and brine, dried over Na2SO4, evaporated. The residue was purified on FC (10% EtOAc/Hexane) to yield a mixture of cis and trans isomers (24.0 g, 65%). The mixture was separated into single cis (fast-eluted, 5.6 g) and trans (slow-eluted, 4.2 g) isomers on MPLC (5% EtOAc/Hexane). $^1$H NMR (400 MHz, CDCl$_3$): cis: 7.40 (m, 5), 5.68 (m, 1H), 5.18 (s, 2H), 5.04 (m, 2H), 4.85 (br s, 1H), 4.10 (br s, 1H), 2.50 (dd, J=7.2 Hz, 1H), 2.30 (dd, J=7.3 Hz, 1H), 2.20 (m, 1H), 2.00 (m, 3H), 1.70–1.43 (m, 2H), 1.44 (s, 9H). trans: 7.38 (m, 5H), 5.65 (m, 1H), 5.12 (s, 2H), 5.03 (m, 2H), 4.50 (br s, 1H), 4.00 (br s, 1H), 2.62 (dd, J=6.1 Hz, 1H), 2.24 (m, 8H), 2.10 (m, 2H), 1.70 (m, 1H), 1.41 (s, 9H), 1.42–1.30 (m, 2H).

Step B

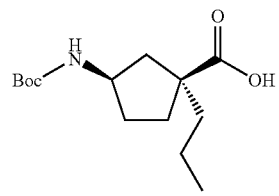

A mixture of the cis ester (Step A, Example 13) (0.65 g) and 10% Pd/C (0.2 g) in methanol (mL) was shaken on a Parr shaker for 2 h under 50 lb of hydrogen. The catalyst was removed by filtration, the filtrate was evaporated and dried in vacuum to yield the desired acid as a white solid which was used in next step without further purification.

Step C

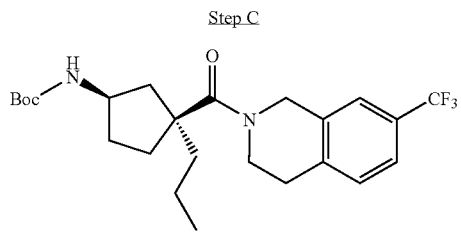

A mixture of the cis acid (Step B, Example 13) (108 mg, 0.4 mmol), the INTERMEDIATE 1(160 mg, 0.8 mmol), PyBroP (370 mg, 0.8 mmol) and DMAP (360 mg, 3.0 mmol) in dichloromethane (10 mL) was stirred at RT under nitrogen overnight., diluted with dichloromethane, washed with water, 1N aq. HCl and brine, dried over Na2SO4, evaporated, purified on preparative TLC (5% MeOH/Hexane). The desired product was obtained as a gummy solid (120 mg, 66%). LC MS for C24H33F3N2O3 for [M+H]$^+$ calc. 455, found 455.

Step D

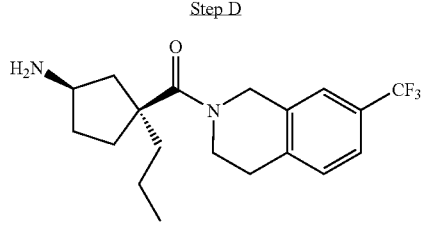

This compound was prepared starting from the intermediate (Step C, Example 13) according to the procedure described in INTERMEDIATE 6-Step B. LC MS for C19H25F3N2O for [M+H]+ calc. 355, found 355.

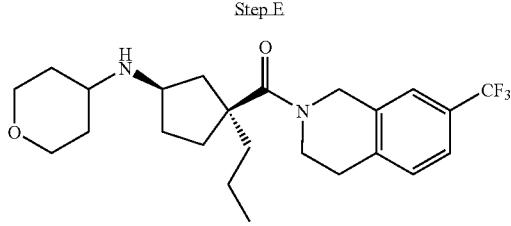

This compound was prepared starting from the intermediate (Step D, Example 13) according to the procedure described in Example 1, Procedure A. LC MS for C24H33F3N2O2 for [M+H]+ calc. 439, found 439.

EXAMPLE 14

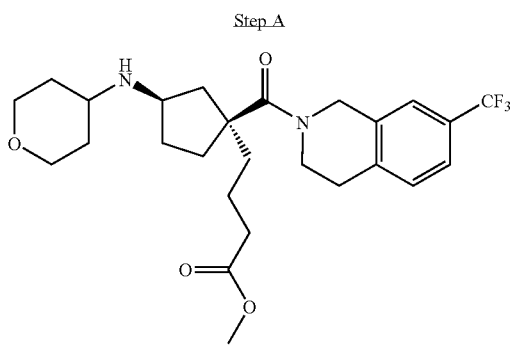

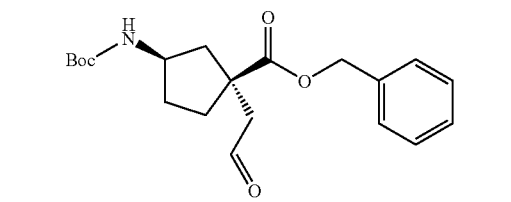

To a solution of the alkene (Step A, Example 13) (0.9 g, 0.25 mmol) in 50 mL of dichloromethane at −78° C. was bubbled into O₃ until the blue solution was observed. Excessive O3 was removed by nitrogen flow, dried over sodium sulfate, evaporated, redissolved in dichloromethane and mixed with triphenyl phosphine (2.0 g), stirred until complete conversion. Dichloromethane was remove and the residue was purified on FC (30% then 50% ethyl acetate/hexane) to yield the title compound as colorless oil (0.66 g, 67%). ¹H NMR (400 MHz, CDCl₃): 9.69 (s, 1H), 7.36 (m, 5H), 5.14 (s, 2H), 5.04 (br, 1H), 4.16 (br, 1H), 2.97 (d, J=18.2 Hz, 1H), 2.74 (m, J=18.2 Hz, 1H), 2.12 (m, 2H), 2.02 (m, 1H), 1.90 (m, 1H), 1.60 (m, 2H), 1.44 (s, 9H).

A solution of methyl(triphenylphosphoranylidene)acetate was prepared by treatment of the corresponding phosphonium bromide (0.83 g, 2.0 mmol) in THF (20 mmol) and lithium bis(trimethylsilyl)amide THF solution (1.0 M, 2.0 mL, 2.0 mmol). To the above solution was added the aldehyde (Step A, Example 14) (0.66 g, 2.0 mmol) in THF (5 mL) at −78° C. The reaction was warmed to RT overnight, evaporated and purified on FC (10% EtOAc/hexane) to yield a mixture of cis and trans isomers (0.6 g, 72%). ¹H NMR (400 MHz, CDCl₃): more polar: 7.95 (m, 5H), 6.79 (q, J=7.8 Hz, 1H), 5.80 (d, J=6.6 Hz, 1H), 5.15 (s, 2H), 4.90 (br, 1H), 4.10 (br, 1H), 3.72 (s, 3H), 2.60 (m, 1H), 2.45 (m, 1H), 2.20 (m, 1H), 2.00 (m, 3H), 1.60 (m, 2H), 1.44 (s, 1H). Less polar: 7.38 (m, 5H), 6.05 (m, 1H), 5.80 (d, J=11.6 Hz, 1H), 5.15 (s, 2H), 4.90 (br, 1H), 4.15 (br, 1H), 3.69 (s, 3H), 3.04 (m, 2H), 2.20 (m, 1H), 2.00 (3H), 1.60 (2H), 1.43 (s, 9H).

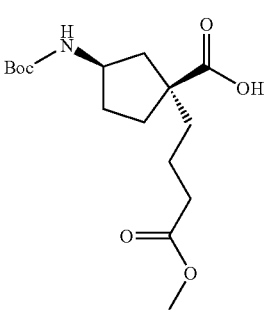

The unsaturated ester (Step B, Example 14) (260 mg, 0.62 mmol) was hydrogenated with 10% Pd/C (0.1 g) in methanol (20 mL) under 50 lb of hydrogen for 2 h, filtered and evaporated to yield the title compound as an oil (202 mg, 100%).

Step D

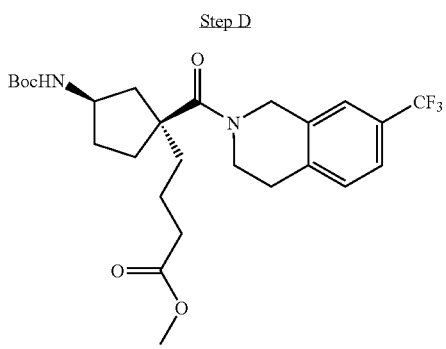

The Boc-amino acid (Step C, Example 14) (200 mg, 0.61 mmol), the INTERMEDIATE 1 (123 mg, 0.61 mmol), PyBrOP (285 mg, 0.61 mmol), DMAP (45 mg, 0.366 mmol) and DIEA (236 mg, 0.183 mmol) was mixed with 10 mL of dichloromethane under nitrogen and stirred for 2 days. The reaction was quenched with water, washed with 1N aq. HCl, brine, dried over sodium sulfate and evaporated. The residue was purified on preparative TLC (20% EtOAc/hexane) to yield the title compound as an oil (120 mg, 38%). $^1$H NMR (400 MHz, CDCl$_3$): 7.42 (d, J=8.0 Hz, 2H), 7.27 (d, J=8.0 Hz, 2H), 4.92 (br, 1H), 4.79 (m, 2H), 4.00 (m, 1H), 3.80 (m, 2H), 3.58 (s, 3H), 2.95 (m, 2H), 2.42–2.10 (m, 4H), 1.90 (m, 3H), 1.75 (m, 1H), 1.50 (m, 3H), 1.20 (ss, 9H).

Step E

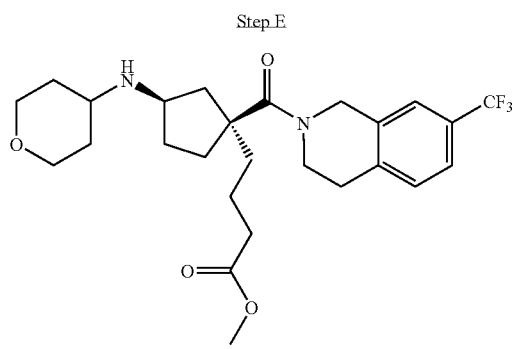

This compound was prepared starting from the Intermediate (Step D, Example 14) according to the procedure described in Example 13, Step D and E. LC MS for C26H35F3N2O4 for [M+H]$^+$ calc. 496, found 496.

EXAMPLE 15

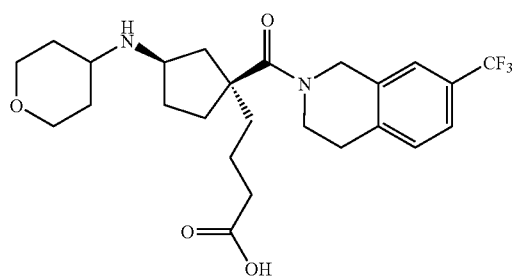

The Example 14 (40 mg) was mixed with lithium hydroxide mono hydrate (20 mg), methanol (2 mL) and water (0.5 mL), stirred overnight, evaporated and purified on preparative TLC (methanol) to yield the title compound as a white solid (37 mg). LC MS for C25H33F3N2O4 for [M+H]$^+$ calc. 483, found 483.

INTERMEDIATE 12

Step A

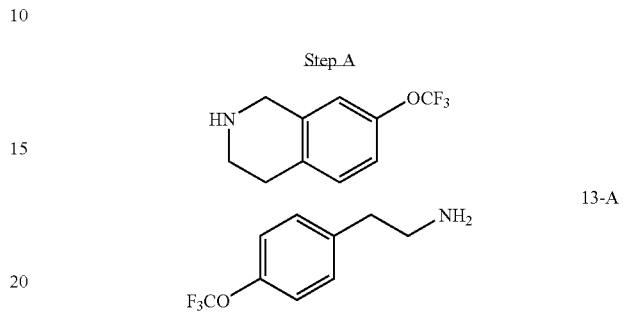

To a solution of 4-trifluoromethoxy phenylacetonitrile (5 g, 24.4 mmol), EtOH (80 mL), and NH$_4$OH (20 mL), was added Raney Ni (one scoop). The reaction mixture was placed in a par-shaker and shook under 40 Lb pressure overnight. The solution was filtered through celite and concentrated in vacuo to yield the title compound (4.36 g, 85.5%). 1H NMR (400 MHz, CD3OD) δ 7.30 (d, J=8.5 Hz, 2H), 7.19(d, J=8.0 Hz, 2H), 2.87 (app. d, J$_{ave}$=7.0 Hz, 2H), 2.78 (app t, J$_{ave}$x7.2 Hz, 2H). LC-MS for C$_9$H$_{10}$F$_3$NO [M$^+$H$^+$] calculated 206.07, found 206.15.

Step B

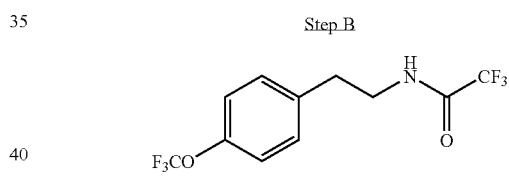

The amine (Step A, Intermediate 12) (4.36 g, 21.3 mmol) and pyridine (3.44 mL, 42.5 mmol) were dissolved in DCM (40 mL). The solution was cooled to 0° C. before TFAA (4.5 mL, 31.9 mmol) was added slowly. The reaction mixture was stirred in the ice bath for another 10 minutes before warmed up to room temperature. The reaction was completed in 30 minutes and dumped in water and extracted with DCM (2×). The organic layer was washed with 1N HCl and saturated NaCl solution, dried over MgSO$_4$, and concentrated in vacuo to yield the title compound (5.79 g, 90.4%). 1H NMR (400 MHz, CDCl3) δ 7.23 (m, 4H), 6.34 (s, 1H), 3.63 (q, J=13.5 Hz, 6.9 Hz), 2H), 2.92 (t, J=7.0 Hz, 2H).

Step C

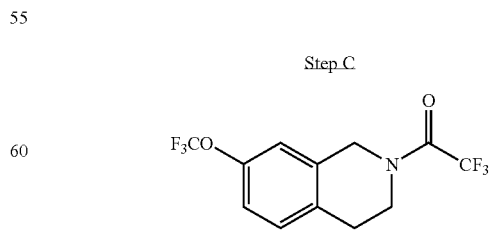

To a mixture of the amide (Step B, Intermediate 12) (4 g, 13.3 mmol) and paraformaldehyde (604 mg, 19.3 mmol) was added in one portion a mixture of conc. sulfuric acid (27 mL) and glacial acetic acid (18 mL). The reaction mixture was stirred at room temperature for 36 hrs before poured onto ice water (250 mL) and extracted with EtOAc (3×). Combined organic layer was washed with water (2×), saturated NaHCO₃, and brine, dried over MgSO₄, filtered, and evaporated. The concentrate was purified by column chromatography to yield the title compound (3.1 g, 75%). 1H NR (400 MHz, CDCl3) δ 7.22 (q, J=11.67 Hz, 8.46 Hz, 1H), 7.11 (t, J=10.53 Hz, 1H), 7.03 (d, J=11.67 Hz, 1H), 4.79 (d, J=23.57 Hz, 2H), 3.91 (t, J=6.18 Hz, 1H), 3.87 (t, J=5.72 Hz, 1H), 2.97 (m, 2H).

Step D

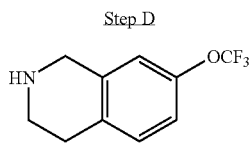

The amide (Step C, Intermediate 12) (2.37 g, 7.57 mmol) was dissolved in EtOH (25 mL) before a solution of K₂CO₃ (5.23 g, 37.9 mmol) in H₂O (25 mL) was added. The reaction mixture was refluxed for 1½ hours before concentrated in vacuo. The concentrate was diluted with H₂O and extracted with DCM (5×). Combined organic layer was dried over MgSO₄, filtered, and concentrated to yield the title compound (1.34 g, 81.7%). %). 1H NMR (400 MHz, CDCl3) δ 7.11 (d, J=8.4 Hz, 1H), 7.01 (bd, J=8.4 Hz, 1H), 6.89 (s, 1H), 4.03 (s, 2H), 3.15 (t, J=6.1 Hz, 2H), 2.80 (t, J=6.5 Hz, 2H), 1.80 (s, 1H).

EXAMPLE 16

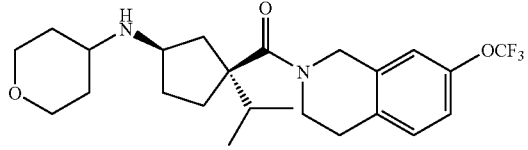

Example 16 was prepared as detailed in Example 1 using Intermediate 12 instead of Intermediate 1. LC-MS for C24H33F3N2O3 [M⁺H⁺] calculated 455, found 455.

INTERMEDIATE 13

Step A

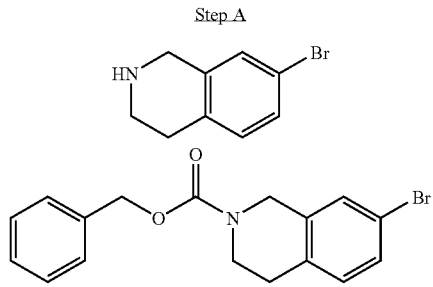

To a solution of 7-bromo-1,2,3,4-tetrahydroisoquinoline (12.43 g, 59 mmol) in tetrahydrofuran (150 ml) was added benzyl chloroformate (10.1 ml, 71 mmol), and the resulting mixture stirred at room temperature for 5 hours. N,N-dimethylethylenediamine (1.5 ml, 13.7 mmol) was added and the mixture stirred at room temperature for a further 1 hour. Ether (500 ml) was added and the mixture washed with water (400 ml), 10% citric acid solution (300 ml), saturated NaHCO₃ (150 ml), sat NaCl (100 ml), dried over MgSO₄, filtered and evaporated to give the product (20 g, 98%); ¹H NMR 500 MHz (CDCl₃) δ=2.82 (2H, br s), 3.73 (2H, br s), 4.61 and 4.64 (2H, s), 5.21 (2H, s), 7.02 (1H, br d, J=7.6 Hz), 7.28 to 7.44 (7H, m).

Step B

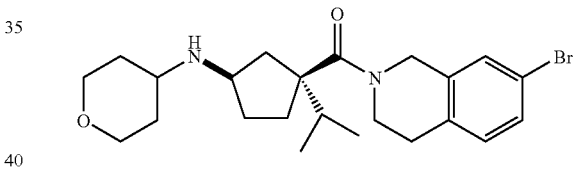

A reaction mixture of the carbamide (Step A, Intermediate 13) (400 mg, 1.16 mmol) in TFA (1.6 mL) and DMS (0.4 mL) was stirred at room temperature overnight. After completion of reaction, the mixture was concentrated in vacuo, redissolved in EtOAc, and washed with saturated NaHCO₃. Combined aqueous layer was back-washed with EtOAc (2×). Combined organic layer was dried over Na₂SO₄, filtered, and concentrated to yield the crude title product which was used on the next step. LC-MS for C₉H₁₁BrN [M⁺H⁺] calculated 212.00, found 213.95.

EXAMPLE 17

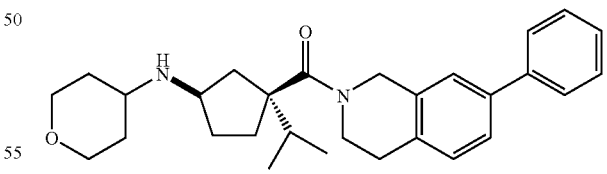

Example 17 was prepared as detailed in Example 1 using Intermediate 13 instead of Intermediate 1. LC-MS for C₂₃H₃₄BrN₂O₂ [M⁺H⁺] calculated 449.17, found 451.17.

EXAMPLE 18

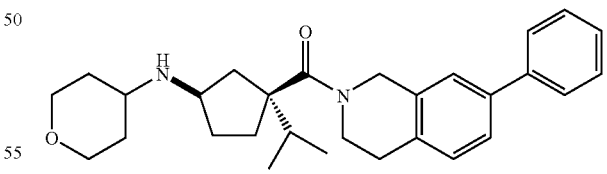

To a solution of Example 17 (100 mg, 0.210 mmol), phenylboronic acid (30 mg, 0.230 mmol), toluene (1.4 mL), and MeOH (0.6 mL) was added a solution of Na₂CO₃ (80 mg, 0.735 mmol) and Pd(PPh₃)₂Cl₂ (8 mg, 0.011 mmol) in H₂O (0.4 mL). The reaction mixture was heated at 80° C. in a high pressure tube for 12 hours before filtered through celite and concentrated to dryness. The concentrate was diluted with DCM, washed with 1N NaOH solution (3×), dried over Na₂SO₄, and concentrated in vacuo. The crude product was purified by preparation plate (5/94.5/0.5, MeOH/DCM/NH₄OH) to yield Example 18 (63.3 mg, 63.3%). LC-MS for $C_{29}H_{39}N_2O_2$ [M⁺H⁺] calculated 447.29, found 447.35.

INTERMEDIATE 14

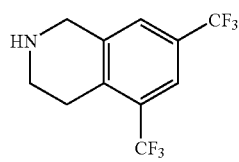

Intermediate 14 was synthesized as detailed in Intermediate 12 using 1,4-bis(trifluoromethyl)phenylacetonitrile as starting material instead of 4-trifluoromethoxy phenylacetonitrile. 1H NMR (500 MHz, CDCl3) δ 7.74 (s, 1H), 7.47 (s, 1H), 4.15 (s, 2H), 3.20 (t, J=6.0 Hz, 2H), 3.02 (app. T, $J_{ave}$=5.6 Hz, 2H)m 1.83 (bs, 1H). LC-MS for $C_{11}H_{11}F_6N$ [M⁺H⁺] calculated 270.06, found 270.05.

EXAMPLE 19

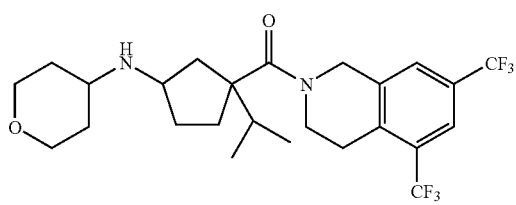

Example 19 as a mixture of four isomers was prepared as detailed in Example 1, Procedure B using Intermediate 14 instead of Intermediate 1. LC-MS for $C_{23}H_{34}BrN_2O_2$ [M⁺H⁺] calculated 449.17, found 451.17.

INTERMEDIATE 15

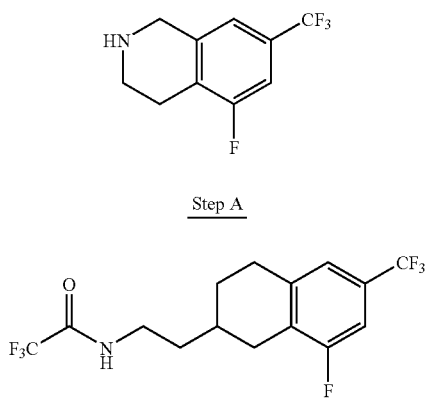

Step A

A solution of 2-fluoro-4-trifluoromethylphenylacetonitrile (10 g, 49 mmol) in a mixture of ethanol (100 ml) and ammonium hydroxide (20 ml of a 29.3% aqueous solution) was hydrogenated over Raney nickel (1 g) for 16 hours. The catalyst was removed by filtration through celite and the filtrate evaporated to dryness. The neat residue was added in a dropwise manner to trifluoroacetic anhydride (25 ml, 177 mmol) cooled at 0° C. and the resulting mixture stirred at 0° C. for 30 mins. The reaction mixture was poured onto ice (250 ml) and the resulting mixture stirred for 30 mins after which the precipitate was removed by filtration and air dried to give the product as a white solid (13.4 g, 90%); ¹H NMR 500 MHz (CDCl₃) δ=3.02 (2H, t, J=7.0 Hz), 3.66 (2H, q, J=6.6 Hz), 6.44 (1H, br s), 7.34 (2H, m), 7.41 (1H, d, J=7.8 Hz).

Step B

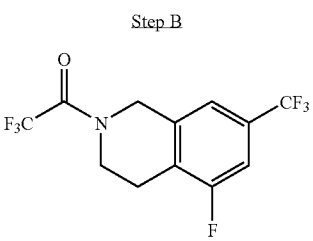

To a mixture of the product from step A, Intermediate 15 (13.4 g, 44 mmol) and paraformaldehyde (2 g, 48 mmol) was added in one portion a mixture of concentrated sulfuric acid (90 ml) and glacial acetic acid (60 ml) and the resulting mixture stirred at room temperature for 16 hours. The reaction mixture was poured onto a mixture of ice and water (1 liter) and extracted with ethyl acetate (3×150 ml); the combined ethyl acetate layers were washed with water (3×500 ml), saturated NaHCO₃ (200 ml), and sat NaCl (100 ml), dried over MgSO₄, filtered and evaporated in vacuo. The residue was purified by column chromatography on silica elution with 10% Et₂O in Hexanes to give the product (8.29 g, 60%); ¹H NMR 500 MHz (CDCl₃) δ=3.01 (2H, m), 3.91 and 3.97 (2H, t, J=6.2 Hz), 4.83 and 4.88 (2H, s), 7.21–7.28 (3H, m).

Step C

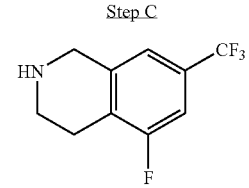

To a solution of the trifluoroacetamide formed in step B (8.29 g, 26 mmol) in ethanol (200 ml) was added a solution of potassium carbonate (20 g, 145 mmol) in water (50 ml), and the resulting mixture stirred at reflux for 1 hour. The ethanol was removed by rotary evaporation and water (150 ml) was added to the residue. Extracted with CH₂Cl₂ (3×100 ml), the combined CH₂Cl₂ layers were washed with sat NaCl (100 ml), dried over Na₂SO₄, filtered and evaporated in vacuo to give the product (5.2 g, 91%); ¹H NMR 500 MHz (CDCl$_3$) δ=1.74 (1H, br s), 2.78 (2H, d, J=6.0 Hz), 3.17 (2H, t, J=6.0 Hz), 4.05 (2H, s), 7.04–7.14 (3H, m).

EXAMPLE 20

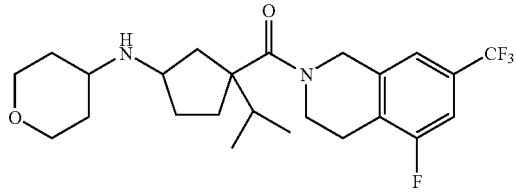

Example 20 as a mixture of four isomers was prepared as detailed in Example 1, Procedure B using Intermediate 15 instead of Intermediate 1. LC-MS for C24H32F4N2O2 [M$^+$H$^+$] calculated 456, found 456. Cis isomers were resolved into two singe isomers by a Gilson HPLC equipped with a preparatory ChiralPak AD column (eluant: 5% EtOAc/hexane/hexane).

EXAMPLE 21

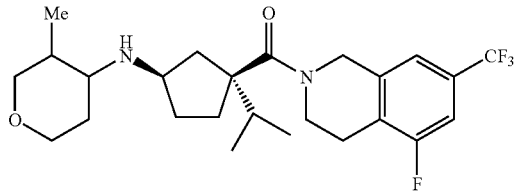

This compound as a mixture of four diastereoisomers was prepared starting from INTERMEDIATE 15 according to the procedure described in Example 6. LC-MS for C25H34F4N2O2 [M$^+$H$^+$] calculated 471, found 471. The cis and trans isomers in reference to pyran ring were separated into four single isomers by a Gilson HPLC equipped with a preparatory ChiralPak AD column (eluant: 5% EtOH/hexane).

EXAMPLE 22

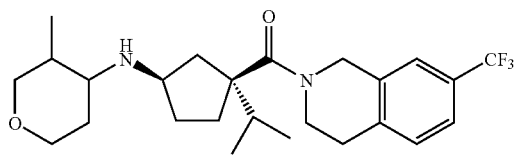

This product was prepared in an analogous fashion to that of Example 1, Procedure A, except tetrahydro-4H-pyran-4-one was replaced with 2-methyl-cyclohexanone. The crude product was purified by Preparative TLC (eluant: 0.5% NH$_4$OH:5% MeOH:94.5% CH$_2$Cl$_2$) to afford the title compound (353 mg, 61%) as a mixture of four diastereomers. LC-MS for C$_{26}$H$_{37}$F$_3$N$_2$O calculated 450.29, found [M+H]$^+$ 451.3.

INTERMEDIATE 16

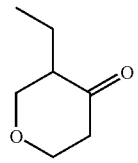

To a solution of pyran-4-one (5.0 g, 50 mmol) and HMPA (8.7 mL) in THF (150 mL) was added slowly a solution of LDA (31.25 mL, 2M solution) in 125 mL of THF at −78° C. Stirred for 5 minutes and then added EtI (16 mL, 200 mmol). The mixture was gradually warmed to 0° C. over 2 h. Reaction mixture was quenched with saturated solution of NH4Cl and then extracted with ether (4×100 mL). The ether layer washed with brine, dried (anhydrous magnesium sulfate), concentrated, purified by flash column chromatography and eluted with 25% ethyl acetate/hexane to yield the title compound (1.20 g, 20%).

EXAMPLE 23

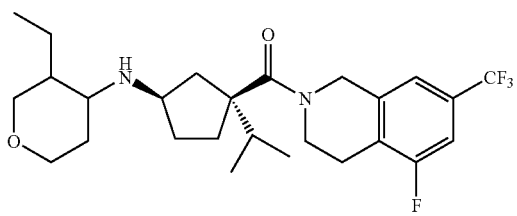

This compound as a mixture of four diastereoisomers was prepared starting from INTERMEDIATE 15 and 16 according to the procedure described in Example 6. LC-MS for C26H36F4N2O2 [M$^+$H$^+$] calculated 485, found 485. The cis and trans isomers in reference to pyran ring were separated into four single isomers by a Gilson HPLC equipped with a preparatory ChiralPak AD column (eluant: 5% EtOH/hexane).

INTERMEDIATE 17

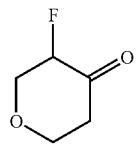

To a mixture of 5,6-dihydro-4-methoxy-2H-pyran (0.5 g, 4.4 mmol) in acetonitrile/water (15 mL, 1:1) at RT was added [1-(chloromethyl)-4-fluoro-1,4-diazoniabicyclo[2.2.2]octane bis(tetrafluoroborate)] (1.5 g, 4.4 mmol, SELECTOR™) in one lot and stirred the reaction to completion. Solid NaCl was added to the reaction mixture, then extracted with ether (4×50 mL). The ether layer dried (anhydrous magnesium sulfate) and concentrated to yield 0.34 g (65%) of the title compound that required no further purification. $^1$H-NMR (500 MHz, CDCl$_3$): δ 4.95 (m, 1H), 4.4–4.21 (m, 2H), 3.72–3.65 (m, 2H), 2.75 (m, 2H).

EXAMPLE 24

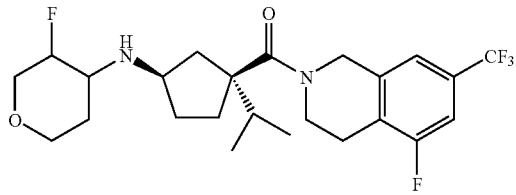

This compound as a mixture of four diastereoisomers was prepared starting from INTERMEDIATE 15 and 17 according to the procedure described in Example 6. LC-MS for C24H31F5N2O2 [M+H+] calculated 475, found 475. The cis and trans isomers in reference to pyran ring were separated into four single isomers by a Gilson HPLC equipped with a preparatory ChiralPak AD column (eluant: 5% EtOH/hexane).

INTERMEDIATE 18

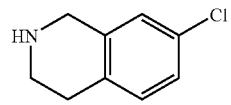

Intermediate 18 was prepared in a similar manner to intermediate 15 replacing 2-Fluoro-4-trifluoromethyl phenylacetonitrile with 4-chlorophenylacetonitrile in step A; $^1$H NMR 500 MHz (CDCl$_3$) δ=1.73 (1H, br s), 2.76 (2H, d, J=6.0 Hz), 3.13 (2H, t, J=6.0 Hz), 3.97 (2H, s), 7.00 (1H, s), 7.02 (1H, d, J=8.2 Hz) 7.10 (1H, dd, J=2.1 and 8.2 Hz).

EXAMPLE 25

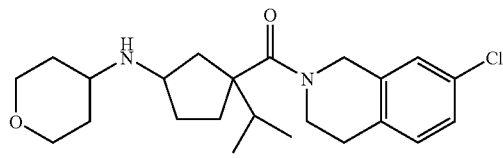

Example 25 as a mixture of four isomers was prepared as detailed in Example 1, Procedure B using Intermediate 18 instead of Intermediate 1. LC-MS for C23H33ClN2O2 [M+H+] calculated 405, found 405.

EXAMPLE 26

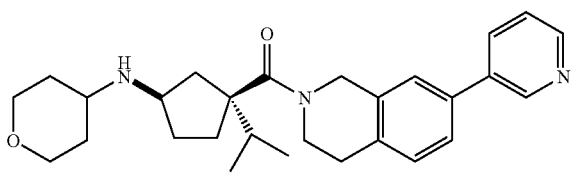

Step A

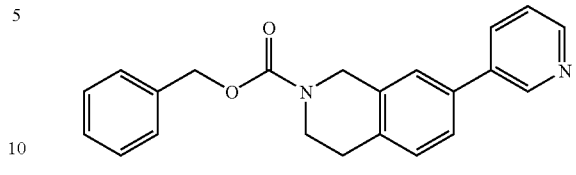

To a solution of diethyl(3-pyridyl)borane (703 mg, 4.782 mmol) and the bromide (Step A, Intermediate 13) (1.5 g, 4.347 mmol) in toluene\methanol (7/3, 30 mL) was added sodium carbonate (1.15 g, 10.89 mmol), Pd(PPh$_3$)$_2$Cl$_2$ (152 mg, 0.217 mmol) and water (6 mL), and the solution was heated at 80° C. overnight. The solution was then filtered through celite, concentrated in vacuo, extracted with methylene chloride, washed with 1N sodium hydroxide, dried over sodium sulfate, concentrated in vacuo and purified via MPLC (0–50% ethyl acetate/hexanes) to yield the title compound (1.5 g, 100%).

Step B

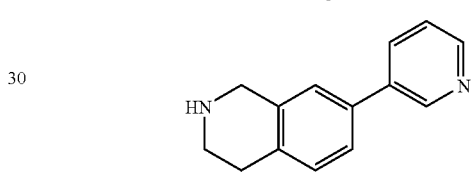

To a solution of the coupling product (Step A, Example 26) (1.5 g, 4.36 mmol) in ethanol (50 mL) was added palladium/carbon (150 mg). This mixture was put under balloon hydrogenation overnight. The mixture was extracted with methylene chloride, washed with 1N sodium hydroxide and concentrated in vacuo to yield the title compound (1.03 g, 100%). The crude product will be used in the next step.

Step C

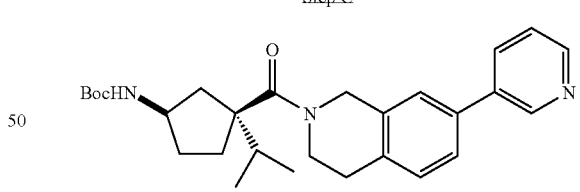

A solution of the amine (Step B, Example 26) (1.03 g, 4.90 mmol) and INTERMEDIATE 4 (1.33 g, 4.90 mmol) in toluene (25 mL) was concentrated in vacuo two times and put under nitrogen. To the mixture was added 4-dimethylaminopyridine (359 mg, 2.94 mmol), methylene chloride (20 mL), bromo-tris-pyrrolidino-phosphonium hexafluorophosphate (2.285 g, 4.90 mmol) and N,N-diisopropylethylamine (1.90 mL, 10.9 mmol), and the resulting mixture was stirred at room temperature for 2 days. The solution was concentrated in vacuo and was purified through MPLC (0–40% ethyl acetate/hexanes) to yield the title compound (460 mg, 22%).

Step D

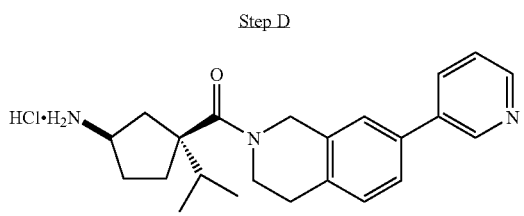

4N hydrochloric acid (10 mL) was added to the Boc amide (Step C, Example 26) (100 mg, 0.216 mmol) and the solution was concentrated in vacuo to yield the title compound (100 mg, 100%).

Step E

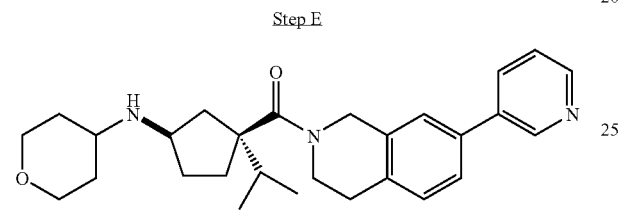

To a solution of the amino amide (Step D, Example 26) (100 mg, 0.230 mmol) in methylene chloride anhydr. (20 mL) was added tetrahydro-4H-pyran-4-one (155 mg, 1.43 mmol) and N,N-diisopropylethylamine (120 μμL, 0.69 mmol). After adding molecular sieves (20 mg), sodium triacetoxyborohydride (488 mg, 2.30 mmol) was added and mixture stirred overnight. The mixture was extracted with methylene chloride, washed with sodium bicarbonate, dried under sodium sulfate and concentrated in vacuo. The crude product was purified on preparation plates (8/91.2/0.8, methanol/methylene chloride/ammonium hydroxide) and 4N hydrochloric acid was added; the solution was concentrated in vacuo to yield the title compound (80 mg, 78%). LC-MS: MW calculated 447.29, found 448.7.

EXAMPLE 27

Step A

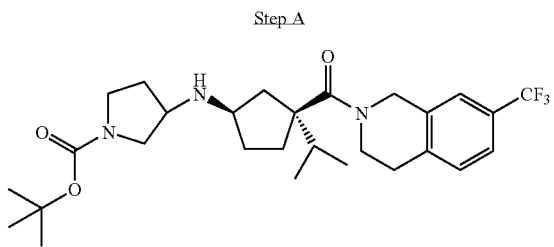

To a solution of INTERMEDIATE 6 (200 mg, 0.512 mmol) in methylene chloride anhydr. (20 mL) was added 1-N-BOC-3-pyrrolidinone (95 mg, 0.512 mmol) and N,N-diisopropylethylamine (268 μL, 1.53 mmol). After adding molecular sieves (20 mg), sodium triacetoxyborohydride (759 mg, 3.58 mmol) was added and mixture stirred overnight. The mixture was extracted with methylene chloride, washed with sodium bicarbonate, dried under sodium sulfate and concentrated in vacuo. The crude product was purified on preparation plates (7/92.3/0.7, methanol/methylene chloride/ammonium hydroxide) to yield the title compound (150 mg, 57%). LC-MS: MW calculated 523.3, found 524.7.

EXAMPLE 28

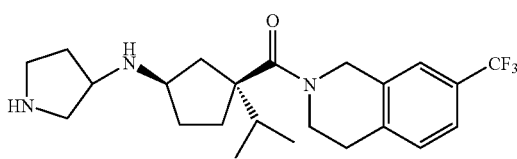

To example 27 (150 mg, 0.287 mmol) was added 4N hydrochloric acid (5 mL), and the solution was concentrated in vacuo to yield example 28 (140 mg, 90%). LC-MS: MW calculated 423.25, found 424.25.

EXAMPLE 29

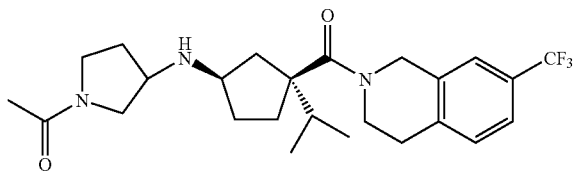

To a mixture of example 28 (40 mg, 0.095 mmol) and N,N-diisopropylethylamine (50 μL, 0.28 mmol) was added pyridine (46 μL, 0.57 mmol) and acetic anhydride (17 μL, 0.190 mmol), and the resulting mixture stirred at room temperature for 8 hours. The mixture was extracted with methylene chloride, washed with water, dried under sodium sulfate and concentrated in vacuo. The crude product was purified on preparation plates (7/92.3/0.7, methanol/methylene chloride/ammonium hydroxide) to yield example 29 (37 mg, 84%). LC-MS: MW calculated 465.3, found 466.3.

A number of examples were prepared starting from the INTERMEDIATE 6 and various ketones commercially available or synthesized in house according to the procedure described in Example 1, Procedure A.

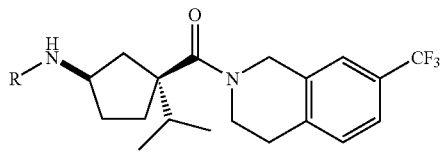
| Example | R | Molecular Formula | Calculated [M+H+] | Found [M+H+] |
|---|---|---|---|---|
| 30 | OH, cyclohexyl | $C_{25}H_{36}F_3N_2O_2$ | 453.27 | 453.25 |
| 31 | OMe, cyclohexyl | $C_{26}H_{38}F_3N_2O_2$ | 467.28 | 467.35 |
| 32 | tetrahydrothiopyran-4-yl | $C_{24}H_{34}F_3N_2OS$ | 455.23 | 455.2 |
| 33 | BocN-piperidin-4-yl | $C_{29}H_{43}F_3N_3O_3$ | 538.32 | 538.3 |
| 34 | cyclopentyl | $C_{24}H_{34}F_3N_2O$ | 423.25 | 423.25 |
| 35 | Me, cyclopentyl | $C_{25}H_{36}F_3N_2O$ | 437.27 | 437.35 |
| 36 | tetrahydrothiophen-3-yl | $C_{23}H_{32}F_3N_2OS$ | 441.21 | 441.25 |
| 37 | HN-piperidin-4-yl | $C_{24}H_{34}F_3N_3O$ | 437.27 | 437.25 |
| 38 | N-Me-piperidin-4-yl | $C_{25}H_{37}F_3N_3O$ | 452.28 | 452.35 |
| 39 | N-acetyl-piperidin-4-yl | $C_{26}H_{37}F_3N_3O_2$ | 480.28 | 480.25 |

EXAMPLE 40

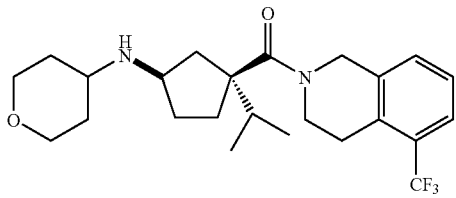

Step A

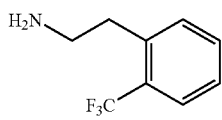

To a hydrogenation vessel was added 2-(trifluoroethyl) phenylacetonitrile (2 g, 10.80 mmol), followed by a solution of ethanol (60 mL) and ammonium hydroxide (20 mL). Raney nickel (catalytic amount) was then added, and the vessel was put under hydrogenation (40 psi) overnight. The mixture was filtered and concentrated in vacuo to yield the desired amine (1.53 g, 75%). The crude product was used in the next step.

Step B

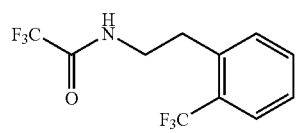

To a cooled suspension (0° C.) of the amine (Step A, Example 40) (1.53 g, 8.09 mmol) and methylene chloride anhydr. (20 mL) was added pyridine (3.27 mL, 40.44 mmol). Trifluoroacetic anhydride (1.72 mL, 12.14 mmol) was then added slowly, and the mixture stirred at room temperature for 6 hours. The mixture was extracted with methylene chloride, washed with iced-water, 1 N hydrochloric acid and sodium chloride (aq), dried under magnesium sulfate and concentrated in vacuo to yield the desired compound (920 mg, 40%). The crude product was used in the next step.

Step C

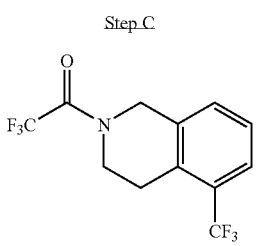

Paraformaldehyde (202 mg, 6.45 mmol) was added to the amide (Step B, Example 40) (920 mg, 3.23 mg), and a solution of acetic acid (6 mL) and sulfuric acid conc. (9 mL) was then added. The mixture was stirred under nitrogen for 2 hours. The mixture was extracted with ethyl acetate, washed with ice-water and saturated sodium bicarbonate, dried over sodium sulfate and concentrated in vacuo to yield the title compound (1.00 g, 100%). The crude product was used in the next step.

Step D

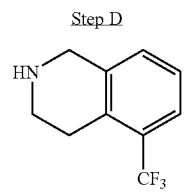

To a solution of the amide (Step C, Example 40) (100 mg, 0.337 mmol) was added ethanol (10 mL), followed by a mixture of potassium carbonate (465 mg, 3.37 mmol) and water (10 mL). The mixture was refluxed at 90° C. for 2 hours, and di-tert-butyl dicarbonate (340 mg, 0.506 mmol) was added to the mixture, which stirred at room temperature overnight. The mixture was concentrated in vacuo, extracted with methylene chloride, washed with water, dried under magnesium sulfate and concentrated in vacuo. The crude product was purified on preparation plates (20/80, ethyl acetate/hexanes); 4N hydrochloric acid was added and the mixture was concentrated in vacuo to yield the title compound (70 mg, 88%).

Step E

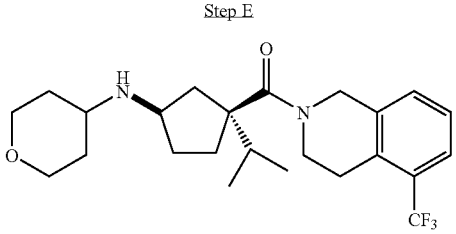

To a mixture of oxalyl chloride (280 μL, 0.560 mmol) and methylene chloride anhydr. (2 mL) was added INTERMEDIATE 5 (147.5 mg, 0.420 mmol) and a drop of DMF. The reaction mixture was stirred at room temperature for three hours, concentrated in vacuo for 2 hours and then dissolved in methylene chloride anhydrous (5 mL). The mixture was put into iced-water bath (0° C.), and to the mixture was added the amine (Step D, Example 40) (70 mg, 0.350 mmol) and N,N-diisopropylethylamine (220 μL, 5.37 mmol). The temperature was raised gradually to room temperature, and the reaction was stirred overnight. Some unused isoquinoline was seen in LCMS. The mixture was extracted with methylene chloride, washed with sodium bicarbonate, dried under sodium sulfate and concentrated in vacuo. A solution of ethanol (20 mL) and sodium borohydride (40 mg, 1.05 mmol) was added and stirred overnight. The solution was extracted with methylene chloride, washed with sodium bicarbonate, dried under sodium sulfate and concentrated in vacuo. The crude product was purified on preparation plates (8/91.2/0.8, methanol/methylene chloride/ammonium hydroxide). 4N hydrochloric acid was added and the mixture was concentrated in vacuo to yield example 40 (50 mg, 53%). LC-MS: MW calculated 438.25, found 439.25.

EXAMPLE 41

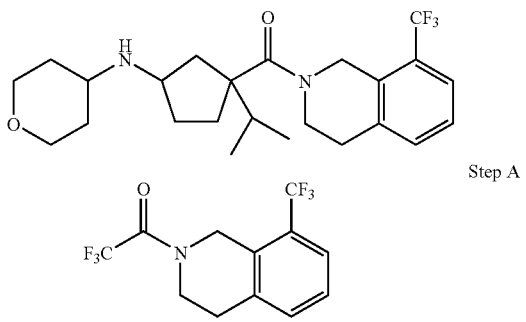

Paraformaldehyde (1.69 g, 54.10 mmol) was added to N-trifluoroacetyl-3-trifluoromethyl-β-phenylethyl amine (7.71 g, 27.05 mmol) in a 250 mL round-bottomed flask before a solution of acetic acid (60 mL) and sulfuric acid conc. (90 mL) was added. The mixture was stirred under nitrogen for 1 hour. The mixture was extracted with ethyl acetate, washed with ice-water and saturated sodium bicarbonate, dried over sodium sulfate and concentrated in vacuo to yield a mixture of two isomers (6.15 g, 77%). The isomers were separated by using MPLC (25/75: ethyl acetate/hexanes) to yield the title compound (minor isomer, 2.03 g, 26%).

Step B

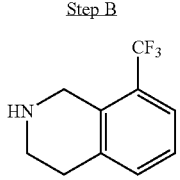

To a solution of the amide (Step A, Example 41) (300 mg, 1.01 mmol) was added ethanol (10 mL), followed by a mixture of potassium carbonate (1.395 g, 10.10 mmol) and water (10 mL). The mixture was refluxed at 90° C. for 2 hours, and di-tert-butyl dicarbonate (340 mg, 1.56 mmol) was added to the mixture, which stirred at room temperature overnight. The mixture was concentrated in vacuo, extracted with methylene chloride, washed with water, dried under magnesium sulfate and concentrated in vacuo. The crude product was purified on preparation plates (30/70, ethyl acetate/hexanes); 4N hydrochloric acid was added and the mixture was concentrated in vacuo to yield the title compound (250 mg, 100%).

Step C

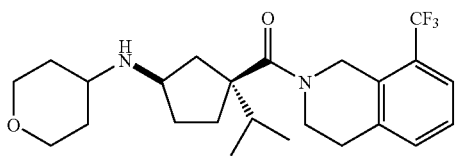

To a mixture of oxalyl chloride (396 μL, 0.795 mmol) and methylene chloride anhydrous. (2 mL) was added INTERMEDIATE 5 (209 mg, 0.596 mmol) and a drop of DMF. The reaction mixture was stirred at room temperature for three hours, concentrated in vacuo for 2 hours and then dissolved in methylene chloride anhydrous (5 mL). The mixture was put into iced-water bath (0° C.), and to the mixture was added the amine (Step B, Example 41) (100 mg, 0.497 mmol) and N,N-diisopropylethylamine (312 μL, 1.79 mmol). The temperature was raised gradually to room temperature, and the reaction was stirred overnight. Some unused isoquinoline was seen in LCMS. The mixture was extracted with methylene chloride, washed with sodium bicarbonate, dried under sodium sulfate and concentrated in vacuo. A solution of ethanol (20 mL) and sodium borohydride (113 mg, 2.98 mmol) was added and stirred overnight. The solution was extracted with methylene chloride, washed with sodium bicarbonate, dried under sodium sulfate and concentrated in vacuo. The crude product was purified on preparation plates (8/91.2/0.8, methanol/methylene chloride/ammonium hydroxide). 4N hydrochloric acid was added and mixture was concentrated in vacuo to yield example 41 (40 mg, 33%). LC-MS: MW calculated 438.25, found 439.25.

EXAMPLE 42

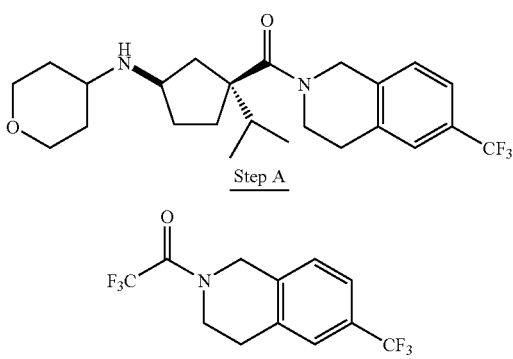

Paraformaldehyde (1.69 g, 54.10 mmol) was added to N-trifluoroacetyl-3-trifluoromethylphenyl-β-ethyl amine (7.71 g, 27.05 mmol) in a 250 mL round-bottomed flask before a solution of acetic acid (60 mL) and sulfuric acid conc. (90 mL) was added. The mixture was stirred under nitrogen for 1 hour. The mixture was extracted with ethyl acetate, washed with ice-water and saturated sodium bicarbonate, dried over sodium sulfate and concentrated in vacuo to yield a mixture of two isomers (6.15 g, 77%). The isomers were separated by using MPLC (25/75: ethyl acetate/hexanes) to yield the title product (major isomer, 4.12 g, 53%).

Step B

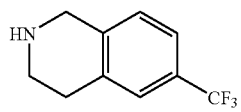

To a solution of the amide (Step A, Example 42) (300 mg, 1.01 mmol) was added ethanol (10 mL), followed by a mixture of potassium carbonate (1.395 g, 10.10 mmol) and water (10 mL). The mixture was refluxed at 90° C. for 2 hours, and di-tert-butyl bicarbonate (340 mg, 1.56 mmol) was added to the mixture, which stirred at room temperature overnight. The mixture was concentrated in vacuo, extracted with methylene chloride, washed with water, dried under magnesium sulfate and concentrated in vacuo. The crude product was purified on preparation plates (30/70, ethyl acetate/hexanes); 4N hydrochloric acid was added and the mixture was concentrated in vacuo to yield the title compound (200 mg, 87%).

Step C

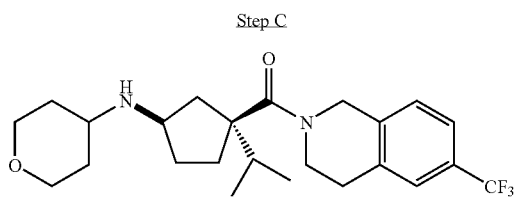

To a mixture of oxalyl chloride (396 μL, 0.795 mmol) and methylene chloride anhydrous. (2 mL) was added INTERMEDIATE 5 (209 mg, 0.596 mmol) and a drop of DMF. The reaction mixture was stirred at room temperature for three hours, concentrated in vacuo for 2 hours and then dissolved in methylene chloride anhydrous (5 mL). The mixture was put into iced-water bath (0° C.), and to the mixture was added the amine (Step B, Example 22) (100 mg, 0.497 mmol) and N,N-diisopropylethylamine (312 μL, 1.79 mmol). The temperature was raised gradually to room temperature, and the reaction was stirred overnight. The mixture was extracted with methylene chloride, washed with sodium bicarbonate, dried under sodium sulfate and concentrated in vacuo. A solution of ethanol (20 mL) and sodium borohydride (113 mg, 2.98 mmol) was added and stirred overnight. The solution was extracted with methylene chloride, washed with sodium bicarbonate, dried under sodium sulfate and concentrated in vacuo. The crude product was purified on preparation plates (8/91.2/0.8, methanol/methylene chloride/ammonium hydroxide). 4N hydrochloric acid was added and the mixture was concentrated in vacuo to yield example 42 (35 mg, 28%). LC-MS: MW calculated 438.25, found 439.25.

INTERMEDIATE 19

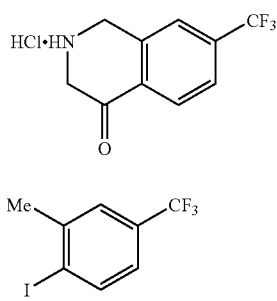

Step A:

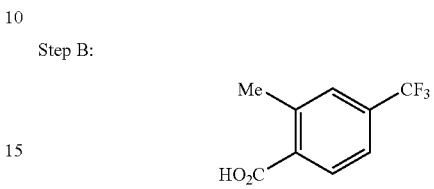

To a cooled (0° C.) mixture of 3-methylbenzotrifluoride (35.7 g, 0.223 mol) and trifluoromethanesulfonic acid (44.7 g, 0.298 mol) was added N-iodosuccinimide (33.4 g, 0.149 mmol) in small portions over 20 min. The ice bath was removed and the reaction mixture was stirred at room temperature overnight. The reaction mixture was poured into ice water and extracted three times with DCM. The organic layers were combined and washed with 10% $Na_2SO_3$ solution, then brine, dried over anhydrous $MgSO_4$, filtered, and concentrated to afford 40.1 g of crude product. This material was combined with the crude product obtained from a second batch prepared in exactly the same way (from 0.155 mol of N-iodosuccinimide, 37.4 g crude product) giving a total of 77.5 g crude material. The combined crude product was then distilled (~1 mm Hg, 52–54° C. head temperature, 75° C. bath temperature) to give 62.8 g of product, which by HNMR contained 10–15% of a second isomer. H NMR ($CDCl_3$, 500 MHz): δ 7.95 (d, J=8.0 Hz, 1H), 7.49 (s, 1H), 7.14 (dd, J=8.0, 1.5 Hz, 1H), 2.51 (s, 3H).

Step B:

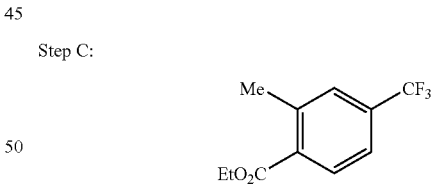

A flask equipped with an addition funnel and condenser and containing Mg turnings (25.4 g, 1.05 mol) was flame dried. To this flask was added 40 mL of THF, a crystal of $I_2$ and 1,2-dibromoethane (~0.25 mL). Approximately ⅛ of the volume of a solution of the 4-iodo-3-methylbenzotrifluoride from Step A, Intermediate 19 (59.85 g, 209.2 mmol) in 220 mL of THF was added to the reaction vessel and the resulting mixture was warmed to reflux. Then the remainder of the solution of 4-iodo-3-methylbenzotrifluoride was added at such a rate as to maintain a gentle reflux. After the addition, the reaction mixture was stirred at reflux for 1.5 h, then was cooled to −10° C. (ice/salt bath). Dry $CO_2$ gas was bubbled through the reaction mixture for 2.5 h at such a rate as to maintain the temperature below 5° C. The reaction mixture was quenched by addition of 150 mL of 6 N HCl solution. The mixture was filtered to remove the remaining Mg. The filtrate was extracted three times with 400 mL of ether. The combined ethereal layers were washed three times with 400 mL of 2 N NaOH solution. The aqueous layers were combined and made acidic while cooling in an ice bath with concentrated HCl solution. The aqueous mixture was then extracted three times with DCM. The combined organic layers were then dried over anhydrous $MgSO_4$, filtered, and concentrated to give 29.5 g (69%) of crude product which was used as is in the following Step C.

Step C:

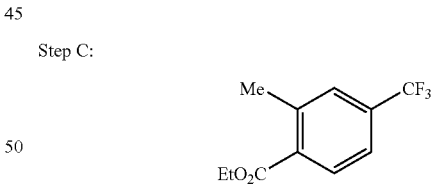

Thionyl chloride (21.2 mL, 290 mmol) was added over 5 minutes to 500 mL of ethanol cooled in an ice bath to 0° C. The resulting ethanolic anhydrous HCl solution was poured in to a flask containing the 2-methyl-4-(trifluoromethyl) benzoic acid from Step B, Intermediate 19 (29.5 g, 145 mmol) and the mixture was stirred at reflux for 5 h and at room temperature overnight. The reaction mixture was concentrated and the residue obtained was purified by flash chromatography (silica, DCM) to afford 28.5 g (85%) of the target ethyl ester.

ESI-MS calc. for $C_{11}H_{11}F_3O_2$: 232; Found: 233 (M+H). H NMR ($CDCl_3$, 500 MHz): δ 8.00 (d, J=8.0 Hz, 1H), 7.52 (s, 1H), 7.51 (d, J=8.0 Hz, 1H), 4.41 (q, J=7.5 Hz, 2H), 2.66 (s, 3H), 1.43 (t, J=7.0 Hz, 3H).

Step D:

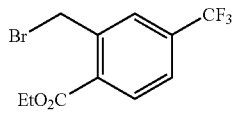

To a solution of the ethyl 2-methyl-4-(trifluoromethyl) benzoate from Step C, Intermediate 19 (28.0 g, 121 mmol) in $CCl_4$ was added N-bromosuccinimide (recently recrystallized from hot water, 22.6 g, 127 mmol), followed by AIBN (~100 mg). The resulting reaction mixture was stirred at reflux for 3 h. Since the reaction had not progressed, a second portion of AIBN (from a different source, ~100 mg) was added and the reaction mixture was stirred at reflux for 4 h, then at room temperature for three days. The reaction mixture was cooled to 0° C. and the succinimide was filtered off. The filtrate was diluted with DCM and washed with 1 N NaOH solution, saturated $NaHCO_3$ solution, and brine. The organic layer was dried over anhydrous $MgSO_4$, filtered, and concentrated giving 37.5 g of crude product, which by HNMR analysis contained about 20% of the starting material.

H NMR ($CDCl_3$, 500 MHz): δ 8.08 (d, J=8.0 Hz, 1H), 7.74 (s, 1H), 7.64 (d, J=8.0 Hz, 1H), 4.97 (s, 2H), 4.46 (q, J=7.0 Hz, 2H), 1.46 (t, J=7.0 Hz, 3H).

Step E:

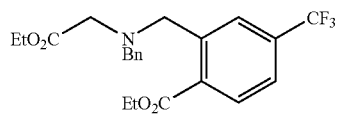

The benzyl bromide from Step D, Intermediate 19 (~80% purity, 37.5 g, ca 97 mmol) was combined with N-benzyl glycine ethyl ester (32.1 g, 166 mmol) and triethylamine (16.9 mL, 121 mmol) in 500 mL of THF. The reaction mixture was stirred at reflux for 2 h then was concentrated. The residue obtained was partitioned between ether and saturated $NaHCO_3$ solution. The aqueous layer was extracted again with ether and the combined ethereal layers were washed three times with water, once with brine, dried over anhydrous $MgSO_4$, filtered, and concentrated. Purification by flash chromatography (silica, 10% ethyl acetate/hexane, then MPLC purification of mixed fractions using 20% ethyl acetate/hexane) provided 28.99 g of tertiary amine.

ESI-MS calc. for $C22H24F3NO4$: 423; Found: 424 (M+H).

Step F:

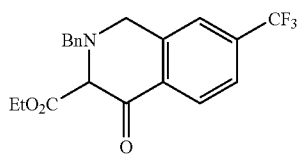

A solution of 21% ethanolic sodium ethoxide (3.38 mL, 10.4 mmol) was concentrated to remove all of the ethanol. A solution of the product from Step E, Intermediate 19 (3.40 g, 8.03 mmol) in 50 mL of toluene was added and the resulting red suspension was warmed to reflux in a flask equipped with a Dean Stark trap and condenser. After stirring for 1 h at reflux (stirring became erratic due to the precipitation of considerable amounts of solid material) the reaction mixture was cooled to room temperature and diluted with ether. Water was added followed by approximately 11 mL of 1 N HCl solution to make the pH ~5. Then 30 mL of saturated $NaHCO_3$ solution were added, bringing the pH to ~7. The layers were separated and the aqueous layer was extracted again with ether. The combined ethereal layers were washed with brine, dried over anhydrous $MgSO_4$, filtered, and concentrated giving 2.80 g of crude product. Purification by MPLC (silica, 20% ethyl acetate/hexane) gave 2.24 g of the desired cyclized product.

H NMR ($CDCl_3$, 500 MHz): δ 7.89 (d, J=8.5 Hz, 1H), 7.65 (d, J=8.5 Hz, 1H), 7.37–7.19 (m, 6H), 4.39 (q, J=7.0 Hz, 2H), 4.12 (s, 2H), 3.84 (s, 2H), 1.45 (t, J=7.5 Hz, 3H).

Step G:

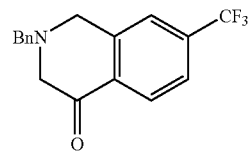

The cyclized product from Step F, Intermediate 19 (460 mg, 1.22 mmol) was dissolved in ethanol (4 mL) and concentrated HCl solution (13 mL) was added. The resulting solution was stirred at reflux under a nitrogen atmosphere for 55 h. The reaction mixture was concentrated to dryness. To the residue was added saturated $NaHCO_3$ solution and the resulting mixture was extracted twice with DCM. The combined organic layers were washed with brine, dried over anhydrous $MgSO_4$, filtered, and concentrated. Purification by MPLC (silica, 35% ethyl acetate/hexane) gave the product which was converted to its hydrochloride salt by dissolving in DCM, adding excess 1 N HCl in ether, and concentrating (255 mg salt collected).

ESI-MS calc. for $C17H14F3NO$: 305; Found: 306 (M+H). Free base H NMR ($CDCl_3$, 500 MHz): δ 8.18 (d, J=8.0 Hz, 1H), 7.67 (d, J=8.0 Hz, 1H), 7.51 (s, 1H), 7.39 (m, 5H), 3.98 (br s, 2H), 3.90 (br s, 2H), 3.57 (br s, 2H).

Step H:

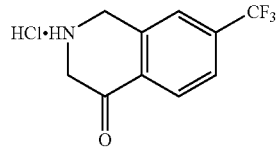

To a solution of the N-benzyl-4-oxo-7-(trifluoromethyl) tetrahydroquinoline from Step G, Intermediate 19 (2.13 g, 6.98 mmol) in 40 mL of glacial acetic acid was added concentrated HCl solution (0.582 mL, 6.98 mmol), and 10% Pd/C (200 mg). The resulting mixture was stirred under a hydrogen atmosphere (balloon) for 3 h. The reaction mixture was filtered through celite and concentrated to afford the product as its hydrochloride salt (2.08 g, some AcOH may remain, 1 peak by HPLC).

ESI-MS calc. for $C10H8F3NO$: 215; Found: 216 (M+H).

EXAMPLE 43

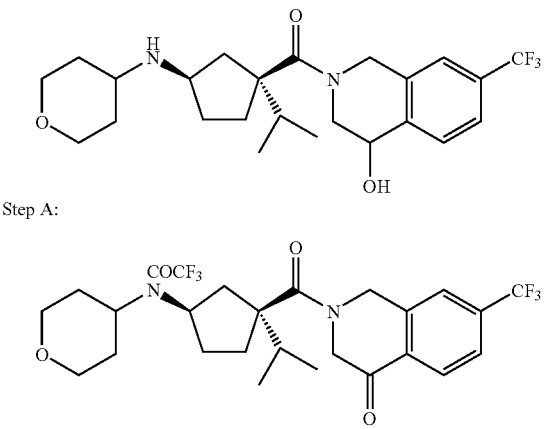

Step A:

To a cooled (ice bath) solution of INTERMEDIATE 5 (281 mg, 0.800 mmol) in 5 mL of DCM was added oxalyl chloride (209 μL, 2.40 mmol) followed by 1 drop of DMF. The reaction mixture was warmed to room temperature, stirred for 2 h, then concentrated. The residue was dissolved in 5 mL of DCM and treated with INTERMEDIATE 19 (0.727 mmol), followed by triethylamine (223 μL, 1.60 mmol). DMAP Was added (~5 mg) and the reaction mixture was stirred overnight at room temperature. The reaction mixture was diluted with DCM and washed with 1 N HCl solution, saturated NaHCO$_3$ solution (twice), then brine. The organic layer was dried over anhydrous MgSO$_4$, filtered, and concentrated. Purification by MPLC (silica, 65% ethyl acetate/hexane) gave 172 mg of target amide.

ESI-MS calc. for C26H30F6N2O4: 548; Found: 549 (M+H).

Step B:

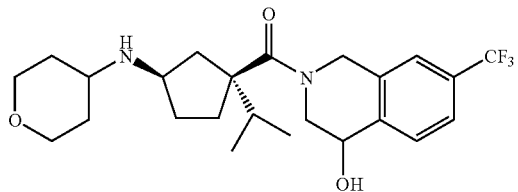

To a solution of the amide from Step A, Example 43 (56.3 mg, 0.124 mmol) in 2 mL of ethanol was added sodium borohydride (28 mg, 0.74 mmol). The reaction mixture was stirred at room temperature for overnight. The reaction mixture was concentrated and the residue obtained was purified by reverse phase HPLC (YMC Pack Pro C18, 100×20 mm ID) afforded the product as its TFA salt. This was converted to its HCl salt by dissolving in DCM and adding 100 μL of 1 N HCl/ether, then concentrating, giving 33 mg of product as a mixture of two stereoisomers.

ESI-MS calc. for C24H33F3N2O3: 454; Found: 455 (M+H).

The mixture of diastereomers from EXAMPLE 43 could be separated into two single isomers by chiral HPLC using a Chiralcel OD column (2 cm×25 cm, Daicel Chemical Industries), eluting with 20% i-propanol/hexane. This was performed in an automated fashion using a Gilson fraction collector integrated with Gilson Unipoint software.

EXAMPLE 44

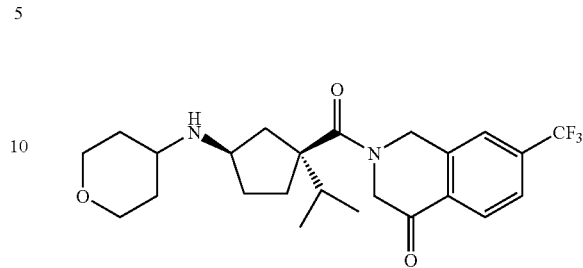

To a solution of the product from EXAMPLE 43 (59.1 mg, 0.120 mmol) in 3 Ml of acetone was added dropwise Jones Reagent (13 drops). The reaction mixture was stirred at room temperature for 20 min, then was quenched by addition of excess i-propanol. This solution was combined with a second batch prepared in the same fashion starting from 5.2 mg of the product from EXAMPLE 43 (a probe reaction). The combined solutions were filtered through celite, washing with acetone. The filtrate was concentrated and the residue obtained was purified by reverse phase HPLC (YMC Pack Pro C18, 100×20 mm ID) affording the product as its TFA salt. This was converted to its HCl salt by dissolving in DCM and adding excess of 1 N HCl/ether, then concentrating, giving 41 mg (63%) of product.

ESI-MS calc. for C24H31F3N2O3: 452; Found: 453 (M+H).

EXAMPLE 45

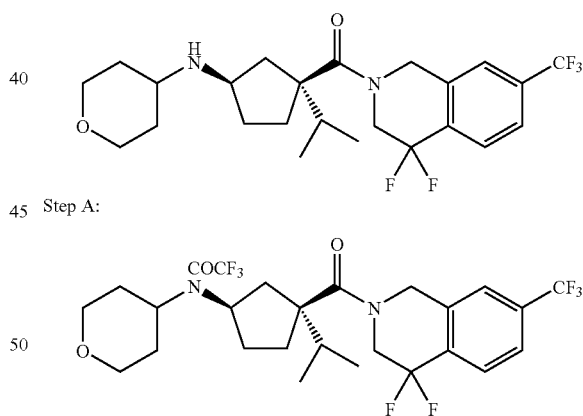

Step A:

A solution of diethylaminosulfur trifluoride (25 μL, 0.19 mmol) in 3 mL of DCM was added to a solution of the product from Step A in the synthesis of EXAMPLE 43 (52 mg, 0.095 mmol) in 2 mL of DCM. After 2.5 h of stirring at room temperature only starting material was observed. The DCM was removed and carbon tetrachloride was added. The reaction mixture was stirred at reflux for 3 h. Still no product was observed by HPLC-MS analysis. At this point, 1 mL of diethylaminosulfur trifluoride was added, followed by 1 drop of ethanol. This mixture was stirred at 70° C. for 3 h, when no starting material could be detected by HPLC-MS analysis. The reaction mixture was diluted with DCM and poured into ice water. The phases were separated and the aqueous layer was extracted with more DCM. The combined organic layers were washed with brine, dried over anhydrous MgSO₄, filtered, and concentrated. The resulting 90 mg of crude product which was not clean by HPLC analysis, was none-the-less carried on to the next step.

ESI-MS calc. for C26H30F8N2O3: 570; Found: 571 (M+H).

Step B:

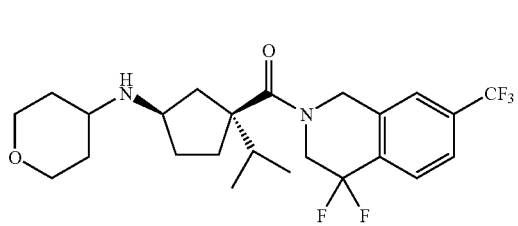

A solution of the crude product from Step A, Example 44 in 1 mL of ethanol was treated with sodium borohydride (69 mg). The resulting mixture was stirred at room temperature for 3 h. The reaction mixture was quenched with 1 N HCl in ether and concentrated. Purification by reverse phase HPLC (YMC Pack Pro C18, 100×20 mm ID) afforded the product as its TFA salt. This was converted to its HCl salt by dissolving in DCM and adding excess of 1 N HCl/ether, then concentrating, giving 8 mg of product.

ESI-MS calc. for C24H31F5N2O2: 474; Found: 475 (M+H).

INTERMEDIATE 20

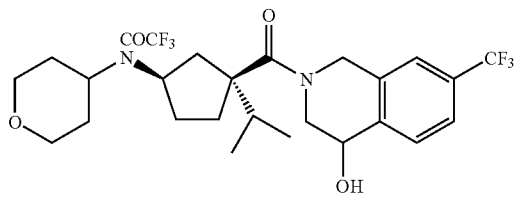

A solution of the product from Step A in the synthesis of EXAMPLE 43 (154 mg, 0.280 mmol) in 2 mL of ethanol was treated with sodium borohydride (10.3 mg, 0.272 mmol) and stirred at room temperature for 1 h. The reaction mixture was concentrated at room temperature and the residue obtained was dissolved in DCM and washed with saturated NaHCO₃ solution, then brine, dried over anhydrous MgSO₄, filtered, and concentrated. Purification by MPLC (silica, ethyl acetate) afforded 110 mg (71%) of product as a mixture of two diastereomeric alcohols.

ESI-MS calc. for C26H32F6N2O4: 550; Found: 551 (M+H).

EXAMPLE 46

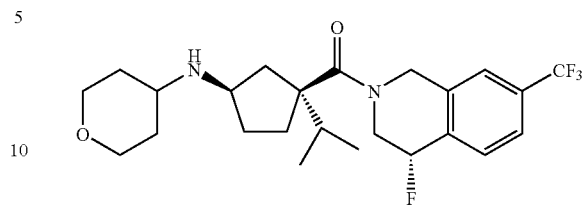

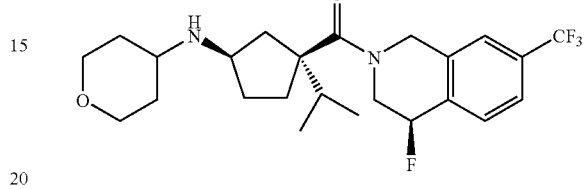

Step A:

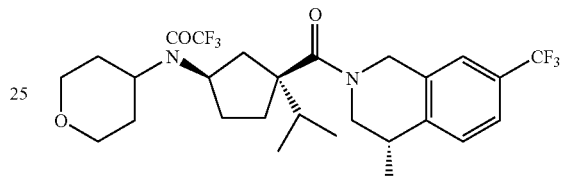

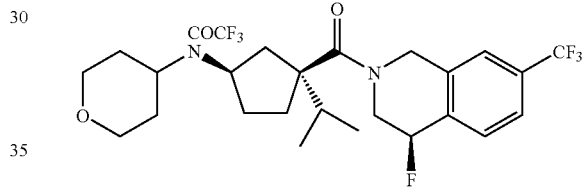

To a cooled (−78° C.) solution of the alcohol INTERMEDIATE 20 (101 mg, 0.183 mmol) in 5 mL of DCM was added diethylaminosulfur trifluoride (97 μL, 0.734 mmol). The reaction mixture was stirred at −78° C. for 2 h, then was quenched with methanol (~5 drops), and warmed to room temperature. The mixture was diluted with DCM and washed with water, then brine, dried over anhydrous MgSO₄, filtered, and concentrated. Purification by preparative TLC (silica, 40% ethyl acetate/hexane) allowed separation of two product bands (top band 28.7 mg, bottom band 31.4 mg).

Faster eluting isomer: ESI-MS calc. for C26H31F7N2O3: 552; Found: 553 (M+H).

Slower eluting isomer: ESI-MS calc. for C26H31F7N2O3: 552; Found: 553 (M+H).

Step B:

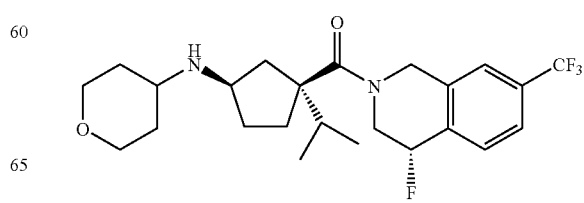

-continued

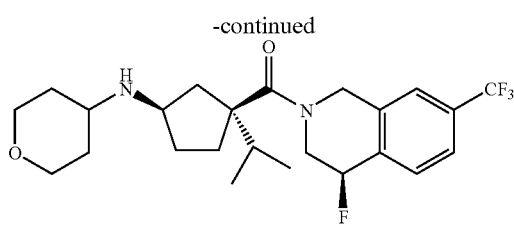

A solution of the faster eluting isomer from Step B, Example 46 (28.7 mg, 0.520 mmol) in 1 mL of ethanol was treated with sodium borohydride (30 mg) and the resulting mixture was stirred at room temperature overnight. The reaction mixture was concentrated and the residue obtained was partitioned between DCM and saturated NaHCO₃ solution. The organic layer was washed with brine, dried over anhydrous MgSO₄, filtered, and concentrated. Purification by reverse phase HPLC (YMC Pack Pro C18, 100×20 mm ID) afforded the product as its TFA salt. This was converted to its HCl salt by dissolving in DCM and adding excess of 1 N HCl/ether, then concentrating, giving 11.6 mg of product as a single isomer.

ESI-MS calc. for C24H32F4N2O2: 456; Found: 457 (M+H).

The slower eluting isomer from Step B (31.4 mg, 0.569 mmol) was similarly deprotected to give 12.3 mg of target compound as its HCl salt.

ESI-MS calc. for C24H32F4N2O2: 456; Found: 457 (M+H).

INTERMEDIATE 21

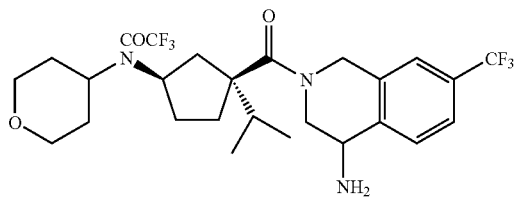

Step A:

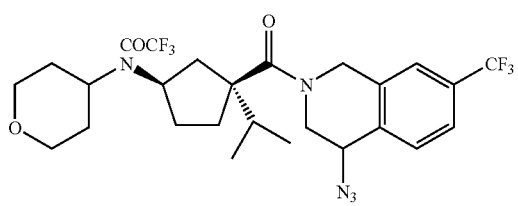

To a solution of INTERMEDIATE 20 (257 mg, 0.467 mmol) in 6 mL of toluene was added diphenylphosporyl azide (251 µL, 1.17 mmol), followed by DBU (175 µL, 1.17 mmol). The reaction mixture was stirred at 60° C. for 2 h, then at room temperature for overnight. The reaction mixture was concentrated and the residue was dissolved in DCM and washed with 2 N HCl solution. The aqueous layer was back-washed with more DCM, the organic layers were combined and washed with saturated NaHCO₃ solution, and brine. The organic layer was dried over anhydrous MgSO₄, filtered, and concentrated. Purification by MPLC (silica, 60% ethyl acetate/hexane) gave 192 mg (71%) of desired azide.

ESI-MS calc. for C26H31F6N5O3: 575; Found: 576 (M+H).

Step B:

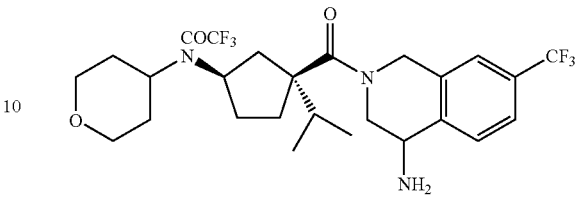

To a solution of the azide from Step A, Intermediate 21 (192 mg, 0.330 mmol) in 6 mL of methanol was added 10% Pd/C (38 mg). The resulting mixture was stirred in a hydrogen atmosphere (balloon) for 1.5 h, then was filtered, and concentrated to give 187 mg of amine product.

ESI-MS calc. for C26H33F6N3O3: 549; Found: 550 (M+H).

EXAMPLE 47

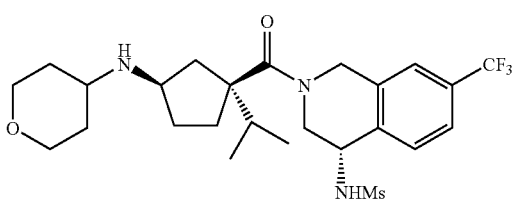

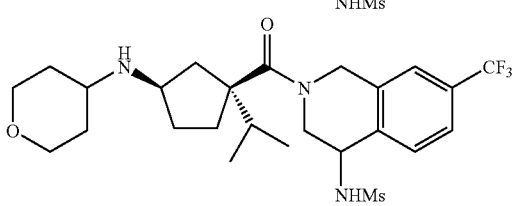

Step A:

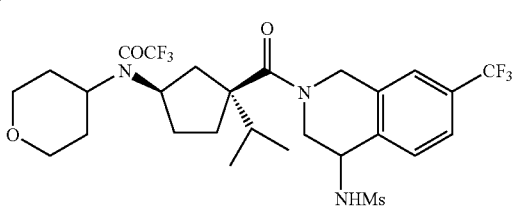

To a solution of INTERMEDIATE 21 (50.8 mg, 0.0924 mmol) in 8 mL of DCM was added pyridine (75 µL, 0.92 mmol), followed by methanesulfonyl chloride (72 µL, 0.92 mmol). After stirring at room temperature for 3 days the reaction mixture was diluted with DCM and washed with 3 N HCl solution. The aqueous layer was back-extracted with DCM and the organic layers were combined and washed with saturated NaHCO₃ solution, then brine, dried over anhydrous MgSO₄, filtered, and concentrated. Purification by MPLC (silica, ethyl acetate) afforded 39.1 mg of methanesulfonamide as a mixture of two diastereomers.

ESI-MS calc. for C27H35F6N3O5S: 627; Found: 628 (M+H).

Step B:

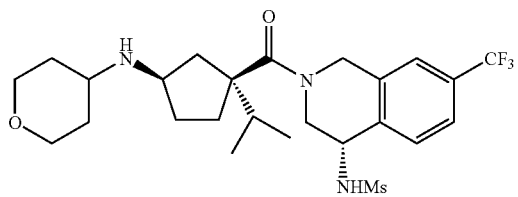

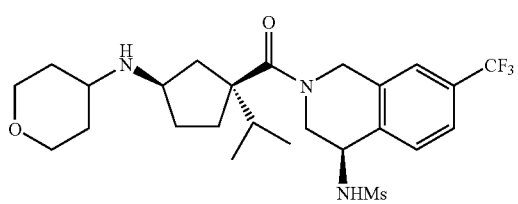

A solution of the mesylate from Step A, Example 47 (0.0382 mmol) in 3 mL of ethanol was treated with sodium borohydride (30 mg) and the resulting mixture was stirred at room temperature for overnight. The reaction mixture was concentrated and the residue obtained was partitioned between DCM and saturated NaHCO$_3$ solution. The organic layer was washed with brine, dried over anhydrous MgSO$_4$, filtered, and concentrated. Purification by preparative TLC (silica, 5% of a 1:9 30% NH$_4$OH solution/methanol in DCM) allowed separation of two bands (7.8 mg faster eluting isomer and 4.7 mg slower eluting isomer).

Faster eluting isomer: ESI-MS calc. for C25H36F3N3O4S: 531; Found: 532 (M+H).

Slower eluting isomer: ESI-MS calc. for C25H36F3N3O4S: 531; Found: 532 (M+H).

EXAMPLE 48

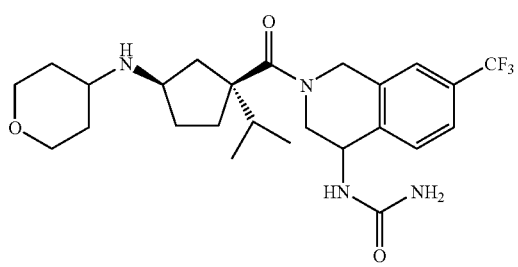

Step A:

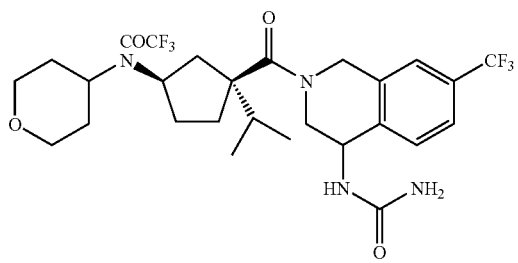

To a solution of INTERMEDIATE 21 (21 mg, 0.038 mmol) in 1.5 mL of DCM was added pyridine (8 μL, 0.1 mmol), followed by p-nitrochloroformate (19 mg, 0.096 mmol). After stirring at room temperature for 2 h more pyridine (8 μL, 0.1 mmol) and p-nitrochloroformate (19 mg, 0.096 mmol) were added and the reaction mixture was stirred overnight at room temperature. More pyridine (8 μL, 0.1 mmol) and p-nitrochloroformate (19 mg, 0.096 mmol) were added and the reaction mixture was stirred for 5 h, then ammonia gas was bubbled through the reaction mixture for 10 min. The reaction mixture was diluted with DCM and washed with water, 1 N HCl solution, saturated NaHCO$_3$ solution, and brine. The organic layer was dried over anhydrous MgSO$_4$, filtered, and concentrated. The crude product was used as is in Step B.

ESI-MS calc. for C27H34F6N4O4: 592; Found: 593 (M+H).

Step B:

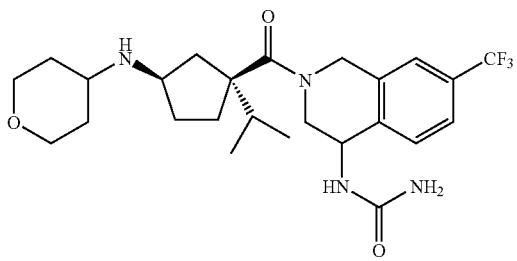

A solution of the crude urea from Step A, Example 48 (calc. 0.038 mmol) in 3 mL of ethanol was treated with sodium borohydride (30 mg) and stirred overnight at room temperature. The reaction mixture was concentrated and the residue obtained was dissolved in DCM and washed with saturated NaHCO$_3$ solution, and brine. The organic layer was dried over anhydrous MgSO$_4$, filtered, and concentrated. Purification by preparative TLC (silica, 7.5% of a 1:9 30% NH$_4$OH solution/methanol in DCM) afforded the product which was converted to its hydrochloride salt (6.8 mg) by dissolving in DCM, adding excess 1 N HCl in ether, and concentrating. The product was obtained as a mixture of two diastereomers.

ESI-MS calc. for C25H35F3N4O3: 496; Found: 497 (M+H).

EXAMPLE 49

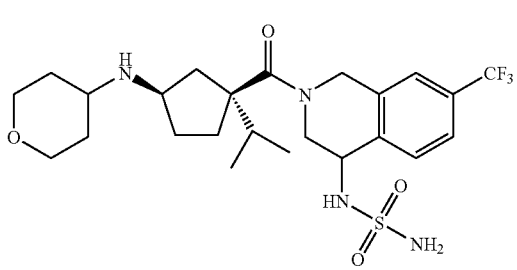

Step A:

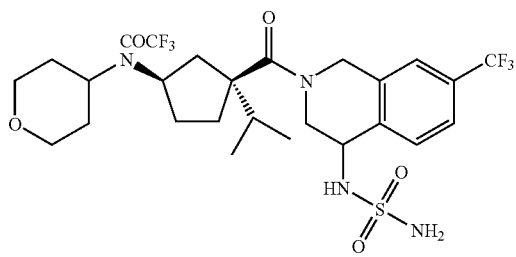

Chlorosulfonylisocyanate (17 µL, 0.19 mmol) was combined neat with formic acid (7.2 µL, 0.19 mmol) and the mixture was stirred at room temperature for 2 h. A solution of INTERMEDIATE 21 (21 mg, 0.038 mmol) and pyridine (15 µL, 0.19 mmol) in 2 mL of THF was added and the resulting mixture was stirred for overnight. HPLC-MS analysis indicated only 50% conversion to sulfamide, therefore more chlorosulfonylisocyanate (34 µL, 0.38 mmol) was combined neat with formic acid (14 µL, 0.38 mmol) and that mixture was stirred at room temperature for 3 h. Then the THF solution with remaining starting material as well as product was added to this followed by more pyridine (30 µL, 0.38 mmol) and the resulting mixture was stirred for 3 h. Since no progress was observed after three h, the reaction mixture was diluted with ethyl acetate and washed with 1 N HCl solution, saturated NaHCO₃ solution, and brine, dried over anhydrous MgSO₄, filtered, and concentrated. The crude product was used as is in Step B.

ESI-MS calc. for $C_{26}H_{34}F_6N_4O_5S$: 628; Found: 629 (M+H).

Step B:

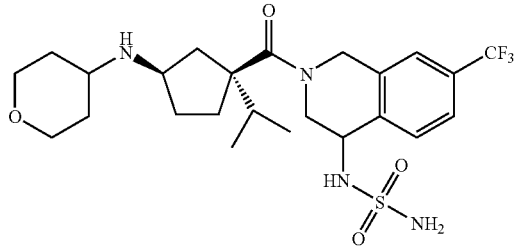

The crude sulfamide from Step A, Example 49 (calc. 0.038 mmol) was deprotected and purified in an identical fashion as described in Step B of the synthesis of EXAMPLE 6 to give two single isomer products (3.02 mg of the faster eluting band and 3.97 mg of the slower eluting band from separation by preparative TLC). The slower eluting band was contaminated with some of the starting amine INTERMEDIATE 21.

Faster eluting isomer: ESI-MS calc. for $C_{24}H_{35}F_3N_4O_4S$: 532; Found: 533 (M+H).

Slower eluting isomer: ESI-MS calc. for $C_{24}H_{35}F_3N_4O_4S$: 532; Found: 533 (M+H).

EXAMPLE 50

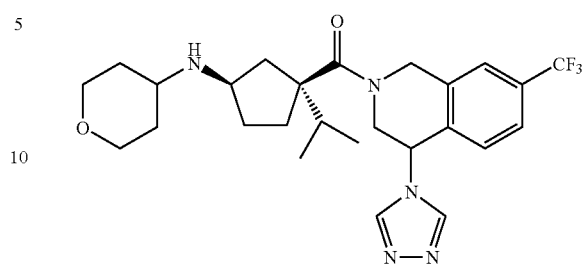

Step A:

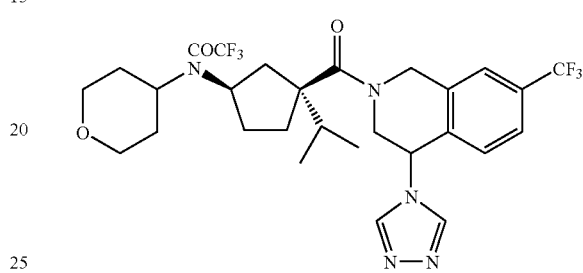

To a solution of INTERMEDIATE 21 (50.8 mg, 0.0924 mmol) in 1 mL of toluene was added N,N-dimethyl-formamide azine (39 mg, 0.28 mmol, prepared according to Bartlett, R. K.; Humphrey, I. R., *J. Chem. Soc. C* (1967), 1664.) and TsOH.H₂O (1 crystal, ~1 mg). The resulting reaction mixture was stirred for 18 h at reflux, then was concentrated. Preparative TLC (silica, 75% ethyl acetate/hexane, eluted twice) afforded 31 mg of product as a mixture of two diastereomers.

ESI-MS calc. for $C_{28}H_{33}F_6N_5O_3$: 601; Found: 602 (M+H).

Step B:

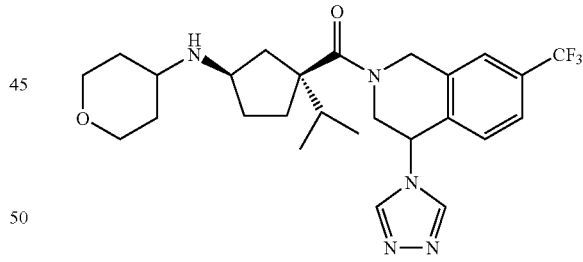

A solution of the triazole from Step A, Example 50 (31 mg, 0.052 mmol) in 2 mL of ethanol was treated with sodium borohydride (30 mg) and the resulting reaction mixture was stirred at 50° C. for 2 h. The reaction mixture was concentrated and the residue obtained was dissolved in DCM and washed with saturated NaHCO₃ solution, then brine, dried over anhydrous MgSO₄, filtered, and concentrated. Purification by reverse phase HPLC (YMC Pack Pro C18, 100×20 mm ID) afforded the product as its TFA salt. This was converted to its HCl salt by dissolving in DCM and adding excess of 1 N HCl/ether, then concentrating, giving 5 mg of product.

ESI-MS calc. for $C_{26}H_{34}F_3N_5O_2$: 505; Found: 506 (M+H).

EXAMPLE 51

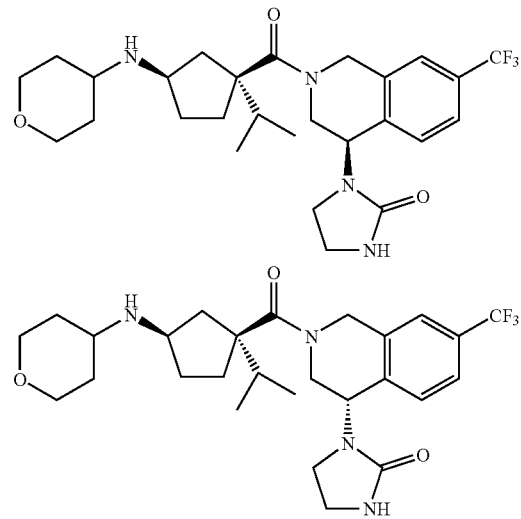

Step A:

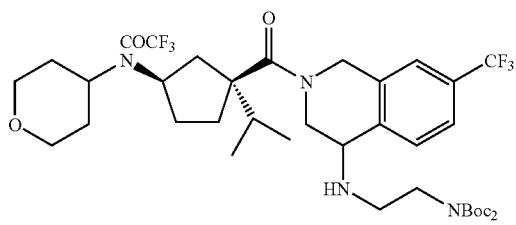

To a solution of INTERMEDIATE 21 (76 mg, 0.14 mmol) in 5 mL of DCM was added N,N-bis(tert-butoxycarbonyl)glycinal (for a preparation see Johnson, Theodore R.; Silverman, Richard B *Bioorg. Med. Chem.*, (1999), 7(8),1625–1636. 43 mg, 0.17 mmol), and sodium triacetoxyborohydride (88 mg, 0.41 mmol). The resulting reaction mixture was stirred at room temperature overnight. The reaction mixture was diluted with DCM and washed with saturated NaHCO$_3$ solution, then brine, dried over anhydrous MgSO$_4$, filtered, and concentrated. Purification by preparative TLC (silica, 35% ethyl acetate/hexane) provided 51.4 mg of target secondary amine as a mixture of two diastereomers.

ESI-MS calc. for C38H54F6N4O7: 792; Found: 793 (M+H).

Step B:

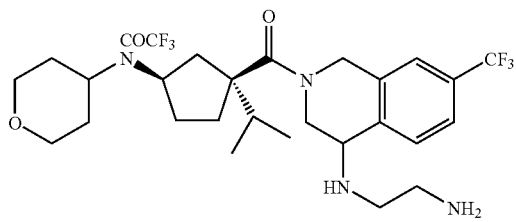

The product from Step A, Example 51 (51.4 mg, 0.0648 mmol) was dissolved in 1 mL of 4 N HCl/dioxane and stirred at room temperature for 1 h. The reaction mixture was concentrated to afford 49.9 mg of product as its bis-hydrochloride salt (a mixture of two diastereomers).

ESI-MS calc. for C28H38F6N4O3: 592; Found: 593 (M+H).

Step C:

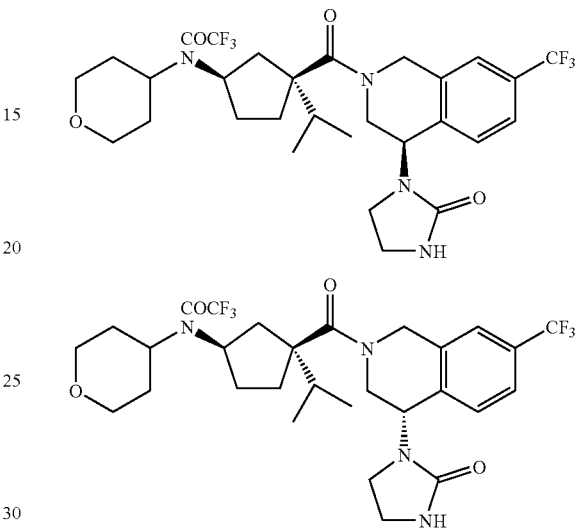

To a solution of the diamine from Step B, Example 51 (calc. 0.0648 mmol) in 10 mL of DCM was added a solution of phosgene in toluene (1.93 M, 50 μL, 0.097 mmol), followed by triethylamine (45 μL, 0.32 mmol). The resulting mixture was stirred at room temperature for 1.5 h, then was washed with 2 N HCl solution. The aqueous layer was back-washed with more DCM and the organic layers were combined. The combined organic layers were washed with saturated NaHCO$_3$ solution, then brine, dried over anhydrous MgSO$_4$, filtered, and concentrated. Purification by preparative TLC (silica, ethyl acetate) allowed separation of the two product isomers (18.5 mg of the faster eluting isomer and 13.3 mg of the slower eluting isomer).

Faster eluting isomer: ESI-MS calc. for C29H36F6N4O4: 618; Found: 619 (M+H).

Slower eluting isomer: ESI-MS calc. for C29H36F6N4O4: 618; Found: 619 (M+H).

Step D:

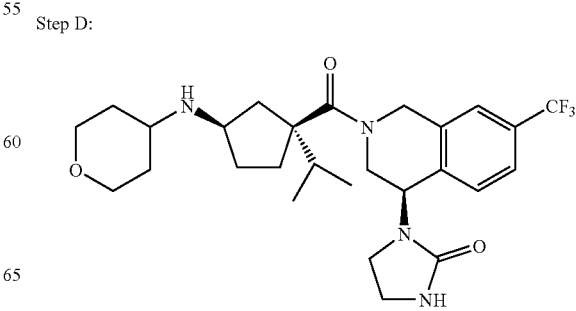

-continued

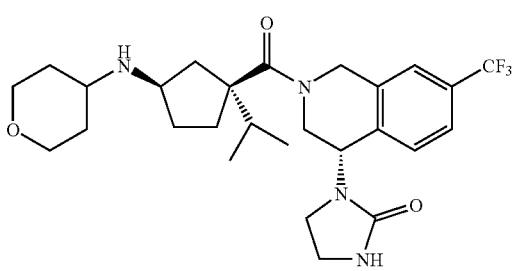

The trifluoroacetate protecting group was removed from both the faster eluting (18.5 mg) and slower eluting isomers (13.3 mg) from Step C, Example 51 according to the same procedure described in EXAMPLE 50 (Step B) to give 13.7 and 10.3 mg, respectively, of the final hydrochloride salts.

From faster eluting isomer, Step C: ESI-MS calc. for C27H37F3N4O3: 522; Found: 523 (M+H).

From slower eluting isomer, Step C: ESI-MS calc. for C27H37F3N4O3: 522; Found: 523 (M+H).

INTERMEDIATE 22

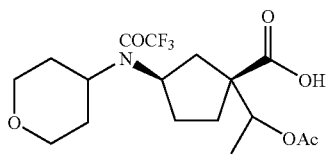

Step A:

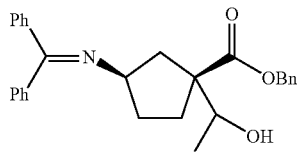

To a precooled (−78° C.) solution of LDA (1.5 M in cyclohexane, 63.3 mL, 94.9 mmol) in 95 mL of THF was added dropwise a solution of the Schiff base (Step D, Procedure A, Intermediate 5) in 45 mL of THF. After stirring the reaction mixture at −78° C. for 1 h 10 min, neat acetaldehyde (8.16 mL, 146 mmol) was added dropwise (accompanied by a color change from orange to yellow). After stirring for an additional 30 min, the cold reaction mixture was poured into 400 mL of 10% citric acid solution. The mixture was extracted twice with ether (400 mL) and the ethereal layers were combined and washed with brine, dried over anhydrous Na2SO4, filtered, and concentrated to give 22.5 g of crude product. Purification in 4 five g batches by MPLC (silica, eluting with 1 L 20% ethyl acetate/hexane, then 500 mL 25% ethyl acetate/hexane, then 1 L 30% ethyl acetate/hexane) allowed separation of a top and bottom band. The top band (6.48 g) was found to contain three of the four stereoisomers and the bottom band contained a single isomer, which was determined to have the undesired trans cyclopentyl stereochemistry.

Step B:

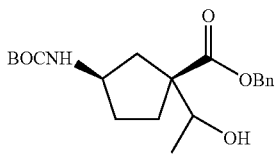

To a solution of the iminoester from Step A, Intermediate 22 (6.48 g, 15.2 mmol) in 80 mL of THF was added 2 N HCl solution (40 mL) and the reaction mixture was stirred overnight at room temperature. Added more 2 N HCl solution (30 mL) and washed twice with hexane to remove the benzophenone. The aqueous layer was concentrated. To the residue was added 100 mL each of DCM and saturated NaHCO3 solution. Then di-tert-butyl dicarbonate (6.63 g, 30.4 mmol) was added and the reaction mixture was stirred for 1.25 h. The layers were separated and the organic layer was washed with brine, dried over anhydrous MgSO4, filtered, and concentrated to give 8.8 g of crude material. Purification by MPLC (silica, 50% ethyl acetate/hexane) allowed separation of two product bands, the top of which (1.76 g) corresponding to a single trans isomer and the bottom (2.90 g) corresponding to a mixture of two cis isomers epimeric at the hydroxyl center.

Step C:

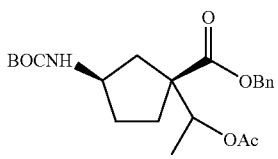

The hydroxy ester prepared as described in Step B, Intermediate 22 (2.66 g, 7.32 mmol) was combined with triethylamine (2.55 mL, 18.3 mmol) and acetic anhydride (1.73 mL, 18.3 mmol) in 50 mL of DCM. The reaction mixture was stirred at room temperature for 2 h. The reaction mixture was then diluted with DCM and washed with 2 N HCl solution, saturated NaHCO3 solution, and brine, dried over anhydrous MgSO4, filtered, and concentrated. Purification by MPLC (silica, 45% ethyl acetate/hexane) gave 2.84 g of desired product.

Step D:

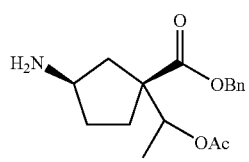

The intermediate from Step C, Intermediate 22 (2.66 g, 6.56 mmol) was dissolved in 4 N HCl/1,4-dioxane (20 mL) and stirred at room temperature for 1.5 h. The reaction mixture was concentrated to afford 2.35 g of crude product as its hydrochloride salt which gave a single peak (>99%) on HPLC and was not further purified.

ESI-MS calc. for C17H23NO4: 305; Found: 306 (M+H).

EXAMPLE 52

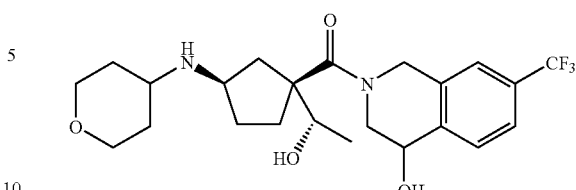

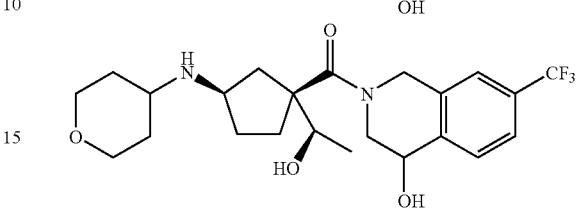

Step A:

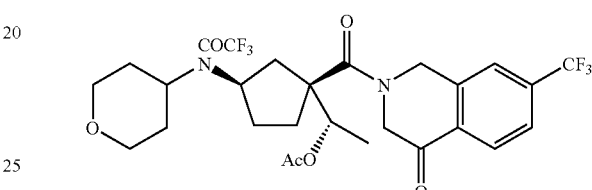

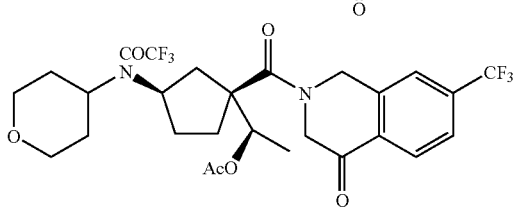

A cooled (0° C.) solution of INTERMEDIATE 22 (250 mg, 0.632 mmol) in 5 mL of DCM was treated with oxalyl chloride (221 µL, 2.53 mmol) followed by 1 drop of DMF. The reaction mixture was warmed to room temperature, stirred for 1.5 h, and concentrated. The residue obtained was dissolved in DCM, cooled to 0° C., and treated with INTERMEDIATE 19 (270 mg, 1.07 mmol), then triethylamine (264 µL, 1.90 mmol), and finally a few crystals of DMAP (~1–2 mg). The reaction mixture was warmed to room temperature and stirred for 1.5 h. The reaction mixture was then diluted with DCM and washed with 1 N HCl solution, then brine, dried over anhydrous MgSO$_4$, filtered, and concentrated. Purification by preparative TLC (silica, 50% ethyl acetate/hexane) allowed separation of two product isomers (92.6 mg of the faster eluting isomer and 94.1 mg of the slower eluting isomer).

Faster eluting isomer: ESI-MS calc. for C27H30F6N2O6: 592; Found: 593 (M+H).

Slower eluting isomer: ESI-MS calc. for C27H30F6N2O6: 592; Found: 593 (M+H).

Step B:

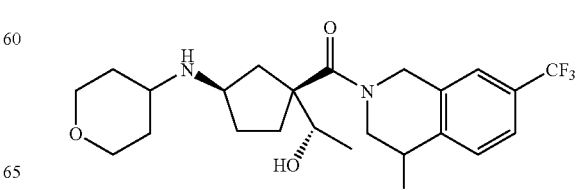

Step E:

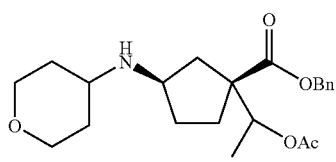

To a solution of the amine hydrochloride from Step D, Intermediate 22 (1.83 g, 5.34 mmol), tetrahydro-4H-pyran4-one (0.74 mL, 8.0 mmol), and triethylamine (0.74 mL, 5.3 mmol) in DCM was added sodium triacetoxyborohydride (4.53 g, 21.4 mmol). The resulting mixture was stirred overnight at room temperature. The reaction mixture was diluted with DCM and washed with saturated NaHCO$_3$ solution, then brine, dried over anhydrous MgSO$_4$, filtered, and concentrated to give 2.19 g of crude product which showed one major peak (>90%) by HPLC.

ESI-MS calc. for C22H31NO5: 389; Found: 390 (M+H).

Step F:

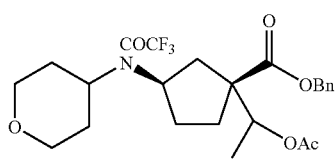

To a solution of the product from Step E, Intermediate 22 (2.19 g, 5.62 mmol) and triethylamine (1.17 mL, 8.43 mmol) in 50 mL of DCM was added trifluoroacetic anhydride (1.19 mL, 8.43 mmol). The resulting reaction mixture was stirred at room temperature for 4 h. The mixture was diluted with DCM and washed with saturated NaHCO$_3$ solution, then brine, dried over anhydrous MgSO$_4$, filtered, and concentrated to give 2.28 g of crude product. Purification by MPLC (silica, 50% ethyl acetate/hexane) provided 2.07 of the protected amine.

ESI-MS calc. for C24H30F3NO6: 485; Found: 486 (M+H).

Step G:

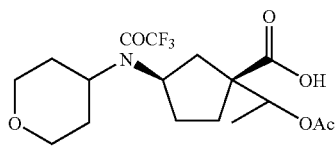

A mixture of the protected amine from Step F, Intermediate 22 (2.07 g, 4.26 mmol) and 10% Pd/C (Degussa, 250 mg) in 30 mL of methanol was stirred under a hydrogen atmosphere using a balloon for 2 h and 10 min. The reaction mixture was filtered through celite and concentrated to give 1.56 g of the crude product which showed a single peak by HPLC (>99%).

ESI-MS calc. for C17H24F3NO6: 395; Found: 396 (M+H).

-continued

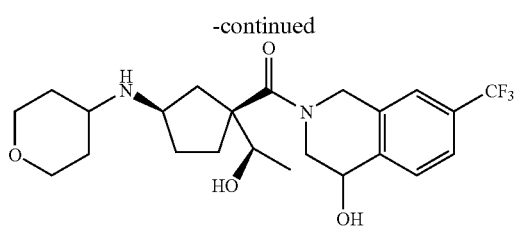

A solution of the faster eluting isomer from Step A, Example 52 (92 mg, 0.16 mmol) in 5 mL of ethanol was treated with sodium borohydride (59 mg, 1.6 mmol) and the resulting mixture was stirred at room temperature for overnight. The reaction mixture was concentrated and the residue obtained was dissolved in DCM and washed with saturated NaHCO$_3$ solution. The aqueous layer was back-washed with DCM four more times. The combined organic layers were dried over anhydrous MgSO$_4$, filtered, and concentrated. Purification by preparative TLC (silica, 12% of a 1:9 30% NH$_4$OH solution/methanol in DCM) afforded the product which was converted to its hydrochloride salt (49 mg) by dissolving in DCM, adding excess 1 N HCl in ether, and concentrating. The product was obtained as a mixture of two diastereomers, epimeric at the benzylic hydroxyl bearing carbon.

ESI-MS calc. for C23H31F3N2O4: 456; Found: 457 (M+H).

The slower eluting isomer from Step A, Example 52 (94 mg, 0.16 mmol) was similarly converted to a mixture of two final diastereomeric products (59.3 mg hydrochloride salt).

ESI-MS calc. for C23H31F3N2O4: 456; Found: 457 (M+H).

INTERMEDIATE 23

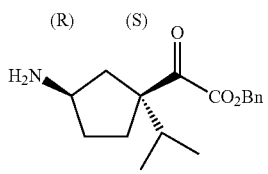

This compound was prepared by treatment of the corresponding Boc-amide with 4N HCl/dioxane (Step F, Intermediate 5).

INTERMEDIATE 24

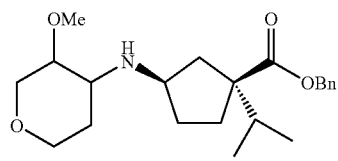

To a solution of INTERMEDIATE 23 (1.79 g, 6.01 mmol), INTERMEDIATE 9 (2.35 g, 18.0 mmol), and triethylamine (0.838 mL, 6.01 mmol) in 30 mL of DCM was added sodium triacetoxyborohydride (5.10 g, 24.0 mmol) and the resulting mixture was stirred for three days. The reaction mixture was diluted with DCM and washed with saturated NaHCO$_3$ solution, then brine, dried over anhydrous MgSO$_4$, filtered, and concentrated to give 2.61 g of crude product, which was primarily a mixture of two isomers (assumed from related work to be the two cis tetrahydropyran isomers). INTERMEDIATE 24 could be used crude as a mixture of two isomers or could be purified and separated into two single isomers (see INTERMEDIATES 25A and 25B) and then carried on.

ESI-MS calc. for C22H33NO4: 375; Found: 376 (M+H).

INTERMEDIATES 25A and 25B

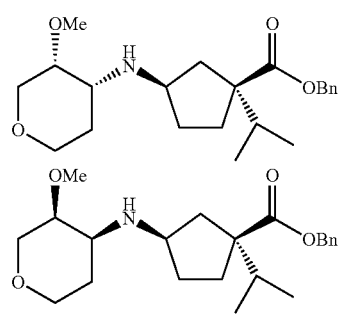

Crude INTERMEDIATE 24 (ca 6.01 mmol) was purified and separated into two major single isomers using a Chiralcel OD column (2 cm×25 cm, Daicel Chemical Industries), eluting with 20% i-propanol/heptane. This required 45 injections of approximately 50 mg of material/injection, and was performed in an automated fashion using a Gilson fraction collector integrated with Gilson Unipoint software. 920 mg Of the faster eluting isomer and 652 mg of the slower eluting isomer were obtained. The faster and slower eluting isomers are designated INTERMEDIATES 25A and 25B, respectively.

Faster eluting isomer (25A): ESI-MS calc. for C22H33NO4: 375; Found: 376 (M+H).

Slower eluting isomer (25B): ESI-MS calc. for C22H33NO4: 375; Found: 376 (M+H).

INTERMEDIATE 26

Step A:

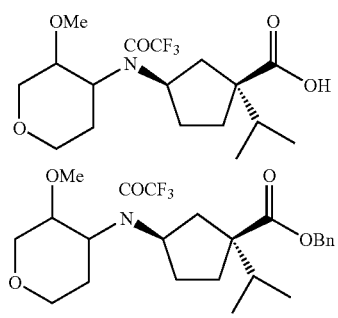

To a solution of unpurified INTERMEDIATE 24 (455 mg, 1.21 mmol) in DCM (10 mL) was added trifluoroacetic anhydride (257 μL, 1.82 mmol) followed by triethylamine (254 μL, 1.82 mmol). The reaction mixture was stirred at room temperature for 2.5 h, then was diluted with DCM and washed successively with 1 N HCl solution, saturated NaHCO$_3$ solution, and brine. The organic layer was dried over anhydrous MgSO$_4$, filtered, and concentrated to afford 554 mg of crude product. Purification by MPLC (silica, 40% ethyl acetate/hexane) provided 405 mg (71%) of product as a mixture of predominantly two isomers (two cis tetrahydropyran isomers).

ESI-MS calc. for C24H32F3NO5: 471; Found: 494 (M+Na$^+$).

Step B:

Step B:

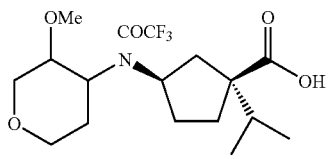

A mixture of ester from Step A above (405 mg, 0.859 mmol) and 10% Pd/C (Degussa, 80 mg) in methanol (5 mL) was stirred under a hydrogen atmosphere (balloon) for 2 h. The reaction mixture was filtered through a syringe equipped with a millipore PTFE 0.45 μm filter, and concentrated to give 310 mg of target acid as a mixture of predominantly two isomers (two cis tetrahydropyran isomers).

ESI-MS calc. for C17H26F3NO5: 381; Found: 404 (M+Na+).

INTERMEDIATES 27A AND 27B

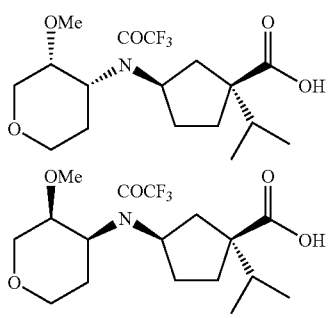

INTERMEDIATES 27A and 27B as single isomers were each individually prepared from INTERMEDIATES 25A and 25B respectively, using the same procedures as described for the synthesis of INTERMEDIATE 26. Note that the absolute stereochemistry of INTERMEDIATE 27A is one of the two shown immediately above and that of INTERMEDIATE 27B is the other, though which is which has not been unequivocally determined.

INTERMEDIATE 27A: ESI-MS calc. for C17H26F3NO5: 381; Found: 382 (M+H).

INTERMEDIATE 27B: ESI-MS calc. for C17H26F3NO5: 381; Found: 382 (M+H).

EXAMPLE 53

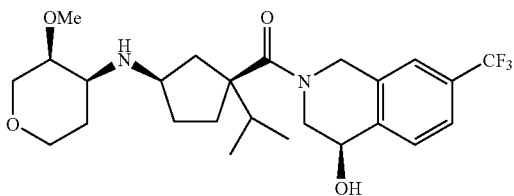

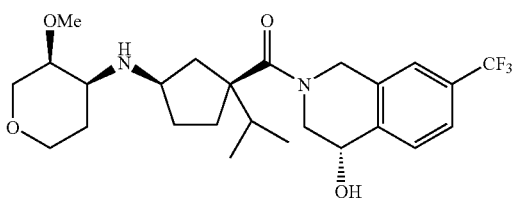

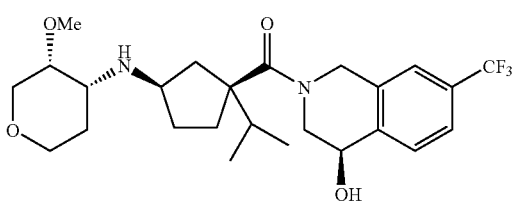

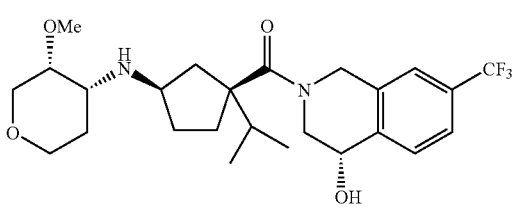

Step A:

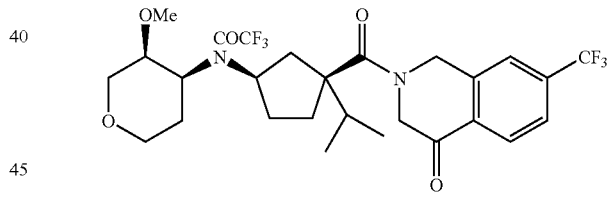

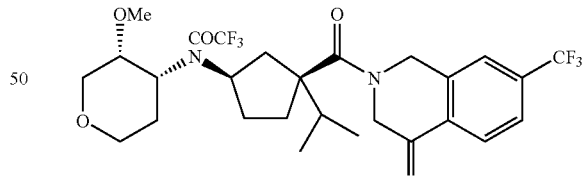

To a cooled (0° C.) solution of INTERMEDIATE 27B (258 mg, 0.676 mmol) in 5 mL of DCM was added oxalyl chloride (254 μL, 2.70 mmol), followed by 1 drop of DMF. The reaction mixture was permitted to warm to room temperature and stir for 2.5 h, then was concentrated. The residue obtained was dissolved in 5 mL of DCM, cooled to 0° C., and INTERMEDIATE 19 (340 mg, 1.35 mmol) was added, followed by triethylamine (283 μL, 2.03 mmol), and DMAP (~5 mg). The resulting reaction mixture was warmed to room temperature and stirred for overnight. The mixture was diluted with DCM and washed with 1 N HCl solution, saturated NaHCO₃ solution, and brine, dried over anhydrous MgSO₄, filtered, and concentrated. Purification by MPLC (silica, 60% ethyl acetate/hexane) afforded 373 mg of desired amide as a single stereoisomer.

ESI-MS calc. for C27H32F6N2O5: 578; Found: 601 (M+Na⁺).

INTERMEDIATE 27A was coupled to INTERMEDIATE 19 in the same way, also giving a single (different) diastereomer as the product.

ESI-MS calc. for C27H32F6N2O5: 578; Found: 601 (M+Na⁺).

Step B:

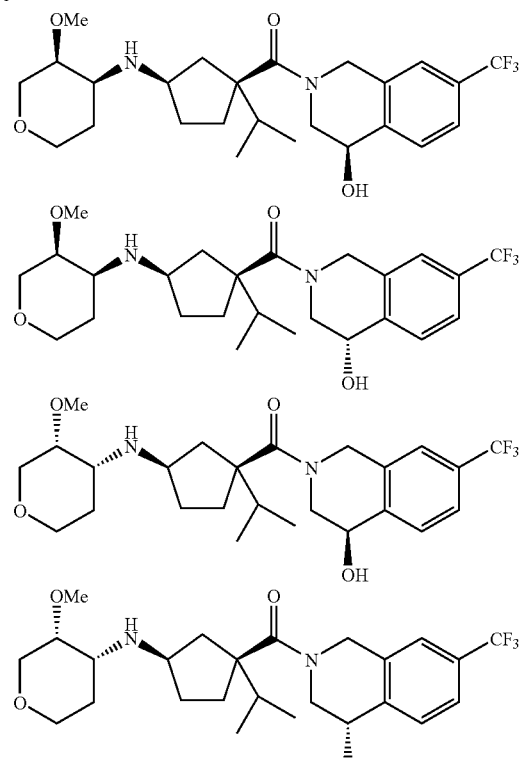

To a solution of the amide from Step A that was derived from INTERMEDIATE 27B (373 mg, 0.645 mmol) in 7 mL of ethanol was added sodium borohydride (244 mg, 6.45 mmol) and the resulting mixture was stirred at room temperature for 5 h. The reaction mixture was concentrated and the residue was dissolved in DCM and washed with saturated NaHCO₃ solution, then brine, dried over anhydrous MgSO₄, filtered, and concentrated. Purification by MPLC (silica, 10% of a 1:9 30% NH₄OH solution/methanol in DCM) afforded the product as a mixture of two isomers (180 mg). Separation of the two diastereomers was accomplished by chiral HPLC using a Chiralcel OD column (2 cm×25 cm, Daicel Chemical Industries), eluting with 60% i-propanol/heptane, 9 mL/min flow rate. For 177 mg of the mixture this required 4 injections of approximately 44 mg of material/injection, and was performed in an automated fashion using a Gilson fraction collector integrated with Gilson Unipoint software. 62 mg Of the faster eluting isomer (19 min) and 78 mg (30 min) of the slower eluting isomer were obtained. These were converted to their HCl salts by dissolving in DCM, adding excess 1 N HCl solution, and concentrating.

Similarly, the amide from Step A that was derived from INTERMEDIATE 27A (195 mg, 0.337 mmol) was also converted to two aminoalcohol final isomers (81 mg) that were separated in the same way except that the solvent system used was 55% i-propanol/heptane (30 mg of the faster eluting isomer [13.6 min] and 28 mg of the slower eluting isomer [30 min] from 78 mg of the mixture).

Isomer 1: ESI-MS calc. for C25H35F3N2O4: 484; Found: 485 (M+H).

Isomer 2: ESI-MS calc. for C25H35F3N2O4: 484; Found: 485 (M+H).

Isomer 3: ESI-MS calc. for C25H35F3N2O4: 484; Found: 485 (M+H).

Isomer 4: ESI-MS calc. for C25H35F3N2O4: 484; Found: 485 (M+H).

INTERMEDIATE 28

Step A:

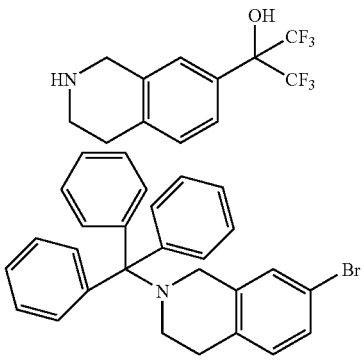

To a solution of the INTERMEDIATE 13 (1.08 g, 5.09 mmol) and triethylamine (0.708 mL, 5.09 mmol) in DCM (20 mL) was added triphenylmethyl chloride (1.42 g, 5.09 mmol). The reaction was stirred at room temperature for 20 h before being concentrated under reduced pressure. The resulting residue was purified by MPLC (silica gel, 0–50% EA/hexanes) to give 1.38 g of product (59.7%).

Step B:

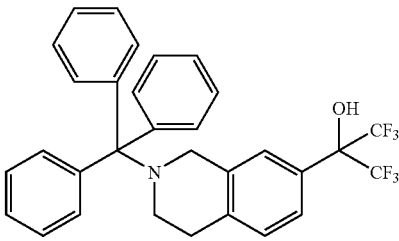

A cooled solution (−78° C.) of the product from Step A, Intermediate 28 (1.0 g, 2.2 mmol) in THF (20 mL) was treated with tert-butyl lithium (1.7 M solution in pentane, 2.6 mL, 4.4 mmol) and stirred at −78° C. After 20 min hexafluoroacetone gas was bubbled through the solution for 30 sec, and the reaction was warmed to room temperature slowly. After 2 h the reaction was quenched with H₂O (2 mL) and resulting solution was evaporated under a stream of nitrogen overnight. The resulting residue was purified by MPLC (silica gel, 0–40% EA/hexanes) to give 380 mg of the desired product (32%).

ESI-MS calc for C31H25F6NO: 541: found 300 (M+H-trityl).

Step C:

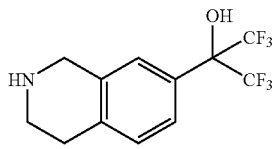

The product from Step B, Intermediate 28 (380 mg, 0.70 mmol) was dissolved in TFA (20 mL) and allowed to stir at room temperature. After 1.5 h the reaction was concentrated under reduced pressure and the resulting residue was partitioned between water and hexanes. The aqueous layer was lyophilized to give 200 mg of product (96%).

EXAMPLE 54

Step A:

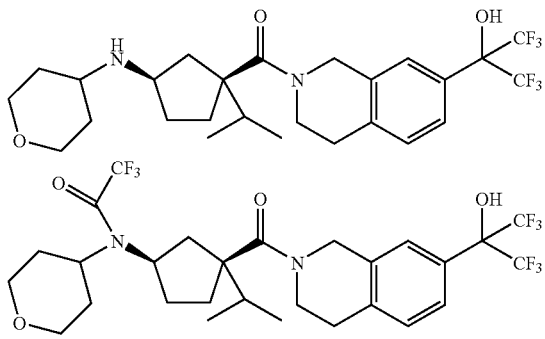

INTERMEDIATE 5 (11 mg, 0.31 mmol) was combined with INTERMEDIATE 28 (9 mg, 0.03 mmol), PyBrop (20 mg, 0.43 mmol), DEA (15 µL, 0.086 mmol), and DMAP (3 mg, 0.25 mmol) in DCM (2 mL) and stirred at room temperature. After 72 h, the reaction was diluted with DCM and washed with saturated aqueous sodium bicarbonate and brine. The organic layer was dried over MgSO4, filtered and concentrated under reduced pressure to give 5 mg of product (26%).

Step B:

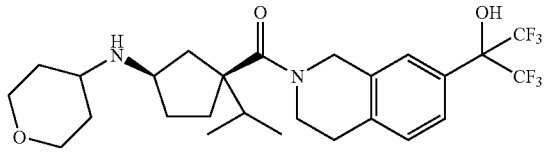

A solution of the product form Step A, Example 54 (5 mg, 0.008 mmol) in TBI (1 mL) and methyl alcohol (1 mL) was treated with a solution of lithium hydroxide monohydrate (1 mg, 0.02 mmol) in water (1 mL). After 18 h at room temperature the reaction was concentrated under reduced pressure and the product was purified by reverse phase HPLC (20–100% MeCN/H2O). The resulting product was converted to its hydrochloride salt by treatment with HCl (2 N in ethyl ether) to give 0.4 mg of a white solid (10%).

ESI-MS calc. for C26H34F6N2O3: 536: found 537 (M+H).

INTERMEDIATE 29

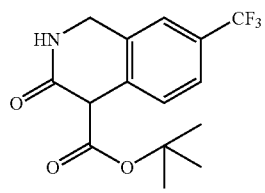

To a solution of sodium hydride (4.60 g, 115 mmol) in DMSO (120 mL) was added tert-butyl methyl malonate dropwise. The resulting solution was heated to 100° C. for 30 min then cooled to room temperature, where 3-cyano-4-fluorobenzotrifluride (9.86 g, 52.0 mmol) was added and the reaction reheated to 100° C. After 2 h the reaction was cooled to room temperature and poured into a mixture of saturated aqueous ammonium chloride (400 mL), EA (100 mL) and hexanes (100 mL). The organic layer was separated and washed once with saturated aqueous ammonium chloride, three times with water and once with brine. Filtration through a short plug of silica gel, followed by concentration under reduced pressure gave a crude yellow oil. This product was dissolved in ethyl alcohol (50 mL), treated with Raney Nickel (~1 g), and placed on a Parr shaker under 50 psi H$_2$. After 18 h the reaction was filtered through celite and concentrated under reduced pressure to give 12.5 g of product (76%).

ESI-MS calc. for C15H16F3NO3: 315; found 631 (2M+H).

H NMR (CDCl$_3$, 500 MHz) δ 7.60 (d, J=10.0 Hz, 1H), 7.50 (s, 1H), 7.44 (d, J=10.0 Hz, 1H), 7.24 (bs, 1H), 4.86 (d, J=14.5 Hz, 1H), 4.46 (t, J=14.5 Hz, 2H), 2.20 (bs, 1H), 1.45 (bs, 9H).

INTERMEDIATE 30

Step A:

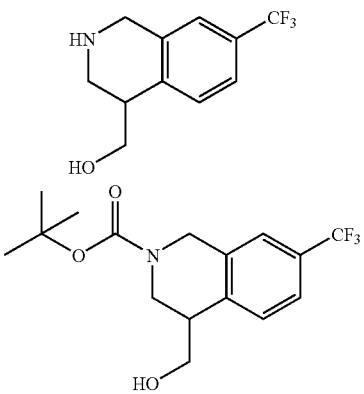

A solution of INTERMEDIATE 29 (5.0 g, 16 mmol) in THF (100 mL) was treated with borane (1.0 M solution in THF, 80 mL, 80 mmol) and stirred at room temperature. After 18 h the reaction was heated to 50° C. for 5.5 h after which time the reaction was concentrated under reduced pressure and re-dissolved in a 1% solution of HCl in methanol. After 18 h at 50° C. the reaction was concentrated under reduced pressure to give a yellow oil which was dissolved in DCM (100 mL) and triethylamine (2.5 mL, 18 mmol) and treated with di-tert-butyl dicarbonate (3.9 g, 18 mmol). After 3.5 h at room temperature the reaction was diluted with DCM, washed with saturated sodium bicarbonate solution, 1N HCl solution, and brine. The organic layer was dried over MgSO4, filtered and concentrated under reduced pressure to give a crude oil which was purified by MPLC (silica gel, 0–50% EA/hexanes) to give 2.2 g of product (37%).

ESI-MS calc. for C16H20F3NO3: 331.14; found 276 (M+H-t-butyl).

Step B:

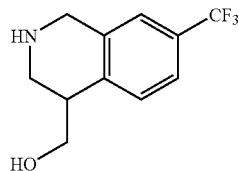

The product from Step A (360 mg, 1.1 mmol) was dissolved in 4 N HCl solution in dioxane (10 mL) and stirred at room temperature. After 18 h, the reaction was concentrated under reduced pressure to give 280 mg of a white salt (100%).

ESI-MS calc. for C11H12F3NO: 231; found 232 (M+H).

INTERMEDIATE 31

Step A:

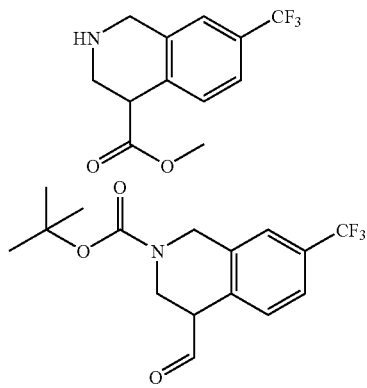

To a cooled (−78° C.) solution of oxalyl chloride (820 μL, 9.42 mmol) in DCM (100 mL) was added DMSO (1.3 mL, 19 mmol) dropwise. After 10 min at −78° C. a solution of the alcohol from Intermediate 30, Step A (2.6 g, 7.9 mmol) in DCM (50 mL) was added to the reaction. After 30 min at −78° C., triethylamine (5.3 mL, 38 mmol) was added and the reaction was warmed to room temperature. After 2 h, the reaction was diluted with DCM and washed three times with 2N HCl, once with saturated sodium bicarbonate, and once with brine. The organic layer was dried over MgSO4, filtered and concentrated under reduced pressure to give a crude product that was purified by MPLC (silica gel, 0–50% EA/hexanes). 1.0 g of a colorless oil was recovered (33%).

H NMR (CDCl3, 500 MHz) δ 9.77 (s, 1H), 7.54 (d, J=8.0 Hz, 1H), 7.56 (s, 1H), 7.35 (d, J=8.0 Hz, 1H), 4.97–4.67 (m, 2H), 4.39 (m, 1H), 3.69 (bs, 1H), 3.42 (bs, 1H), 1.50 (bs, 9H).

Step B:

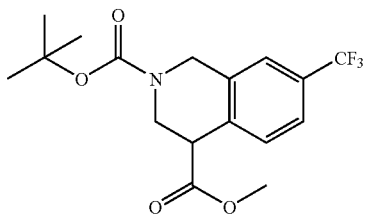

To a solution of the product from Step A (1.0 g, 3.1 mmol) in tert-butyl alcohol was added 2-methyl-2-butene (12 mL) followed by a solution of sodium chlorite (2.42 g, 27 mmol) and sodium dihydrogen sulfate (3.26 g, 27 mmol) in water (12 mL). The resulting solution was stirred at room temperature for 72 h before being concentrated under reduced pressure. The resulting residue was added to a solution of methyl alcohol (25 mL) treated with thionyl chloride (1.1 mL, 16 mmol) and stirred at room temperature. After 18 h the reaction was concentrated under reduced pressure and the residue re-dissolved in DCM. The resulting solution was cooled to 0° C. and treated with triethylamine (0.86 mL, 6.1 mmol) and di-tert-butyl dicarbonate (0.75 g, 3.4 mmol). After being warmed to room temperature the reaction was stirred for 18 h before being diluted with DCM and washed with 1N HCl solution, saturated sodium bicarbonate, and brine. The organic layer was dried over MgSO4, filtered and concentrated under reduced pressure. The product was purified by MPLC (silica gel, 0–80% EA/hexanes) to give 520 mg of a colorless oil (47%).

ESI-MS calc. for C17H20F3NO4: 359; found 360 (M+H).

Step C:

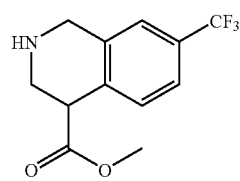

The product from Step B (460 mg, 1.3 mmol) was treated with hydrogen chloride (4 N solution in dioxane, 30 mL) and stirred at room temperature for 1.5 h before being concentrated under reduced pressure to give 390 mg of a white solid.

ESI-MS calc. for C12H12F3NO2: 259; found 260 (M+H).

EXAMPLE 55

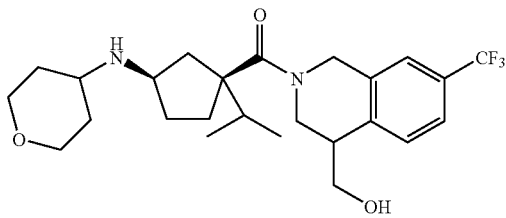

To a cooled (0° C.) solution of INTERMEDIATE 5 (100 mg, 0.28 mmol) was added oxalyl chloride (55 μL, 0.63 mmol) and 1 drop of DMF. The reaction was stirred at room temperature for 2 h before being concentrated under reduced pressure and dried under high vacuum for 1 h. The resulting acid chloride was dissolved in DCM (10 mL) and added dropwise to a solution of INTERMEDIATE 30 (100 mg, 0.38 mmol) in triethylamine (5 mL). After 1 h at room temperature the reaction was concentrated under reduced pressure and the crude residue was dissolved in a mixture of methyl alcohol (1 mL) and THF (1 mL). This solution was treated with a solution of lithium hydroxide monohydrate (59 mg, 1.4 mmol) in water (1 mL). After 18 h at room temperature the reaction was concentrated under reduced pressure and the product was purified by reverse phase HPLC (C18, 20–100% MeCN/H2O) and converted to its hydrochloride salt by addition of HCl (4 N solution in dioxane) to give 8.4 mg of a white solid (6%).

ESI-MS calc. for C25H35F3N2O3: 468; found 469 (M+H).

EXAMPLE 56

Step A:

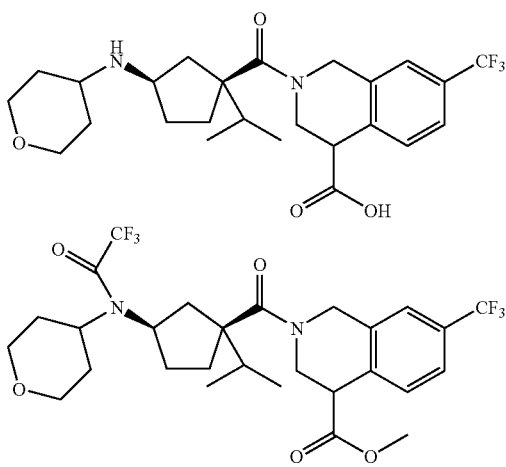

To a cooled (0° C.) solution of INTERMEDIATE 5 (550 mg, 1.6 mmol) was added oxalyl chloride (340 μL, 3.9 mmol) and 1 drop of DMF. The reaction was stirred at room temperature for 2 h before being concentrated under reduced pressure and dried under high vacuum for 1 h. The resulting acid chloride was dissolved in DCM (10 mL) and added dropwise to a solution of INTERMEDIATE 31 (390 mg, 1.3 mmol) in DCM (10 mL) and triethylamine (0.5 mL). After 1.5 h at room temperature the reaction was concentrated under reduced pressure and the product was purified by MPLC (silica gel, 0–50% EA/hexanes) to give 230 mg of a colorless oil (30%).

ESI-MS calc. for C28H34F6N2O5: 592; found 593 (M+H).

Step B:

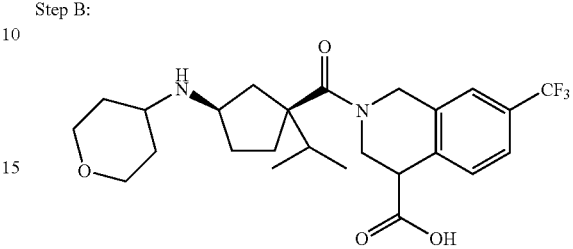

The product from Step A (100 mg, 0.17 mmol) was dissolved in a mixture of methyl alcohol (1 mL) and THF (1 mL). This solution was treated with a solution of lithium hydroxide monohydrate (35 mg, 0.83 mmol) in water (1 mL). After 72 h at room temperature the reaction was concentrated under reduced pressure and the product was purified by reverse phase HPLC (C18, 20–100% MeCN/ H2O) and converted to its hydrochloride salt by addition of HCl (4 N solution in dioxane) to give 46 mg of a white solid (56%).

ESI-MS calc. for C25H33F3N2O4: 482; found 483 (M+H).

EXAMPLE 57

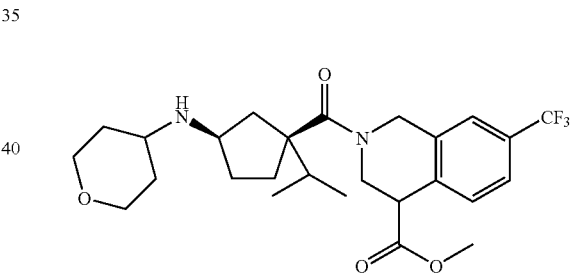

To a cooled (0° C.) solution of thionyl chloride (5 drops) in menthyl alcohol (2 mL) was added Example 56 (3 mg) and the resulting solution was warmed to room temperature. After 72 h the reaction was concentrated under reduced pressure to give 3 mg of a white solid.

ESI-MS calc. for C26H35F3N2O4: 496; 497 (M+H).

EXAMPLE 58

Step A

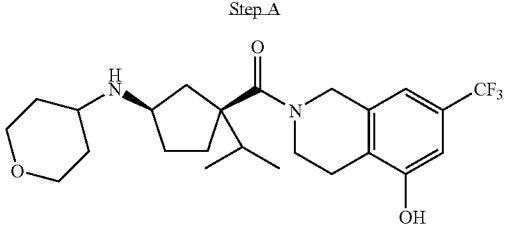

-continued

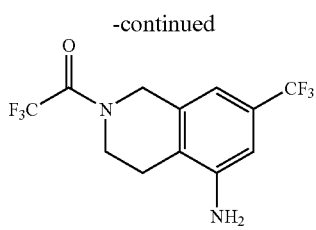

A solution of INTERMEDIATE 7 (2.46 g, 10 mmol) in dichloromethane (50 mL) was treated with TEA (2.73 mL, 20 mmol) and trifluoroacetic anhydride (2.1 mL, 15 mmol). Washed with water, dried over anhydrous sodium sulfate and evaporated. The residue was dissolved in methanol, mixed with 10% Pd/C and hydrogenated with a hydrogen balloon overnight, filtered and evaporated to afford the title compound (2.7 g, 87%). ESI-MS calc. for C12H10F6N2O: 312; found 313 (M+H).

Step B

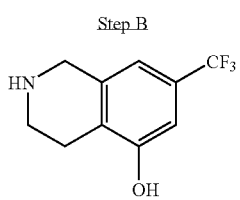

A cooled (0° C.) solution of the product from Step A (380 mg, 1.2 mmol) in 20% aqueous sulfuric acid (10 mL) was treated with a solution sodium nitrite (83 mg, 1.2 mmol) in water (1 mL). The reaction was heated to reflux for 4 h, then cooled to room temperature and neutralized with solid sodium carbonate (to pH ~7). The resulting mixture was extracted with EA three times and the combined organic layers where dried over MgSO4, filtered and concentrated under reduced pressure to give 270 mg of the desired product (100%).

ESI-MS calc. for C10H10F3NO: 217; found 218 (M+H).

Step C:

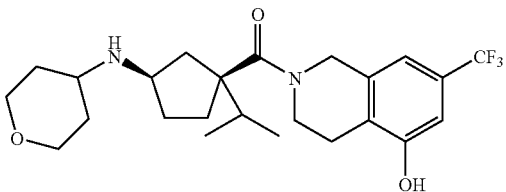

To a cooled (0° C.) solution of INTERMEDIATE 5 (100 mg, 0.28 mmol) was added oxalyl chloride (70 µL, 0.78 mmol) and 1 drop of DMF. The reaction was stirred at room temperature for 2 h before being concentrated under reduced pressure and dried under high vacuum for 1 h. The resulting acid chloride was dissolved in DCM (5 mL) and added dropwise to a solution of the product from Step B (93 mg, 0.42 mmol) in DCM (10 mL) and triethylamine (0.5 mL). After 18 h at room temperature the reaction was concentrated under reduced pressure, and the product was dissolved in ethyl alcohol and treated with sodium borohydride. The resulting solution was stirred for 18 h at room temperature before being concentrated under reduced pressure. The product was purified by reverse phase HPLC (C18, 20–100% MeCN/H2O) and converted to its hydrochloride salt by addition of HCl (4 N solution in dioxane) to give 5 mg of a white solid (4%).

ESI-MS calc. for C24H33F3N2O3: 454; found 455 (M+H).

EXAMPLE 59

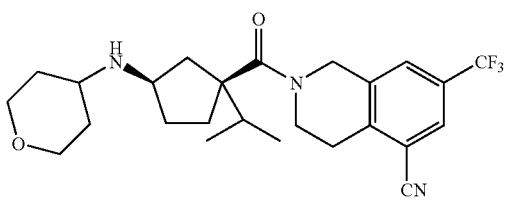

The product from Example 8, Step A (1.1 mg, 0.0020 mmol) was dissolved in ethyl alcohol (1 mL) and treated with sodium borohydride (1.2 mg). The resulting solution was stirred for 18 h at room temperature before being concentrated under reduced pressure. The product was purified by reverse phase HPLC (C18, 20–100% MeCN/H2O) and converted to its hydrochloride salt by addition of HCl (4 N solution in dioxane) to give 0.42 mg of a white solid (45%).

ESI-MS calc. for C25H32F3N3O2: 463; found 464 (M+H).

EXAMPLE 60

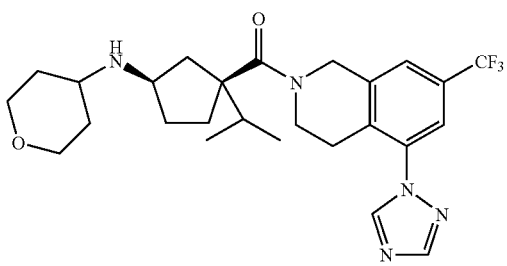

To a cooled (−10° C.) solution of the product from Step B, Example 11 (50 mg, 0.091 mmol) in concentrated aqueous HCl (1 mL) was added a solution of sodium nitrite (6 mg, 0.1 mmol) in concentrated aqueous HCl (1 mL) and the resulting solution was warmed to 0° C. After 2 h the reaction was treated with tin II chloride (67 mg, 0.36 mmol) and the resulting precipitate was removed by filtration. The filter cake was dissolved in ethyl alcohol (1 mL), treated with triazine (5 mg, 0.06 mmol), and heated to reflux. After 12 h the reaction was cooled to room temperature and filtered and the filtrate was treated with sodium borohydride. After 18 h at room temperature the reaction was concentrated under reduced pressure and the produce was purified by reverse phase HPLC (C18, 20–100% MeCN/H2O) and converted to its hydrochloride salt by addition of HCl (4 N solution in dioxane) to give 1.6 mg of a white solid (4%).

ESI-MS calc. for C26H34F3N5O2: 505; found 506 (M+H).

EXAMPLE 61

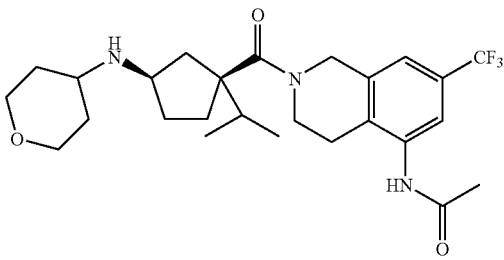

The product from Example 11 Step B (49 mg, 0.089 mmol) was combined with ethyl orthoformate (30 µL, 0.17 mmol) and sodium azide (10 mg, 0.16 mmol) in glacial acetic acid (3 mL) and the resulting solution was heated to reflux. After 18 h, the reaction was poured onto ice and extracted twice with DCM. The combined organic layers where washed with brine, and dried over MgSO4, filtered and concentrated under educed pressure. The resulting residue was dissolved in ethyl alcohol and treated with sodium borohydride. After 18 at room temperature the reaction was concentrated under reduced pressure and the product was purified by reverse phase HPLC (C18, 20–100% MeCN/H2O) and converted to its hydrochloride salt by addition of HCl (4 N solution in dioxane) to give 21 mg of a white solid (48%).

ESI-MS calc. for $C_{26}H_{36}F_3N_3O_3$: 495; found 496 (M+H).

EXAMPLE 62

Step A

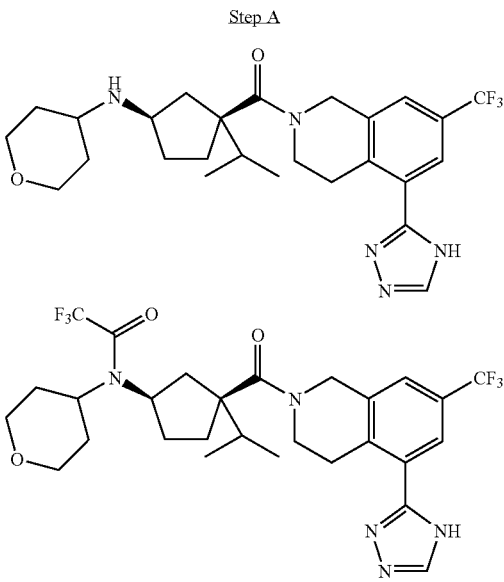

The product from Example 8 Step B (45 mg, 0.078 mmol) was dissolved in N,N-dimethylformamide dimethyl acetal (5 mL) and heated to 120° C. After 50 min the solvent was removed under pressure and the resulting residue was dissolved in glacial acetic acid, treated with hydrazine (4.5 µL, 0.092 mmol), and heated to 70° C. After 18 h the reaction was concentrated under reduced pressure and the product was purified by reverse phase HPLC (C18, 20–100% MeCN/H2O) to give 10 mg of a colorless oil (21%).

ESI-MS calc. for $C_{28}H_{33}F_6N_5O_3$: 601; found 602 (M+H).

Step B

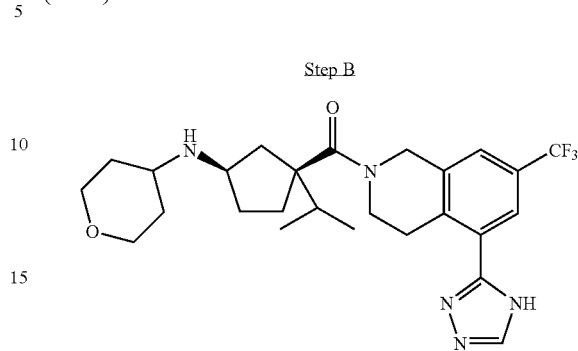

The product form Step A (10 mg, 0.0017 mmol) was dissolved in a mixture of THF (1 mL) and methyl alcohol (1 mL). The resulting solution was treated with lithium hydroxide (10 mg, 0.23 mmol) and stirred for 18 h at room temperature before being concentrated under reduced pressure. The product was purified by reverse phase HPLC (C18, 20–100% MeCN/H2O) and converted to its hydrochloride salt by addition of HCl (4 N solution in dioxane) to give 5.8 mg of a white solid (68%).

ESI-MS calc. for $C_{26}H_{34}F_3N_5O_2$: 505; found 506 (M+H).

EXAMPLE 63

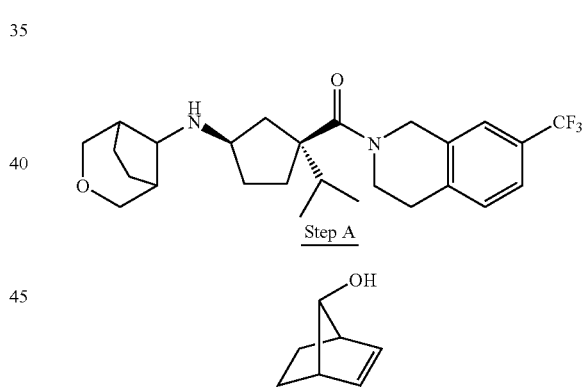

Step A

To a stirred solution of phenyl magnesium bromide (3 M solution in ether, 680 mL, 2 mol) in ethyl ether (500 mL) was added exo-epoxynorbornane (150 g, 1.36 mol) in ethyl ether (250 mL) slowly. After the initial exotherm, the reaction was heated to reflux for 3 h, after which time it was cooled in an ice bath and quenched with water (25 mL). The resulting solution was diluted with ethyl ether and washed with aqueous 3 N HCl twice. The combined aqueous layers where back extracted with ethyl ether twice and the combined organic layers where washed with brine, dried over MgSO$_4$, filtered, and concentrate under reduced pressure (100 mmHg, 30° C.) to give 230 g of a crude orange oil. This material was subject to flash chromatography (silica gel, 40% ethyl ether/hexanes) to give 67 g of pure product (45%). $^1$H NMR (CDCl$_3$, 500 MHz): 6.06 (d, J=1.0 Hz, 2 H), 3.76 (s, 1H), 2.75 (d, J=2.0 Hz, 2H), 1.86 (bs, 2H), 1.71–1.68 (m, 2H).

Step B

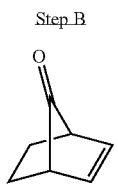

To a cooled (~−78° C.) solution of oxalyl chloride (83 g, 660 mmol) in DCM (500 mL) was added DMSO (78 mL, 1.1 mol) in DCM (200 mL) rapidly but keeping the temperature below −50° C. To this solution was immediately added the product from Step A (67 g, 610 mmol) in DCM (600 mL) rapidly, but keeping the temperature below −50° C. After stirring for 15 minutes at −78° C. this solution was treated with triethylamine (310 mL, 2.1 mol) and allowed to warm to room temperature. After 1 h at room temperature, the reaction was quenched with water and concentrated under reduced pressure. The crude residue was dissolved in a 3:1 solution of ethyl ether and petroleum ether and washed 3 times with aqueous 1 N HCl then with brine. The organic layer was dried over $Na_2SO_4$, filtered, and concentrated under reduced pressure. The resulting residue was quickly chromatographed (short column—silica gel, 15% ethyl ether/hexanes) and concentrated under reduced pressure. Final purification was achieved by distillation (collecting the 60° C. to 70° C. fractions at 30 mm Hg) to give 18.5 g of pure product as a colorless liquid (28%). $^1$H NMR (CDCl$_3$, 500 MHz): 6.53 (bs, 2H), 2.82 (bs, 2H), 1.97 (d, J=7.0 Hz, 2H), 1.21 (dd, =4.5, 6.5 Hz, 2H).

Step C

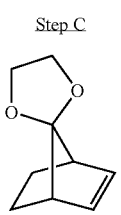

The product from Step B (17.5 g, 162 mmol) was combined with p-toluenesulfonic acid (4.9 g, 26 mmol) and ethylene glycol (13.1 mL, 243 mmol) in benzene (200 mL) and heated to reflux. After 5 h, the solution was allowed to cool to room temperature and stir overnight, after which time it was partitioned between ethyl ether and aqueous saturated NaHCO$_3$. The organic phase was washed with brine, dried over MgSO$_4$, filtered and concentrated. The product was purified by flash chromatography (silica gel, 10% ethyl ether/hexanes) to give 19.0 g of a colorless oil (83%). $^1$H NMR (CDCl$_3$, 500 MHz): 6.18 (bs, 2H), 3.92 (t, J=6.0 Hz, 2H), 3.85 (t, J=6.0 Hz, 2H), 2.53 (bs, 2H), 1.92 (d, J=7.5 Hz, 2H), 0.97 (dd, J=3.5, 10.5 Hz, 2H).

Step D

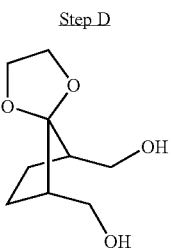

A solution of the product from Step C (2.0 g, 13 mmol) in a mixture of methanol (30 mL) and DCM (24 mL) was cooled to −78° C. and treated with ozone gas (7.5 psi, 2 L/min) until a blue tint to the solution was apparent. At this time, the reaction was purged with nitrogen gas to remove the excess ozone and sodium borohydride (600 mg, 16 mmol) was added to the reaction. The reaction was allowed to warm to 0° C. on an ice bath before acetone was added to quench the excess reducing agent. The resulting solution was concentrated under reduced pressure and the product was purified by flash chromatography (silica gel, eluting with EA) to give 1.9 g of a colorless oil which upon cooling to −20° C. became a colorless solid (78%). $^1$H NMR (CDCl$_3$, 500 MHz): 4.02 (m, 4H), 3.67 (m, 4H), 2.22 (t, J=6.0 Hz, 2H), 1.83 (m, 2H), 1.63 (m, 2 H).

Step E

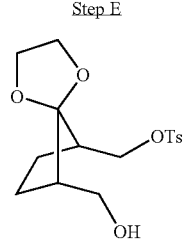

To a cooled (−15° C.) solution of the product from Step D (1.26 g, 6.71 mmol) in THF (21 mL) was added n-butyllithium (2.5 M in hexanes, 2.8 mL, 7.0 mmol). After the reaction was stirred for 30 minutes at −15° C., tosyl chloride (1.28 g, 6.71 mmol) in THF (10 mL) was added dropwise and the reaction was warmed to room temperature and stirred for an additional 30 minutes before being concentrated under reduced pressure. The mono-tosylate product was separated from small amounts of starting material and di-tosylation product by medium pressure liquid chromatography (silica gel, 40–100% EA/hexanes) to give 900 mg of a colorless oil (39%) which was used directly in the next step.

Step F

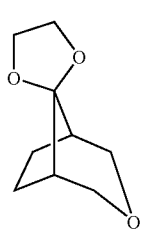

The product from Step E (707 mg, 2.07 mmol) was combined with sodium hydride (60% dispersion in mineral oil, 250 mg) in THF and stirred at room temperature. After 2 h the reaction was quenched with hydrogen chloride (2 N solution in ethyl ether, 4 mL) and the resulting precipitate was filtered off. The filtrate was concentrated and purified by flash chromatography (silica gel, 20% ethyl ether/hexanes) to give 320 mg of product (91%). $^1$H NMR (CDCl$_3$, 500 MHz): 3.97 (m, 4H), 3.93 (d, J=10.5 Hz, 2H), 3.57 (dd, J=2.5, 11.0 Hz, 2H), 1.84–1.81 (m, 2H), 1.75 (m, 4H).

Step G

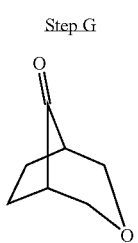

The product from Step F (250 mg, 1.47 mmol) was dissolved in a mixture of THF (4 mL) and aqueous 5% HCl (2 mL) and stirred at room temperature. After 18 h the reaction was diluted with ethyl ether, washed with brine, and dried over MgSO$_4$, filtered and concentrated under reduced pressure. The product was purified by flash chromatography (silica gel, 30% ethyl ether/hexanes) to give 51 mg of a volatile liquid (28%). $^1$H NMR (CDCl$_3$, 500 MHz): 3.99 (dd, J=2.5, 11.0 Hz, 2H), 3.87 (d, J=11 Hz, 2H), 2.28 (bs, 2H), 2.03 (m, 2H), 1.99 (m, 2H).

Step H

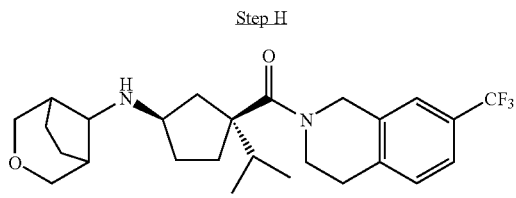

INTERMEDIATE 6 (HCl salt) (38 mg, 0.097 mmol) was combined with the product from Step G (10 mg, 0.08 mmol), N,N-diisopropylethylamine (30 μL, 0.18 mmol), 4 Å powdered molecular sieves (50 mg), and sodium triacetoxyborohydride (84 mg, 0.40 mmol) in 5 mL DCM. The reaction mixture was stirred at room temperature for 3 days, then filtered through celite, washed with saturated sodium bicarboante and brine, and dried over MgSO$_4$, filtered and concentrated under reduced pressure. The product was purified by preparative TLC (silica gel, 0.3% NHOH/3.7% MeOH/97% DCM) and converted to its hydrochloride salt by the addition of hydrogen chloride (2 N solution in ethyl ether) to give 6.0 mg of a white solid (17%). ESI-MS calc. for C$_{26}$H$_{35}$F$_3$N$_2$O$_2$: 464.27; found 465(M+H).

EXAMPLE 64

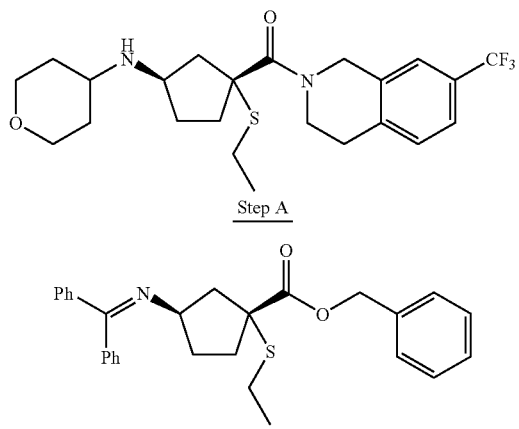

Step A

LDA was prepared by adding 11.5 ml of 2.5 N nBuLi (in Hexane) slowly to a stirred solution of 4 ml of diisopropyl amine in 60 ml of THE at −78°. After 20 minutes, a solution of 9.56 g of the Schiff base (Step B, Intermediate 5) in 5 ml of THE was added portionwise to LDA at −78°. After 30 minutes at −78°, 9.2 ml of ethyl sulfide was added, stirred for 1 hr and then was allowed to stir at room temperature overnight. The reaction mixture was quenched by addition of sat NH4Cl, extracted with EtOAc (3×). The combined organic layers were washed with sat NaCl, dried (NaSO4), filtered and evaporated to afford the crude product. Column chromatography (silica gel, Hexane: Ethyl acetate:93:7) afforded 4.5 gm of the title compound as a mixture alkylated products. m/e=443 (M+1).

Step B

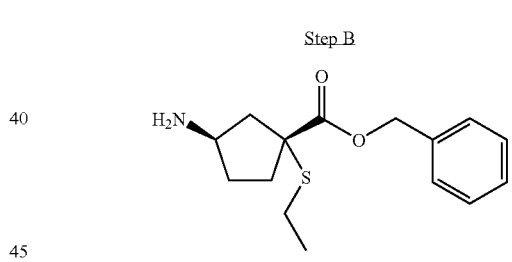

To a solution of 2.5 g. of the product from Step A in 25 ml of THF was added 20 ml of 2N HCl portionwise. After 1 hr the reaction mixture was evaporated to a small volume. The residue was extracted with hexanes (3×) in order to remove neutral material. The aqueous layer was made basic with 5N NaOH and extracted with EtOAc (3×). The combined organic layers were washed with sat NaCl, dried (NaSO4), filtered and evaporated to afford 750 mg of the title compound. m/e=280 (M+1).

Step C

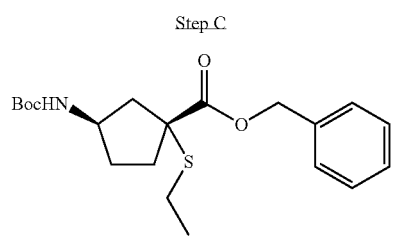

To a stirred solution of 755 mg of the product from Step B in 4 ml of CH2Cl2 was added 1.1 ml of Et3N followed by a solution of 1.77 g of Boc2O in 5 ml of CH2Cl2. The reaction mixture was stirred at room temperature overnight, extracted with sat NaHCO3 followed by sat NaCl. The organic layer was dried (NaSO4), filtered and evaporated to afford the crude. Flash column chromatography (silica gel, Hexane:Ethyl acetate:88:12) afforded 780 mg of 3 as a mixture of isomers.

Step D

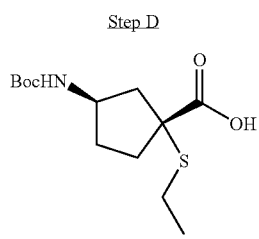

To a stirred solution of 715 mg of the product from Step C in 4 ml of methanol and 4 ml of THF at room temperature was added portionwise a solution of 0.395 g of LiOH in 4 ml of water. The reaction mixture was refluxed for 3 days, cooled to room temperature and evaporated to a small volume. The residue was diluted with water and extracted with EtOAc to remove the neutral material. The aqueous layer was treated with 0.5N HCl to a pH of ca 5 and extracted with CH2Cl2 (3×). The combined organic layers were washed with sat sodium chloride, dried (Na2SO4), filtered and evaporated to affored 0.5 g of the acid. NMR (CD3OD) δ1.20 (m, 3H), 1.43 (s, 9 H), 2.63 (m.2H).

Step E

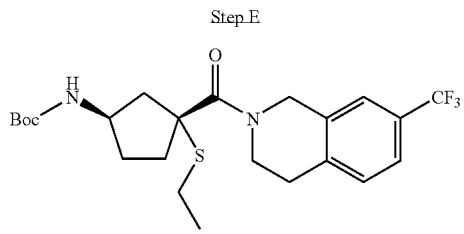

To a stirred solution of the acid (Step D) (0.493 g) in 4 ml of CH2Cl2 was added INTERMEDIATE 1 (0/475 g), 0.950 g of PyBrop and 0.48 ml of Et3N. The reaction mixture was stirred at r.t. overnight, diluted with CH2Cl2, washed with sat NH4Cl, sat NaHCO3 followed by sat NaCl, dried (Na2SO4) filtered and evaporated to afford 0.695 g of the crude product. Preparative tic (SiO2 gel) afford 0.275 g of the top spot and 0.335 g of the bottom spot. Top spot: NMR (CD3OD) 6 1.41 (s, 9H), 7.36 (d, 1H), 7.47(m,2 H).

Step F

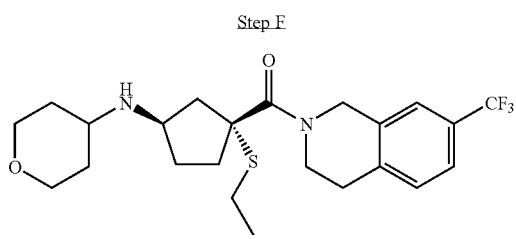

A solution of 100 mg of the product from Step E, top spot, in 2 ml of 4N HCl in Dioxane was allowed to stir at stir at room temperature for 2 h. The reaction mixture was evaporated and residue was dissolved in 3 ml of CH2Cl2. Triethyl amine (60 ul), 40, 40 µl of tetrrahydropyranone, 224 mg of Na(OAc)3 and 50 mg of molecular sieves 4A were added and was allowed to stir at room temperature overnight. The reaction mixture was diluted with CH2Cl2, washed with sat NaHCO3, sat NaCl, dried (Na2SO4), filtered and evaporated to afford the crude product. Purification of the crude compound by prep tlc (silica gel, CH2Cl2:CH3OH:NH4OH:90: 10:1) afforded 97 mg of the free amine. Mass spectrum: m/e 457 (m+1).

EXAMPLE 65

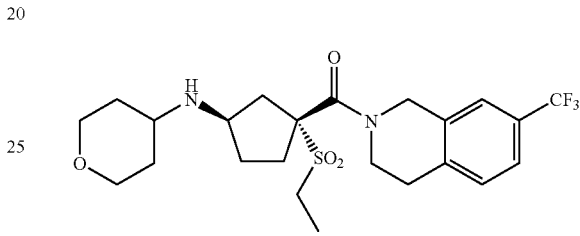

Step A

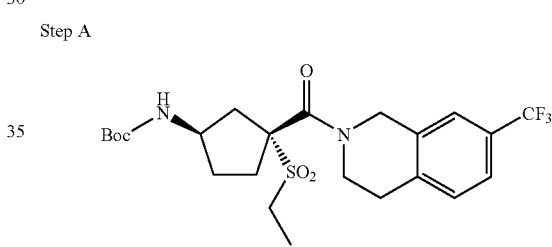

To a stirred solution of the product from Step E, Example 64 (top spot) in 2 ml of CH2Cl2 at room temperature was added 86 mg (2 eq) of 3-chloroperbenzoic acid (72%). After 2 hr the reaction mixture was extracted with sat NaHCO3, washed with sat NaCl, dried (Na2SO4), filtered and evaporated to afford the crude product. Preparative tlc (SiO2, Hexane: Ethyl acetate: 1:1) afforded 102 mg of the title compound. Mass spectrum: m/e=405 (m−Boc+1).

Step B

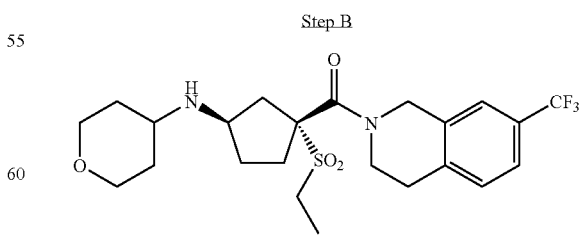

The product from Step A was converted to Example 65 as described for the preparation of Example 64 from the product (Step E, Example 64).

EXAMPLE 66

Step A

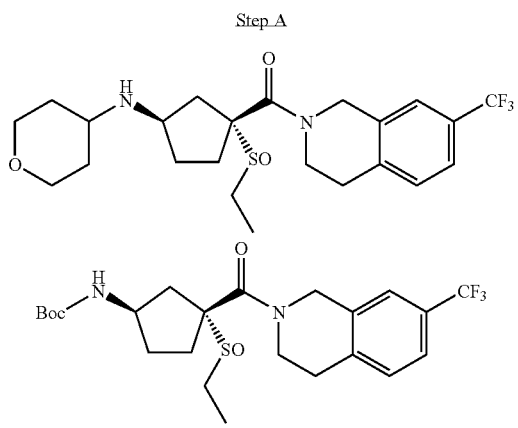

To a stirred solution of 71 mg of the product (Step E, Example 64) in 3 ml of methanol was added dropwise a solution of 51 mg (1.5 eq) of NaIO4 in 0.6 ml of water. After 18 hr at room temperature the reaction mixture was evaporated to a small volume. The residue was suspended in ethyl acetate. The organic layer was washed with sat sodium chloride, dried (Na2SO4), filtered and evaporated to provide the crude product. Preparative tlc (Sio2 gel, Hexane: Ethyl acetate: 20:80) afforded 60 mg of 9. Mass spectrum: m/e=389 (m−Boc+1).

Step B

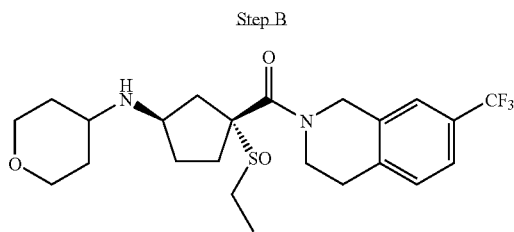

The product from Step A was converted to Example 66 as described for the preparation of Example 64 from the product (Step E, Example 64).

EXAMPLE 67

Step A

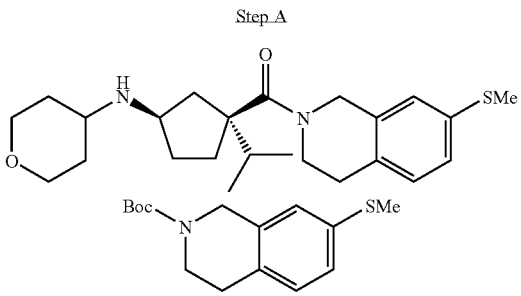

A stirred mixture of Cu, (2.5 g, 0.04 mol), (CH3)2S2 (2.75 g, 0.029 mol) and 20 ml of 2,6-Lutidine was refluxed for 4 hr. A solution of 2.6 g (0.0083 mol) of N-Boc-7-bromo-1, 2,3,4-tetrahydroisoquinoline in lutidine was added to the cooled reaction mixture and refluxed for 7 days under N2, cooled to room temperature and filtered through celite. The filtrate was evaporated and the residue was suspended in CH2Cl2 and filtered through celite again. The filtrate was evaporated and the residue was purified by flash column chromatography (SiO2 gel, Hexane:Ethyl acetate:90:10) to afford 0.360 g of the title compound. 1H-NMR (CDCl3)=δ 1.5 (s, 9H), 2.48(s, 3H).

Step B

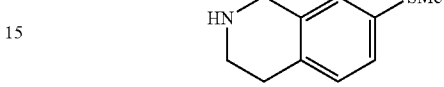

A mixture of 0.360 g of the product from Step A in 10 ml of 4 N HCl in dioxane was stirred at room temperature for 2 h. The reaction mixture became heterogenous due to separation of solid. The mixture was evaporated and the residue was purified by prep tlc (SiO2 gel, CH2Cl2: CH3OH:NH4OH:90:10:1) to afford 160 mg of the title compound.

Step C

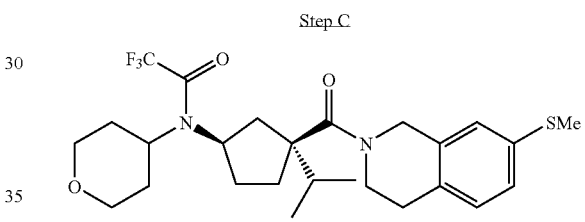

To a stirred solution of 0.160 g of the product from the above Step B, 0.376 g (1.2 eq) of the INTERMEDIATE 5, 0.50 g(1.2 eq) of PyBrop in 3 ml of CH2Cl2 was added 0.248 ml (2 eq) of Et3N. After 48 hr the reaction mixture was diluted with CH2Cl2, extracted with sat NaHCO3 and washed with sat NaCl, and dried (NaSO4), filtered and evaporated to afford 0.835 mg of the crude product. Preparative tlc (SiO2 gel, Hexane:Ethyl acetate:6:4) afforded 0.510 g of 4. Mass spectrum=m/e=513 (m+1). 1H-NMR (500 MHz, CD3OD) δ 0.80 (d, 3 H), 1.05 (d, 3 H), 2.45 (s, 3H).

Step D

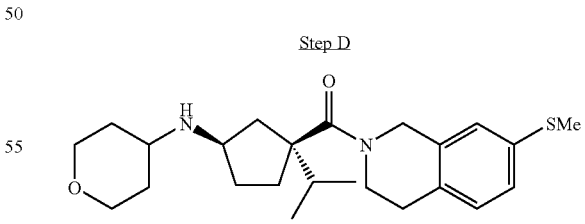

A solution of 68 mg of the product from the above Step C in 2 ml of ethanol was treated with 50 mg (10 mol) of NaBH4 overnight at room temperature. The reaction mixture was evaporated to a small volume, the residue was suspended in CH2Cl2, washed with sat NaCl, dried (NaSO4), filtered and evaporated to afford crude product. Preparative tlc (SiO2 gel, CH2Cl2:CH3OH:NH4OH:90:10: 1) afforded 49 mg of the title compound, mass spectrum=m/ e=417 (m+1). The free amine was converted to the hydrochloride salt by treatment with 1.5 eq of 1 N HCl in ether.

EXAMPLE 68

Step A

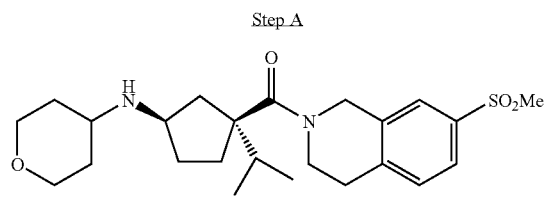

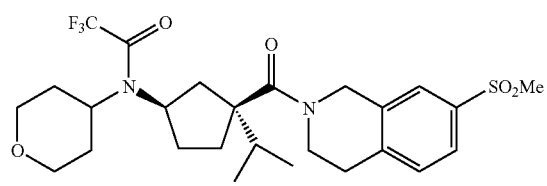

A stirred solution of 79 mg of the product (Step C, Example 67) in 2 ml of CH2Cl2 was treated with 79 mg (2.2 eq) of 72% of 3-chloroperbenzoic acid. After 3 hr the reaction mixture was extracted with sat NaHCO3, washed with sat NaCl, dried Na2SO4, filtered and evaporated to afford the crude product. Preparative tlc (SiO2 gel, Hexane: Ethyl acetate: 20:80) afforded 72 mg of the title compound. 1H-NMR (500 MHz, CD3OD) δ 3.10 (s, 3 H).

Step B

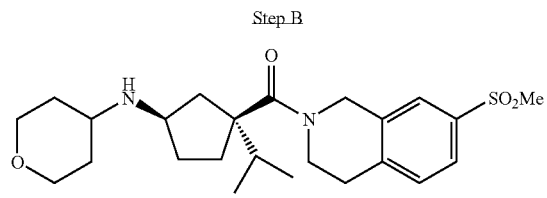

The intermediate from Step A was converted to the Example 68 as described for the preparation of Example 67 (Step D).

EXAMPLE 69

Step A

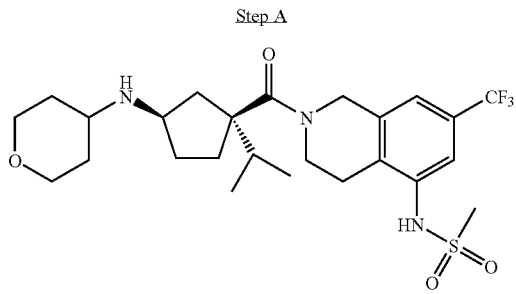

-continued

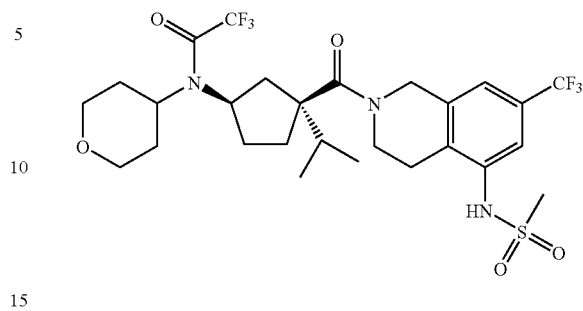

To a mixture of the product from Step B, Example 11 (200 mg, 0.363 mmol) and pyridine (287 µL, 3.82 mmol) in DCM (5 mL), was slowly added methanesulfonyl chloride (280 µL, 3.82 mmol) at 0° C. The reaction mixture was stirred at room temperature overnight and concentrated under vacuum. The residue was purified by flash column chromatography (silica gel, 100% EtOAc) to yield the title compound (241 mg, 100%). LC-MS calc. For C27H35F6N3O5S: 627.22; Found: 628 (M+H).

Step B

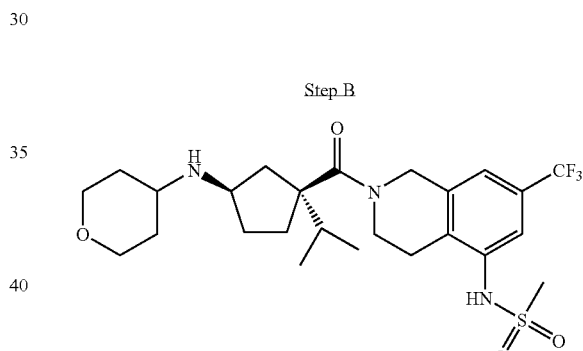

To a solution of the product from Step A, Example 69 (220 mg, 0.351 mmol) in ethanol (20 mL), was added sodium borohydride (300 mg, 7.93 mmol). The reaction mixture was stirred for 16 hr, and diluted by methanol. The extra sodium borohydride was destroyed by 4N HCl in dioxane and then the solvent was evaporated under vacuum. The residue was purified by preparative TLC (silica gel, 1000 micron) (developed by 8% [aq. NH4OH/MeOH 1/9]/ DCM) to yield the final product of the title compound as a free base. Its HCl salt (127 mg) was formed by treatment with 4N HCl/dioxane. $^1$H NMR (CDCl$_3$, 500 MHz): δ 7.54 (s, 1H), 7.22 (s, 1H), 4.75 (s, 2H), 3.92–3.98 (m, 2H), 3.82 (s, 2H), 3.55 (br s, 1H), 3.38 (m, 2H), 3.18 (m, 1H), 3.04 (s, 3H), 2.87 (m, 2H), 2.74 (m, 1H), 2.48 (br s, 1H), 2.02–2.16 (m, 2H), 1.74–1.90 (m, 4H), 1.57 (m, 1H), 1.37 (m, 2H), 1.25 (m, 1H), 0.86 (dd, 6H). LC-MS calc. for C25H36F3N3O4S: 531.24; Found: 532 (M+H).

EXAMPLE 70

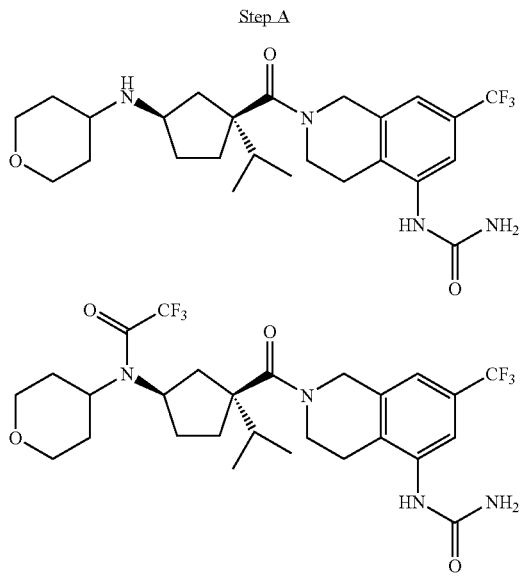

To a mixture of the product from Step B, Example 11 (100 mg, 0.182 mmol) and pyridine (36 mg, 0.455 mmol) in DCM (5 mL), was slowly added p-nitrophenyl chloroformate (73.4 mg, 0.364 mmol). The reaction mixture was stirred at room temperature for 2 hr. The reaction was stirred for another 1 hr after the $NH_3$ gas was bubbled into the reaction mixture for 1 min. The reaction was quenched by water, diluted by DCM, and separated the organic portion. After the aqueous portion was extracted by DCM, the combined organic portion was washed by water, 1N HCl solution, saturated $NaHCO_3$ solution, and brine, dried over $Na_2SO_4$, and concentrated. The residue was purified by preparative TLC (silica gel, 1000 micron) (developed by 100% EtOAc) to yield the title compound (108 mg, 100%). LC-MS calc. for C27H34F6N4O4: 592.25; Found: 593 (M+H).

Step B

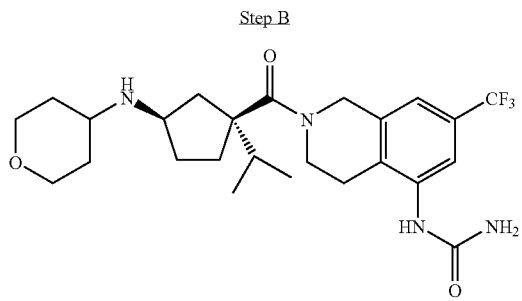

Example 70 was prepared starting from the above Step A as detailed in Example 69, Step B. $^1$H NMR (CDCl$_3$, 500 MHz): δ 8.17 (s, 1), 7.76 (s, 1H), 7.07 (s, 1), 5.50 (s, 2H), 4.75 (m, 2H), 3.90–4.08 (m, 3H), 3.73 (m, 1H), 3.36 (m, 2H), 3.17 (m, 1H), 2.62–2.82 (m, 3H), 2.42 (br s, 1H), 2.17 (m, 1H), 1.54–2.05 (m, 7H), 1.17–1.37 (m, 3H), 0.70–0.92 (m, 6H). LC-MS calc. For C25H35F3N4O3: 496.27; Found: 497 (M+H).

EXAMPLE 71

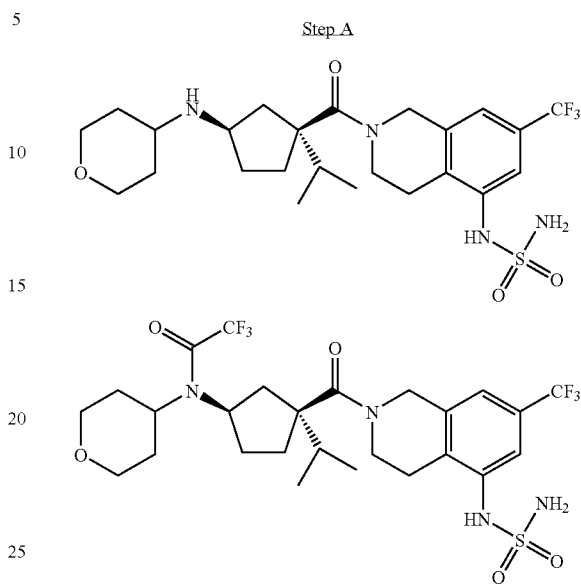

To a mixture of chlorosulfonyl isocyanate (79 μL, 0.91 mmol) in THF (5 mL), was added formic acid (34 μL, 0.91 mmol) at 0° C. The reaction mixture was warmed to room temperature and stirred for 2 hr. Then a solution of the product from Step B, Example 11 (100 mg, 0.182 mmol) and pyridine (74 μL, 0.91 mmol) in THF (5 mL) was slowly added into the reaction mixture. The reaction mixture was stirred for another 2 hr, diluted by EtOAc and added by 1N HCl. The aqueous layer was extracted by EtOAc. The combined organic portion was washed by saturated $NaHCO_3$ and brine, dried over $Na_2SO_4$, filtered and concentrated. The residue was purified by preparative TLC (silica gel, 1000 micron) (developed by 100% EtOAc) to yield the title compound (38 mg, 33%). LC-MS calc. for C26H34F6N4O5S: 628.22; Found: 629 (M+H).

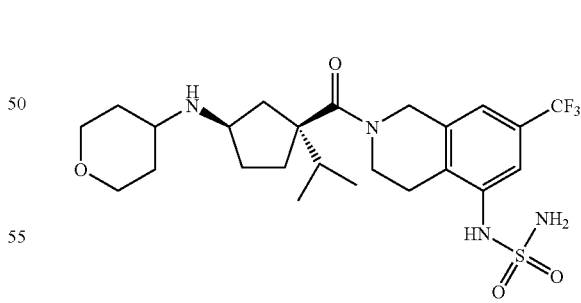

Example 71 was prepared starting from the above Step A as detailed in Example 69, Step B. $^1$H NMR (CDCl$_3$, 500 MHz): δ 7.64 (s, 1H), 7.22 (s, 1H), 4.74 (m, 2H), 3.80–3.97 (m, 4H), 2.66–3.40 (m, 10H), 2.44 (m, 1H), 2.07 (m, 2H), 1.55–1.80 (m, 5H), 1.30 (m, 3H), 2.17 (m, 1H), 0.80–0.94 (m, 6H). LC-MS calc. For C24H35F3N4O4S: 532.23; Found: 533 (M+H).

Example 72

Step A

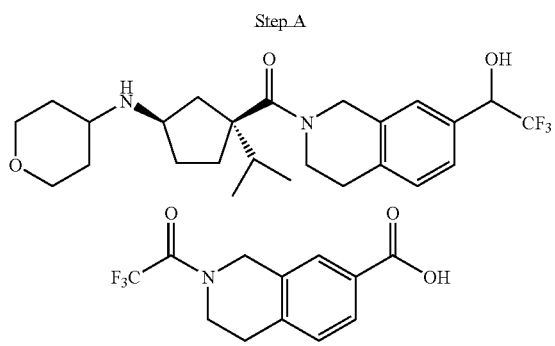

To a flask was added the solid amide (Step C, Intermediate 1) (6.0 g, 20 mmol), cooled at −78° C., then ClSO₂OH (8 mL, 120 mmol). The reaction mixture was stirred at RT for 3 days, dumped into ice-water, extracted with ethyl acetate, dried with anhydrous sodium sulfate and evaporated under reduced pressure. The title compound was obtained as a dark oil (6.15 g) which was used in next step without further purification.

Step B

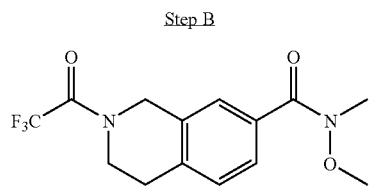

A mixture of the above acid (Step A, Example 72) (6.15 g, 22.5 mmol) and thionyl chloride (8.21 mL, 112.6 mmol) in benzene (100 mL) was refluxed for 1.5 hr. Then SO₂, HCl, solvent and extra thionyl chloride were removed under vacuum. The residue as acid chloride was dissolved by DCM (80 mL) and slowly added into a solution of N,N-dimethylhydroxylamine HCl salt (6.59 g, 67.53 mmol) and DIEA (11.76 mL, 67.53 mmol) in DCM (40 mL) at 0° C. The reaction mixture was stirred for 1 hr, diluted by DCM, washed by 10% NaHCO₃ and brine, dried over Na₂SO₄, filtered, and concentrated. The residue was purified by column chromatography (silica gel, 50% EtOAc/hexane) to yield the title compound (2.33 g, 32.7%). ¹H-NMR (400 MHz, CDCl₃) δ 7.50–7.61 (m, 2H), 7.22 (m, 1H), 4.81 (m, 2H), 3.86–3.94 (m, 2H), 3.57 (s, 3H), 3.38 (s, 3H), 3.01 (m, 2H). ESI-MS calc. For C14H15F3N2O3: 316.10; Found: 317 (M+H).

Step C

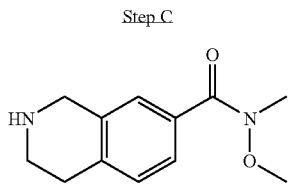

To a solution of the Weinrib amide (Step B, Example 72) (2.27 g, 7.18 mmol) in ethanol (44 mL), was added a solution of potassium carbonate (5.36 g, 38.77 mmol) in water (11 mL). The reaction mixture was refluxed at 95° C. for 5 hr, concentrated under vacuum, extracted by DCM (three times). The organic portion was washed by water and brine, dried over Na₂SO₄, filtered, and concentrated. The residue was purified by column chromatography (silica gel, 10% [aq. NH₄OH/MeOH 1/9]/DCM) to yield the title product (1.82 g, 100%). ESI-MS calc. For C12H16N2O2: 220.12; Found: 221 (M+H).

Step D

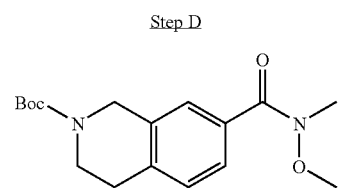

To a solution of the isoquinoline (Step B, Example 72) (1.80 g, 8.17 mmol) in DCM (100 mL), was added di-tert-butyl dicarbonate (2.68 g, 12.26 mmol). The reaction mixture was stirred overnight, and concentrated. The residue was purified by column chromatography (silica gel, 40% EtOAc/hexane) to yield the title product (1.68 g, 64%). ¹H-NMR (400 MHz, CDCl₃) δ 7.49 (d, J=8.0 Hz, 1H), 7.45 (s, 1H), 7.17 (d, J=8.0 Hz, 1H), 4.61 (s, 2H), 3.68 (t, J=5.8 Hz, 2H), 3.58 (s, 3), 3.37 (s, 3H), 2.88 (t, J=5.8 Hz, 2H), 1.51 (s, 9H).

Step E

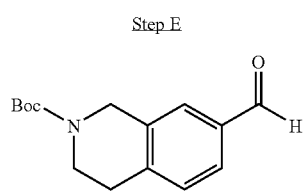

To a solution of the Boc-amide (Step D, Example 72) (1.65 g, 5.15 mmol) in THF (25 mL), cooled to −40° C., was added 1M lithium aluminum hydride in THF (5.15 mL, 5.15 mmol). The reaction was stirred for 30 min and then stirred at −20° C. for 1 hr. Iced-water was used to quench the reaction and the solvent was evaporated. The left aqueous portion was extracted by DCM (three times). The combined organic portion was dried over Na₂SO₄, filtered, and concentrated. The residue was purified by column chromatography (silica gel, 30% EtOAc/hexane) to yield the title product (587 mg, 43.8%). ¹H-NMR (400 MHz, CDCl₃) δ 9.99 (s, 1H), 7.70 (d, J=8.0 Hz, 1H), 7.65 (s, 1H), 7.32 (d, J=8.0 Hz, 1H), 4.66 (s, 2H), 3.70 (t, J=5.8 Hz, 2H), 2.93 (t, J=5.8 Hz, 2H), 1.51 (s, 9H).

Step F

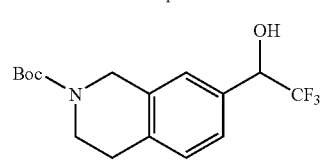

To a solution of the aldehyde (Step E, Example 72) (560 mg, 2.14 mmol) in THF (10 mL), was added 0.5M trimethyl (trifluoromethyl)silane in THF (5.14 mL, 2.57 mmol). The reaction was cooled to 0° C., and then 1.0 M tetrabutylammonium fluoride in THF (100 μL, 15 mg) was added. The reaction mixture was stirred at room temperature for 4 hr, and then concentrated. The residue was purified by column chromatography (silica gel, 30% EtOAc/hexane) to yield the title compound (557 mg, 64.5%). ¹H-NMR (400 MHz, CDCl₃) δ 7.18–7.32 (m, 3H), 5.01 (m, 1H), 4.60 (s, 2H), 3.67 (t, J=5.5 Hz, 2H), 2.84–2.98 (m, 3H), 1.52 (s, 9H).

Step G

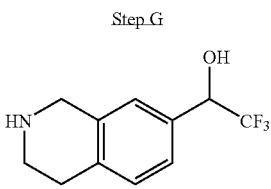

A mixture of the alcohol (Step F, Example 72) (100 mg, 0.302 mmol) in 4N HCl/Dioxane was stirred at room temperature overnight. Solvent was evaporated to yield the title product (87 mg, 100%). ESI-MS calc. For C11H12F3NO: 231.09; Found: 232 (M+H).

Step H

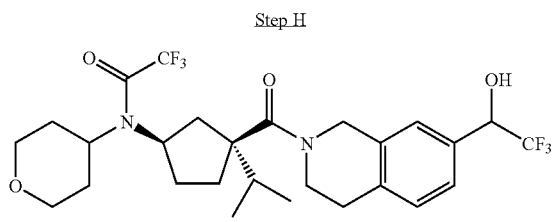

To a solution of INTERMEDIATE 5 (106 mg, 0.302 mmol) in DCM (2 mL), was added 2.0 M oxalyl chloride in DCM (226 μL, 0.453) and trace amount of DMF. The reaction mixture was stirred for 1 hr, and concentrated. The residue was put on high vacuum for 2 hr and dissolved in DCM (40 mL). The formed acid chloride was added into a solution of the amine (Step G, Example 72) (HCl salt, 81 mg, 0.302 mmol) and DIEA (63 μL, 0.363 mmol) in DCM (2 mL) at 0° C. The reaction mixture was stirred overnight, diluted by DCM, washed by 10% NaHCO₃ and brine, dried over Na₂SO₄, filtered and concentrated. The residue was purified by preparative TLC (1000 micron) (developed by 50% EtOAc/hexane) to yield the title product (113 mg, 66%). LC-MS calc. For C27H34F6N2O4: 564.24; Found: 565 (M+H).

Step H

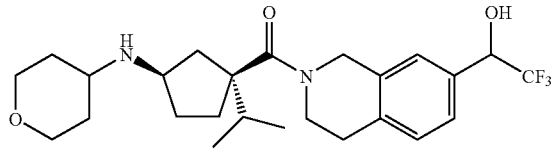

To a solution of the amide (Step H, Example 72) (110 mg, 0.195 mmol) in ethanol (4 mL), was added sodium borohydride (147.5 mg, 3.90 mmol). The reaction was stirred for 4 hr and then quenched by methanol. The extra sodium borohydride was destroyed by 4N HCl in dioxane. After the solvent was evaporated under vacuum, the residue was dissolved in DCM, washed by 10% NaHCO3 solution, water, and brine, dried over Na₂SO₄, filtered and concentrated. The residue was purified by preparative TLC (1000 micron) (developed by 6% [aq. NH₄OH/MeOH 1/9]/DCM) to yield the final product of the title compound as a free base. Its HCl salt (81.5 mg) was formed by treatment with 4N HCl/dioxane. ¹H-NMR (400 MHz, CDCl₃) δ 7.29 (d, J=8.0 Hz, 1H), 7.22 (s, 1H), 7.15 (d, J=8.0 Hz, 1H), 4.95 (m, 1H), 4.66 (s, 2H), 3.95 (d, J=11.5 Hz 2H), 3.72 (m, 2H), 3.38 (t, J=11.0 Hz, 2H), 3.16 (m, 1H), 2.84 (m, 2H), 2.75 (m, 1H), 2.47 (br s, 1H), 2.09 (m, 2H), 1.88 (m, 2H), 1.77 (m, 2H), 1.57 (m, 1H), 1.38 (m, 2H), 1.26 (m, 1H), 0.78–0.92(m, 6H). LC-MS calc. For C25H35F3N2O3: 468.26; Found: 469 (M+H).

EXAMPLE 73

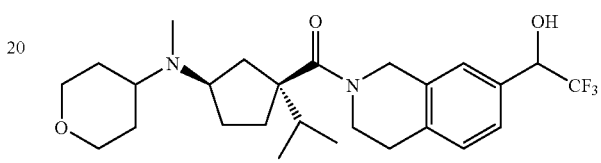

To a solution of Example 72 (58 mg, 0.124 mmol) in DCM (4 mL) was added formaldehyde (37%, 100 mg, 1.24 mmol) and molecular sieve (4 Å, 800 mg). After the reaction mixture was stirred for 2 hr, the sodium triacetoxyborohydride (140 mg, 0.620 mmol) was added. The reaction was stirred overnight, diluted by DCM, washed by 10% NaHCO3, water and brine, dried over Na₂SO₄, filtered, and concentrated. The residue was purified by preparative TLC (1000 micron) (developed by 5% [aq. NH₄OH/MeOH 1/9]/DCM) to yield the final product of the title compound as a free base. Its HCl salt (42.7 mg) was formed by treatment with 4N HCl/dioxane. 1H-NMR (400 MHz, CDCl₃) δ 7.10–7.30 (m, 3H), 4.94 (m, 1H), 4.56–4.70 (m, 3H), 4.02 (d, J=10.5 Hz, 2H), 3.74 (m, 2H), 3.38 (m, 2H), 2.84 (m, 4H), 2.62 (m, 1H), 2.02–2.22 (m, 5H), 1.84 (m, 2H), 1.64 (m, 4H), 1.43 (m, 2H), 0.76–0.95(m, 6H). LC-MS calc. For C26H37F3N2O3: 482.28; Found: 483 (M+H).

EXAMPLE 74

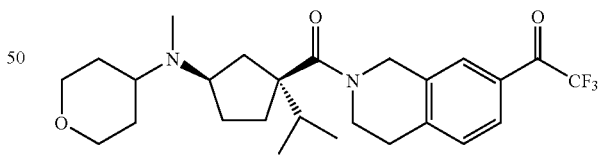

To a solution of Example 73 (29.8 mg, 0.0618 mmol), and triethylamine (51.6 μL, 0.371 mmol) in DMSO (1 mL), was slowly added sulfur trioxide pyridine complex (140 mg, 0.880 mmol) in DMSO (1 mL). The reaction was stirred overnight, diluted by DCM, washed by water (twice) and brine, dried over Na₂SO₄, filtered, and concentrated. The residue was purified by preparative TLC (1000 micron) (developed by 5% [aq. NH₄OH/MeOH 1/9]/DCM) to yield a mixture of the final title compound and starting materials. Reversed phase HPLC (C18 column) separation to yield the title compound as trifluoroacetic acid salt (2.1 mg). LC-MS calc. For C26H35F3N2O3: 480.26; Found: 481 (M+H).

EXAMPLE 75

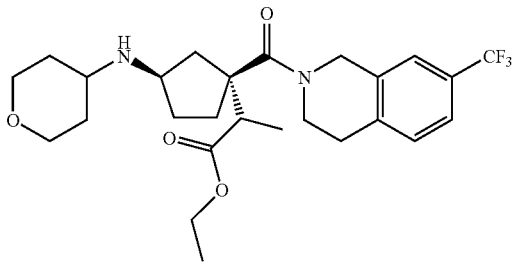

Step A

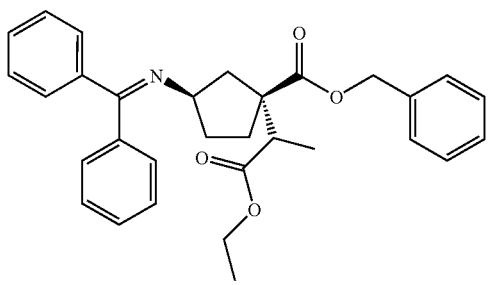

A solution of diisopropylamine (2.58 mL, 18.14 mmol) in THF (50 mL) was cooled to −78° C. and a solution of nBuLi (2.5 M, 7.25 mL, 18.14 mmol) was added via syringe. After 15 minutes at −78° C. a solution of the benzyl ester Intermediate 5, Step B (5.35 g, 13.95 mmol) in THF (50 mL) was added, and the stirring at −78° C. was continued for another 1 hr. To this solution of the enolate was added 3.62 mL (27.90 mmol) of ethyl 2-bromopropionate and the alkylation was allowed to come to completion at −17° C. overnight. The reaction was quenched by pouring onto saturated solution of ammonium chloride, and the crude product was extracted with ethyl acetate. After drying (anhydrous magnesium sulfate), the solution was concentrated and the crude product was purified by flash chromatography (Kieselgel LoBar column, ethyl acetate:hexanes/1:4) to yield 1.66 g (25%) of the higher eluting, 1,3-cis-diastereoisomer. LC MS: for $C_{31}H_{33}NO_4$ calculated: 483.24, found 484.15 $[M+H]^+$.

Step B

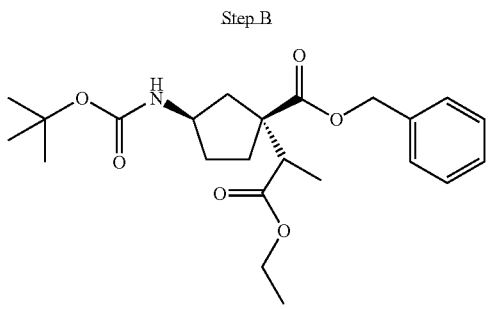

A solution of the Schiff base from previous step (1.66 g, 3.411 mmol) in THF (30 mL) was treated 2N HCl (10 mL) and stirred at room temperature for 6 hrs. The volatiles were removed in vacuo, and the residue was dissolved in dichloromethane (50 mL). Solid $BOC_2O$ (1.81 g) was added, followed by 50 mL of saturated solution of sodium bicarbonate. The reaction mixture was vigorously stirred overnight, the organic phase was separated and the solvent was removed in vacuo. The pure product was obtained by gradient column chromatography (silica gel, ethyl acetate: hexanes/0% to 50%), 849 mg (59%). LC MS: for $C_{23}H_{33}NO_6$ calculated: 419.23, found 320.20 [M+H-BOC]$^+$.

Step C

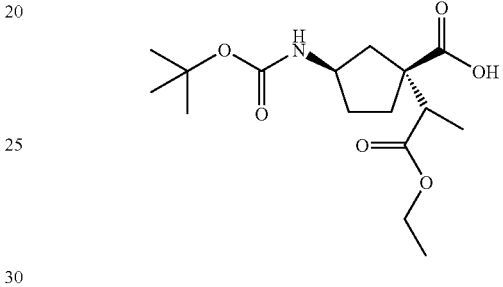

The benzyl ester from previous step (830 mg, 1.98 mmol) was hydrogenated under balloon pressure in the presence of Pd/C (130 mg, 10% Pd) in ethanol for 3 hrs. The catalyst was filtered off, and the filtrate was evaporated to dryness. The remaining crude product (617 mg, 95%) was used in the next step without further purification.

Step D

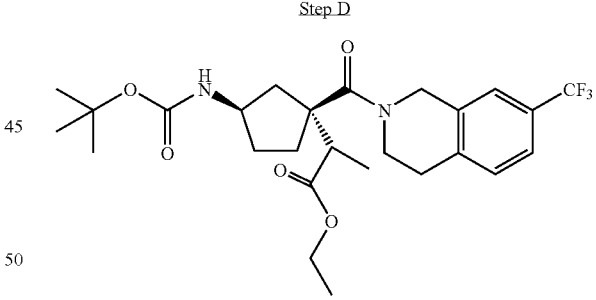

A solution of the acid from the previous step (308 mg, 0.934 mmol), Intermediate 1 (188 mg, 0.934 mmol) and DMAP (68 mg, 0.56 mmol) in dichloromethane (10 mL) was treated with PyBrop (435.4 mg, 0.934 mmol) and diisopropyl ethylamine (174 µL, 2.80 mmol) and stirred overnight at room temperature. The reaction mixture was quenched by pouring onto saturated solution of sodium bicarbonate, and extracted with dichloromethane. After drying (anhydrous magnesium sulfate) the solvent was evaporated in vacuo to yield 276 mg (58%) of the pure product. LC MS: for $C_{26}H_{35}N_3FO_5$ calculated: 512.25, found 513.25 $[M+H]^+$.

Step E

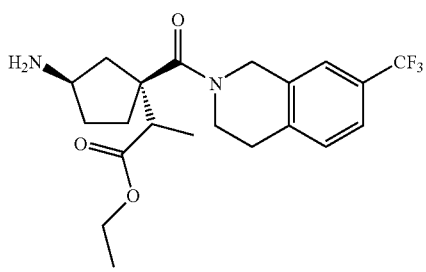

A solution of the BOC-protected amine from previous step (275 mg, 0.5363 mmol) in dichloromethane (3 mL) was treated with trifluoroacetic acid (3 mL) and stirred at room temperature for 1 hr. The volatiles were removed in vacuo, and the crude product (300 mg) was used in the next step as obtained. LC MS: for $C_{21}H_{27}F_3N_2O_3$ calculated: 412.20, found 313.20 $[M+H]^+$.

Step F

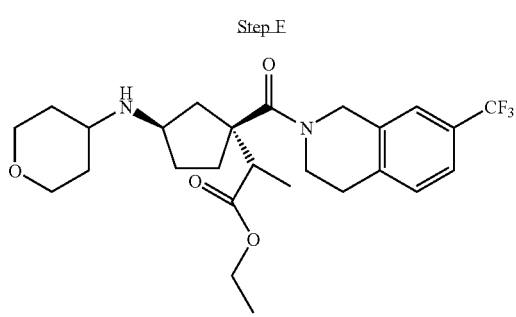

A solution of the amine trifluoroacetate from previous step (300 mg, app. 0.537 mmol), tetrahydropyran-4-one (149 μL, 1.611 mmol), 4 A molecular sieves (crushed, 540 mg) and diisopropyl ethylamine (95 μL, 1.611 mmol) in dichloroethane (6 mL) was treated with sodium triacetoxyborohydride (569 mg, 2.685 mmol) and stirred at room temperature for 24 hrs. The reaction was quenched with saturated solution of sodium bicarbonate and the crude product was extracted into dichloromethane. The combined organic extracts were back-washed with brine, dried with anhydrous sodium sulfate and the solvent was removed in vacuo. The residue was purified by preparative TLC (eluent: ethyl acetate:ethanol:ammonium hydroxide/90:8:2) to yield 75.2 mg (28%) of the higher eluting and 132 mg (50%) of the lower eluting enantiomer. LC MS: for $C_{26}H_{35}F_3N_2O_4$ calculated: 496.25, found 497.35 $[M+H]^+$ (higher eluting enantiomer) and 497.35 $[M+H]^+$ (lower eluting enantiomer).

EXAMPLE 76

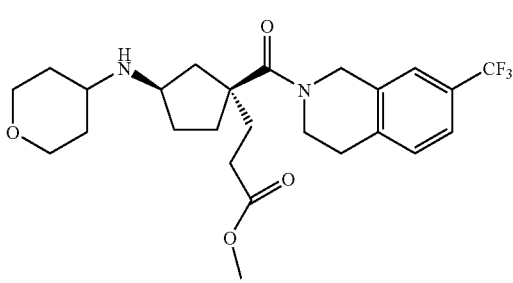

This compound was synthesized in a procedure analogous to that described for Example 75, except that in Step A ethyl 2-bromopropionate was replace by methyl 3-bromopropionate. LC MS: for $C_{25}H_{33}F_3N_2O_4$ calculated: 482.24, found 483.25 $[M+H]^+$.

EXAMPLE 77

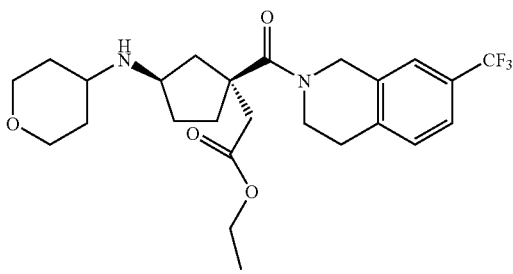

This compound was synthesized in a procedure analogous to that described for Example 75, except that in Step A ethyl 2-bromopropionate was replace by ethyl 2-bromoacetate. LC MS: for $C_{25}H_{33}F_3N_2O_4$ calculated: 482.24, found 483.25 $[M+H]^+$.

EXAMPLE 78

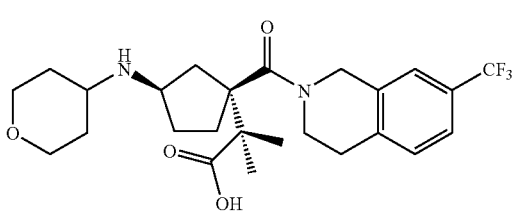

Step A

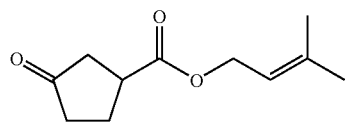

A solution of 3-oxocyclopentanecarboxylic acid (6.20 g, 48.4, Stetter, H., Kuhlman, H., *Liebigs Ann. Chemie,* 1979, 7, 944–9) and 3-methyl-2-buten-1-ol (5.90 mL, 58.1 mmol) and DMAP (140 mg) in dichloromethane (50 mL) was treated with EDC and stirred at room temperature overnight. The reaction was quenched by pouring onto 100 mL of water, and the product was extracted with dichloromethane. The combined organic extracts were washed with brine and dried with anhydrous magnesium sulfate. Evaporation of the solvent in vacuo gave 10.51 g (100%) of the desired ester. $^1$H NMR (CDCl$_3$, 500 MHz): 5.33 (bt, J=7.33 Hz, 1M), 4.62 (d, J=7.32 Hz, 2H), 3.12 (ddd, J=14.9, 8.0, 6.9 Hz, 1H), 2.55 to 2.10 (m, 6H0, 1.77 (s, 3H), 1.72 (s, 3H).

Step B

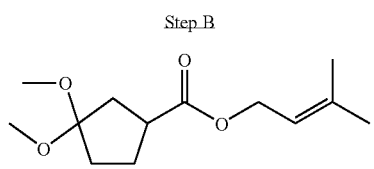

A solution of the ester from the previous step (10.50 g, 53.78 mmol) and TsOH (500 mg) in dichloromethane (50 mL) was treated with trimethyl orthoformate (24 mL, 220 mmol) and stirred at room temperature overnight. The reaction was quenched by pouring onto a saturated solution of sodium bicarbonate and the crude product was extracted with dichloromethane. The combined organic layers were washed with brine, dried with anhydrous magnesium sulfate, and the solvent was evaporated in vacuo. The residue was further purified by distillation (b.p.: 123° C.@4 mm Hg) to give 8.27 g (63%) of the desired acetal. $^1$H NMR (CDCl$_3$, 500 MHz): 5.33 (bt, J=7.09 Hz, 1H), 4.57 (d, J=7.32 Hz, 2H), 3.21 (s, 3), 3.19 (s, 3H), 2.87 m, 1H), 2.15 to 1.80 (bm, 6H), 1.76 (s, 3H), 1.70 (s, 3H).

Step C

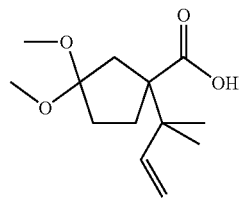

A solution of diisopropylamine (14.28 mL, 101.9 mmol) in THF (200 mL) was cooled to −78° C. and n-butyllithium (40.76 mL, 2.5 M in hexane, 110 mmol) was added via syringe. After 10 minutes, the neat ester from the previous step (12.34 g, 50.94 mmol) was added via syringe, followed after 20 minutes by neat chloro trimethylsilane (12.93 mL, 101.9 mmol). The solution was allowed to warm up to room temperature over 3 h, after which time it was quenched by pouring onto a 10% aqueous solution of citric acid. The crude product (19.75 g) was obtained by extraction with diethyl ether, drying (magnesium sulfate) and evaporation of the solvent in vacuo. It was further purified by flash chromatography (silica gel, ethyl acetate:hexane/2:3) to yield 5.25 g (43%) of the pure product. $^1$H NMR (CDCl$_3$, 500 MHz): 5.95 (dd, J=17.2, 10.8 Hz, 1H), 5.07 (dd, J=10.75, 0.9 Hz, 1H), 5.25 (dd, J=17.40, 0.9 Hz, 1H), 3.21 (s, 3H), 3.14 (s, 3H), 2.58 (d, J=13.73 Hz, 1H), 2.28 (m, 1H), 1.88 to 1.76 (bm, 3H), 1.73 to 1.66 (bm, 2H), 1.084 (s, 3H), 1.00 (s, 3H). $^{13}$C NMR (CDCl$_3$, 125 MHz): 174.7, 143.9, 113.1, 112.3, 58.7, 53.8, 50.7, 41.4, 36.5, 31.4, 24.7, 23.1, 22.0.

Step D

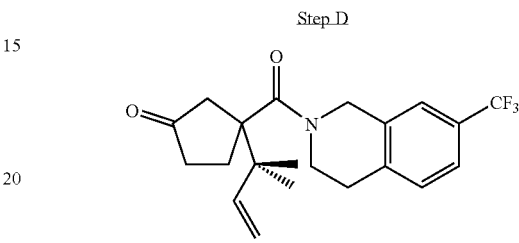

A solution of the crude acid, from previous step (2.80 g, 14.27 mmol) was dissolved in benzene (20 mL) and thionyl chloride (2.08 mL, 28.53 mmol) was added. The reaction mixture was heated to reflux for 3 hrs, whereupon a small quench with methanol indicated 100% ester formation. The volatiles were removed in vacuo, and the crude acid chloride was dissolved in benzene (20 mL) and ethyl diisopropylamine (5.41 mL, 31.08 mmol) was added. This solution was treated with Intermediate 1, and the resulting mixture was stirred at room temperature for 1 hr. The reaction was quenched with water, and the crude product was extracted into ethyl acetate. The solvent was removed in vacuo, and the residue (4.50 g) was further purified by flash chromatography to yield 2.373 g (60%) of the pure product. $^1$H NMR (CDCl$_3$, 500 MHz): 7.46 (d, J=8.01 Hz, 1H), 7.34 (s, 1H), 7.28 (d, J=6.41 Hz, 1H), 5.71 (dd, J=17.0, 11.0 Hz, 1H), 5.08 (d, J=17.4 Hz, 1H), 5.02 (d, J=10.8 Hz, 1H), 4.79 (d, J=17.0 Hz, 1H), 4.71 (d, J=17.0 Hz, 1H), 3.90 (m, 1H), 3.75 (m, 1H), 2.93 (m, 2H), 2.80 (d, J=18.8 Hz, 1H), 2.75 (d, J=18.5 Hz, 1H), 2.50 (m, 2H), 2.30 (m, 2H), 1.08 (s, 6H).

Step E

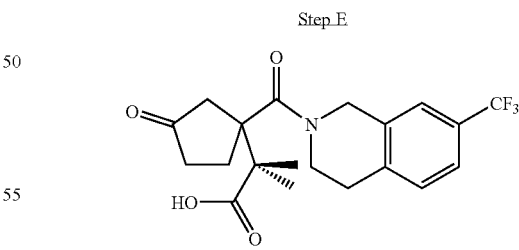

A solution of the olefin from previous step (760 mg, 2.00 mmol) in acetonitrile (4 mL) tetrachloromethane (4 mL) and water (6 mL) was treated under vigorous stirring with solid RuCl$_3$ (11 mg, 0.03 mmol, followed by sodium periodate (1.75 g, 8.20 mmol) and the stirring was continued for 3 hrs. The reaction mixture was diluted with dichloromethane and the phases were separated. The volatiles were removed in vacuo, and the dark residue was purified by preparative TLC (ethyl acetate:hexanes/1:1) to yield 145 mg (16%) of the desired acid. LC MS: for $C_{20}H_{22}F_3NO_3$ calculated: 381.16, found 382.15 $[M+H]^+$.

Step F

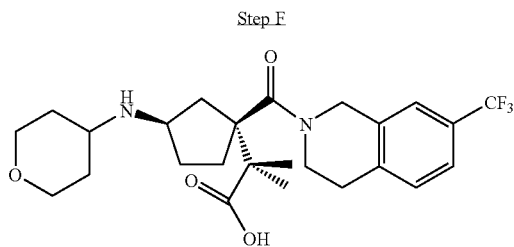

This compound was synthesized starting from the previously described ketone and Intermediate 3 in a procedure analogous to that described for Example 75, Step F. LC MS: for $C_{25}H_{33}F_3N_2O_4$ calculated: 482.24, found 483.25 $[M+H]^+$.

EXAMPLE 79

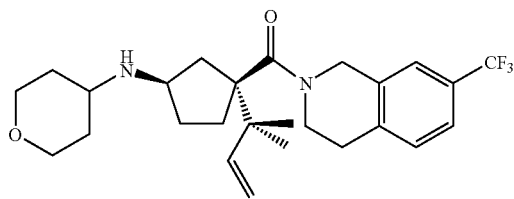

This compound was synthesized starting from the ketone described in Example 78, Step D and Intermediate 3 in a procedure analogous to that described for Example 75, Step F. LC MS: for $C_{26}H_{35}F_3N_2O_2$ calculated: 464.27, found 465.30 $[M+H]^+$.

EXAMPLE 80

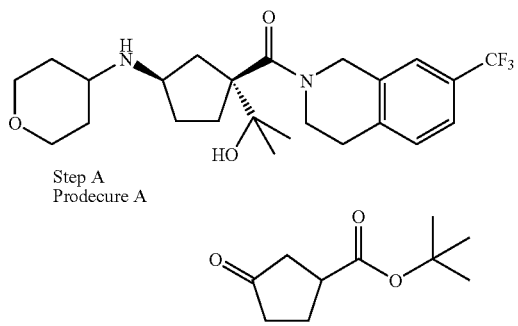

Step A
Prodecure A

A solution of 3-oxo-cyclopentane carboxylic acid (Stetter, H., Kuhlmann, H. Liebigs Ann. Chem., 1979, 7, 944–9) (5.72 g, 44.6 mmol) in dichloromethane (30 mL) was treated with N,N'-di-iso-propyl-O-tert-Butyl-iso-urea (21.2 mL, 89.3 mmol) and the reaction mixture was stirred at ambient temperature overnight. The precipitated N,N'-di-iso-propyl urea was filtered off, the filtrate concentrated in vacuo and the residue was purified by distillation (b.p.: 125–129° C.@18 mmHg) to yield 4.7446 g (58%) of the pure product.

$^1$H NMR (500 MHz, CDCl$_3$): 3.02 (p, J=7.8 Hz, 1H), 2.05–2.50 (m, 6H), 1.45 (s, 9H). $^{13}$C NMR (125 MHz, CDCl$_3$): 217.00, 173.47, 80.99, 41.88, 41.14, 27.94, 26.57.

Procedure B

A 2 L round RBF was charged with anhydrous magnesium sulfate (113 g, 940 mmol) and dichloromethane (940 mL). While stirring, the suspension was treated with concentrated sulfuric acid (12.5 mL, 235 mmol) followed after 15 minutes by 3-oxo-cyclopentane carboxylic acid (30.1 g, 235 mmol). After stirring for 15 minutes, tert-butanol (87 g, 1.2 mol) was added. The reaction vessel was closed with a stopper to aid retention of isobutylene, and stirred at ambient temperature for 72 h The solid was filtered off through a plug of Celite and the volume of the filtrate was reduced to approximately 500 mL, and washed with a saturated solution of sodium bicarbonate (2×150 mL). The organic phase was dried with anhydrous magnesium sulfate, filtered, and the solvent was removed by distillation at reduced pressure (180 mmHg). The crude product was purified by distillation to yield 39.12 g (90%) of pure product.

Step B

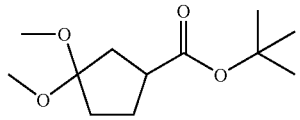

A solution of tert-Butyl 3-oxocyclopentane carboxylate (11.54 g, 62.64 mmol) in dichloromethane (200 mL) was treated with trimethyl orthoformate (41.4 mL, 251 mmol) in the presence of p-toluenesulfonic acid (400 mg) and stirred at room temperature for 48 h. The dark reaction mixture was poured onto a saturated solution of sodium bicarbonate, and the crude product was extracted with dichloromethane. The combined organic extracts were dried with anhydrous magnesium sulfate, the solvent was removed in vacuo, and the crude product was purified by distillation (b.p.: 104° C.@4 mmHg) to yield 12.32 g (85%) of the desired product. $^1$H NMR (500 MHz CDCl$_3$): 3.21 (s, 3H), 3.20 (s, 3H), 2.80 (m, 1H), 2.10 to 1.80 (bm, 6H), 1.46 (s, 9H). $^{13}$C NMR (125 MHz, CDCl$_3$): 174.9, 111.2, 80.3, 67.8, 49.2, 42.5, 37.4, 33.8, 28.3, 22.0.

Step C

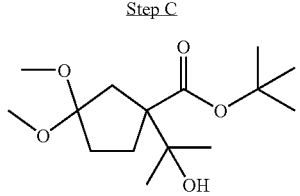

A solution of diisopropylamine (5.6 mL, 40 mmol) in dry tetrahydrofuran (40 mL) was cooled to −78° C. and it was treated with n-butyllithium (16 mL, 40 mmol, 2.5M solution in hexanes). The neat ester from the previous step (5.8 g, 25 mmol) was added via syringe, and the enolate was allowed to form for 30 minutes at −15° C. The temperature of the reaction mixture was lowered to −78° C. once again, and acetone (5.5 mL, 75 mmol) was added via syringe. The reaction was allowed to proceed at −15° C. overnight, and it was quenched by pouring the mixture onto 150 mL of 10% aqueous citric acid. The crude product was extracted into diethyl ether, the combined extracts were dried and the solvent was removed in vacuo. The crude product (8.31 g) was further purified by column chromatography (Silica gel, ethyl acetate+hexanes/1:1) to yield 4.31 g (60%) of pure product. $^1$H NMR (500 MHz, CDCl$_3$): 3.21 (s, 3H), 3.18 (s, 3H), 2.46 (d, J=14.2 Hz, 1H), 2.20 (m, 1H), 1.99 (d, J=13.96 Hz), 1.85 (m, 3H), 1.50 (s, 9H), 1.21 (bs, 6H). $^{13}$C NMR (125 MHz, CDCl$_3$): 175.9, 110.4, 81.8, 73.3, 60.6, 49.5, 49.0, 39.5, 33.6, 28.2, 27.9, 26.7, 25.6.

Step D

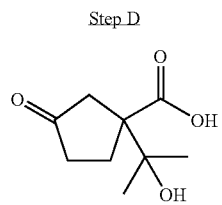

The solution of the ester-acetal (4.31 g, 14.9 mmol) from the previous step in dichloromethane (4 mL) was treated with trifluoroacetic acid (4.0 mL) and stirred at room temperature overnight. The solvent was evaporated in vacuo, and the residue was co distilled several times with hexane to yield 4.14 g of the desired acid. $^1$H NMR (500 MHz, CDCl$_3$): 2.84 (d, J=18.31 Hz), 2.26 (d, J=18.76 Hz), 2.48 to 2.28 (m, 4H), 1.41 (s, 3H), 1.37 (s, 3H).

Step E

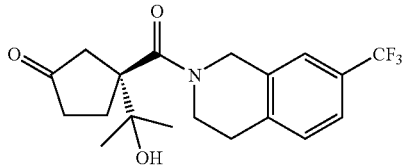

A solution of the acid from previous step (271 mg, 1.4543 mmol) in benzene (8 mL) was treated with thionyl chloride (848 µL, 11.6344 mmol) and the resulting mixture was heated to 65° C. for 30 minutes. The reaction progress was monitored by MeOH quench and TLC comparison of the amount of formed methyl ester vs. the remaining acid. The reaction mixture was then evaporated to dryness, co-distilled with benzene (3×) and the residue was dissolved in dichloromethane (8 mL). To this was added 292 mg (1.4543 mmol) of Intermediate 1, and the reaction mixture was stirred at room temperature for 30 minutes. It was diluted with dichloromethane and washed with 2N HCl and brine, dried with anhydrous magnesium sulfate and the solvent was removed in vacuo. Purification by preparative TLC (four plates, 1000 µm, dichloromethane:acetone/4:1) gave 437 mg of pure product. $^1$H NMR (500 MHz, CDCl$_3$): 7.43 (bd, J=7.78 Hz, 1H), 7.35 (bs, 1H), 7.26 (bd, J=7.78 Hz, 11), 4.87 (d, J=16.7 Hz, 1H), 4.80 (d, J=16.70 Hz, 1H), 3.97 (m, 1H), 3.80 (m, 1H), 2.94 (m, 2H), 2.78 (m, 2H), 2.61 (m, 1H), 2.50 to 2.35 (bm, 3H), 1.25 (s, 6H). $^{13}$C NMR (125 MHz, CDCl$_3$): 217.6, 175.0, 134.1, 129.2, 123.4, 123.1, 74.6, 59.0, 47.9, 46.6, 43.4, 37.1, 29.0, 28.7, 27.1, 26.8. LC MS: for C$_{19}$H$_{22}$F$_3$NO$_3$ calculated: 369.16, found 370.15 [M+H]$^+$.

Step F

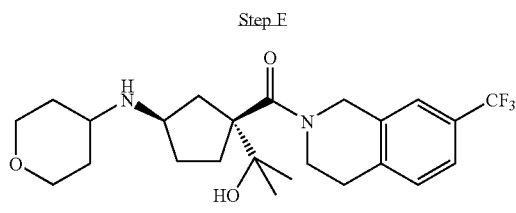

A solution of the ketone synthesis of which was described in step E of this example (320 mg, 0.866 mmol), Intermediate 3 (357 mg, as hydrochloride, 2.598 mmol) 4 A molecular sieves (crushed, 618 mg), diisopropylethylamine (452 µL, 2.598 mmol) in dichloroethane (10 mL) was treated with sodium triacetoxyborohydride (918 mg, 4.33 mmol) and the reaction mixture was stirred at room temperature for 18 hrs. It was diluted with dichloromethane, washed with saturated solution of sodium bicarbonate, this was back-washed with dichloromethane. The combined organic extracts were dried with anhydrous sodium sulfate and the solvent was evaporated to dryness. The remaining crude product was purified by preparative TLC (ethyl acetate:ethyl alcohol:ammonium hydroxide/90:8:2) to yield 140 mg (36%) of the higher eluting cis-racemic pair and 156.8 mg (40%) of the lower eluting trans-isomer. LC MS: for C$_{24}$H$_{33}$F$_3$N$_2$O$_3$ calculated: 454.24, found 455.20 (both isomers) [M+H]$^+$.

EXAMPLE 80

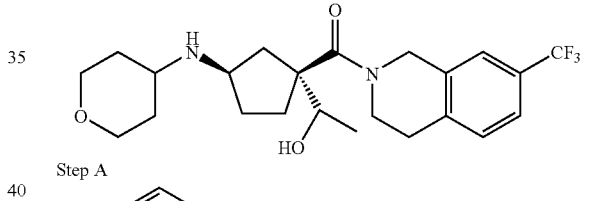

Step A

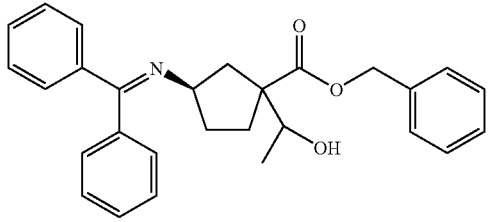

A solution of diisopropylamine (2.70 mL, 19.27 mmol) in tetrahydrofuran (20 mL) was cooled to −78° C. and a solution of nBuLi in hexanes (7.70 mL, 2.5M, 19.27 mmol) was added via syringe, followed by a solution of the Schiff base, preparation of which was described in Intermediate 9, Steps A to C (5.685 g, 14.82 mmol) in THF (10 mL). The enolate was allowed to form for 3 hrs at −78° C., after which time the neat acetaldehyde (1.00 mL, 29.65 mmol) was added. The reaction was quenched with addition of aqueous citric acid (200 mL, 10%) and the crude product was extracted into diethyl ether. Drying (anhydrous magnesium sulfate) and evaporation of the solvent gave the crude desired product (6.16 g). This was further purified by flash chromatography (deactivated silica gel, ethyl acetate:hexanes/3:7) to yield the desired cis-isomer (2.32 g, 54%). This Schiff base was found to be unstable, and was used in the next step without delay. LC-MS for C$_{28}$H$_{29}$NO$_3$ [M +H]$^+$ calculated: 428.21, found 428.20.

Step B

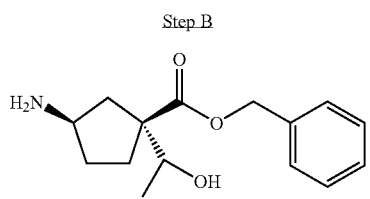

The Schiff base preparation of which was described in the previous step (2.323 g, 5.4334 mmol) was dissolved in THF (20 mL) and 2N HCl was added. The reaction mixture was stirred at room temperature 2 hrs, after which time the volatiles were removed in vacuo. The resulting mixture of the desired amine hydrochloride and benzophenone was used in the next step without further purification.

Step C

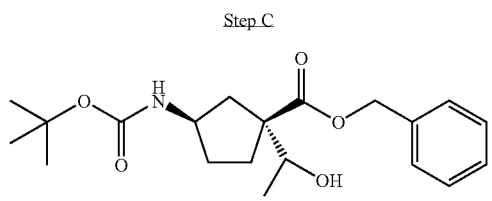

The crude product from the previous step (max 5.4334 mmol) was dissolved in dichloromethane (50 mL), $BOC_2O$ (2.371 g, 10.8668 mmol) were added followed by 50 mL of saturated solution of sodium bicarbonate. The reaction mixture was vigorously stirred at root temperature for 1 hr. The layers were separated, the aqueous phase was washed with dichloromethane. The combined organic extracts were dried (anh. magnesium sulfate) and the solvent was evaporated in vacuo. Final purification by gradient flash chromatography (ethyl acetate:hexanes/0% to 40%) gave the desired BOC-protected amine (619 mg, 32%, two steps) as a diastereoisomeric mixture (3:2) of two isomers. LC-MS for $C_{20}H_{29}NO_5$ [M +H]$^+$ calculated: 364.20, found 264.20 (loss of the BOC group).

Step D

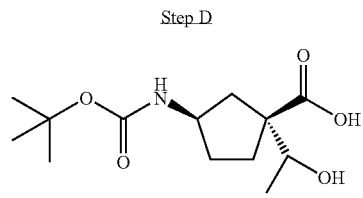

This acid was prepared by standard hydrogenation of the benzyl ester (the above step 3) on 10% Pd/C in methanol. The crude product was used in next step without further purification.

Step E

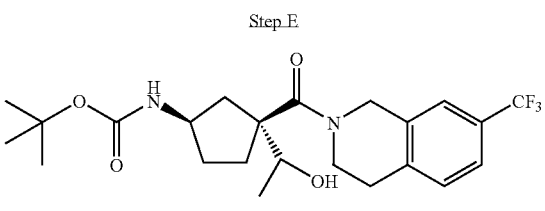

A solution of the acid from the previous step (760 mg, max 2.50 mmol), Intermediate 1 (1.00 g, 5.00 mmol) and 1-hydroxy-7-azobenzotriazole (340 mg, 2.50 mmol) in dichloromethane (20 mL) was treated with EDC (1.44 g, 7.50 mmol) and the resulting mixture was stirred at room temperature overnight. The reaction was quenched with water, and the product was extracted into dichloromethane. The combined organic extracts were dried (anh. magnesium sulfate) and the solvent was removed in vacuo. The residue (1.4383 g) was purified by MPLC (eluant gradient 20–100% ethyl acetate/hexane to afford 282 mg (25%) of the pure product. $^1$H NMR (CDCl$_3$, 500 MHz) indicated a mixture of isomeric alcohols in a ratio of about 2 to 3. LC-MS for $C_{23}H_{31}F_3N_2O_4$ [M +H]$^+$ calculated: 457.22, found 357.10 (loss of the BOC group).

Step F

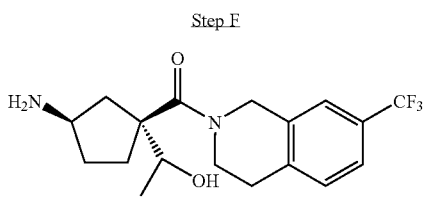

The solution of the BOC-protected amine from the previous step (81 mg, 0.177 mmol) in dichloromethane (3 mL) was treated with TFA (3 mL) and the resulting mixture was stirred at room temperature for 2 hrs. The volatiles were removed in vacuo to yield 86 mg (100%) of the crude product. LC-MS for $C_{18}H_{23}F_3N_2O_2$ [M+H]$^+$ calculated: 357.17, found 357.25.

Step G

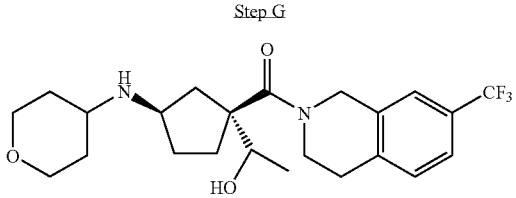

This compound was synthesized from the previously described amine and tetrahydropyran-4-one according to the procedure described in Example 75, Step F. The respective diastereoisomers were separated by preparative TLC (dichloromethane:methanol:ammonium hydroxide/90:9:1). LC-MS for $C_{23}H_{31}F_3N_2O_2$ [M+H]$^+$ calculated: 441.23, found (both isomers) 441.25.

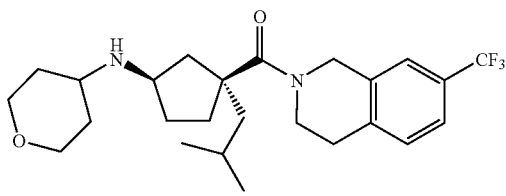

Step A

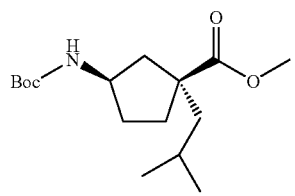

A solution of the product from Step B Intermediate 4 (5.0 g, 15.2 mmol) in anhydrous THF (20 ml) was added to a solution of freshly prepared LDA (19.52 mmol in 35 ml of THF at −78° C. and the resulting dark-brown mixture stirred for 45 min. A solution of 1-Iodo-2-methylpropane (2.25 ml) was then added and the resulting mixture stirred at −78° C. for 3 h. The mixture was then stirred at −25° C. for 1 hr (yellow solution) and quenched with saturated aqueous ammonium chloride. The mixture was extracted with ethylacetate (×3) and the combined organic layers washed with brine, dried (MgSO$_4$) and conc. in vacuo. The resulting oil was dissolved in THF (30 ml) and treated with 10 ml of 2N HCl and stirred for 3 h. The aqueous THF was evaporated to afford a clear brown oil, which was dissolved in DCM (60 ml) and treated with a saturated solution of sodium bicarbonate (60 ml) and Boc-anhydride (17.7 g, 81.3 mmol). The resulting mixture was stirred overnight and the layers separated. The organic layer was washed with brine, dried (MgSO$_4$) and conc. in vacuo. Flash chromatography eluting with hexane ethylacetate (0 to 8%) afforded 0.78 g of the cis diastereomer and 1.69 g of the trans (with some cis) diastereomers (51%). $^1$H NMR (CDCL$_3$, 500 MHz) δ 4.88–4.96 (b, 1H), 4.06–4.16 (b, 1H), 3.71 (s, 3H), 2.21 (m, 1H), 2.14 (d, 1H), 2.15 (d, 1H), 2.06 (m, 1H), 1.85–1.92 (m, 1H), 1.72–1.79 (m, 1H), 1.58 (s, 2H), 1.48–1.54 (m, 1H), 1.45 (s, 9H), 0.82–0.87 (d,d, 6H).

Step B

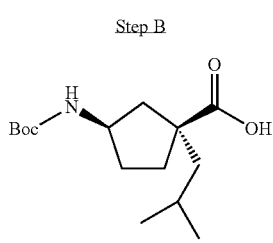

To a solution of 0.45 g (1.5 mmol) of the cis Intermediate from step A in THF/MeOH (5.0 ml) was added an aqueous solution of lithium hydroxide (0.10 g in 2.0 ml water). The mixture was stirred overnight at 60° C. and cooled to RT. The pH was adjusted to pH 7 and the methanol evaporated. The resulting suspension was extracted with ethylacetate (×3). The combined organic layers washed with brine, dried (MgSO$_4$) and conc. in vacuo to afford 0.27 g (57%) of the title product as an oil. LC-MS for C$_{15}$H$_{27}$NO$_4$ [M+H]$^+$ calculated 286.19, found 186.05 (loss of Boc group).

Step C

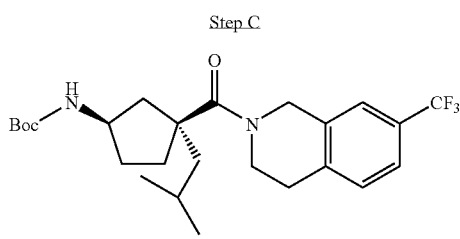

A solution of the Intermediate from step B (0.145 g, 0.508 mmol) in dry DCM (3.0 ml) at RT was treated with Intermediate 1 (0.204 g, 1.01 mmol) and HOAT (0.069 g, 0.508 mmol). After 10 min of stirring, EDC.HCl (0.292 g, 1.52 mmol) was added to the mixture and the reaction quenched with sodium bicarbonate after, 18 h. The layers were separated and the organic layer was dried (MgSO$_4$) and concentrated in vacuo. Flash chromatograph eluting with hexane/ethyl acetate (15–20%) afforded 0.182 g of the title product as an oil.

Step D

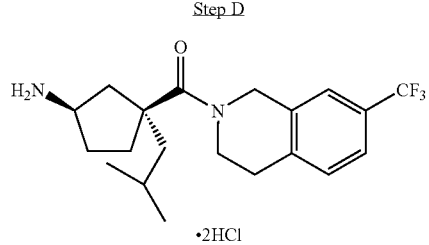

·2HCl

To a solution of the Intermediate from step C in ethylacetate (1.0 ml) was added a saturated solution of ethylacetate/HCl and the mixture stirred for 30 min. Volatiles upon removal under vacuo gave the desired product as the HCl salt. LC-MS for C$_{20}$H$_{27}$F$_3$N$_2$O [M+H]$^+$ calculated 369.21, found 369.2.

Step E

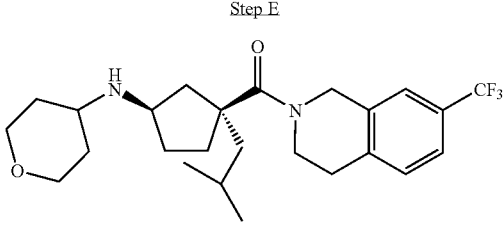

A solution of the Intermediate from step D (0.161 g, 0.40 mmol) in DCM (3.0 ml) and DIEA (0.104 ml) was treated with pyran 4-one (0.055 ml, 0.59 mmol) and 4A° molecular sieve. After stirring the mixture for 45 min, sodium triacetoxyborohydride (0.167 g, 0.79 mmol) was added. The mixture was stirred for 18 h, filtered and the filtrate was extracted with water. The organic layer was dried (MgSO$_4$) and conc. in vacuo. Reverse phase HPLC purification of the crude afforded 0.086 g of the title product (Example 81) which was subsequently transformed to the HCl salt. LC-MS for C$_{24}$H$_{35}$F$_3$N$_3$O$_2$ [M+H]$^+$ calculated 453.27, found 453.25.

EXAMPLE 82

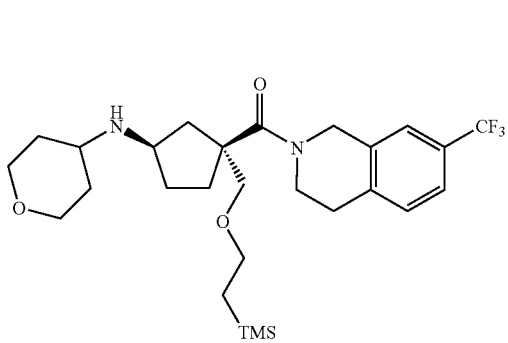

Step A

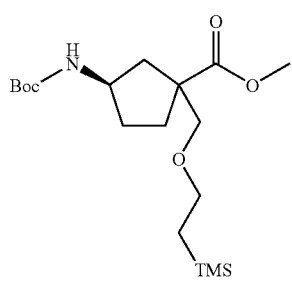

The procedure in Step A (Example 81) was used to prepare the title compound but using 2-(Trimethylsilyl) ethoxy methyl chloride instead of I-Iodo-2-methylpropane. The two diastereomers (1.24 g) were inseparable by flash chromatography. LC-MS for $C_{18}H_{35}NO_5Si$ [M+H]$^+$ calculated 374.23, found 390.15 (loss of Boc plus sodium).

Step B

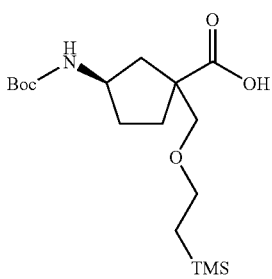

To a solution of 0.38 g (1.5 mmol) of the intermediate from step A in THF/MeOH (5.0 ml) was added an aqueous solution of lithium hydroxide (0.052 g in 2.0 ml water) The mixture was stirred overnight at 60° C. and cooled to RT. The pH was adjusted to pH 7 and the methanol evaporated. The resulting suspension was extracted with ethylacetate (×3). The combined organic layers was washed with brine, dried (MgSO$_4$) and conc. in vacuo to afford 0.375 g of the crude title product as an oil. LC-MS for $C_{17}H_{33}NO_5Si$ [M+H]$^+$ calculated 360.21, found 382.15 (plus sodium).

Step C

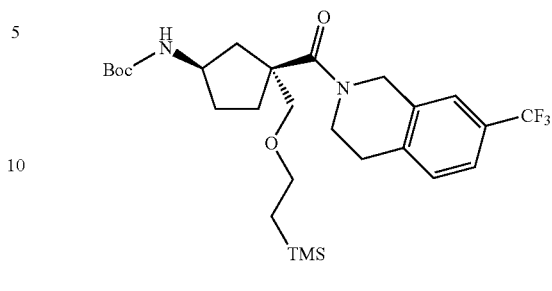

The acid from Step B (0.113 g, 0.31 mmol) in dry DCM (4.0 ml) at RT was treated with Intermediate 1 (0.126 g, 0.62 mmol) and HOAt (0.42 g, 0.31 mmol). After 10 min of stirring, EDC.HCl (0.178 g, 0.93 mmol) was added to the mixture and the reaction quenched with sodium bicarbonate, after 18 h. The suspension was extracted with DCM (×2) and the combine organic layers dried (MgSO$_4$) and conc. in vacuo. Flash chromatograph eluting with hexane ethyl acetate (5–15%) afforded 0.015 g of the cis and 0.140 g of the trans title products. LC-MS for $C_{24}H_{41}F_3N_2O_4$ Si [M+H]$^+$ calculated 543.28, found 443.2 (loss Boc group).

Step D

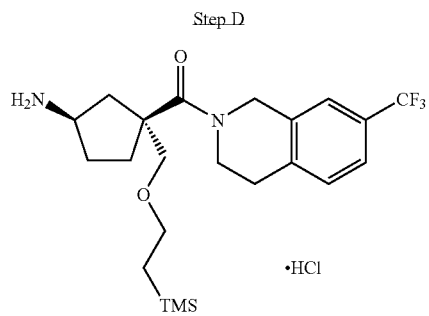

To a solution of intermediate from Step C in ethylacetate (1.0 ml) was added a saturated solution of ethylacetate/HCl and the mixture stirred for 30 min. Volatiles upon removal under vacuo gave the desired product as the HCl salt. LC-MS for $C_{22}H_{33}F_3N_2O_2$ Si [M+H]$^+$ calculated 443.23, found 443.2.

Step E

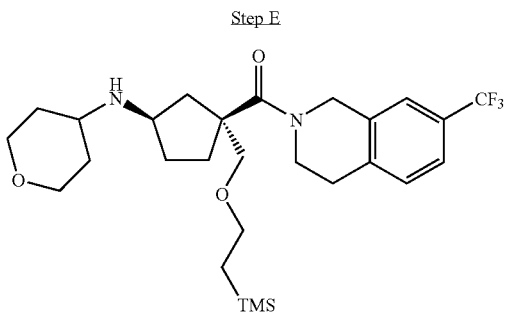

A solution of intermediate from Step D (0.012 g, 0.025 mmol) in DCM (1.0 ml) and DIEA (6.4 μl) was treated with pyran 4-one (3.5 μl, 0.037 mmol) and 4A⁰ molecular sieve. After stirring the mixture for 45 min, sodium triacetoxyborohydride (0.010 g, 0.050 mmol) was added. The mixture was stirred for 18 h, filtered and the filtrate was extracted with water. The organic layer was dried (MgSO₄) and concentrated in vacuo. Reverse phase HPLC purification of the crude afforded 0.010 g of the title product (Example 82) which was subsequently transformed to the HCl salt. LC-MS for $C_{27}H_{41}F_3N_2O_3Si$ [M+H]$^+$ calculated 527.28, found 527.2.

EXAMPLE 83

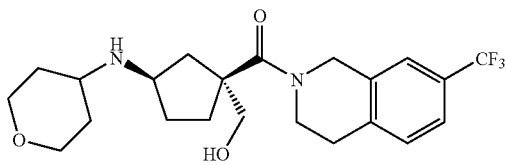

To a solution of a second batch of crude Example 82 (~0.041 mmol) in DCM (1.0 ml) was added 1.5 eq. of boron trifluoride in ether and the mixture stirred for 1 h. The reaction was quenched with sodium bicarbonate and extracted with DCM. The combined organic layers was dried (MgSO₄) and conc. in vacuo. Gilson purification afforded 1.8 mg of the title product (Example 83) which was subsequently transformed to the HCl salt. LC-MS for $C_{22}H_{29}F_3N_2O_3$ [M+H]$^+$ calculated 427.21, found 427.15.

EXAMPLE 84

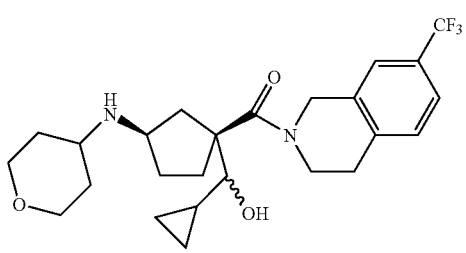

Step A

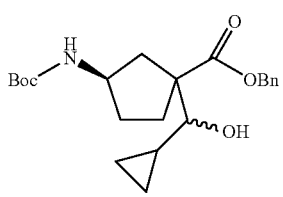

The procedure in Step A (Example 81) was used to prepare the title compound but using the product from Step D Intermediate 5 instead of (Step D Intermediate 4) and cyclopropanecarboxaldehyde instead of 1-Iodo-2-methyl-propane. The two trans diastereomers (0.595 g) were collected in pure form while the two cis diastereomers (0.90 g), as shown, were inseparable by flash chromatography. LC-MS for $C_{22}H_{31}NO_5$ [M+H]$^+$ calculated 390.22, found 412.15 (plus sodium).

Step B

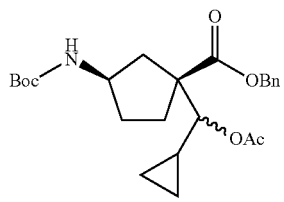

A mixture of the 2 cis diastereomers (0.390 g, 0.10 mmol), from Step A, in pyridine (5 ml) was treated with 0.28 ml (0.30 mmol) acetic anhydride. After 24 h, the solvent was evaporated and chromatography, eluting with hexane/ethyl acetate (15%), afforded 0.323 g of the title product. LC-MS for $C_{24}H_{33}NO_6$ [M+H]$^+$ calculated 432.23, found 332.2 (loss of Boc group).

Step C

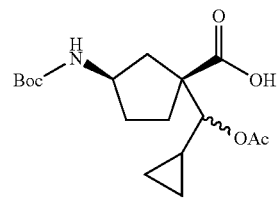

A solution of the Intermediate from step B was dissolve in ethylacetate (5 ml) and treated with 40 mg of 10% Palladium on carbon. The mixture was hydrogenated on a Parr shaker with 50 psi of hydrogen and filtered through celite. The filtrate was concentrated to afford 0.270 g of the crude title acid as foam.

Step D

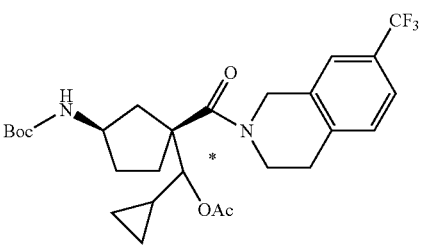

The procedure in Step C (Example 81) was used to synthesized the title compound which afforded the two cis diastereomers, as shown, following column chromatography (eluting with hexane/ethylacetate (10–15%)). 70 mg of the upper band and 51 mg of the lower band was collected (66%). LC-MS for $C_{27}H_{35}F_3N_2O_5$ [M+H]$^+$ calculated 525.25, found 425.2 (loss of Boc group).

Step E

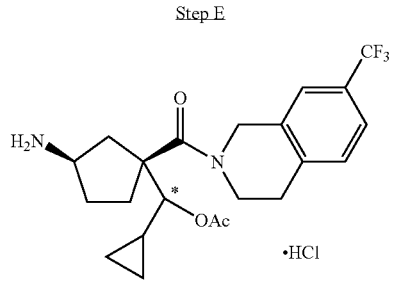

To a solution of Intermediate from step D in ethylacetate (1.0 ml) was added a saturated solution of ethylacetate/HCl and the mixture stirred for 30 min. Volatiles upon removal under vacuo gave the desired product as the HCl salt.

Step F

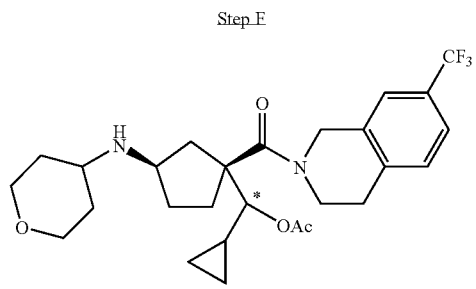

solution of Intermediate from step E (0.061 g, 0.130 mmol) in DCM (2.0 ml) and DIEA (0.033 ml) was treated with pyran 4-one (0.018 ml, 0.19 mmol) and 4A⁰ molecular sieve. After stirring the mixture for 45 min, sodium triacetoxyborohydride (0.055 g, 0.26 mmol) was added. The mixture was stirred for 18 h, filtered and the filtrate was extracted with water. The organic layer was dried (MgSO$_4$) and concentrated in vacuo to afford 0.078 g of the crude title product that was taken to the next step without further purification.

Step G

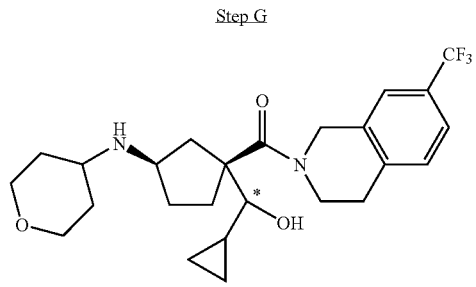

The crude Intermediate from step F was dissolved in MeOH (2.0 ml) and treated with potassium carbonate. After 2 h, the solid was filtered off and the filtrate concentrated. Reverse phase HPLC purification of the crude afforded 0.035 g of the title product (Example 84) which was subsequently transformed to the HCl salt. The other cis diastereomer was also made following steps E to G. LC-MS for $C_{25}H_{33}F_3N_3O_3$ [M+H]$^+$ calculated 467.24, found 467.2.

EXAMPLE 85

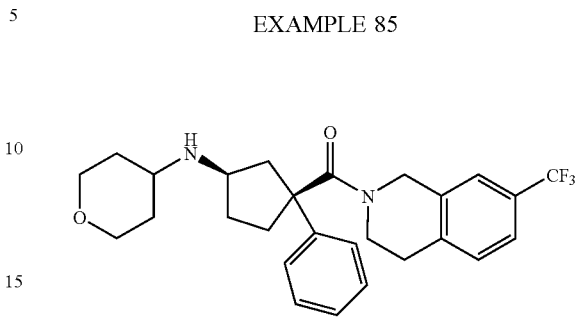

Step A

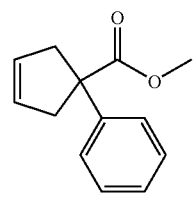

A solution of methyl phenylacetate (15 g, 99 mmol) in THF (200 ml) and DMPU (50 ml) at 0° C. was treated with sodium hydride (7.99 g, 199 mmol) and the mixture stirred for 2 h at 50° C. (hydrogen gas evolution). After cooling to RT cis-1,4-dichloro-2-butene was added to the mixture (exothermic reaction) and the mixture stirred at 50° C. for 3 h. The mixture was cool to RT, quenched with saturated ammonium chloride and extracted with ethyl acetate (×2). The combined organic layers was washed with brine, dried (NgSO$_4$) and concentrated. Flash chromatography eluting with 3% ethyl acetate in hexane afforded 7 g of the title product.

$^1$H NMR (CDCl$_3$, 500 MHz) δ 7.35 (m, 5H), 5.78 (s, 2H), 3.65 (s, 3H), 3.42 (d, 2H), 2.78 (d, 2H).

Step B

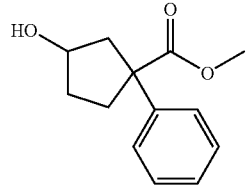

A solution of the Intermediate from step A (2.0 g, 9.89 mmol) in THF(5 ml) at 0° C. was treated with 4.94 ml of 1.0 M borane-THF complex. The mixture was stirred at RT overnight and quenched with 5 ml of water. Borax (2.28 g, 14.84 mmol) was added to the mixture and after 18 h the mixture was diluted with water and extracted with ethyl acetate (×2). The organic layer was dried (MgSO$_4$) and concentrated. Flash chromatography eluting with hexane/ethylacetate (15%) in hexane afforded 1.2 g of a cis/trans mixture of the title alcohol.

Step C

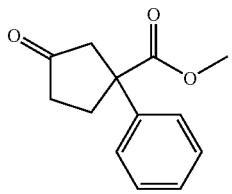

A solution of the Intermediate in step B (1.2 g, 5.4 mmol) in acetone (5.0 ml) was treated with 2 ml of Jones' reagent (10.3 g CrO$_3$ in 35 ml water and 8.8 ml of H$_2$SO$_4$) and the mixture stirred for 2 h. The acetone was evaporated and the residue diluted in ethylacetate and extracted with water (×3). The combine organic layers was washed with brine, dried (MgSO$_4$) and concentrated in vacuo. Column chromatography eluting with hexane/ethylacetate (10–20%) afforded 0.34 g of the title ketone.

$^1$H NMR (CDCl$_3$, 500 MHz) δ 7.35 (m, 5H), 3.68 (s, 3H), 3.27 (d, 2H), 3.0 (m, 2H), 2.65 (d, 2H).

Step D

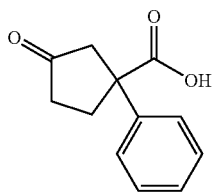

To a solution of the Intermediate from step C (0.19 g, 0.87 mmol) in THF/MeOH (5.0 ml) was added an aqueous solution of lithium hydroxide (0.074 g in 2.0 ml water). The mixture was stirred for 6 h at 60° C. and cooled to RT. The pH was adjusted to pH 7 and the methanol evaporated. The resulting suspension was extracted with ethylacetate (×3). The combined organic layers was washed with brine, dried (MgSO$_4$) and conc. in vacuo to afford 0.145 g (82%) of the title keto acid as an oil.

$^1$H NMR (CDCl$_3$, 500 MHz) δ 7.38 (m, 5H), 3.28 (d, 2H), 3.05 (m, 2H), 2.63 (d, 2H).

Step E

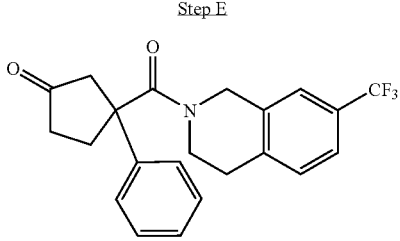

The acid from Step D (0.138 g, 0.67 mmol) in dry DCM (3.0 ml) at RT was treated with Intermediate 1 (0.37 g, 1.35 mmol) and HOAt (0.091 g, 0.67 mmol). After 10 min of stirring, EDC.HCl (0.38 g, 2.1 mmol) was added to the mixture and the reaction quenched with sodium bicarbonate, after 18 h. The suspension was extracted with DCM (×2) and the combine organic layers dried (MgSO$_4$) and conc. in vacuo. Flash chromatograph eluting with hexane ethyl acetate (25–30%) afforded 0.193 g (74%) of the title product. LC-MS for C$_{22}$H$_{20}$F$_3$NO$_2$ [M+H]$^+$ calculated 388.14, found 388.15.

Step F

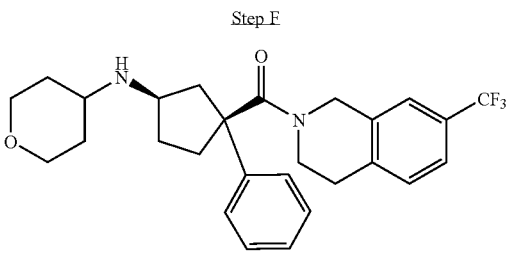

A solution of intermediate from Step E (0.1 g, 0.25 mmol) in DCM (2.0 ml) was treated with DIEA (0.075 ml) tetrahydro-2H-pyran-4-ylamine HCl salt (0.052 g, 0.38 mmol) and 4A° molecular sieve. After stirring the mixture for 45 min, sodium triacetoxyborohydride (0.105 g, 0.5 mmol) was added. The mixture was stirred for 18 h, filtered and the filtrate was extracted with water. The organic layer was dried (MgSO$_4$) and conc. in vacuo. Column chromatography eluting with ethyl acetate/methanol (3%) afforded 0.021 g of the two cis products and 0.015 g of the two trans title products (Example 85), which were subsequently transformed to the HCl salt. LC-MS for C$_{27}$H$_{31}$F$_3$N$_2$O$_2$ [M+H]$^+$ calculated 473.23, found 473.4.

EXAMPLE 86

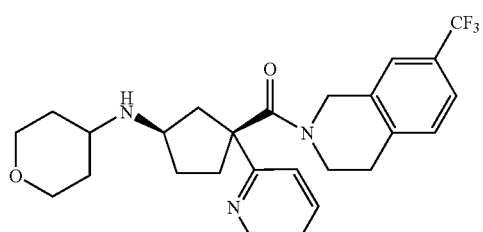

Step A

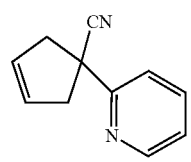

A solution of 2-cyanomethyl pyridine (10.0 g, 84.6 mmol) in THF (200 ml) and DMPU (20 ml) at RT was treated with lithium hydride (1.77 g, 211.6 mmol) and the resulting green suspension stirred at 50° C. for 3 h. Cis-1,4-dichloro-2-butene (8.96 ml, 84.6 mmol) was then added via a syringe and the mixture stirred at 50° C. overnight. The reaction was quenched with saturated ammonium chloride and extracted with ethyl-acetate (×2). The combined organic layers were dried (MgSO$_4$) and concentrated in vacuo. Flash chromatography eluting with hexane/ethyl acetate (15%) afforded 5.33 g of the title product (38%).

$^1$H NMR (CDCl$_3$, 500 MHz) δ 3.24 (s, 4H), 5.82 (s, 2H), 7.25 (t, 1H), 7.64 (d, 1H), 7.74 (t, 1H), 8.63 (d, 1H).

Step B

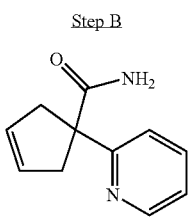

A solution of the Intermediate from step A (4.0 g, 23.5 mmol) in t-butanol (80 ml) was treated with 10 g (70.5 mmol)of potassium fluoride (40% on alumina) and the mixture stirred at 80° C. for 48 h. The precipitate was filtered, washed with methanol and the filtrate concentrated in vacuo. Flash chromatography eluting with hexane:ethyl acetate:methanol (85:10:5) afforded 3.21 g (73%) of the title amide. LC-MS for $C_{11}H_{12}N_2O$ [M+H]$^+$ calculated 189.09, found 189.05.

Step 3

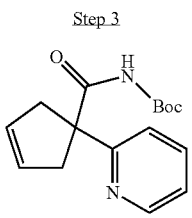

To a solution of the Intermediate in step B (1.0 g, 5.3 mmol) in DCM (5 ml) at RT was added DMAP (0.1 eq), TEA (1.12 ml, 7.96 mmol) and Boc anhydride(1.39 g, 6.37 mmol). The resulting deep, red mixture was stirred for 4 h and the reaction quenched with water. The layers were separated, the organic dried (MgSO$_4$) and concentrated in vacuo. TLC showed 2 spots. Flash chromatography eluting with hexane/ethyl acetate (15%) afforded 0.364 g of spot 1 and 0.384 g of spot 2. Spot 1 was bis-Boc while spot 2 was mono-Boc, the title product.

$^1$H NMR (CDCl$_3$, 400 MHz) δ 9.13 (broad, 1H), 8.62–8.63 (d, 1H), 7.67–7.72 (d, t, 1H), 7.36–7.38 (d, 1H), 7.24 (m, 1H), 5.72 (s, 2H), 3.40–3.43 (d, 2H), 2.99–3.05 (d, 2H), 1.47 (s, 9H).

Step D

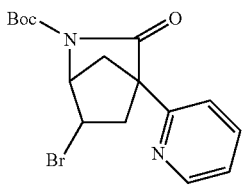

To a flame dried 3 neck flask under N$_2$ was added 0.152 g (3.81 mmol) of sodium hydride (60% dispersion in mineral oil) in TBF (40 ml). A solution of the Intermediate from step 3 (1.0 g, 3.46 mmol) in THF(15 ml) was then added via a cannula and the resulting mixture stirred at RT for 30 min. NBS (0.68 g, 3.81 mmol) dissolved in THF was then added via a cannula at −78° C. and the resulting slurry stirred at RT overnight. The reaction was quenched with water, extracted with ethyl acetate (×3) and the combined layers dried (MgSO$_4$) and concentrated in vacuo. Flash chromatography eluting with hexane/ethylacetate (15%) afforded 0.5 g of starting material and 0.51 g of the title product as a white solid. LC-MS for $C_{16}H_{19}BrN_2O_3$ [M+H]$^+$calculated 367.06, found 367.0.

Step E

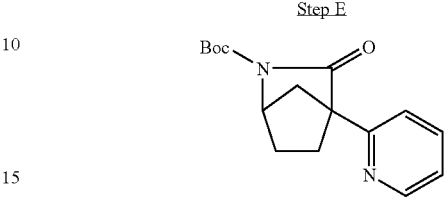

A solution of the Intermediate in step D (0.51 g, 1.38 mmol) in benzene (15 ml) at RT was treated with tributyltin hydride(0.75 ml, 2.77 mmol) and catalytic amount of AIBN. The mixture was stirred at 80° C. for 2 h and the benzene evaporated. Flash chromatography eluting with hexane/ethyl acetate (10%) afforded 0.343 g (86%) of the title product. LC-MS for $C_{16}H_{20}N_2O_3$ [M+H]$^+$ calculated 289.15, found 189.3.

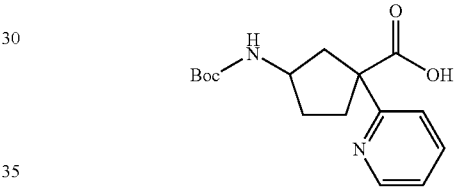

A mixture of the lactam from step E (0.142 g, 4.92 mmol) was stirred with 2 ml of 12N HCl for 3 h and evaporated. The resulting oil was dissolved in a 1:1 mixture of MeOH: DCM (10 ml) and stirred with Boc anhydride (2 eq) for 18 h. The solvents were evaporated and extracted with DCM and water. The desired title acid (cis/racemate) were found in the aqueous layer possibly as a zwitterion.

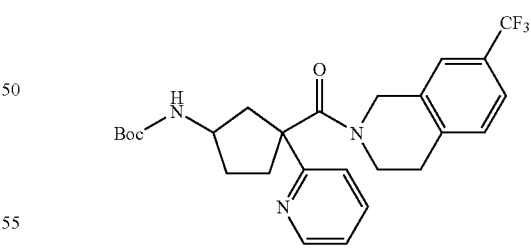

A suspension of the crude acid from step F in DCM (5 ml) was treated with DMAP (catalytic amount) excess Intermediate 1 and excess TEA. The resulting solution was then treated with PYBrOP and the mixture stirred overnight. The reaction was quenched with water and extracted with DCM. Flash chromatography (1:1) hexane ethyl acetate afforded 0.055 g of the 2 cis title products. LC-MS for $C_{26}H_{30}F_3N_3O_3$ [M+H]$^+$ calculated 490.22, found 390.1 (loss of Boc group).

Step H

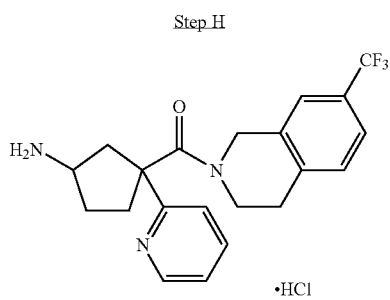

To a solution of intermediate from step G in ethylacetate (1.0 ml) was added a saturated solution of ethylacetate/HCl and the mixture stirred for 30 min. Volatiles upon removal under vacuo gave the desired product as the HCl salt.

Step I

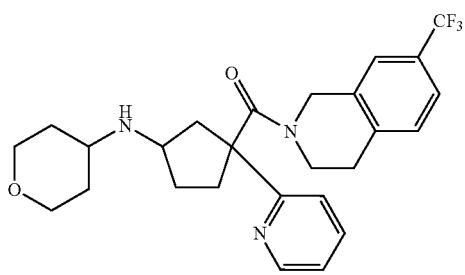

A solution of intermediate from Step H (0.043 g, 0.112 mmol) in DCM (2.0 ml) and DIEA (0.029 ml, 0.168 mmol) was treated with pyran 4-one (0.015 ml, 0.168 mmol) and 4A° molecular sieve. After stirring the mixture for 45 min, sodium triacetoxyborohydride (0.047 g, 0.224 mmol) was added. The mixture was stirred for 18 h, filtered and the filtrate was extracted with water. The organic layer was dried (MgSO$_4$) and conc. in vacuo. Reverse phase HPLC purification of the crude afforded 0.022 g of the racemic title product (Example 86) which was subsequently transformed to the HCl salt. LC-MS for $C_{26}H_{30}F_3N_3O_2$ [M+H]$^+$ calculated 474.23, found 474.25.

EXAMPLE 87

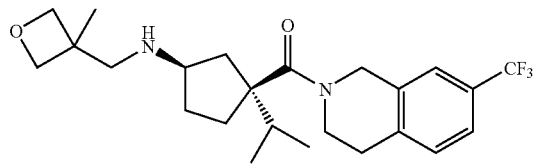

A solution of Intermediate 2 (cis/trans) mixture (0.13 g, 0.037 mmol) in DCM (2.0 ml) was treated with 1-(3-methyloxetan-3-yl) methylamine (0.074 g, 0.73 mmol) and 4A° molecular sieve. After stirring the mixture for 45 min, sodium triacetoxyborohydride (0.154 g, 0.73 mmol) was added. The mixture was stirred for 18 h filtered and the filtrate was concentrated in vacuo. Preparative plate chromatography eluting with hexane/ethylacetate (20%) afforded 0.045 g of the two cis products and 0.031 g of the two trans title products. The cis diastereomers were separated by reverse phase HPLC on a Chiralcel OD column eluting with heptane/isopropanol (20%). LC-MS for $C_{24}H_{33}F_3N_2O_2$ [M+H]$^+$ calculated 439.25, found 439.2.

EXAMPLE 88

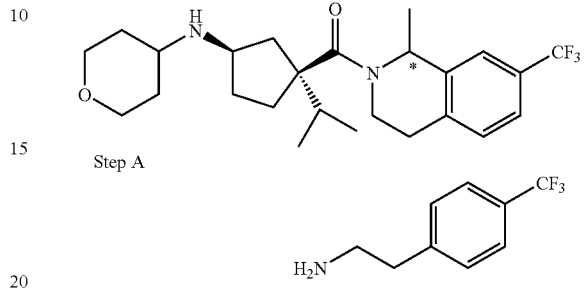

Step A

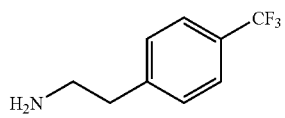

A solution of 4-(trifluoromethyl)phenyl acetonitrile (5.0 g, 27 mmol) in 2M MeOH/NH$_3$ (60 ml) was treated with Raney Nickel (0.7 g) and the mixture hydrogenated (50 psi) on a Parr Shaker for 18 h. The catalyst was filtered of over celite and the filtrate concentrated to afford 4.62 g (90%) of the title product as an oil. $^1$H NMR (CDCl$_3$, 400 MHz. δ 7.56–7.59 (d, 2 H), 7.35–7.38 (d, 2H), 3.05–3.21 (t, 2H), 2.86–2.89 (t, 2H), 2.15–2.62 (b, 2H).

Step 2

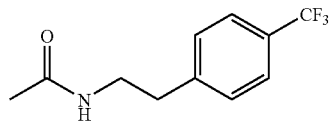

2.0 g (10.57 mmol) of the intermediate from step A was dissolved in DCM (5.0 ml) and the resulting solution treated with acetic anhydride (1.09 ml, 11.62 mmol) and TEA (1.64 ml, 11.62 mmol) at 0° C. The mixture was stirred at RT overnight and conc. in vacuo. The resulting cream solid was chromatograph, eluting with hexane/ethylacetate (20–30%) and MeOH (10%). 1.77 g (72%) of the title product was collected as a cream foam. LC-MS for $C_{11}H_{12}F_3NO$ [M+H]$^+$ calculated 232.09, found 232.1.

Step C

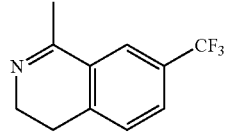

A mixture of the intermediate from step B (1.50 g, 6.84 mmol), 2.66 (32.4 mmol) ml phosphorus oxychloride and 1.99 g (12.97 mmol) zinc (11) chloride was stirred at 98° C. for 24 h, then at 120° C. for 4 days. The resulting black slurry was cooled to RT, diluted with DCM. The mixture was then treated with 5 ml of 5N NaOH and extracted repeatedly with DCM. The combined organic layers was dried (MgSO$_4$) and conc. in vacuo. Flash chromatography eluting with hexane:ethylacetate:methanol (75:15:10)

afforded 0.153 g of the title product. LC-MS for $C_{11}H_{10}F_3N$ [M+H]$^+$ calculated 214.08, found 214.05.

Step D

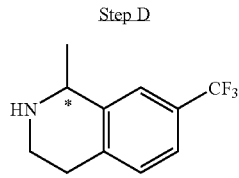

To a solution of the intermediate from step C (0.15 g, 0.7 mmol) in DCM (5.0 ml) was added 0.3 g (1.75 mmol) of sodium triacetoxyborohydride and the mixture stirred overnight. The solid was filtered off and washed with warm DCM and the filtrate concentrated to afford the title racemic amine as an oil. No further purification. LC-MS for $C_{11}H_{12}F_3N$ [M+H]$^+$ calculated 216.09, found 216.05

Step E

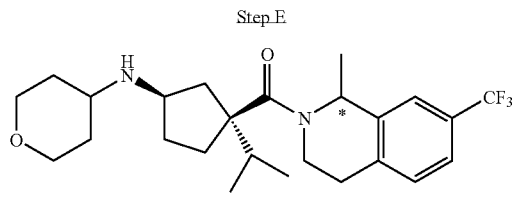

A solution of intermediate 5 (0.19 g, 0.54 mmol) in methylene chloride (3.0 ml) at 0° C. under nitrogen, was treated with oxalylchloride (0.096 ml, 1.08 mmol) and the mixture stirred for 2 h at rt. The solvent was evaporated under a nitrogen atmosphere to dryness and the intermediate from step 4, (0.15 g, 0.69 mmol) dissolved in triethylamine, added to the yellowish brown oil. After stirring for 18 h the reaction was quenched with water, extracted with methylene chloride dried (MgSO$_4$) and conc. in vacuo. The resulting oil was redissolved in ethanol (3.0 ml) and treated with sodium borohydride (~2 eq). After stirring at RT for 1 h, the reaction was quenched with water and the ethanol evaporated. The resulting aqueous suspension was extracted with DCM (×3) and the combined organic layers dried (MgSO$_4$) and conc. in vacuo. Reverse phase HPLC purification of the crude afforded the racemic title product (Example 88), which was subsequently transformed to the HCl salt (0.0042 g). LC-MS for $C_{25}H_{35}F_3N_2O_2$ [M+H]$^+$ calculated 453.27, found 453.25.

EXAMPLE 89

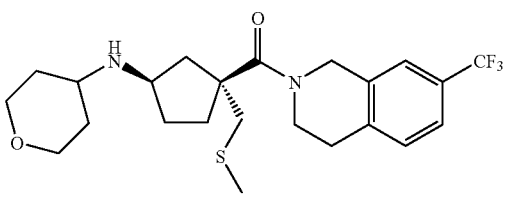

Step 1

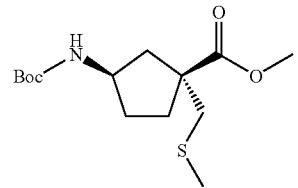

A solution of the methyl ester (Step B, Intermediate 4) (5.0 g, 15.2 mmol) in anhydrous THF (20 ml) was added to a solution of freshly prepared LDA (19.52 mmol in 35 ml of THF) at −78° C. and the resulting dark-brown mixture stirred for 45 min. A solution of chloromethyl thiomethyl-ether (2.0 ml, 2.4 mmol) was then added and the resulting mixture stirred at −78° C. for 1 h and then gradually warmed to 0° C. and held there for 1 hr. The reaction mixture was quenched with saturated aqueous ammonium chloride and extracted with ethylacetate (×3) and the combined organic layers washed with brine, dried (MgSO$_4$) and concentrated in vacuo. The resulting oil was dissolved in THF (10 ml) and treated with 1 ml of 12N HCl and stirred for 30 minutes. After the evaporation of the volatiles, the clear brown oil which was dissolved in DCM (100 ml) and treated with a saturated solution of sodium bicarbonate (100 ml) and (Boc)$_2$O (1.2 Eq.). After the mixture was stirred overnight and the layers were separated. The organic layer was washed with brine, dried (MgSO$_4$) and concentrated in vacuo. Flash chromatography and eluting with hexane ethylacetate (0 to 10%) afforded 0.67 g of the desired cis compound.

$^1$H NMR (CDCl$_3$, 500 MHz) 4.93 (b, 1H), 4.18–4.12 (m, 1H), 3.75 (s, 3H), 2.92–2.74 (dd, 2H), 2.14 (d, 1H), 2.14 (m, 1H), 2.13 (s, 3H), 2.09 (m, 3H), 1.69–1.52 (m, 1H), 1.44 (s, 9H).

Step B

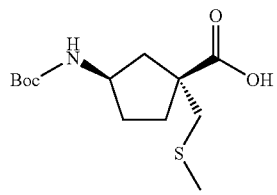

Starting from Step A intermediate (0.21 g, 0.1.3 mmol) and following the procedure under Example 81 (Step B) gave 0.19 g of the title compound.

Step C

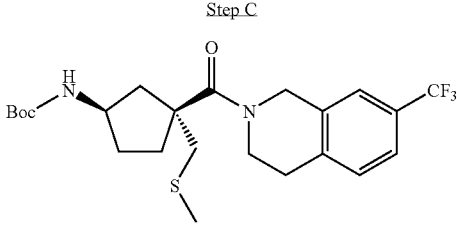

The acid from Step B (0.19 g, 0.66 mmol) in dry DCM (5.0 ml) at RT was treated with Intermediate 1 (0.13 g, 0.66 mmol) and Hunig base (0.25 ml, 1.4 mmol). After 10 min of stirring, PyBrop (0.38 g, 0.83 mmol) was added to the mixture and stirred for 48 h at RT. The suspension was extracted with DCM (×2) and the combine organic layers dried (MgSO$_4$) and concentrated in vacuo. Flash chromatograph eluting with hexane ethyl acetate (3:1) afforded 0.15 g of the title product. LC-MS for C$_{23}$H$_{31}$F$_3$N$_2$O$_3$S [M+H]$^+$ calculated 473.20, found 373.2 (loss of Boc group).

Step D

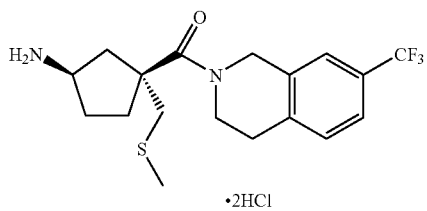

•2HCl

To a solution of intermediate from Step C (0.032 g) in ethylacetate (2.0 ml) was added a saturated solution of ethylacetate/HCl and the mixture stirred for 30 min. Volatiles upon removal under vacuum gave 0.030 g the desired product as the HCl salt. LC-MS for C$_{18}$H$_{23}$F$_3$N$_2$OS [M+H]$^+$ calculated 373.16, found 373.2.

Step E

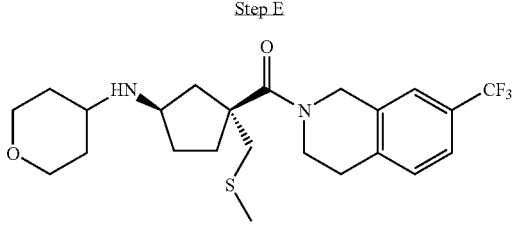

A solution of intermediate from Step D (0.030 g, 0.073 mmol) in DCM (3.0 ml) and DIEA (0.123 ml) was treated with pyran 4-one (0.015 g, 1.5 mmol) and 4A$^0$ molecular sieve. After stirring the mixture for 45 min, sodium triacetoxyborohydride (0.03 g, 1.5 mmol) was added. The mixture was stirred for 18 h, filtered and the filtrate was extracted with water. The organic layer was dried (MgSO$_4$) and concentrated in vacuo. Reverse phase HPLC purification of the crude afforded the title product (Example 89) which was subsequently transformed to the HCl salt (0.020 g). LC-MS for C$_{23}$H$_{31}$F$_3$N$_2$O$_2$S [M+H]$^+$ calculated 457.21, found 457.15.

EXAMPLE 90

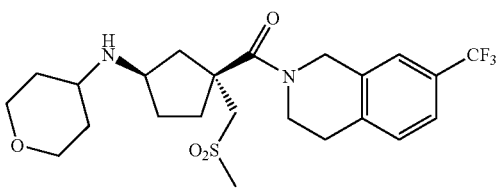

-continued

Step A

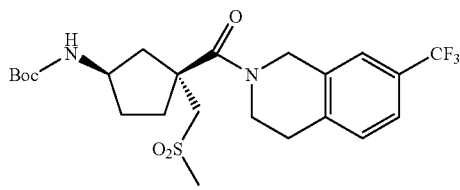

The amide (0.06 g, 0.13 mmol) from Step C and Example 89, in dry DCM (5.0 ml) at RT was treated with m-CPBA (0.1 g, 0.58 mmol, 85%) and stirred for 16 h at RT. The suspension was concentrated in vacuo. Reverse phase HPLC purification afforded 24 mg of the title product. LC-MS for C$_{23}$H$_{31}$F$_3$N$_2$O$_5$S [M+H]$^+$ calculated 505.20, found 405.1 (M-loss of Boc group).

Step B

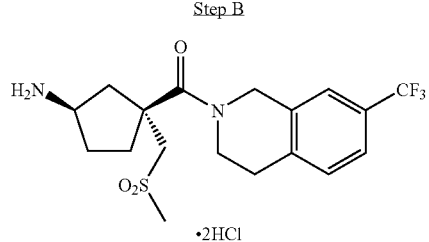

•2HCl

To a solution of intermediate from Step A (0.024 g) in ethylacetate (2.0 ml) was added a saturated solution of ethylacetate/HCl and the mixture stirred for 30 min. Volatiles upon removal under vacuum gave 21 mg of the desired product as the HCl salt. LC-MS for C$_{18}$H$_{24}$F$_3$N$_2$O$_3$S [M+H]$^+$ calculated 405.15, found 405.2.

Step C

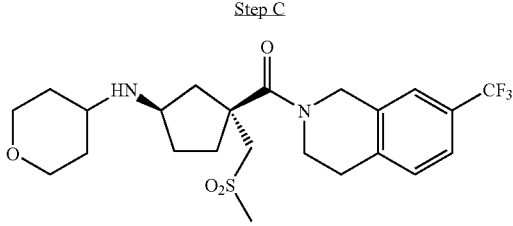

A solution of intermediate from Step B (0.020 g, 0.046 mmol) in DCM (3.0 ml) and DIEA (0.123 ml) was treated with pyran 4-one (0.010 g, 0.092 mmol) and 4A$^0$ molecular sieve. After stirring the mixture for 45 min, sodium triacetoxyborohydride (0.02 g, 0.092 mmol) was added. The mixture was stirred for 18 h, filtered and the filtrate was extracted with water. The organic layer was dried (MgSO$_4$) and concentrated in vacuo. Reverse phase HPLC purification of the crude afforded the title product (Example 90) which was subsequently transformed to the HCl salt (0.016 g). LC-MS for C$_{23}$H$_{32}$F$_3$N$_2$O$_4$S [M+H]$^+$ calculated 489.21, found 485.25.

EXAMPLE 91

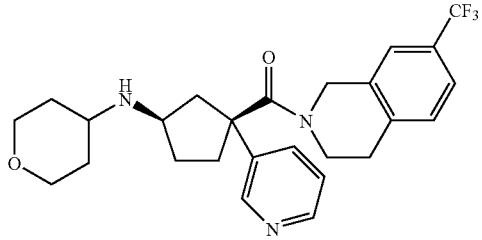

Step A

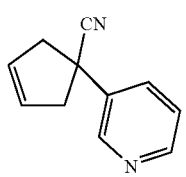

A solution of 3-cyanomethyl pyridine (6.0 g, 50.7 mmol) in THF (100 ml) and DMPU (10 ml) at RT was treated with lithium hydride (1.2 g, 150.0 mmol) and the resulting suspension was stirred at 50° C. for 2 h. Cis-1,4-dichloro-2-butene (5.3 ml, 50.7 mmol) was then added and the mixture was stirred at 50° C. for an additional 3 h. The reaction was quenched carefully with saturated ammonium chloride and extracted with ethyl-acetate (×2). The combined organic layers was washed with brine, dried (MgSO$_4$) and concentrated in vacuo. Flash chromatography eluting with hexane/ethyl acetate (3:2) afforded 3.54 g of the title product (38%).

$^1$H NMR (CDCl$_3$, 500 MHz) 8.78 (d, 1H), 8.60 (d, 1H), 7.81 (dd, 1H), 7.35 (dd, 1H), 5.86 (s, 2H), 3.39 (d, 2H), 2.90 (d, 2H).

Step B

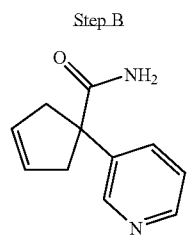

A solution of the Intermediate from step A (1.4 g, 8.23 mmol) in t-butanol (15 ml) was treated with 4.2 g of potassium fluoride/alumina (40%) and the resulting mixture was stirred at 80° C. for 48 h. The precipitate was filtered, washed with methanol and the filtrate was concentrated in vacuo. Flash chromatography eluting with hexane/ethyl acetate/methanol (1:1+10%) afforded 1.24 g of the title amide. LC-MS for C$_{11}$H$_{12}$N$_2$O [M+H]$^+$ calculated 189.09, found 189.1.

Step C

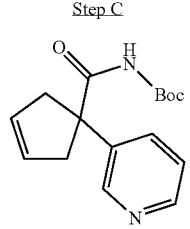

To a solution of the Intermediate in step B (1.0 g, 5.3 mmol) in THF (10 ml) at RT was added NaH (250 mg, 10.4 mmol, 60% in oil) in one lot and stirred for 30 minutes. The reaction mixture was cooled to 0° C. and a solution of xx (1.27 g, 5.3 mmol) in THF (5.0 ml) and then gradually warmed to RT and stirred for an additional 2 h. The reaction mixture was quenched with water and extracted with ethylacetate (2×). The solvent layer was washed with brine, dried (MgSO$_4$) and concentrated in vacuo. Flash chromatography eluting with hexane/ethylacetate/methanol (7:3+5%) afforded 1.1 g of the title product.

$^1$H NMR (CDCl$_3$, 500 MHz) 8.56 (s, 1H), 8.54 (d, 1H), 7.64 (d, 1H), 7.31 (dd, 1H), 7.29 (brs, 1), 5.77 (s, 2H), 3.36 (d, 2H), 2.88 (d, 2H), 1.45 (s, 9H).

Step D

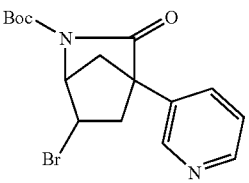

To a flame dried 3 neck flask under N$_2$ was added 0.072 g (1.77 mmol) of sodium hydride (60% dispersion in mineral oil) in THF (40 ml). A solution of the Intermediate from step C (0.51 g, 1.77 mmol) in THF (10 ml) was then added via a cannula and the resulting mixture stirred at RT for 30 min. NBS (0.32 g, 1.77 mmol) dissolved in THF (8 ml) was then added via a cannula at −78° C. and the resulting slurry was gradually warmed and stirred at RT overnight. The reaction was quenched with water, extracted with ethyl acetate (×3) and the combined layers dried (MgSO$_4$) and concentrated in vacuo. Flash chromatography eluting with hexane/ethylacetate (15%) afforded 0.33 g of the title product as a white solid. LC-MS for C$_{16}$H$_{19}$BrN$_2$O$_3$ [M+H]$^+$ calculated 367.07, found 367.0.

Step E

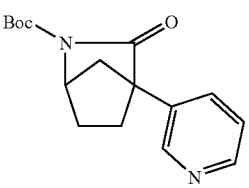

A solution of the Intermediate in step D (0.33 g, 0.9 mmol) in benzene (10 ml) at RT was treated with tributyltinhydride (0.50 ml, 1.8 mmol) and catalytic amount of AIBN. The mixture was stirred at 80° C. for 1 h and the benzene was evaporated. Flash chromatography eluting with hexane/ethyl acetate/methanol (1:1+4%) afforded 0.22 g of the title product. LC-MS for $C_{16}H_{20}N_2O_3$ [M+H]$^+$ calculated 289.15, found 289.1.

Step E

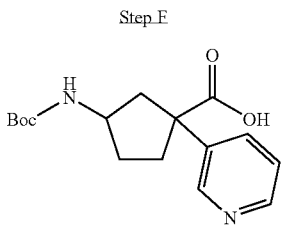

The lactam from step E (0.21 g) was stirred with 2 ml of 12N HCl for 3 h at 70° C. and evaporated. The resulting oil was dissolved in a 1:1 mixture of MeOH:DCM (10 ml), triethylamine (5 eq) and stirred with Boc anhydride (2 eq) for 18 h. The solvents were evaporated and purified. Flash chromatography eluting with hexane/ethyl acetate/acetic acid (1:1+10%) afforded 0.12 g of the title product. LC-MS for $C_{16}H_{22}N_2O_4$ [M+H]$^+$ calculated 307.17, found 307.3.

Step G

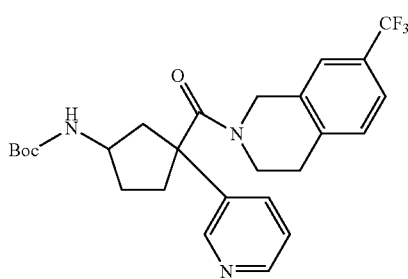

To a suspension of acid (0.1 g, 0.32 mmol) from step F in DCM (5 ml) was treated with Intermediate 1 (0.08 g, 0.4 mmol), HOAT (0.06 g, 0.4 mmol), Hunig base (5 eq) and EDC (0.11 g, 0.6 mmol). The resultant mixture was stirred for 18 h. The volatiles were removed under vacuo. Flash chromatography with hexane ethyl acetate (1:1+2% MeOH) afforded 0.12 g of the desired product as racemate. LC-MS for $C_{26}H_{30}F_3N_3O_3$ [M+H]$^+$ calculated 490.22, found 490.3.

Step H

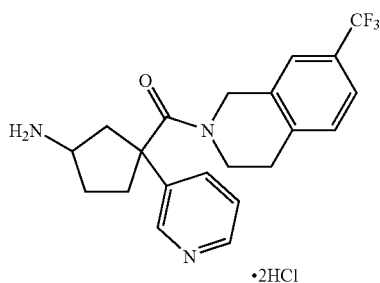

To a solution of intermediate (0.12 g) from step G in ethylacetate (2.0 ml) was added a saturated solution of ethylacetate/HCl and the mixture stirred for 30 min. Volatiles upon removal under vacuo gave 0.11 g of the desired product as the HCl salt. LC-MS for $C_{21}H_{23}F_3N_3O$ [M+H]$^+$ calculated 390.18, found 390.2.

Step I

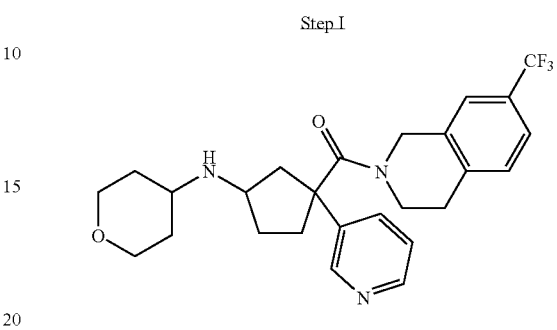

A solution of intermediate from Step H (0.11 g, 0.24 mmol) in DCM (5.0 ml) and Hunig base (0.087 ml, 0.5 mmol) was treated with pyran 4-one (0.24 g, 0.24 mmol) and 4A° molecular sieve. After stirring the mixture for 45 min, sodium triacetoxyborohydride (0.10 g, 0.5 mmol) was added. The mixture was stirred for 18 h, filtered and the filtrate was extracted with water. The organic layer was dried (MgSO$_4$) and concentrated in vacuo. Reverse phase HPLC purification of the crude afforded the racemic title product (Example 91) which was subsequently transformed to the HCl salt (0.071 g). LC-MS for $C_{26}H_{30}F_3N_3O_2$ [M+H]$^+$ calculated 474.23, found 474.2.

EXAMPLE 92

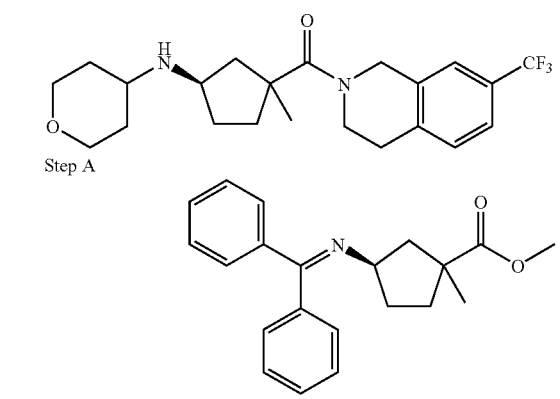

Step A

A flame dried 500 mL round bottom flask was charged with 100 mL of dry THF, and then, set under nitrogen and cooled to −78° C. using an acetone/dry ice bath. Diisopropylamine (1.68 mL, 12.00 mmol) was added to the cooled solvent via syringe followed by the slow addition of 2.5M n-BuLi in hexane (4.80 mL, 12.00 mmol). After 5 minutes stirring, the product described in Step B, Intermediate 4 (3.00 g, 10.00 mmol) in 50 mL of THF was added dropwise via syringe and the resulting mixture stirred at −78° C. for 2 hours. Iodomethane (871 μL, 14.00 mmol) was then added dropwise via syringe and the resulting mixture was stirred overnight allowing to warm slowly to room temperature. The reaction was quenched with a saturated solution of ammonium chloride (100 mL) and the organics separated. The aqueous layer was extracted with ethyl acetate (3×50 mL) and all the organics combined, dried over anhydrous sodium sulfate, filtered, and evaporated under reduced pressure. The crude product was used in the next step without further purification. LC-MS for $C_{21}H_{23}NO_2$ calculated 321.17, found [M+H$^+$] 322.2

Step B

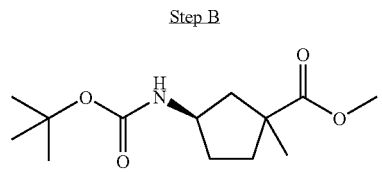

To a solution of the product from Step A, Example 92 (10.00 mmol, assuming 100% conversion) in 30 mL THF was added 30 mL of 2N hydrochloric acid and the resulting mixture stirred overnight at room temperature. The solution was concentrate in vacuo to remove the THF and the aqueous layer was then diluted with DCM (100 mL). The pH of the aqueous layer was adjusted to pH=10 by slow addition of 5N sodium hydroxide with vigorous stirring. The organic layer was removed using a separatory funnel and the aqueous layer was extracted with dichloromethane (2×50 mL). The organics were combined, dried over anhydrous sodium sulfate, and filtered. To the filtrate was added DIEA (1.74 mL, 10.00 mmol) and Boc-anhydride (2.62 g, 12.00 mmol) and the resulting solution was stirred at room temperature overnight. The mixture was washed with 1N hydrochloric acid, followed by saturated solution of sodium bicarbonate, and brine. The organic layer was dried over anhydrous sodium sulfate, filtered, and evaporated under reduced pressure. Purification by MPLC (eluant: 15% ethyl acetate: 85% hexane) afforded 1.23 g (48%) of the product as a mixture of 2 diastereomers.

Step C

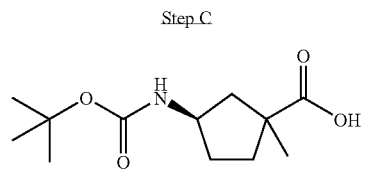

To a mixture of the product described in Step B, Example 92 (1.20 g, 4.66 mmol) in a 1:1:1 solution of THF:methanol:water (45 mL) was added solid LiOH (560 mg, 23.31 mmol) and the resulting solution was heated to 60° C. and stirred for 18 hours. The mixture was left standing to cool to room temperature and then concentrated to remove the organic solvent. The aqueous layer was acidified by slow addition of 6N hydrochloric acid to adjust the pH to 4 or 5. The acidic aqueous layer was extracted with DCM (3×50 mL) and the organics were combined, dried over anhydrous sodium sulfate, filtered, and evaporated under reduced pressure to afford the product (986 mg, 87%) as a yellow oil. $^1$H NMR (CDCl$_3$, 500 MHz) δ 4.56 (br s, 1H), 4.18–4.10 (m, 1H) 4.03 (br s, 1H), 3.78–3.74 (m, 1H), 2.60 (dd, J=7.8, 13.3 Hz, 1H), 2.20–2.00 (m, 2H), 1.62–1.55 (m, 1H), 1.43 (s, 9H), 1.31 (s, 3H).

Step D

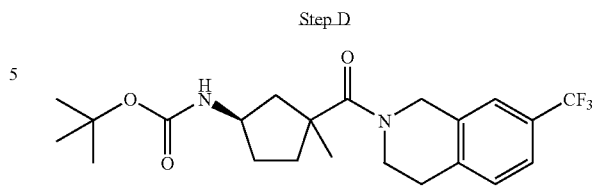

The product described in Step C, Example 92 (100 mg, 0.41 mmol) and Intermediate 1 (83 mg, 0.44 mmol) were first dried by azeotroping with toluene (2×20 mL) and placing under high vacuum for 30 minutes. Under nitrogen, DMAP (30 mg, 0.25 mmol), anhydrous DCM (15 mL), DIEA (214 µL, 1.23 mmol), and PyBrop (192 mg, 0.41 mmol) were added sequentially and the resulting mixture was stirred at room temperature overnight. The reaction was quenched with saturated NaHCO$_3$ and the organics separated. The aqueous layer was back washed with DCM (3×20 mL) and the organic layers were combined, dried over Na$_2$SO$_4$, filtered, and evaporated in vacuo. The residue was purified by preparative TLC (eluant: 30% ethyl acetate: 70% hexanes) to afford the product (85 mg, 49%) as a yellow foam. LC-MS for $C_{22}H_{29}F_3N_2O_3$ calculated 426.21, found [M+H]$^+$ 427.2 and [M+H−100(Boc)]$^+$ 327.2.

Step E

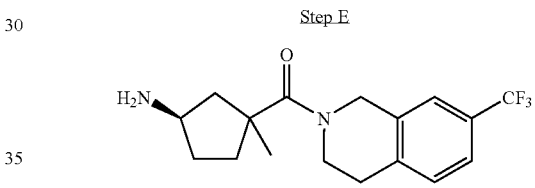

The product described in step D, Example 92 (80 mg, 0.19 mmol) was dissolved with 4N HCl in dioxane (4 mL) and the resulting solution was stirred at room temperature for one hour. The reaction was evaporated under vacuum to afford the product (83 mg, 99%) as a white powder. LC-MS calculated for $C_{17}H_{21}F_3N_2O$ is 326.16, found [M+H]$^+$ 327.15.

Step F

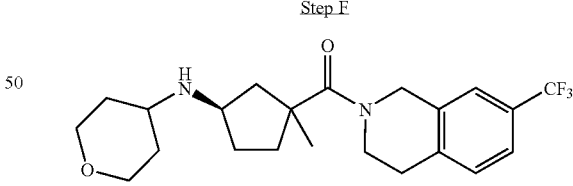

A solution of the product described in Step E, Example 92 (80 mg, 0.18 mmol), tetrahydro4H-pyran-4-one (27 µL, 0.27 mmol), diisopropylethylamine (48 µL, 0.27 mmol) and crushed molecular sieves (4 A, 50 mg) in dichloromethane (4 mL) was treated with sodium triacetoxyborohydride (291 mg, 1.38 mmol) and stirred at room temperature overnight. The reaction was quenched with saturated sodium bicarbonate solution (10 mL) and diluted with an additional 15 mL of DCM. The organic layer was separated and the aqueous washed with dichloromethane (2×15 mL). The organics were combined, dried over anhydrous sodium sulfate, filtered and evaporated under reduced pressure. The residue was purified by preparative TLC (eluant: 0.5% NH₄OH: 5% MeOH: 94.5% CH₂Cl₂) to yield the title compound 81 mg (68%) as a mixture of two diastereomers. LC-MS for $C_{22}H_{29}F_3N_2O_2$ calculated 410.21, found [M+H]⁺ 411.2.

EXAMPLE 93

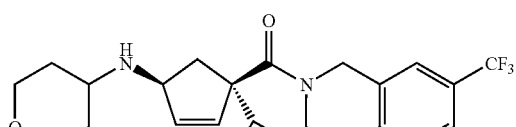

Step A

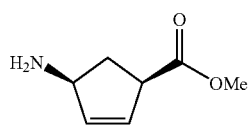

Thionyl chloride (20.1 mL, 275 mmol) was slowly introduced to 175 mL of methanol and the resulting solution was allowed to stir for 10 minutes. To this solution, (1R, 4S)-4-amino-cyclopent-2-ene (commercial, 10 g, 79 mmol) was added and the mixture was heated to reflux for 15 hours. After allowing to cool to room temperature, the solution was evaporated in vacuo to afford the crude product (13.95 g, 99%) which was used for the next step without further purification.

Step B

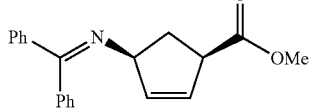

To a suspension of intermediate from step A (13.95 g, 78.8 mmol) in dry dichloromethane (100 mL) was added benzophenone imine (13.47 g, 78.5 mmol) at RT and the resultant mixture was stirred for 24 h. The reaction mixture was filtered and the filtrate was evaporated, to leave behind yellow oil that was triturated with ether (100 mL), filtered and evaporated. This operation was repeated twice to ensure that the product was free of ammonium chloride impurities. The resultant oil was thoroughly dried under high vacuum to yield the title compound (18.03 g, >100%) and required no further purification. ¹H NMR (500 MHz, CDCl₃): δ 7.64 (d, J=7.1 Hz, 2H), 7.52–7.44 (m, 3H), 7.38 (t, J=7.1 Hz, 1H), 7.33 (t, J=7.1 Hz, 2H), 7.20 (d, J=7.1 Hz, 2H), 5.97 (ddd, J=2.1, 4.1, 5.7 Hz, 1H), 5.78 (ddd, J=2.3, 4.8, 5.5 Hz, 1H), 4.52 (br ddd, J=2.1, 5.3, 7.3 Hz, 1H), 3.74 (s, 3H), 3.52 (ddd, J=2.2, 5.95, 8.4 Hz, 1H), 2.40–2.33 (m, 1H), 2.29–2.22 (m, 1H).

Step C

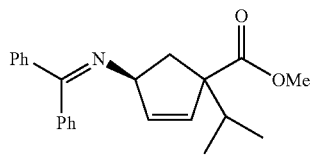

A flame dried 500 mL round bottom flask was charged with 100 mL of dry THF, and then, set under nitrogen and cooled to −78° C. using an acetone/dry ice bath.

Diisopropylamine (2.74 mL, 19.50 mmol) was added to the cooled solvent via syringe followed by the slow addition of 2.5M n-BuLi in hexane (7.80 mL, 19.50 mmol). After 5 minutes stirring, the product described in Step B, Example 93 (5 g, 16.25 mmol) in 30 mL of THF was added dropwise via syringe and the resulting mixture stirred at −78° C. for 2 hours. 2-iodopropane (2.26 mL, 22.75 mmol) was then added dropwise via syringe and the resulting mixture was stirred overnight allowing to warm slowly to room temperature. The reaction was quenched with a saturated solution of ammonium chloride (100 mL) and the organics separated. The aqueous layer was extracted with ethyl acetate (3×100 mL) and all the organics combined, dried over anhydrous sodium sulfate, filtered, and evaporated under reduced pressure. The crude product was used in the next step without further purification. LC-MS for $C_{23}H25NO_2$ calculated 347.19, found [M+H]⁺ 348.2.

Step D

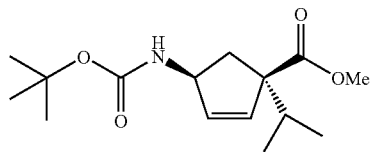

To a solution of the product from Step C, Example 93 (16.25 mmol, assuming 100% conversion) in 100 mL THF was added 100 mL of 2N hydrochloric acid and the resulting mixture stirred overnight at room temperature. The solution was concentrate in vacuo to remove the THF and the aqueous layer was then diluted with DCM (300 mL). The pH of the aqueous layer was adjusted to pH=10 by slow addition of 5N sodium hydroxide with vigorous stirring. The organic layer was removed using a separatory funnel and the aqueous layer was extracted with dichloromethane (2×150 mL). The organics were combined, dried over anhydrous sodium sulfate, and filtered. To the filtrate was added DIEA (2.83 mL, 16.25 mmol) and Boc-anhydride (4.26 g, 19.50 mmol) and the resulting solution was stirred at room temperature overnight. The mixture was washed with 1N hydrochloric acid, followed by saturated solution of sodium bicarbonate, and brine. The organic layer was dried over anhydrous sodium sulfate, filtered, and evaporated under reduced pressure. Purification by MPLC (gradient eluant: 0–25% ethyl acetate/hexane) afforded 1.58 g (34%) of the desired cis (R, S) isomer and 1.37 g (30%) of the undesired trans (S, S) isomer.

Step E

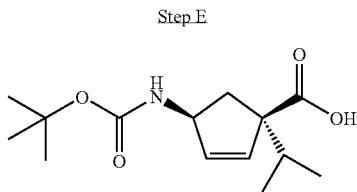

To a mixture the desired cis (R, S) product described in Step D, Example 93 (1.51 g, 5.33 mmol) in a 1:1:1 solution of THF:methanol:water (60 mL) was added solid LiOH (1.12 g, 26.65 mmol) and the resulting solution was heated to 60° C. and stirred for 18 hours. The mixture was left standing to cool to room temperature and then concentrated to remove the organic solvent. The aqueous layer was acidified by slow addition of 6N hydrochloric acid to adjust the pH to 4 or 5. The acidic aqueous layer was extracted with DCM (3×100 mL) and the organics were combined, dried over anhydrous sodium sulfate, filtered, and evaporated under reduced pressure to afford Intermediate 21 (1.30 g, 91%) as a yellow oil. After two weeks standing at room temperature, the material solidified.

Step F

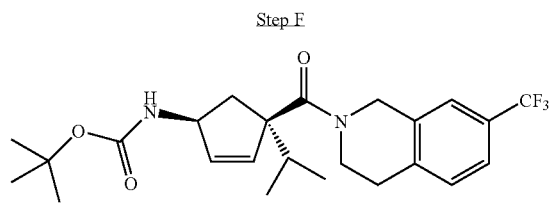

The product described in Step E, Example 93 (300 mg, 1.12 mmol) and Intermediate 1 (673 g, 3.36 mmol) were first dried by azeotrophing with toluene (3×25 mL) and placing under high vacuum for 30 minutes. Under nitrogen, DMAP (82 mg, 0.67 mmol), anhydrous DCM (30 mL), DIEA (584 μL, 3.36 mmol), and PyBroP (522 mg, 1.12 mmol) were added sequentially and the resulting mixture stirred at room temperature overnight. The reaction mixture was washed with 2N HCl, saturated sodium bicarbonate solution, and brine. The organic layer was dried over $Na_2SO_4$, filtered, and evaporated in vacuo. The crude product was purified by preparative TLC (eluant: 35% EtOAc:65% hexanes) to afford the product (337 mg, 69%) as a yellow foam. LC-MS for $C_{24}H_{31}F_3N_2O_3$ calculated 452.23, found $[M+H]^+$ 453.3.

Step G

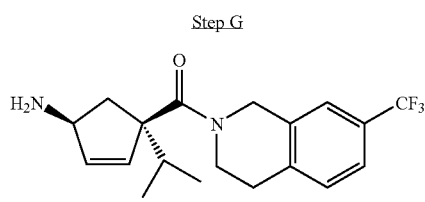

The product described in step F, Example 93 (330 mg, 0.73 mmol) was dissolved with 4N HCl in dioxane (10 mL) and the resulting solution was stirred at room temperature for one hour. The reaction was evaporated under vacuum to afford the product (280 mg, 99%) as a white powder. LC-MS for $C_{19}H_{23}F_3N_2O$ calculated 352.18, found $[M+H]^+$ 353.2.

Step H

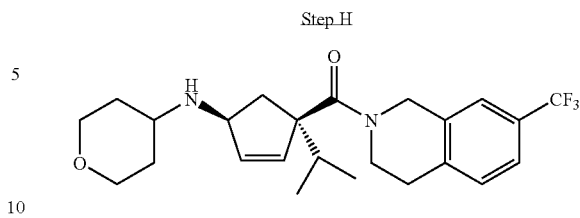

This product was prepared in an analogous fashion to that of Procedure B of Example 92, except Intermediate 6 was replaced with the product described in Step G, Example 93. The crude product was purified by Preparative TLC (eluant: 0.5% $NH_4OH$: 5% MeOH: 94.5% $CH_2Cl_2$) to afford the title compound (Example 93, 53 mg, 92%). LC-MS for $C_{24}H_{31}F_3N_2O_2$ calculated 436.24, found $[M+H]^+$ 437.2.

EXAMPLE 94

Step H

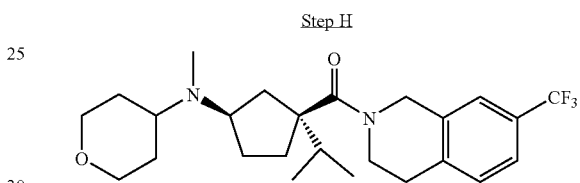

To a solution of product described in Example 1 (100 mg 0.17 mmol) and crushed 4A molecular sieves (400 mg) in dichloromethane (10 mL) was added Formalin (0.2 mL) and the resulting suspension was stirred for 30 minutes at room temperature. This mixture was then treated with sodium triacetoxyborohydride (180 mg, 0.85 mmol) and stirred an addition 15 hours at room temperature. The reaction was quenched with saturated sodium bicarbonate solution (20 mL) and diluted with an additional 10 mL of DCM. The organic layer was separated and the aqueous washed with dichloromethane (2×10 mL). The organics were combined, dried over anhydrous sodium sulfate, filtered and evaporated under reduced pressure. The crude product was purified by preparative TLC (eluant: 0.25% $NH_4OH$: 2.5% MeOH: 97.25% $CH_2Cl_2$) to yield Example 94 (65 mg, 63%). $^1H$ NMR (500 MHz, $CDCl_3$) δ 7.44 (d, J=8.0 Hz, 1H), 7.39 (br s, 1H), 7.26 (dd, J=8.0 Hz, 1H), 4.83 (br s, 1H), 4.68 (d, J=17.2 Hz, 1H), 4.08–4.01 (m, 2H), 3.88–3.80 (m, 2H), 3.41 (d, J=11.2 Hz, 1H), 3.36 (d, J=11.2 Hz, 1H), 2.93 (t, J=5.5 Hz, 2H), 2.65 (dd, J=5.5, 11.9 Hz, 1H), 2.24 (s, 3H), 2.16 (dd, J=7.4, 12.6 Hz, 1H), 2.05 (br s, 1H), 1.94–1.82 (m, 2H), 1.74–1.58 (m, 4H), 1.54–1.40 (m, 2H), 0.97 (d, J=6.6 Hz, 3H), 0.79 (d, J=6.5 Hz, 3H). LC-MS for $C_{25}H_{35}F_3N_2O_2$ calculated 452.26, found $[M+H]^+$ 453.3.

INTERMEDIATE 32

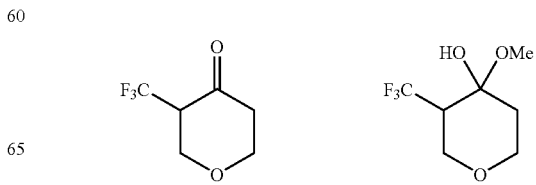

-continued

Step A

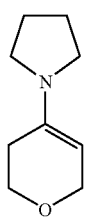

A mixture of tetrahydro-4H-pyran-4-one (106, 100 mmol) and pyrrolidine (11 g, 150 mmol) was stirred at room temperature for one hour. Excess of pyrrolidine was removed in vacuo and the residue dried overnight under high vacuum. The enamine was obtained as a yellow liquid (14.7 g) which was used in the next step without further purification.

Step B

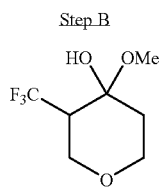

The enamine, prepared in step A, Intermediate 32 (1.54 g, 10 mmol) and 4-N,N-dimethylpyridine (DMAP, 1.22 g) was treated with DMF (25 ML). The mixture was cooled to 0° C. and solid 5-(trifluoromethyl)dibenzothiophenium trifluoromethanesulfonate (4.02 g, 10 mmol) was added. The resulting mixture was stirred at 0° C. for one hour, then quenched with 30 mL of concentrated aqueous HCl, which was stirred for two hours and then extracted with ether (4×70 mL). The combined ether layers were washed with water (50 mL) and brine (50 mL), dried over $Na_2SO_4$, filtered, and evaporated. The residue was purified on silica gel (eluant: 10% ether/hexane) to yield two components. The more polar component (200 mg) was the desired product. $^1$H-NMR showed that it might exist in a semi-ketal form. $^1$H NMR (500 MHz, $CDCl_3$) δ 4.43–3.38 (m, 5H), 3.24, 3.18 (ss, 3H) 2.52 (m, 1H), 1.82 (m, 1H). The less polar product (100 mg) was confirmed as alpha-alpha' di-trifluoromethyl tetrahydro-4H-pyran-4-one. $^1$H NMR (500 MHz, $CDCl_3$) δ 4.59 (dd, 2H), 3.24, 3.80 (t, J=11.3 Hz, 2H) 3.42 (m, 2H).

EXAMPLE 95

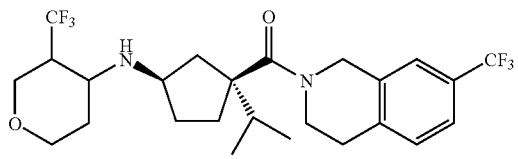

A solution of Intermediate 6 (70 mg, 0.18 mmol), Intermediate 32 (60 mg, 0.36 mmol), diisopropylethylamine (32 μL, 0.18 mmol) and crushed molecular sieves (4A, 50 mg) in dichloromethane (4 mL) was treated with sodium triacetoxyborohydride (191 mg, 0.90 mmol) and stirred at room temperature overnight. The reaction was quenched with saturated sodium bicarbonate solution (10 mL) and diluted with an additional 15 mL of DCM. The organic layer was separated and the aqueous washed with dichloromethane (2×15 mL). The organics were combined, dried over anhydrous sodium sulfate, filtered and evaporated under reduced pressure. The residue was purified by preparative TLC (eluant: 100% ethyl acetate) to yield a higher eluting product 18 mg (20%) as a mixture of two tralis isomers of the tetrahydropyran ring and a lower eluting product 10 mg (11%) as a mixture of two cis isomers.

(higher eluting product) LC-MS for $C_{25}H_{32}F_6N_2O_2$ calculated 506.24, found $[M+H]^+$ 507.25

(lower eluting product) LC-MS for $C_{25}H_{32}F_6N_2O_2$ calculated 506.24, found $[M+H]^+$ 507.25.

EXAMPLE 96

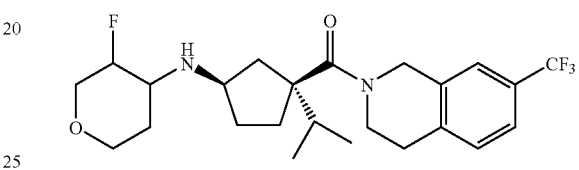

This product was prepared in an analogous fashion to that of Example 95, except Intermediate 32 was replaced with Intermediate 17. The crude product was purified by Preparative TLC (eluant: 0.5% $NH_4OH$: 5% MeOH: 94.5% $CH_2Cl_2$) to afford the title compound as a mixture of four diastereomers. The pure single diastereoisomers were obtained by separation on chiral HPLC (ChiralPak AD, 10% ethyl alcohol in hexanes, 9.0 mL/min). $^1$H NMR (500 MHz, $CDCl_3$) δ 7.44 (d, J=7.7 Hz, 1H), 7.38 (br s, 1H), 7.27 (dd, J=7.6 Hz, 1H), 4.80 (br d, J=17.2 Hz, 1H), 4.75 (br d, J=17.1 Hz, 1H), 3.98 (br d, J=11.5 Hz, 2H), 3.86–3.80 (m, 2H), 3.40 (app dt, J=1.4, 11.6 Hz, 2H), 3.23 (p, J=6.7 Hz, 1H), 2.93 (t, J=5.5 Hz, 2M), 2.85–2.76 (m, 1H), 2.50 (br s, 1H), 2.18–2.06 (m, 3H), 1.95 (br s, 3H), 1.84–1.78 (m, 2H), 1.66–1.57 (m, 2H), 1.51–1.33 (m, 3H), 0.92 (d, J=6.7 Hz, 3H), 0.84 (d, J=6.7 Hz, 3H). LC-MS for $C_{24}H_{32}F_4N_2O_2$ calculated 456.24, found $[M+H]^+$ 457.3.

EXAMPLE 97

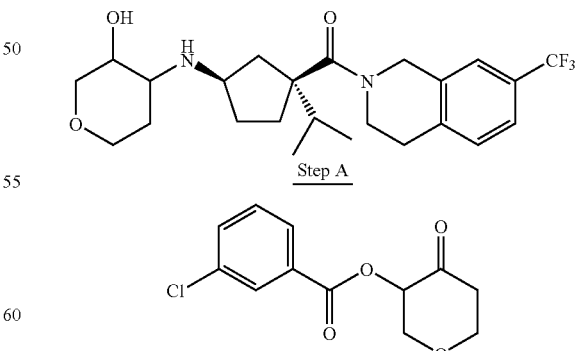

To a suspension of $Na_2HPO_4$ (24.85 g, 175.08 mmol) and 5,6-dihydro-4-methoxy-2H-pyran (10.0 g, 87.5 mmol) in dichloromethane (200 mL) at 0° C. was added dropwise a solution of m-CPBA (30.2 g, 175.06 mmol) in dichloromethane (50 mL) via addition funnel. The resulting solution was stirred for 5 hours allowing to warm to room temperature. The reaction was quenched with water (200 mL) and the organics separated. The aqueous layer was extracted with dichloromethane (200 mL) and the organics combined, dried over anhydrous sodium sulfate, filtered, and evaporated in vacuo to afford the title compound (19.12 g, 86%) as a white solid.

Step B

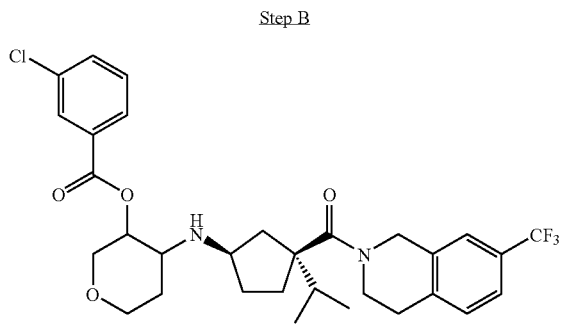

This product was prepared in an analogous fashion to that of Example 95, except the product described in Intermediate 32 was replaced with that of the product described in Step A, Example 97. Purification by preparative TLC (eluant: 5% methanol: 95% dichloromethane) afforded 135 mg (87%) of the product as a mixture of four diastereomers. LC-MS for $C_{31}H_{37}ClF_3N_2O_4$ calculated 592.23, found [M+H]$^+$ 593.3 and [M+H+2]$^+$ 595.3.

Step C

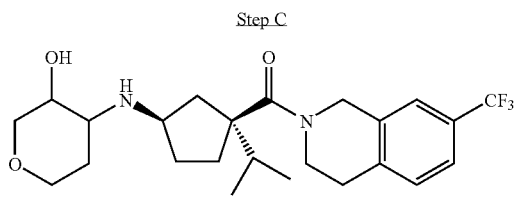

To the solution of the product described in Step B, Example 97 (100 mg, 0.17 mmol) in methanol (5 mL) was added a solution of 0.5 M NaOMe in MeOH (0.40 mL, 0.20 mmol) and the resulting mixture stirred at room temperature for two hours. After completion of reaction, the mixture was evaporated in vacuo and purified by preparative TLC (eluant: 1.0% NH$_4$OH: 10% MeOH: 89% CH$_2$Cl$_2$) to yield the product (69 mg, 90%) as a mixture of four diastereomers. The pure single diastereoisomers were obtained by separation on chiral HPLC (ChiralPak AD, 5% ethyl alcohol in hexanes, 9.0 mL/min). LC-MS for $C_{24}H_{34}F_3N_2O_3$ calculated 454.24, found [M+H]$^+$ 455.2.

EXAMPLE 98

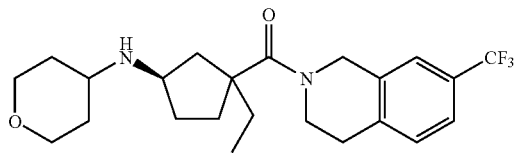

This product was prepared in an analogous fashion to that of Example 92, except iodomethane was replaced with iodoethane. The crude product was purified by Preparative TLC (eluant: 0.5% NH$_4$OH: 5% MeOH: 94.5% CH$_2$Cl$_2$) to afford the title compound (104 mg, 82%) as a mixture of two diastereomers. LC-MS for $C_{23}H_{31}F_3N_2O_2$ calculated 424.23, found [M+H]$^+$ 425.2.

EXAMPLE 99

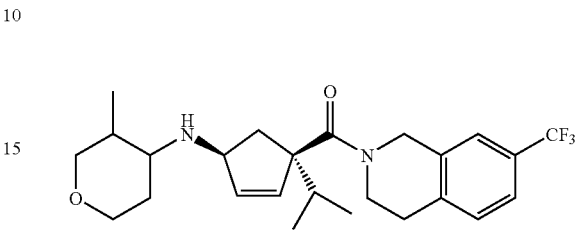

This product was prepared in an analogous fashion to that of Example 93, except tetrahydro-4H-pyran-4-one was replaced with 3-methyl-tetrahydro-4H-pyran-4-one. Purification by preparative TLC (eluant: 0.5% NH$_4$OH: 5% MeOH: 94.5% CH$_2$Cl$_2$) afforded 78 mg (77%) of the product as a mixture of four diastereomers. The pure single diastereoisomers were obtained by separation on chiral HPLC (first by ChiralPak AD, 5% ethyl alcohol in hexanes, 9.0 mL/min, to remove and separated the trans isomers, and then to separate the cis isomers by ChiralCel OD, 8% ethyl alcohol in hexanes, 9.0 mL/min). ). LC-MS for $C_{25}H_{33}F_3N_2O_2$ calculated 450.26, found [M+H]$^+$ 451.2.

EXAMPLE 100

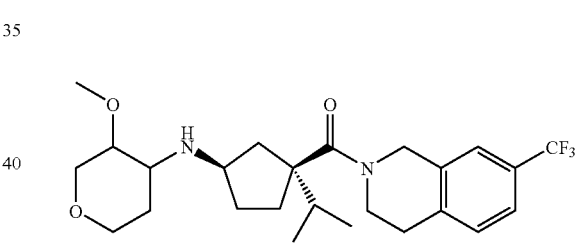

This product was prepared in an analogous fashion to that of Example 95, except the product described in Intermediate 32 was replaced with that of Intermediate 9. Purification by preparative TLC (eluant: 0.5% NH$_4$OH: 5% MeOH: 94.5% CH$_2$Cl$_2$) afforded 26 mg (68%) of the product as a mixture of four diastereomers. ). LC-MS for $C_{25}H_{35}F_3N_2O_3$ calculated 468.26, found [M+H]$^+$ 469.3.

EXAMPLE 101

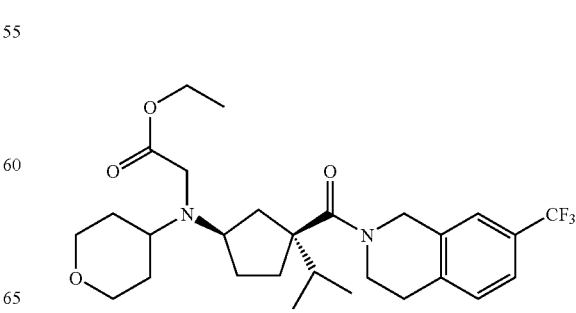

To a suspension of the product described in Procedure B, Example 92 (50 mg, 0.11 mmol) and potassium carbonate (50 mg, 0.37 mmol) in DMF (2 mL) was added ethyl bromo acetate (11.6 µL, 0.11 mmol) via micron pipetter and the resulting solution was stirred at room temperature overnight. The reaction was transfer into 50 mL of water and the product extracted out with ethyl acetate (2×30 mL). The organic layers were combined, washed with water and then brine, dried over anhydrous sodium sulfate, filtered, and evaporated in vacuo. Purification by preparative TLC (eluant: 60% ethyl acetate: 40% hexane) afforded the title compound (43 mg, 73%). LC-MS for $C_{28}H_{39}F_3N_2O_4$ calculated 524.29, found [M+H]$^+$ 525.3.

EXAMPLE 102

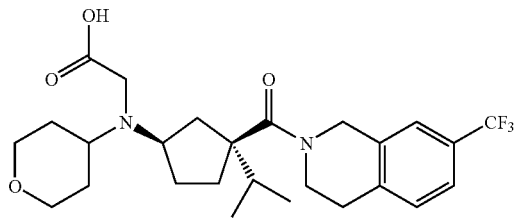

To a solution of the product described in Example 101 (30 mg, 0.06 mmol) in methanol:THF:water (1:1:1 solution, 3 mL), was added LiOH (12 mg, 0.29 mmol) and the resulting mixture stirred overnight at room temperature. The mixture was evaporated under reduced pressure and the residue purified by Gilson reverse phase HPLC to afford the title compound (14 mg, 48%). LC-MS for $C_{26}H_{35}F_3N_2O_4$ calculated 496.17, found [M+H]$^+$ 497.2.

EXAMPLE 103

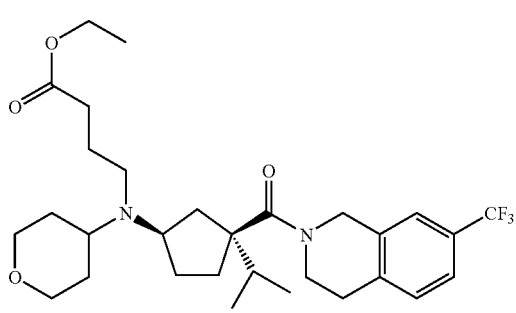

This product was prepared in an analogous fashion to that of Example 101, except ethyl bromo acetate was replaced with ethyl 4-bromo butyrate. Purification by preparative TLC (eluant: 40% ethyl acetate: 60% hexane) afforded the title compound (14 mg, 44%). LC-MS for $C_{30}H_{43}F_3N_2O_4$ calculated 552.32, found [M+H]$^+$ 553.3.

EXAMPLE 104

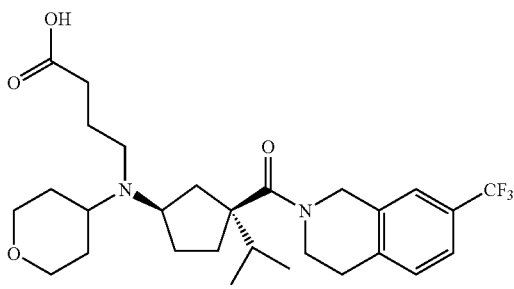

This product was prepared in an analogous fashion to that of Example 102. Purification by Gilson reverse phase HPLC afforded the title compound (6 mg, 63%). LC-MS for $C_{28}H_{39}F_3N_2O_4$ calculated 524.29, found [M+H]$^+$ 525.3.

EXAMPLE 105

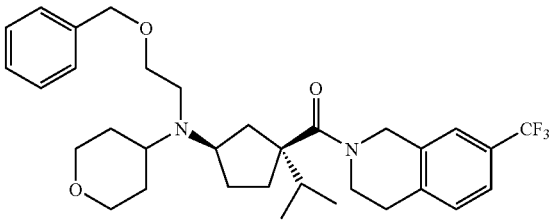

A solution of the product described in Procedure B, Example 92 (50 mg, 0.11 mmol), Benzyloxyacetaldehyde (21 µL, 0.15 mmol), diisopropylethylamine (18 µL, 0.11 mmol) and crushed molecular sieves (4A, 50 mg) in dichloromethane (2 mL) was treated with sodium triacetoxyborohydride (112 mg, 0.53 mmol) and stirred at room temperature overnight. The reaction was quenched with saturated sodium bicarbonate solution (5 mL) and diluted with an additional 10 mL of DCM. The organic layer was separated and the aqueous washed with dichloromethane (10 mL). The organics were combined, dried over anhydrous sodium sulfate, filtered and evaporated under reduced pressure. The residue was purified by preparative TLC (eluant: 70% ethyl acetate: 30% hexane) to yield the title compound (35.2 mg, 55%).

LC-MS for $C_{33}H_{43}F_3N_2O_3$ calculated 572.32, found [M+H]$^+$ 573.4.

EXAMPLE 106

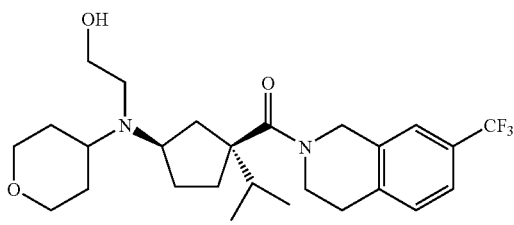

To a suspension of the product described as Example 105 (30 mg, 0.05 mmol) and 10% palladium on carbon (10 mg)

in ethyl alcohol (2 mL) was added 2.0 M HCl in ether (10 µL) and the reaction set under hydrogen atmosphere via hydrogen balloon and stirred at room temperature for 5 hours. The catalyst was filtered off by using a Gilman 0.45 µM PTFE syringe filter and the filtrate evaporated in vacuo. Purification by preparative TLC (eluant: 0.5% NH₄OH: 5% MeOH: 94.5% CH₂Cl₂) afforded the title compound (21 mg, 85%). LC-MS for $C_{26}H_{37}F_3N_2O_3$ calculated 482.28, found [M+H]⁺ 483.3 and [M+H+Na]⁺ 505.3.

EXAMPLE 107

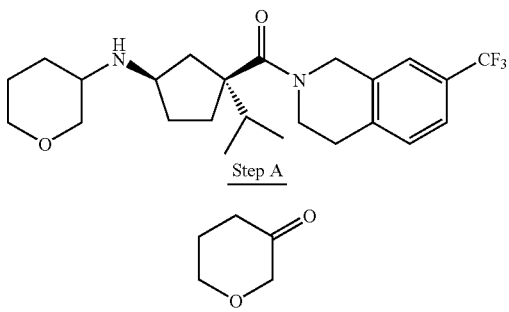

Step A

To 3,4-dihydro-2H-pyran (1.68 g, 20 mmol) was added Borane-THF complex (1.0M solution in THF, 10 mL, 10 mmol) and the resulting mixture stirred for two hours at room temperature. The mixture was evaporated under reduced pressure and residue dissolved into dichloromethane (50 mL). To this solution was added solid magnesium sulfate (30 g) and PCC (8.6 g, 40 mmol) and the resulting slurry stirred at room temperature overnight. The suspension was filtered through celite and then the filtrate passed through a small plug of silica gel. The silica gel plug was washed with 75 mL of dichloromethane and the organics were combined and evaporated in vacuo. The residue was purified by flash chromatography with a small column of silica gel (eluant: 0–50% ether: hexane) to yield the product (127 mg, 6%) as a dark oil. ¹H NMR (500 MHz, CDCl₃) δ 4.03 (s, 2H), 3.86 (t, J=5.6 Hz, 2H) 2.54 (t, J=6.9 Hz, 2H), 2.11 (app dt, J=6.5, 5.6 Hz, 2H).

Step B

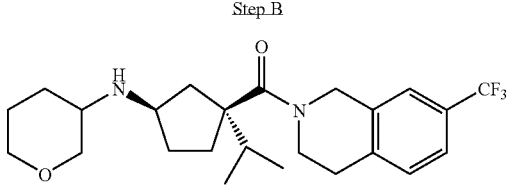

A solution of the product described in Intermediate 6 (100 mg, 0.26 mmol), the product described in Step A, Example 107 (51 mg, 0.51 mmol), diisopropylethylamine (45 µL, 0.26 mmol) and crushed molecular sieves (4A, 50 mg) in dichloromethane (5 mL) was treated with sodium triacetoxyborohydride (271 mg, 1.26 mmol) and stirred at room temperature overnight. The reaction was quenched with saturated sodium bicarbonate solution (10 mL) and diluted with an additional 10 mL of DCM. The organic layer was separated and the aqueous washed with dichloromethane (10 mL). The organics were combined, dried over anhydrous sodium sulfate, filtered and evaporated under reduced pressure. The residue was purified by preparative TLC (eluant: 0.5% NH₄OH: 5% MeOH: 94.5% CH₂Cl₂) to yield the title compound (98 mg, 83%). LC-MS for $C_{24}H_{33}F_3N_2O_2$ calculated 438.25, found [M+H]⁺ 439.3.

EXAMPLE 108

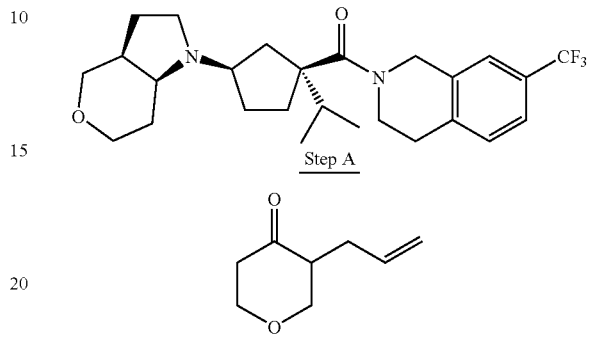

Step A

To 150 mL of THF in a 500 mL round bottom flask was added diiopropylamine (8.76 mL, 62.5 mmol) via syringe. The solution was set under nitrogen and cooled to −78° C. by dry ice/acetone bath. n-Butyl lithium (25 mL, 62.5 mmol) was added to the solution and the resulting mixture stirred at −78° C. for 10 minutes. Tetrahydro-4H-pyran-4-one (5.0 g, 50.0 mmol) in 25 mL of THF was added dropwise via syringe over a 10 minute period and the resulting solution was stirred at −78° C. for one hour. After one hour, allyl bromide (6.47 mL, 75.0 mmol) was added to the cool solution and the resulting mixture was stirred overnight allowing to warm to room temperature. The reaction was quenched with saturated ammonium chloride solution (100 mL) and the organic layer was separated. The aqueous was washed with ethyl acetate (2×50 mL) and the organics were combined, dried over anhydrous sodium sulfate, filtered, and evaporated in vacuo. MPLC purification (eluant 15% ethyl acetate: 85% hexane) afforded the product (1.93 g, 28%) as a clear oil. ¹H NMR (500 MHz, CDCl₃) δ 5.80–5.71 (m, 1H), 5.09–5.02 (m, 2H), 4.21–4.16 (m, 2H), 3.76 (ddd, J=3.7, 11.0, 14.6 Hz, 1H) 3.44 (dd, J=9.6, 11.2, 1H), 2.65–2.55 (m, 3H), 2.44 (ddd, J=3.4, 6.9, 14.4 Hz, 1H), 2.05 (ddd, J=7.5, 14.4, 15.0 Hz, 1H).

Step B

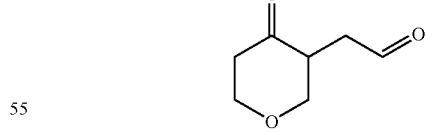

A solution of the product described in Step A, Example 108 (1.9 g, 13.8 mmol) in dichloromethane (50 mL) cooled to 0° C. was introduced ozone by bubbling until the solution turn light blue. Air was then bubbled into the solution to remove excess ozone which cause the blue color to disappear. The reaction was allowed to warm to room temperature at which time triphenylphosphine (3.8 g, 14.5 mmol) was then added. The resulting mixture stirred for two hours at room temperature, and then was evaporated under reduced pressure. The residue was purified by flash chromatography (eluant 2:1 ether: hexane) to yield 1.02 g (52%) of the product as a yellow oil. ¹H NMR (500 MHz, CDCl₃) δ 9.79 (s, 1H), 4.33–4.28 (m, 1H), 4.23 (ddd, J=1.4, 6.6, 11.0 Hz, 1H), 3.69 (ddd, J=2.7, 11.9, 14.6 Hz, 1H) 2.90 (dd, J=6.8, 18.3, 1H), 2.73 (dddd, J=0.9, 7.1, 12.7, 13.5, 1H), 2.47–2.39 (m, 1H), 2.27 (dd, J=5.5, 18.3 Hz, 1H), 2.22–2.10 (m, 2H).

Step C

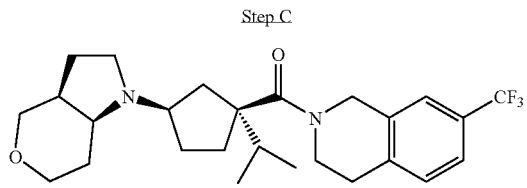

A solution of the product described in Intermediate 6 (100 mg, 0.26 mmol), the product described in Step B, Example 108 (72.8 mg, 0.51 mmol), diisopropylethylamine (45 µL, 0.26 mmol) and crushed molecular sieves (4A, 50 mg) in dichloromethane (5 mL) was treated with sodium triacetoxyborohydride (271 mg, 1.26 mmol) and stirred at room temperature overnight. The reaction was quenched with saturated sodium bicarbonate solution (10 mL) and diluted with an additional 10 mL of DCM. The organic layer was separated and the aqueous washed with dichloromethane (10 mL). The organics were combined, dried over anhydrous sodium sulfate, filtered and evaporated under reduced pressure. The residue was purified by preparative TLC (eluant: 0.5% NH₄OH: 5% MeOH: 94.5% CH₂Cl₂) to yield the title compound (55 mg, 46%). The pure single diastereoisomers were obtained by separation on chiral BPLC (ChiralPak AD, 7% ethyl alcohol in hexanes, 9.0 mL/min). LC-MS for C₂₆H₃₅F₃N₂O₂ calculated 464.27, found [M+H]⁺ 465.2.

EXAMPLE 109

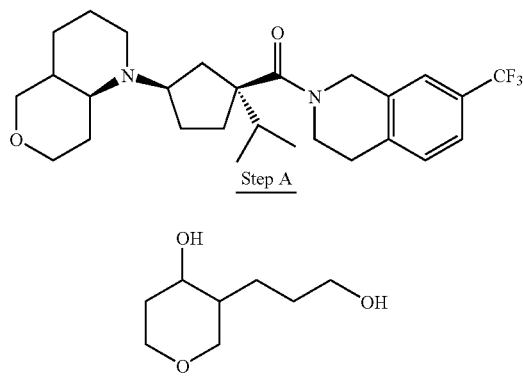

Step A

To a cooled (0° C.) solution of olefin (Step A, Example 108) (1.98 g, 14.1 mmol) in THF (70 mL) was added dropwise 1.0 M BH₃.THF in THF (8.46 mL, 8.46 mmol). The reaction mixture was warmed to room temperature and stirred for 1 h. Then a second portion of 1.0 M BH₃.THF in THF (8.46 mL, 8.46 mmol) and the reaction mixture was stirred over the weekend. The reaction was quenched by the addition of water (70 mL), then was treated with NaBO₃.4H₂O (7.80 g, 50.8 mmol). The resulting suspension was vigorously stirred for 4.25 h, then was concentrated to dryness. The residue was purified by flash chromatography (silica, 5% methanol/DCM, then 8% methanol/DCM, then 10% methanol/DCM) to give 1.92 g (85%) of diol as a mixture of isomers.

Step B

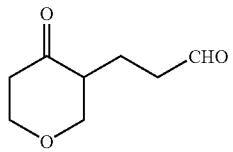

Oxalyl chloride (110 µL, 1.26 mmol) was dissolved in DCM (8 mL), precooled to −78° C. Then a solution of DMSO (179 µL, 2.52 mmol) in DCM (1.5 mL) was added dropwise. After 5 min, a solution of the diol from Step A immediately above (50.5 mg, 0.315 mmol) in DCM (1.5 mL) was added dropwise. The reaction mixture was stirred at −78° C. for 20 min, then triethylamine (702 µL, 5.04 mmol) was added dropwise. The reaction mixture was stirred for an additional 10 min, then was warmed to rt. After 45 min, the reaction mixture was poured into 2 N HCl solution and extracted three times with DCM. The combined organic layers were washed with brine, dried over MgSO₄, filtered, and concentrated, giving 45.4 mg of crude product.

Step C

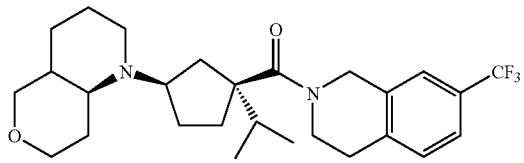

A solution of the product described in Intermediate 6 (100 mg, 0.26 mmol), the product described in Step B, Example 109 (80 mg, 0.51 mmol), diisopropylethylamine (45 µL, 0.26 mmol) and crushed molecular sieves (4A, 50 mg) in dichloromethane (5 mL) was treated with sodium triacetoxyborohydride (271 mg, 1.26 mmol) and stirred at room temperature overnight. The reaction was quenched with saturated sodium bicarbonate solution (10 mL) and diluted with an additional 10 mL of DCM. The organic layer was separated and the aqueous washed with dichloromethane (10 mL). The organics were combined, dried over anhydrous sodium sulfate, filtered and evaporated under reduced pressure. The residue was purified by preparative TLC (eluant: 0.5% NHOH: 5% MeOH: 94.5% CH₂Cl₂) to yield the title compound (59 mg, 48%) as a mixture of isomers. ). LC-MS for C₂₇H₃₇F₃N₂O₂ calculated 478.28, found [M+H]⁺ 479.3.

EXAMPLE 110

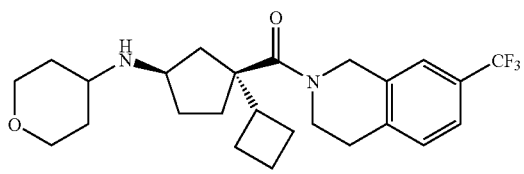

Step A

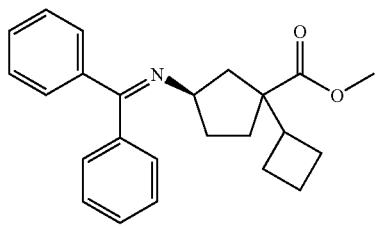

A flame dried 250 mL round bottom flask was charged with 50 mL of dry THF, and then, set under nitrogen and cooled to −78° C. using an acetone/dry ice bath. Diisopropylamine (3.19 mL, 22.76 mmol) was added to the cooled solvent via syringe followed by the slow addition of 2.5M n-BuLi in hexane (9.10 mL, 22.76 mmol). After 5 minutes stirring, the product described in Step B, Intermediate 4 (5.00 g, 16.40 mmol) in 35 mL of THF was added dropwise via syringe and the resulting mixture stirred at −78° C. for 2 hours. Bromo-cyclobutane (5.35 mL, 56.85 mmol) was then added dropwise via syringe and the resulting mixture was stirred overnight allowing to warm slowly to room temperature. The reaction was quenched with a saturated solution of ammonium chloride (75 mL) and the organics separated. The aqueous layer was extracted with ethyl acetate (3×50 mL) and all the organics combined, dried over anhydrous sodium sulfate, filtered, and evaporated under reduced pressure. The crude product was used in the next step without further purification. LC-MS for $C_{24}H_{27}NO_2$ calculated 361.20, found $[M+H]^+$ 362.2

Step B

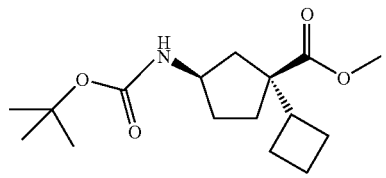

To a solution of the product from Step A, Example 110 (16.40 mmol, assuming 100% conversion) in 40 mL THF was added 40 mL of 2N hydrochloric acid and the resulting mixture stirred overnight at room temperature. The solution was concentrate in vacuo to remove the THF and the aqueous layer was then diluted with DCM (100 mL). The pH of the aqueous layer was adjusted to pH=10 by slow addition of 5N sodium hydroxide with vigorous stirring. The organic layer was removed using a separatory funnel and the aqueous layer was extracted with dichloromethane (2×50 mL). The organics were combined, dried over anhydrous sodium sulfate, and filtered. To the filtrate was added DIEA (5.22 mL, 30.00 mmol) and Boc-anhydride (6.58 g, 30.16 mmol) and the resulting solution was stirred at room temperature overnight. The mixture was washed with 1N hydrochloric acid, followed by saturated solution of sodium bicarbonate, and brine. The organic layer was dried over anhydrous sodium sulfate, filtered, and evaporated under reduced pressure. Purification by MPLC (gradient eluant: 0–30% ethyl acetate/hexane) afforded 103 mg (3%) of the higher eluting desired cis (R, S) isomer and 205 mg (6%) of a 1:1 mixture of the 2 diastereomers. $^1$H NMR (500 MD, $CDCl_3$) (higher eluting desired cis isomer) δ 4.85 and 4.02 (singlets, 1H), 3.70 (s, 3H), 2.28–2.21 (m, 1H), 2.13 (dd, J=5.0, 14.0 Hz, 1H) 2.05–1.90 (m, 2H), 1.68–1.56 (m, 2H), 1.53 (dd, J=7.2, 13.6 Hz, 1H), 1.46 (br s, 10H), 0.64–0.56 (m, 1H), 0.46–0.37 (m, 2H), 0.06–0.00 (m, 2H).

Step C

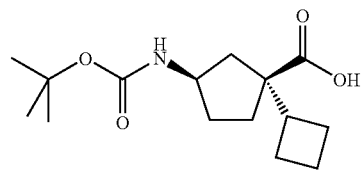

To a mixture of the desired cis (R, S) product described in Step B, Example 110 (100 mg, 0.34 mmol) in a 1:1:1 solution of THF:methanol:water (3 mL) was added solid LiOH (70 mg, 1.68 mmol) and the resulting solution was heated to 60° C. and stirred for 18 hours. The mixture was left standing to cool to room temperature and then concentrated to remove the organic solvent. The aqueous layer was acidified by slow addition of 6N hydrochloric acid to adjust the pH to 4 or 5. The acidic aqueous layer was extracted with DCM (3×25 mL) and the organics were combined, dried over anhydrous sodium sulfate, filtered, and evaporated under reduced pressure to afford the product (89 mg, 94%) as a yellow oil. $^1$H NMR (500 MHz, $CDCl_3$) δ 4.85 and 4.10 (singlets, 1H), 2.28–2.21 (m, 1H), 2.13 (dd, J=5.0, 14.0 Hz, 1H) 2.10–2.04 (m, 1H), 1.99 (dd, J=8.0, 13.7 Hz, 1H), 1.68–1.56 (m, 2H), 1.53 (dd, J=7.2, 13.6 Hz, 1H), 1.46 (br s, 10H), 0.64–0.56 (m, 1H), 0.46–0.37 (m, 2H), 0.08–0.01 (m, 2H).

Step D

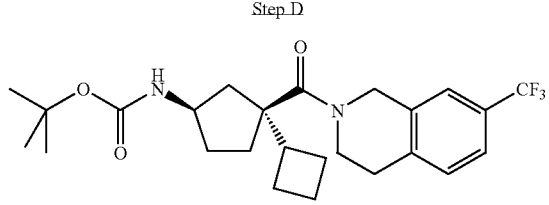

The product described in Step C, Example 110 (25 mg, 0.09 mmol) and Intermediate 1 (28 mg, 0.10 mmol) were first dried by azeotroping with toluene (20 mL) and placing under high vacuum for 30 minutes. Under nitrogen, DMAP (7 mg, 0.05 mmol), anhydrous DCM (0.5 mL), DIEA (62 μL, 0.35 mmol), and PyBrop (42 mg, 0.09 mmol) were added sequentially and the resulting mixture was stirred at room temperature overnight. The reaction was quenched with saturated $NaHCO_3$ solution, diluted with 10 mL of DCM, and the organics separated. The aqueous layer was back washed with DCM (10 mL) and the organic layers were combined, dried over $Na_2SO_4$, filtered, and evaporated in vacuo. The residue was purified by preparative TLC (eluant:

20% ethyl acetate: 80% hexanes) to afford the product (14 mg, 34%) as a yellow film. LC-MS calculated for $C_{25}H_{33}F_3N_2O_3$ is 466.24, found [M+H]+ 467.3.

Step E

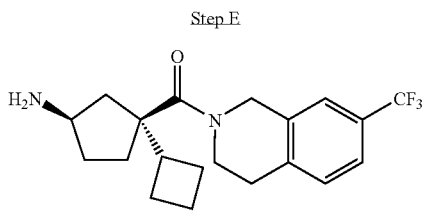

The product described in step D, Example 110 (14 mg, 0.03 mmol) was dissolved with 4N HCl in dioxane (1 mL) and the resulting solution was stirred at room temperature for one hour. The reaction was evaporated under vacuum to afford the product (quantitative) as a white powder. LC-MS calculated for $C_{20}H_{25}F_3N_2O$ is 366.19, found [M+H]+ 367.2.

Step F

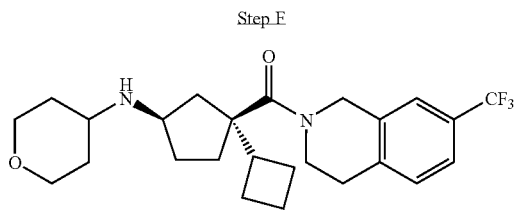

A solution of the product described in Step E, Example 110 (13.70 mg, 0.03 mmol), tetrahydro-4H-pyran-4-one (6 μL, 0.06 mmol), diisopropylethylamine (5.5 μL, 0.03 mmol) and crushed molecular sieves (4A, 10 mg) in dichloromethane (1 mL) was treated with sodium triacetoxyborohydride (32 mg, 0.15 mmol) and stirred at room temperature overnight. The reaction was quenched with saturated sodium bicarbonate solution (2 mL) and diluted with an additional 5 mL of DCM. The organic layer was separated and the aqueous washed with dichloromethane (5 mL). The organics were combined, dried over anhydrous sodium sulfate, filtered and evaporated under reduced pressure. The residue was purified by preparative TLC (eluant: 0.5% $NH_4OH$: 5% MeOH: 94.5% $CH_2Cl_2$) to yield the title compound 9.61 mg (71%). LC-MS for $C_{25}H_{33}F_3N_2O_2$ calculated 450.25, found [M+H]+ 451.2.

EXAMPLE 111 AND 112

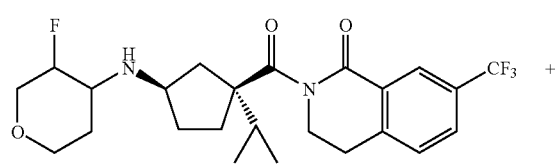

-continued

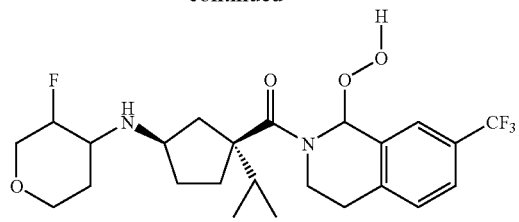

After storing the product from Example 96 in a scintillation vial at room temperature for three months, analysis of the compound by LC-MS exhibited degradation of the product by air oxidation. Separation by Gilson reverse phase HPLC provided two new products (Example 114 and 115) and 60% of the parent compound recovered. These compounds were analyzed by NMR and LC-MS to determine the structures.

See Example 96 for parent compound's NMR and LC-MS.

Example 114: $^1$H NMR (500 MHz, CDCl$_3$) δ 8.38 (s, 1), 7.71 (br dd, J=2.3, 7.6 Hz, 1H), 7.38 (d, J=7.8 Hz, 1H), 6.24 (br s, 1H), 4.13–4.06 (m, 1H), 4.05–3.97 (m, 2H), 3.90 (s, 1H), 3.62 (app dt, J=2.8, 6.6 Hz, 2H), 3.51–3.40 (m, 2H), 3.10 (t, J=6.6 Hz, 2H), 2.17 (p, J=6.8 Hz, 1H), 1.91–1.84 (m, 1H), 1.82–1.56 (m, 5H), 1.42–1.36 (m, 1H), 1.32 (d, J=8.9 Hz, 1H), 1.27 (s, 1H), 1.05 (d, J=6.5 Hz, 3H), 1.03 (d, J=6.3 Hz, 3H). LC-MS for $C_{24}H_{30}F_4N_2O_3$ calculated 470.24, found [M+H]+ 471.2. Example 115: $^1$H NMR (500 MHz, CDCl$_3$) (mixture of isomers at hydroperoxy substituent): δ 7.90–7.75 (m, 1H), 7.58–7.48 (m, 2H), 6.70 (br s, 1H), 6.38 (br s, 1H), 4.20–3.95 (m, 3H), 3.62–3.35 (m, 6H), 2.98–2.80 (m, 2H), 2.12 (p, J=6.6 Hz, 1H), 2.00–1.80 (m, 3H), 1.62–1.26 (m, 3H), 0.90–0.80 (m, 6H). LC-MS for $C_{24}H_{32}F_4N_2O_3$ calculated 488.24, found [M+H]+ 489.2.

INTERMEDIATE 33

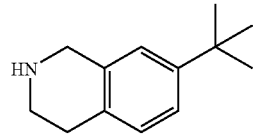

Step A

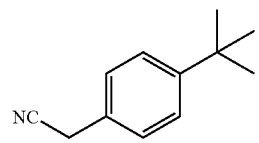

To a mixture of sodium cyanide (5.39 g, 110 mmol) and 4-(tert-butyl)benzyl bromide (25.0 g, 110 mmol) in DMSO (100 mL), was added 2 drops of water. The reaction mixture was stirred and heated at 80° C. for 3 hr, poured into 400 mL of iced water, and extracted by DCM (twice) and EtOAc/hexane (1:1, twice). The organic portion was washed by water and brine, dried over $Na_2SO_4$, filtered, and concentrated. The residue was purified by column chromatography (silica gel, 20% EtOAc/hexane to 30% EtOAc/hexane) to yield the title compound (10.12 g, 53%). $^1$H-NMR (400 MHz, CDCl$_3$) δ 7.44 (d, J=8.2 Hz, 2H), 7.30 (d, J=8.2 Hz, 2H), 3.72 (s, 2H), 1.37 (s, 9H).

Step B

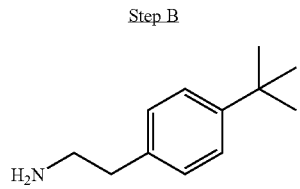

To a solution of the nitrile product from Step A (10.12 g, 58.41 mmol) in ethanol (100 mL) and 30% ammonium hydroxide solution (25 mL), was added Raney Ni (~400 mg). The reaction mixture was placed in a par-shaker and shook under 50 lb pressure of H$_2$ overnight. The solution was diluted by methanol, filtered through celite and concentrated under vacuum to yield the title product (10.1 g, 97%). $^1$H-NMR (400 MHz, CDCl$_3$) δ 7.34 (d, J=8.2 Hz, 2H), 7.15 (d, J=8.2 Hz, 2H), 2.97 (t, J=6.8 Hz, 2H), 2.74 (t, J=6.8 Hz, 2H), 1.71 (br m, 2H), 1.33 (s, 9H).

Step C

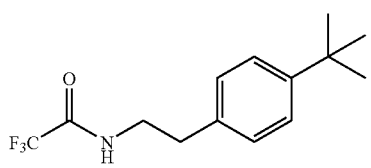

To a solution of the amine from Step B (10.1 g, 56.97 mmol) and pyridine (9.22 mL, 113.9 mmol) in DCM (120 mL), cooled to 0° C., was slowly added trifluoroacetic anhydride (12.07 mL, 85.45 mmol). The reaction mixture was stirred at room temperature for 3 hr, diluted by DCM, washed by 2N HCl, water and brine, dried over Na$_2$SO$_4$, filtered, and concentrated to yield the title compound (7.95 g, 51%). $^1$H-NMR (400 MHz, CDCl$_3$) δ 7.38 (d, J=8.2 Hz, 2H), 7.14 (d, J=8.2 Hz, 2H), 6.35 (br s, 1H), 3.63 (q, J=6.6 Hz, 2H), 2.87 (t, J=6.8 Hz, 2H), 1.34 (s, 9H).

Step D

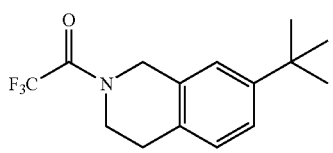

To a solution of acetic acid (113 mL) and concentrated sulfuric acid (28 mL), cooled to 0–5° C., was added a mixture of the amide from Step C (7.90 g, 28.91 mmol) and paraformaldehyde (1.302 g, 43.36 mmol). The reaction mixture was stirred at room temperature overnight and poured into iced-water. The mixture was extracted by EtOAc (three times). The organic portion was washed by water and brine, dried over Na$_2$SO$_4$, filtered, and concentrated to yield the title compound (8.11 g, 98%). $^1$H-NMR (400 MHz, CDCl$_3$) δ 7.26–7.34 (m, 1H), 7.11–7.18 (m, 2H), 4.80 (d, 2H), 3.88 (m, 2H), 2.95 (m, 2H), 1.33 (s, 9H).

Step E

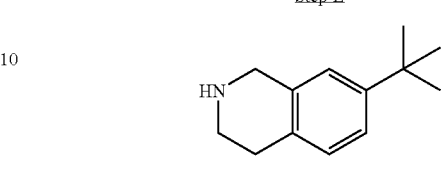

To a solution of the amide from Step D (890 mg, 3.12 mmol) in ethanol (20 mL), was added a solution of potassium carbonate (2.37 g, 17.16 mmol) in water (5 mL). The reaction mixture was refluxed overnight and then concentrated. The residue was diluted by water, extracted by DCM (three times). The combined organic portion was washed by water and brine, dried over MgSO$_4$, filtered, and concentrated. The residue was purified by flash column chromatography (silica gel, 5% [aq. NH4OH/MeOH 1/9]/DCM to 8% [aq. NH4OH/MeOH 1/9]/DCM) to yield the title compound (402 mg, 68%). $^1$H-NMR (400 MHz, CD$_3$OD) δ 7.20 (d, J=8.0 Hz, 1H), 7.05 (m, 2H), 4.03 (s, 2H), 3.50 (s, 1H), 3.16 (t, J=6.0 Hz, 2H), 6.80 (t, J=6.0 Hz, 2H), LC-MS calc. For C13H19N: 189.15; Found: 190 (M+H).

EXAMPLE 113

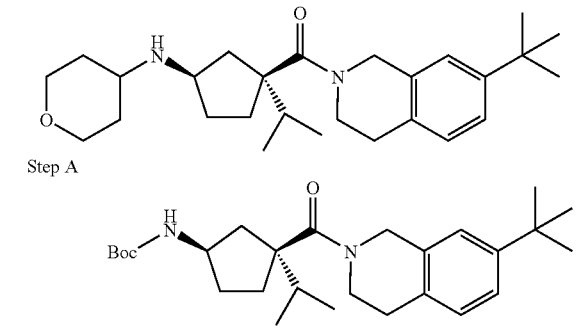

Step A

This compound was prepared starting from INTERMEDIATE 4 and INTERMEDIATE 33 as detailed in Intermediate 6, Step A. LC-MS calc. For C27H42N2O3: 442.32; Found: 443 (M+H).

Step B

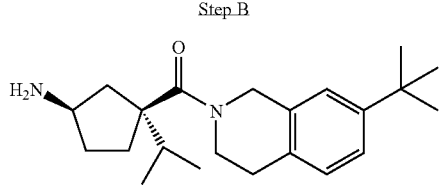

This compound was prepared as detailed in Intermediate 6, Step B.

Step C

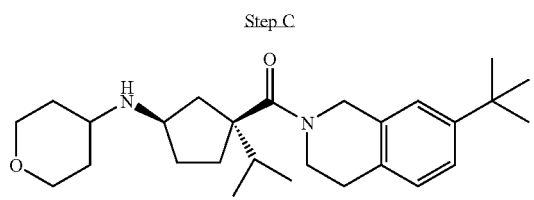

This compound was prepared from the above intermediate from Step B as detailed in Example 1, Procedure A. LC-MS calc. For C27H42N2O2: 426.32; Found: 427 (M+H).

INTERMEDIATE 34

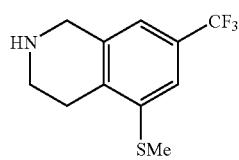

Step A

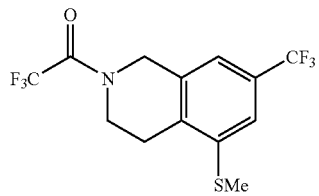

N-Trifluoracetyl-7-trifluoromethyl-5-IodoTIQ (Step A, Intermediate 10) (530 mg, 1.25 mmol) was dissolved in pyridine (8 mL) and Cu powder (500 mg) and methyldisulfide (500 mg) were added. The suspension was heated to 95 degrees C. for 6 h. Filtered off insolubles and taken up in dichloromethane and 2N HCl added. Wash organic layer with 2N HCl until neutral. The organic layer was dried and concentrated. Chromatography gave the title product (360 mg).

NMR (500 MHz, CD$_3$OD) δ: 7.33 (s, 1H); 7.28 (s, 1H); 4.57 (s, 2H); 3.59 (t, J=6, 2H); 2.92 (s, 2H); 2.90 (t, J=6 2H); 2.53 (s, 3H). MS (ES) m/z: 344.05 [MH$^+$].

Step B

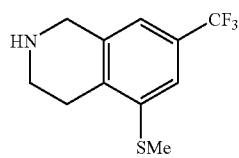

The amide from Step A (360 mg) was mixed with NaBH4 (100 mg) in 10 mL of EtOH overnight. The mixture was evaporated and the residue was purified on chromatography (silica gel, 10% [aq. NH4OH/MeOH 1/9]/DCM. The title compound was obtained as an oil (210 mg). MS (ES) m/z: 248.0 [MH$^+$].

EXAMPLE 114

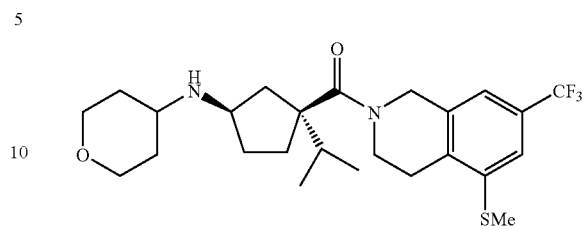

This compound was prepared starting from INTERMEDIATE 5 and INTERMEDIATE 34 according to the procedure described in Example 58, Step C. ESI-MS calc. for C25H35F3N2O2S: 484; found 485 (M+H).

INTERMEDIATE 35

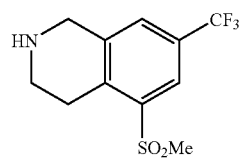

Step A

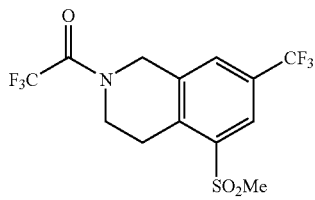

INTERMEDIATE 34 (105 mg, 0.3 mmol) was dissolved in a mixture of Isopropanol and water (2 mL) and Oxone (600 mg) was added and the mixture was stirred for 48 h. Dichloromethane and brine were added and the organic phase was separated dried and evaporated gave after prepTLC with 4:1 hexane: ethyl acetate the product 115 mg. MS (ES) m/z: 376.0[MH$^+$].

Step B

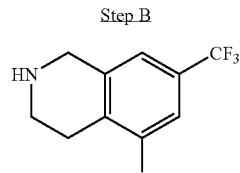

The amide from Step A was deblocked using NaBH4 in EtOH (Step B, Intermediate 34). MS (ES) m/z: 279.95 [MH$^+$].

EXAMPLE 115

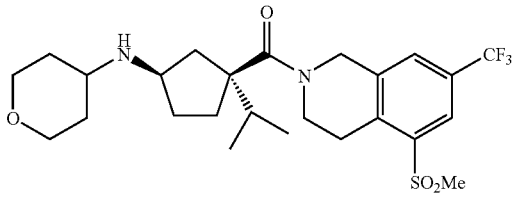

This compound was prepared starting from INTERMEDIATE 5 and INTERMEDIATE 35 according to the procedure described in Example 58, Step C. ESI-MS calc. for C25H35F3N2O4S: 516; found 517 (M+H).

INTERMEDIATE 36

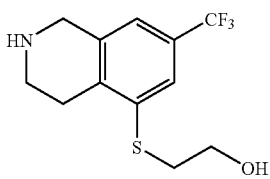

Step A

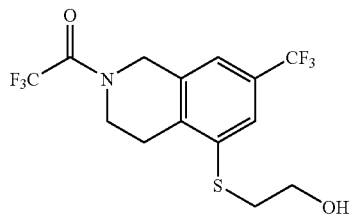

N-Trifluoracetyl-7-trifluoromethyl-5-IodoTIQ (Step A, Intermediate 10) (1000 mg, 2.4 mmol) was dissolved in DME (10 mL) and Cu powder (1000 mg) and hydroxyethyldisulfide (1000 mg) were added. The suspension was heated to reflux for 16 h. Filtered off insolubles and concentrated to small volume and partition between ether hexane 1:1 and water. The organic layer was separated dried and evaporated. Flash chromatography afforded the product (800 mg). MS (ES) m/z: 374.0 [MH+].

Step B

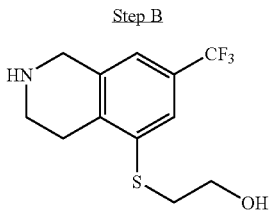

The amide from Step A was deblocked using NaBH4 in EtOH (Step B, Intermediate 34) and used as is.

EXAMPLE 116

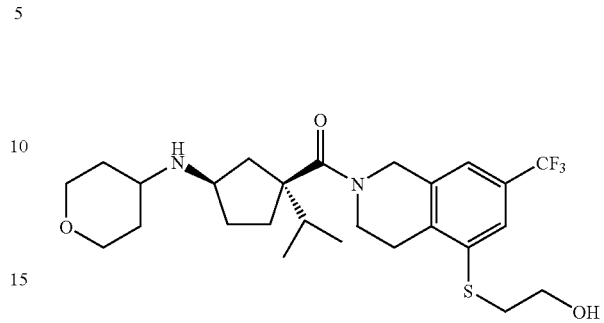

This compound was prepared starting from INTERMEDIATE 5 and INTERMEDIATE 36 according to the procedure described in Example 58, Step C. ESI-MS calc. for C26H37F3N2O3S: 514; found 515 (M+H).

INTERMEDIATE 37

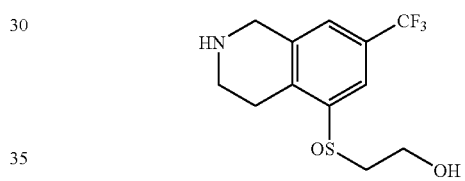

The amide (Step A, Intermediate 36) (120 mg, 0.32 mmol) was dissolved in dichloromethane (2 mL) and 3-chloroperbenzoic acid (220 mg of 77% pure) was added and the mixture was stirred for 18 h. The organic phase was washed with 1N NaOH, separated dried and evaporated, then EtOH (2 mL) and NaBH4 (20 mg) was added and stirred overnight. The product was obtained after Chromatography (50 mg). MS (ES) m/z: 294.05 [MH+].

EXAMPLE 117

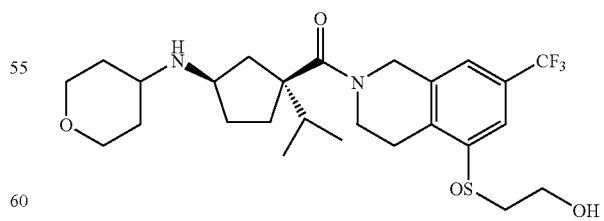

This compound was prepared starting from INTERMEDIATE 5 and INTERMEDIATE 37 according to the procedure described in Example 58, Step C. ESI-MS calc. for C26H37F3N2O4S: 530; found 531 (M+H).

INTERMEDIATE 38

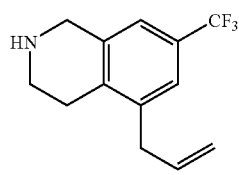

N-Trifluoracetyl-7-trifluoromethyl-5-IodoTIQ (Step A, Intermediate 10) (846 mg, 2 mmol), allyl tributyltin (740 uL, 2.4 mmol), Pd{P(Ph)₃}Cl₂ (70 mg 0.1 mmol) and Et₃N (500 ul) were combined in DMF (2.5 mL) and heated at 90 degrees C. for 4 h, then cooled and partitioned between ether and brine. The ether layer was dried and concentrated and the residue was Flash Chromatographed Hexane/Ethyl Acetate 80:20 yielding product (450 mg). MS (ES) m/z: 338.05 [MH⁺]. Then 100 mg was deblocked under standard conditions (Step B, Intermediate 34) to give the title product (80 mg). MS (ES) m/z: 242.3 [MH⁺].

EXAMPLE 118

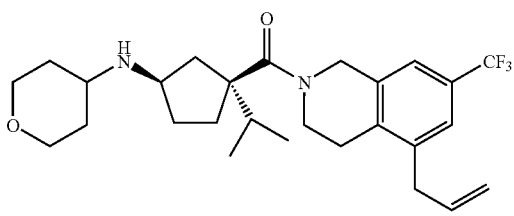

This compound was prepared starting from INTERMEDIATE 5 and INTERMEDIATE 38 according to the procedure described in Example 58, Step C. ESI-MS calc. for C27H37F3N2O2: 478; found 479 (M+H).

INTERMEDIATE 39

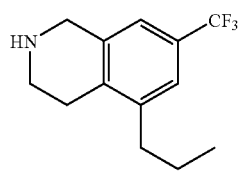

N-trifluoroacetyl-7-trifluoromethyl-5-allylTIQ (40 mg, 0.3 mmol) was dissolved in ethyl acetate (1 mL) and hydrogenated at atmospheric pressure with Pd/C. The mixture was filtered over celite and concentrated to dryness to give the product. MS (ES) m/z: 340.1 [MH⁺]. Standard deblocking using NaBH4 in EtOH afforded the title compound.

EXAMPLE 119

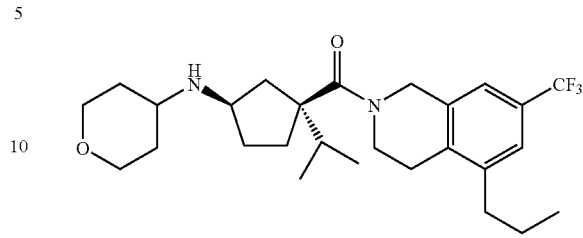

This compound was prepared starting from INTERMEDIATE 5 and INTERMEDIATE 39 according to the procedure described in Example 58, Step C. ESI-MS calc. for C27H39F3N2O2: 480; found 481 (M+H).

INTERMEDIATE 40

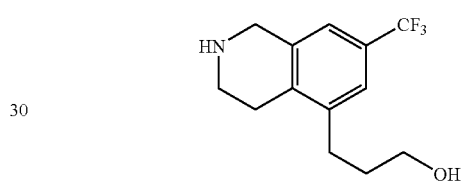

N-trifluoroacetyl-7-trifluoromethyl-5-allylTIQ (100 mg, 0.3 mmol) was dissolved in THF (1 mL) and cooled to 0 decrees C, then BH3/THF 1M (220 uL, 220 mmol) after warming to room temperature and stirring for 3 h water (1 mL) and NaBO₃4H₂O (75 mg, 0.45 mmol) was added. The mixture was stirred until complete by LC/MS. Dichloromethane and brine were added and the organic layer was separated and dried and evaporated to give the product (79 mg) after PrepTLC. MS (ES) m/z: 356.1 [MH⁺]. Standard deblocking using NaBH4 in EtOH. MS (ES) m/z: 260.1 [MH⁺].

EXAMPLE 120

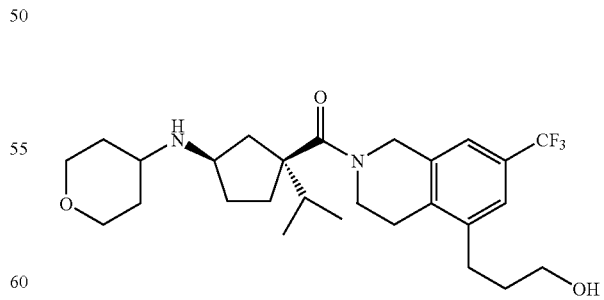

This compound was prepared starting from INTERMEDIATE 5 and INTERMEDIATE 40 according to the procedure described in Example 58, Step C. ESI-MS calc. for C27H39F3N2O3: 496; found 497 (M+H).

INTERMEDIATE 41

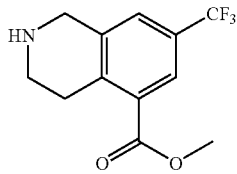

Step A

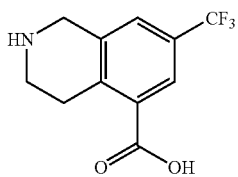

Intermediate 10 (1.95 g, 8.5 mmol) was refluxed with 50 mL of concentrated aq. HCl for 48 h. LC-MS showed a complete hydrolysis. The mixture was cooled to RT and the resultant precipitate was collected by filtration and washing with concentrated aq. HCl. The desired product as its HCl salt (1.75 g, 73%) was obtained after dryness in high vacuum. $^1$H NMR (CD$_3$OD, 400 MHz): 8.20 (s, 1H), 7.80 (s, 1H), 4.51 (s, 2H), 3.55 (m, 4H). LC-MS for C11H10F3NO2 calculated 245, found [M+H]$^+$ 246.

Step B

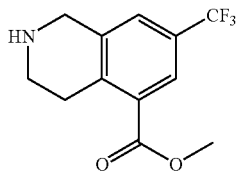

To a suspension of the amino acid HCl salt (Step A, Intermediate 41) (1.75 g, 6.25 mmol) in 50 mL of methanol was added slowly a neat solution of acetyl chloride (5 mL). The resultant mixture was refluxed until LC-MS showed a complete esterification (~3 h), evaporated and dried in high vacuum to yield the title compound as a white solid (1.85 g, 100%). $^1$H NMR (CD$_3$OD, 400 MHz): 8.19 (s, 1H), 7.82 (s, 1H), 4.50 (s, 2H), 3.94 (s, 3H), 3.53 (s, 4H). LC-MS for C12H12F3NO2 calculated 259, found [M+H]$^+$ 260.

EXAMPLE 121

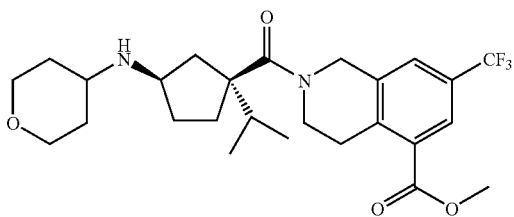

Step A

-continued

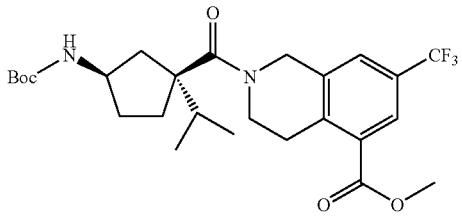

A mixture of the INTERMEDIATE 41 (as HCl salt, 1.2 g, 4 mmol), the acid (Intermediate 4, 1.1 g, 4 mmol), PyBrOP (1.85 g, 4 mmol), DMAP (0.29 g, 2.4 mmol) and DIEA (2.77 mL, 16 mmol) in 10 mL of dichloromethane was stirred at RT overnight. The entire mixture was dumped on a silica gel column and eluted with 20% ethyl acetate/hexane. The title compound was obtained as a white solid (1.7 g, 83%). LC-MS for C26H35F3N2O5 calculated 512, found [M+H−100]$^+$ 413.

Step B

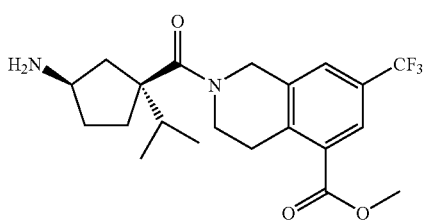

The above amide (Step A, Example 121) (1.7 g, 3.3 mmol) was mixed with 20 mL of 4N HCl/dioxane for one hour, evaporated and dried in high vacuum to yield the title product as a white solid (1.45 g, 100%). LC-MS for C21H27F3N2O3 calculated 412, found [+H]$^+$ 413.

Step C

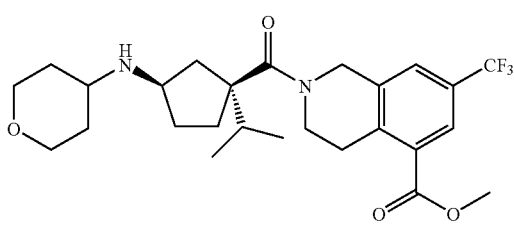

This compound was prepared starting from the above amino amide (Step B, Example 121) and tetrahydro-4H-pyran-4-one according to the Procedure A described in Example 1. LC-MS for C26H35F3N2O4 calculated 496, found [M+H]$^+$ 497.

EXAMPLE 122

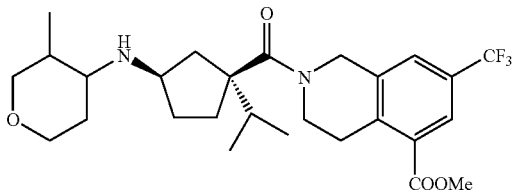

This compound as a mixture of 4 isomers was prepared according to the procedure as detailed in Example 121, except the tetrahydro-4H-pyran-4-one was replaced by 3-methyl-tetrahydro-4H-pyran-4-one. LC-MS for C27H37F3N2O4 calculated 510, found [M+H]$^+$ 511.

EXAMPLE 123

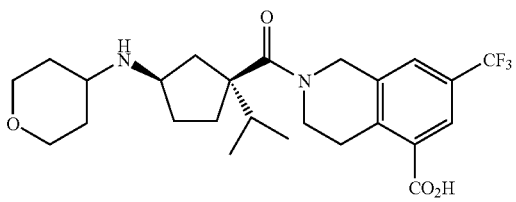

The ester (Example 121, 86 mg, 0. mmol) was stirred with LiOH.H2O (100 mg) in a mixture of 0.1 mL water and 0.5 mL of methanol overnight. The mixture was loaded on preparative TLC (1000 micron) directly, developed by methanol. The title product was obtained as a white solid (74 mg, 88%). LC-MS for C25H33F3N2O4 calculated 482, found [M+H]$^+$ 483.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula I:

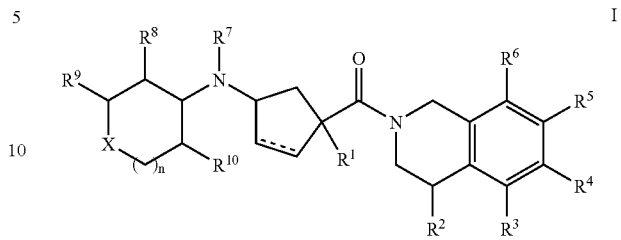

wherein:

X is selected from the group consisting of:
—O—, —NR$^{20}$—, —S—, —SO—, —SO$_2$—, and —CR$^{21}$R$^{22}$—, —NSO$_2$R$^{20}$—, —NCOR$^{20}$—, —NCO$_2$R$^{20}$—, —CR$^{21}$CO$_2$R$^{20}$—, —CR$^{21}$OCOR$^{20}$—, —CO—, where R$^{20}$ is selected from: hydrogen, C$_{1-6}$ alkyl, benzyl, phenyl, C$_{3-6}$ cycloalkyl where the alkyl, phenyl, benzyl, and cycloalkyl groups can be unsubstituted or substituted with 1–3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl, where R$^{21}$ and R$^{22}$ are independently selected from: hydrogen, hydroxy, C$_{1-6}$ alkyl, —O—C$_{1-6}$alkyl, benzyl, phenyl, C$_{3-6}$ cycloalkyl where the alkyl, phenyl, benzyl, and cycloalkyl groups can be unsubstituted or substituted with 1–3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl;

R$^1$ is selected from:
—C$_{1-6}$alkyl, —C$_{0-6}$alkyl-O—C$_{1-6}$alkyl-, —C$_{0-6}$alkyl-S—C$_{1-6}$alkyl-, —(C$_{0-6}$alkyl)-(C$_{3-7}$cycloalkyl)-(C$_{0-6}$alkyl), hydroxy, heterocycle, —CN, —NR$^{20}$R$^{26}$, —NHSO$_2$R$^{20}$, —NHCOR$^{20}$, —NHCO$_2$R$^{20}$, —CO$_2$R$^{20}$, —CR$^{21}$CO$_2$R$^{20}$, —CR$^{21}$OCOR$^{20}$ and phenyl, where R$^{26}$ is selected from: hydrogen, C$_{1-6}$ alkyl, benzyl, phenyl, C$_{3-6}$ cycloalkyl where the alkyl, phenyl, benzyl, and cycloalkyl groups can be unsubstituted or substituted with 1–3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl where the alkyl and the cycloalkyl are unsubstituted or substituted with 1–7 substituents where the substituents are independently selected from:
(a) halo,
(b) hydroxy,
(c) —O—C$_{1-3}$alkyl,
(d) trifluoromethyl,
(f) C$_{1-3}$alkyl,
(g) —O—C$_{1-3}$alkyl,
(h) —CO$_2$R$^{20}$,
(i) —SO$_2$R$^{20}$,
(j) —NHCOCH$_3$,
(k) —NHSO$_2$CH$_3$,
(l) -heterocycle,
(m) =O,
(n) —CN, and where the phenyl and pyridyl are unsubstituted or substituted with 1–3 substituents where the substituents are independently selected from: halo, hydroxy, $C_{1-3}$alkyl, $C_{1-3}$alkoxy and trifluoromethyl;

$R^2$ is selected from:
- (a) hydrogen,
- (b) hydroxy,
- (c) halo,
- (d) $C_{1-3}$alkyl, where the alkyl is unsubstituted or substituted with 1–6 substituents independently selected from: fluoro, and hydroxy,
- (e) —$NR^{20}R^{26}$,
- (f) —$CO_2R^{20}$,
- (g) —$CONR^{20}R^{26}$,
- (h) —$NR^{20}COR^{21}$,
- (i) —$OCONR^{20}R^{26}$,
- (j) —$NR^{20}CONR^{20}R^{26}$,
- (k) -heterocycle,
- (l) —CN,
- (m) —$NR^{20}$—$SO_2$—$NR^{20}R^{26}$,
- (n) —$NR^{20}$—$SO_2$—$R^{26}$,
- (o) —$SO_2$—$NR^{20}R^{26}$, and
- (p) =O, where $R^2$ is connected to the ring via a double bond;

$R^3$ is selected from:
- (a) hydrogen,
- (b) hydroxy,
- (c) halo,
- (d) $C_{1-6}$alkyl,
- (e) —O—$C_{1-6}$alkyl,
- (f) —$NR^{20}R^{21}$,
- (g) —$NR^{20}CO_2R^{21}$,
- (h) —$NR^{20}CONR^{20}R^{21}$,
- (i) —$NR^{20}$—$SO_2$—$NR^{20}R^{21}$,
- (j) —$NR^{20}$—$SO_2$—$R^{21}$,
- (k) heterocycle,
- (l) —CN,
- (m) —$CONR^{20}R^{21}$,
- (n) —$CO_2R^{20}$,
- (o) —$NO_2$,
- (p) —S—$R^{20}$,
- (q) —SO—$R^{20}$,
- (r) —$SO_2$—$R^{20}$, and
- (s) —$SO_2$—$NR^{20}R^{21}$;

$R^4$ is selected from:
- (a) hydrogen,
- (b) $C_{1-6}$alkyl,
- (c) trifluoromethyl,
- (d) trifluoromethoxy,
- (e) chloro,
- (f) fluoro,
- (g) bromo, and
- (h) phenyl;

$R^5$ is selected from:
- (a) $C_{1-6}$alkyl, where alkyl may be unsubstituted or substituted with 1–6 fluoro and optionally substituted with hydroxyl,
- (b) —O—$C_{1-6}$alkyl, where alkyl may be unsubstituted or substituted with 1–6 fluoro,
- (c) —CO—$C_{1-6}$alkyl, where alkyl may be unsubstituted or substituted with 1–6 fluoro,
- (d) —S—$C_{1-6}$alkyl, where alkyl may be unsubstituted or substituted with 1–6 fluoro,
- (e) -pyridyl, which may be unsubstituted or substituted with one or more substituents selected from the group consisting of: halo, trifluoromethyl, $C_{1-4}$alkyl, and $CO_2R^{20}$,
- (f) fluoro,
- (g) chloro,
- (h) bromo,
- (i) —$C_{4-6}$cycloalkyl,
- (j) —O—$C_{4-6}$cycloalkyl,
- (k) phenyl, which may be unsubstituted or substituted with one or more substituents selected from the group consisting of: halo, trifluoromethyl, $C_{1-4}$alkyl, and $CO_2R^{20}$,
- (l) —O-phenyl, which may be unsubstituted or substituted with one or more substituents selected from the group consisting of: halo, trifluoromethyl, $C_{1-4}$alkyl, and $CO_2R^{20}$,
- (m) —$C_{3-6}$cycloalkyl, where alkyl may be unsubstituted or substituted with 1–6 fluoro,
- (n) —O—$C_{3-6}$cycloalkyl, where alkyl may be unsubstituted or substituted with 1–6 fluoro,
- (o) -heterocycle,
- (p) —CN, and
- (q) —$CO_2R^{20}$;

$R^6$ is selected from:
- (a) hydrogen,
- (b) $C_{1-6}$alkyl, and
- (c) trifluoromethyl
- (d) fluoro
- (e) chloro, and
- (f) bromo;

$R^7$ is selected from:
- (a) hydrogen, and
- (b) $C_{1-6}$alkyl, which is unsubstituted or substituted with 1–3 substituents where the substituents are independently selected from: halo, hydroxy, —$CO_2H$, —$CO_2C_{1-6}$alkyl, and —O—$C_{1-3}$alkyl;

$R^8$ is selected from:
- (a) hydrogen,
- (b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
- (c) fluoro,
- (d) —O—$C_{1-3}$alkyl, where alkyl may be unsubstituted or substituted with 1–3 fluoro, and
- (e) $C_{3-6}$ cycloalkyl,
- (f) —O—$C_{3-6}$cycloalkyl,
- (g) hydroxy,
- (h) —$CO_2R^{20}$,
- (i) —$OCOR^{20}$,
or $R^7$ and $R^8$ may be joined together via a $C_{2-4}$alkyl or a $C_{0-2}$alkyl-O—$C_{1-3}$alkyl chain to form a 5–7 membered ring;

$R^9$ is selected from:
- (a) hydrogen,
- (b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
- (c) $CO_2R^{20}$,
- (d) hydroxy, and
- (e) —O—$C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
or $R^8$ and $R^9$ may be joined together by a $C_{1-4}$alkyl chain or a $C_{0-3}$alkyl-O—$C_{0-3}$alkyl chain to form a 3–6 membered ring;

$R^{10}$ is selected from:
- (a) hydrogen, and (b) $C_{1-6}$alkyl, where alkyl may be unsubstituted or substituted with 1–6 fluoro,
(c) fluoro,
(d) —O—$C_{3-6}$cycloalkyl, and
(e) —O—$C_{1-3}$alkyl, where alkyl may be unsubstituted or substituted with 1–6 fluoro,
or $R^8$ and $R^{10}$ may be joined together by a $C_{2-3}$alkyl chain to form a 5–6 membered ring, where the alkyl are unsubstituted or substituted with 1–3 substituents where the substiuents are independently selected from: halo, hydroxy, —$CO_2R^{20}$, $C_{1-3}$alkyl, and $C_{1-3}$alkoxy, or $R^8$ and $R^{10}$ may be joined together by a $C_{1-2}$alkyl-O—$C_{1-2}$alkyl chain to form a 6–8 membered ring, where the alkyl are unsubstituted or substituted with 1–3 substituents where the substituents are independently selected from: halo, hydroxy, —$CO_2R^{20}$, $C_{1-3}$alkyl, and $C_{1-3}$alkoxy,
or $R^8$ and $R^{10}$ may be joined together by a —O—$C_{1-2}$alkyl-O-chain to form a 6–7 membered ring, where the alkyl are unsubstituted or substituted with 1–3 substituents where the substiuents are independently selected from: halo, hydroxy, —$CO_2R^{20}$, $C_{1-3}$alkyl, and $C_{1-3}$alkoxy;
n is selected from 0, 1 and 2;
the dashed line represents a single or a double bond; and pharmaceutically acceptable salts thereof and individual diastereomers thereof.

2. The compound of claim 1 of the formula Ia:

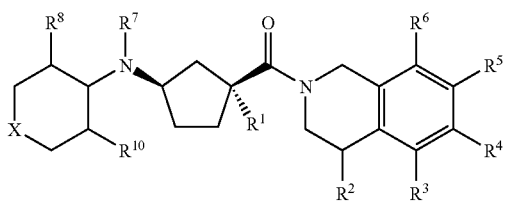

wherein $R^1, R^2, R^3, R^4, R^5, R^6, R^7, R^8, R^{10}$ and X are defined in claim 1.

3. The compound of claim 1 wherein:
X is selected from the group consisting of: —O—, and —$CH_2$—.

4. The compound of claim 1 wherein X is —O—.

5. The compound of claim 1 wherein:
(1) —$C_{1-6}$alkyl, which is unsubstituted or substituted with 1–6 substituents where the substituents are independently selected from:
(a) halo,
(b) hydroxy,
(c) —O—$C_{1-3}$alkyl, and
(d) trifluoromethyl,
(2) —$C_{0-6}$alkyl-O—$C_{1-6}$alkyl-, which is unsubstituted or substituted with 1–6 substituents where the substituents are independently selected from:
(a) halo, and
(b) trifluoromethyl,
(3) —$C_{0-6}$alkyl-S—$C_{1-6}$alkyl-, which is unsubstituted or substituted with 1–6 substituents where the substituents are independently selected from:
(a) halo, and
(b) trifluoromethyl,
(4) —($C_{3-5}$cycloalkyl)-($C_{0-6}$alkyl), which is unsubstituted or substituted with 1–7 substituents where the substituents are independently selected from:
(a) halo,
(b) hydroxy,
(c) —O—$C_{1-3}$alkyl, and
(d) trifluoromethyl.

6. The compound of claim 1 wherein $R^1$ is $C_{1-6}$alkyl which is unsubstituted or substituted with 1–5 substituents where the substituents are independently selected from:
(a) hydroxy, and
(b) fluoro.

7. The compound of claim 1 wherein:
$R^1$ is selected from:
(a) isopropyl,
(b) —CH(OH)$CH_3$, and
(c) —$CH_2CF_3$.

8. The compound of claim 1 wherein $R^1$ is isopropyl.

9. The compound of claim 1 wherein:
$R^2$ is selected from:
(a) hydrogen,
(b) hydroxy,
(c) —$NH_2$,
(d) —$CO_2H$,
(e) -triazolyl,
(f) -tetrazolyl,
(g) —$CO_2$—$C_{1-6}$alkyl,
(h) —$CONH_2$,
(i) —CONH—$C_{1-6}$alkyl,
(j) —NHCO—$C_{1-6}$alkyl,
(k) —$NHCONH_2$,
(l) —NHCONH—$C_{1-6}$alkyl
(m) —OCONH—$C_{1-6}$alkyl,
(n) —NH—$SO_2$—$C_{1-6}$alkyl, and
(o) —$SO_2$—NH—$C_{1-6}$alkyl.

10. The compound of claim 1 wherein:
$R^2$ is selected from:
(a) hydrogen,
(b) hydroxy,
(c) —$NH_2$,
(d) —$CO_2H$,
(e) -triazolyl,
(f) -tetrazolyl,
(g) —$NHCOCH_3$,
(h) —$NHCONH_2$,
(i) —$CONH_2$,
(j) —NH—$SO_2$—$CH_3$, and
(k) —$SO_2$—NH—$CH_3$.

11. The compound of claim 1 wherein $R^2$ is hydrogen.

12. The compound of claim 1 wherein $R^3$ is selected from:
(a) hydrogen,
(b) —$NH_2$,
(c) —$NO_2$,
(c) —$NHSO_2$—$C_{1-6}$alkyl,
(d) fluoro,
(e) -triazolyl, and
(f) -tetrazolyl.

13. The compound of claim 1 wherein $R^3$ is selected from:
(a) hydrogen,
(b) —$NH_2$,
(b) —$NO_2$,
(c) —$NHSO_2$—$CH_3$, and
(d) fluoro.

14. The compound of claim 1 wherein $R^4$ is hydrogen.

15. The compound of claim 1 wherein:
$R^5$ is selected from:
(a) $C_{1-3}$alkyl substituted with 1–6 fluoro,
(b) chloro,
(c) bromo, (d) —O-phenyl, which may be unsubstituted or substituted with one or more substituents selected from the group consisting of: halo and trifluoromethyl,
(e) phenyl, which may be unsubstituted or substituted with one or more substituents selected from the group consisting of: halo and trifluoromethyl, and
(f) —O—C$_{1-3}$alkyl substituted with 1–6 fluoro.

16. The compound of claim 1 wherein:
R$^5$ is selected from:
(a) trifluoromethyl,
(b) trifluoromethoxy,
(c) bromo, and
(d) chloro.

17. The compound of claim 1 wherein:
R$^5$ is trifluoromethyl.

18. The compound of claim 1 wherein R$^6$ is hydrogen.

19. The compound of claim 1 wherein:
R$^7$ is hydrogen or methyl.

20. The compound of claim 1 wherein:
R$^8$ is selected from:
(a) hydrogen,
(b) C$_{1-3}$alkyl, which is unsubstituted or substituted with 1–6 fluoro,
(c) —O—C$_{1-3}$alkyl, and
(d) fluoro, and
(e) hydroxy.

21. The compound of claim 1 wherein:
R$^8$ is selected from:
(a) hydrogen,
(d) trifluoromethyl,
(c) methyl,
(d) methoxy,
(e) ethoxy,
(f) ethyl,
(g) fluoro, and
(h) hydroxy.

22. The compound of claim 1 wherein:
R$^9$ is hydrogen and R$^{10}$ is hydrogen.

23. The compound of claim 1 wherein:
R$^8$ and R$^{10}$ are joined together by a —CH$_2$CH$_2$— chain or a —CH$_2$CH$_2$CH$_2$— chain to form a cyclopentyl ring or a cyclohexyl ring.

24. A compound which is selected from the group consisting of:

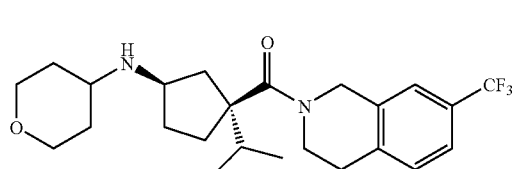

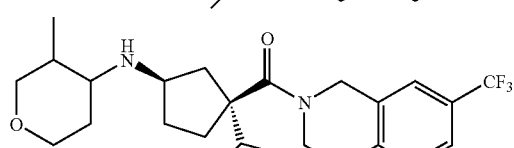

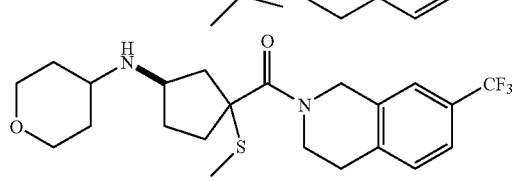

-continued

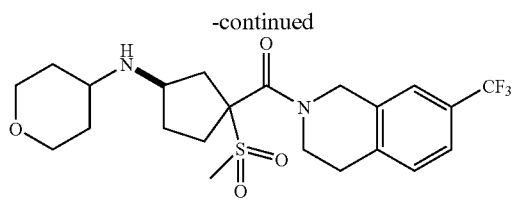

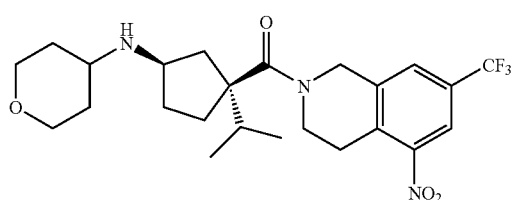

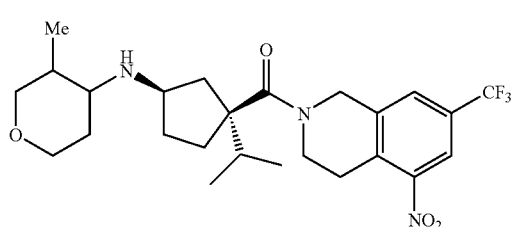

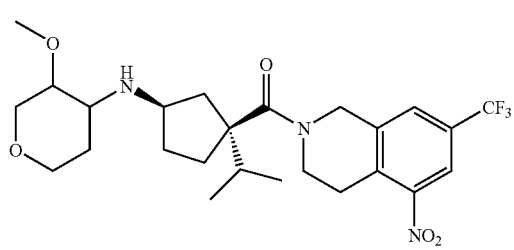

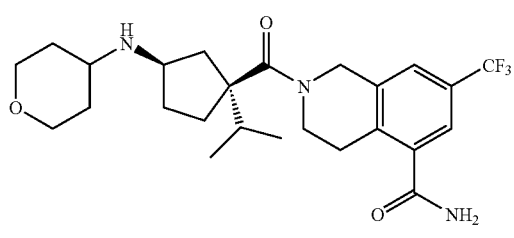

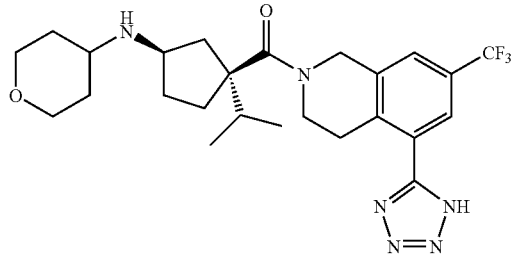

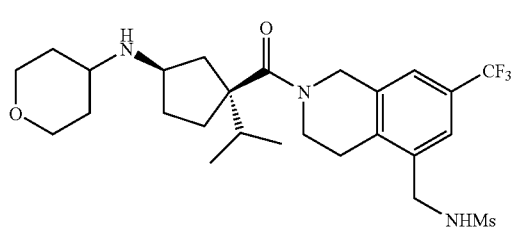

-continued
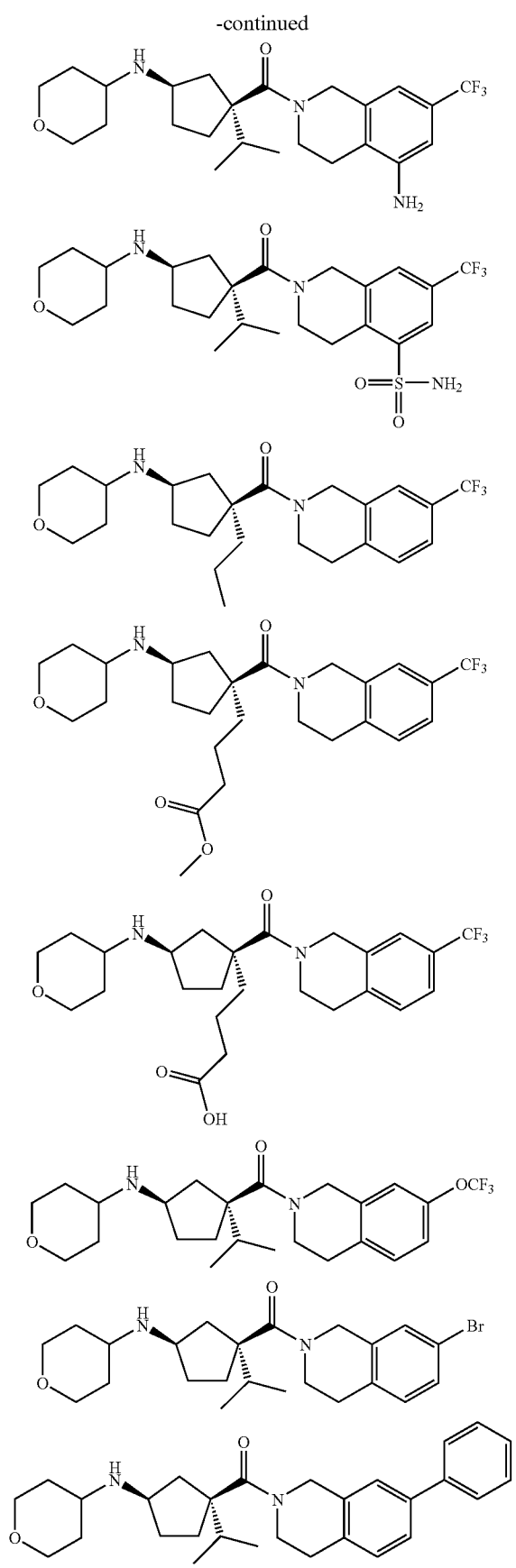
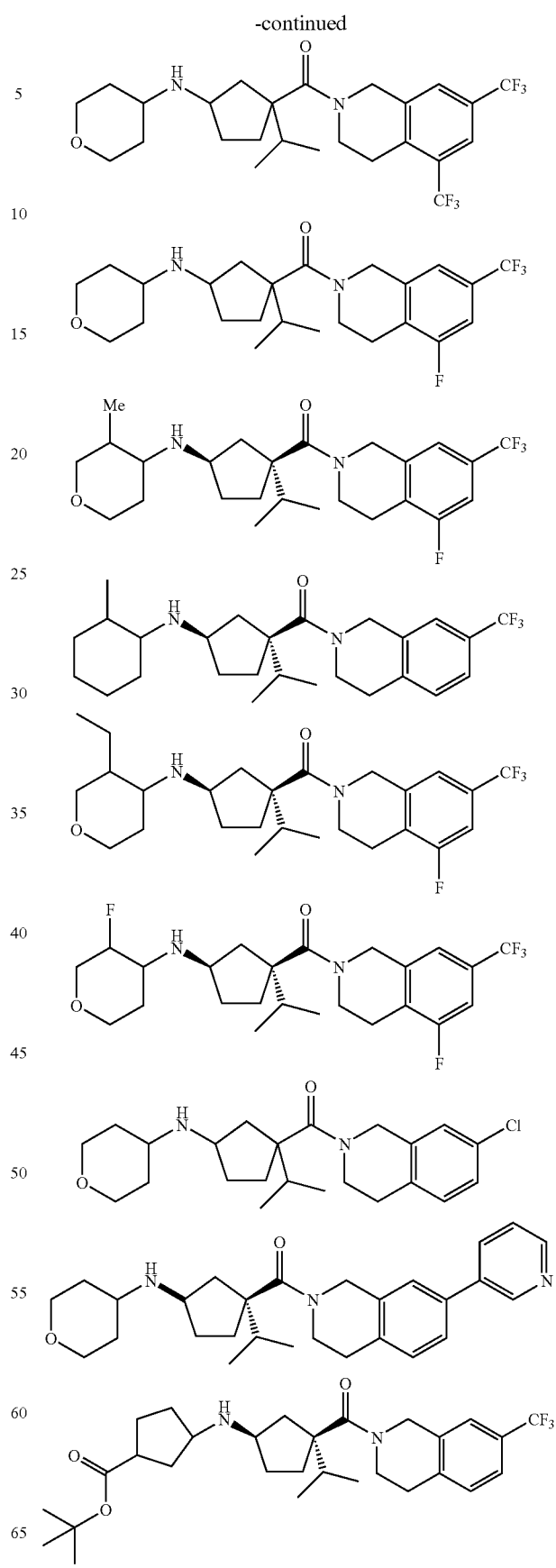

-continued
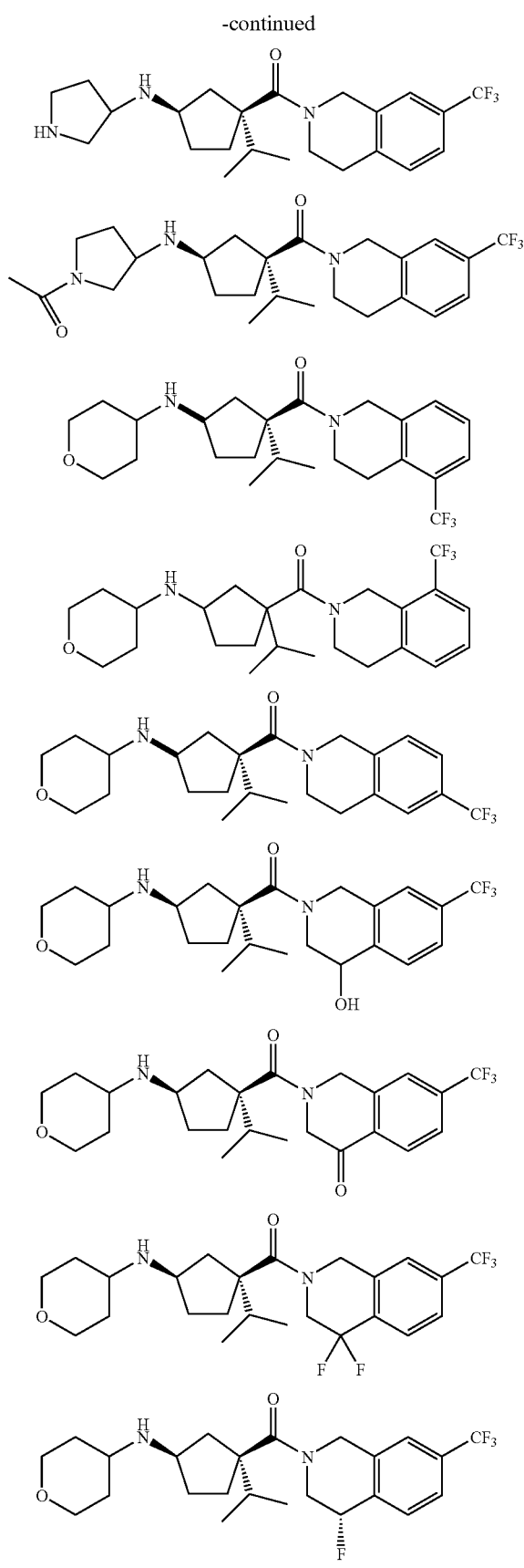
-continued
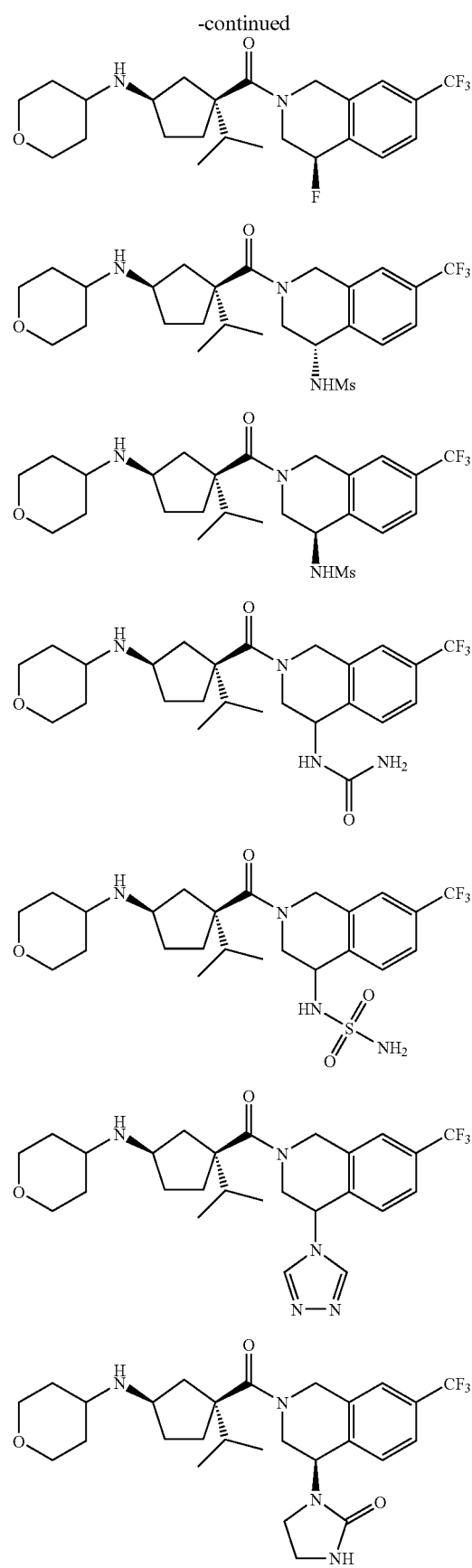

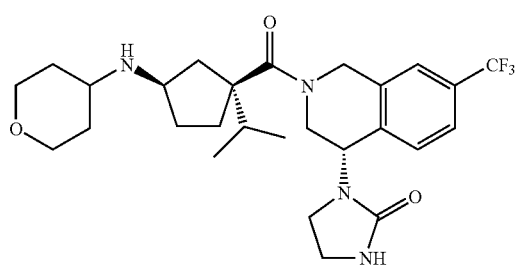
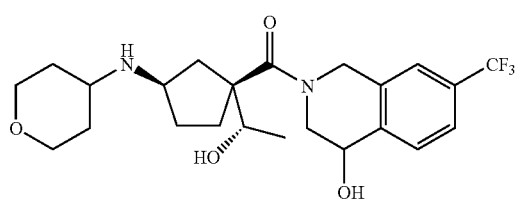
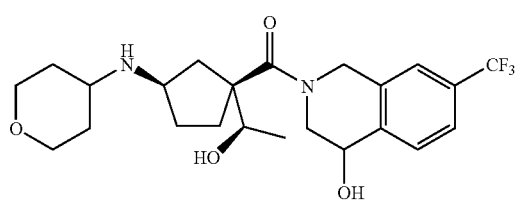
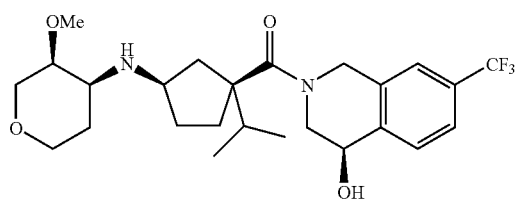
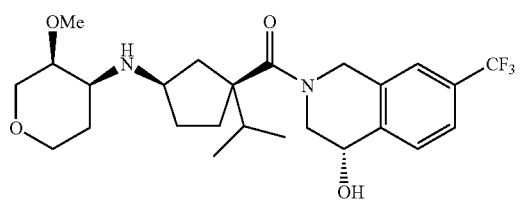
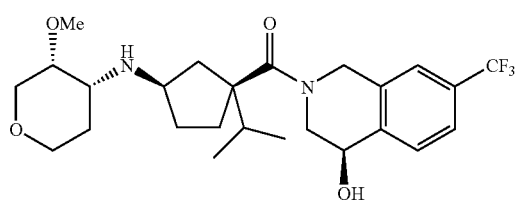
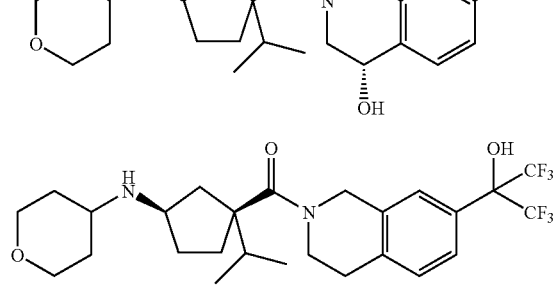
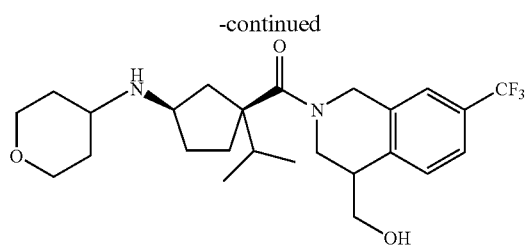
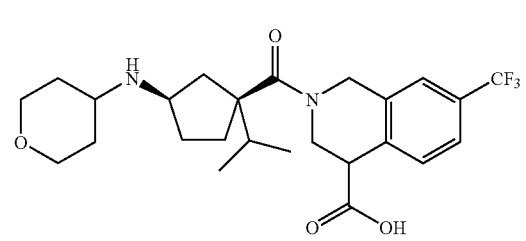
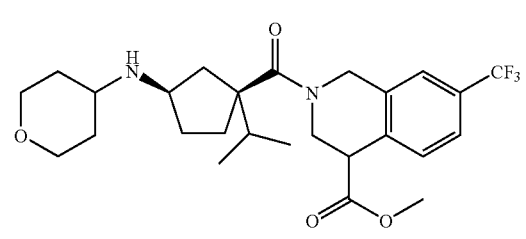
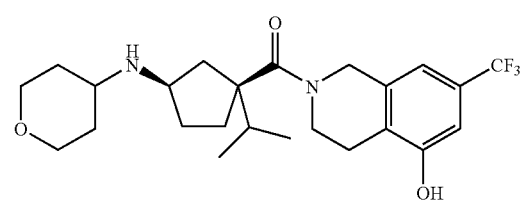
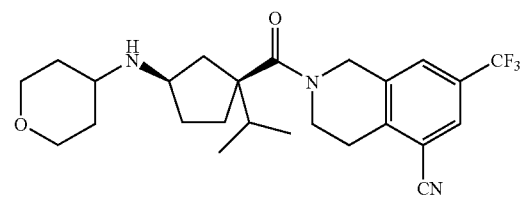
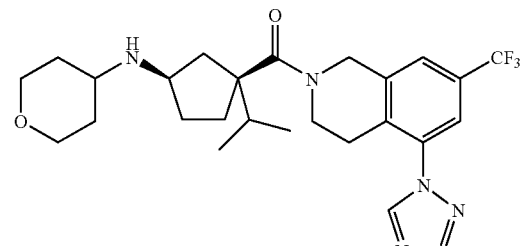
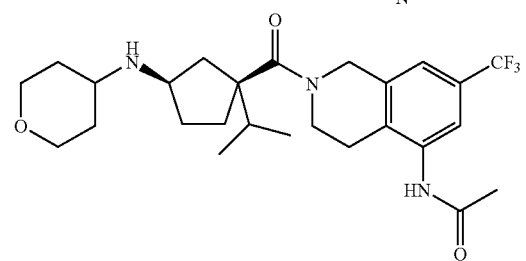

221 -continued
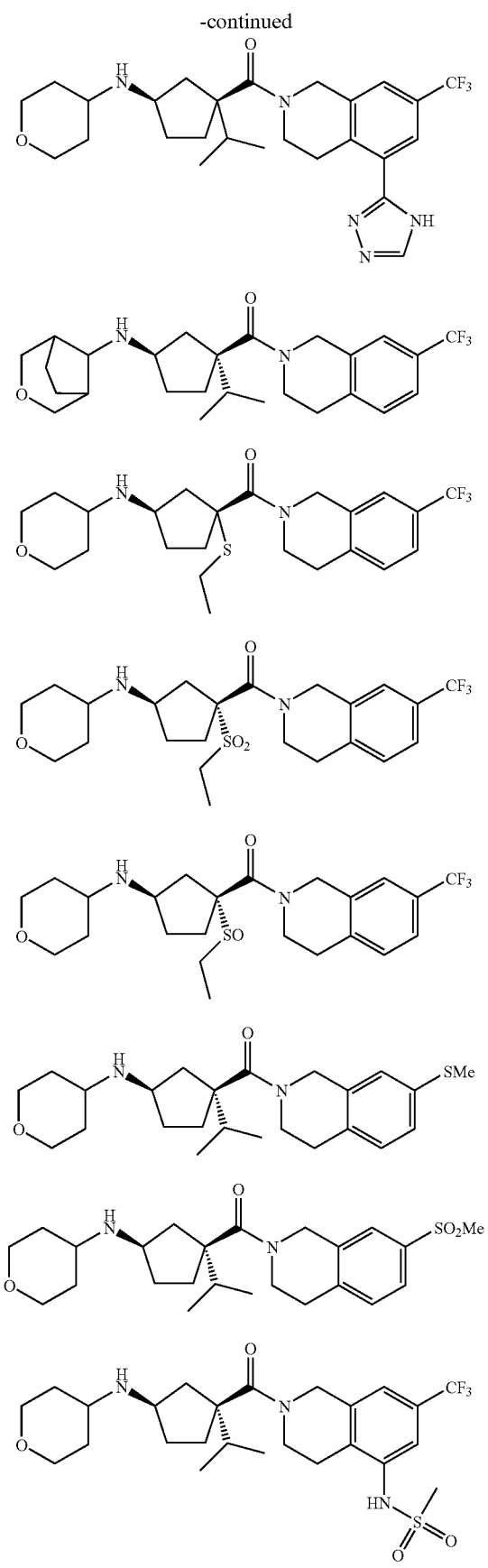
222 -continued
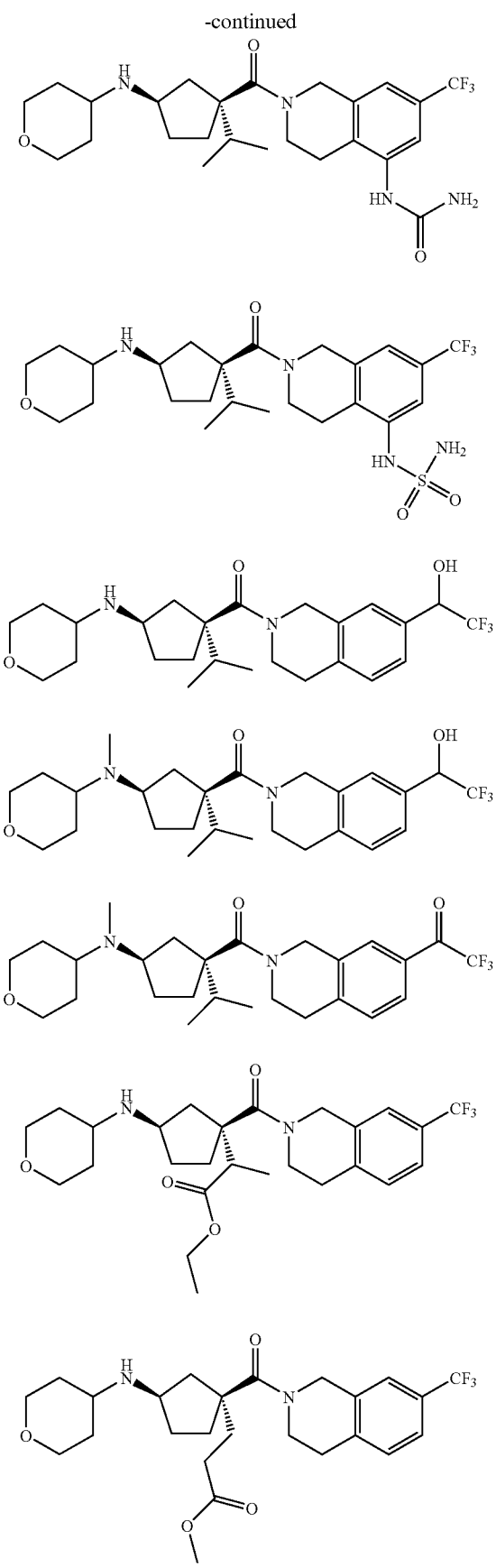

223
-continued
224
-continued
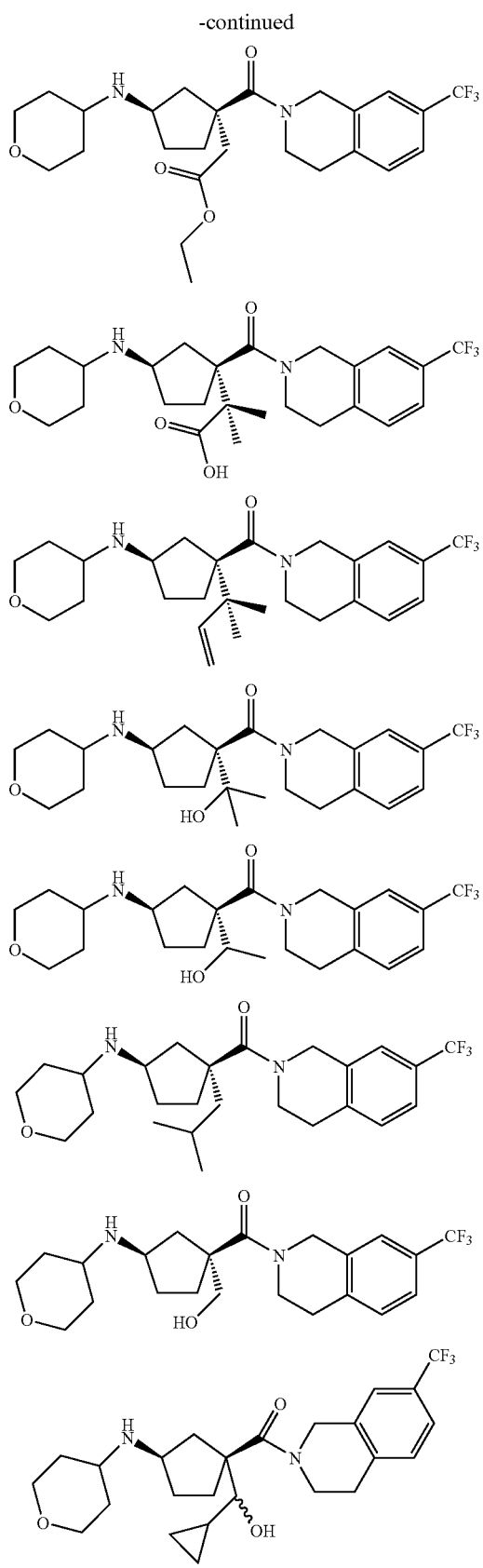
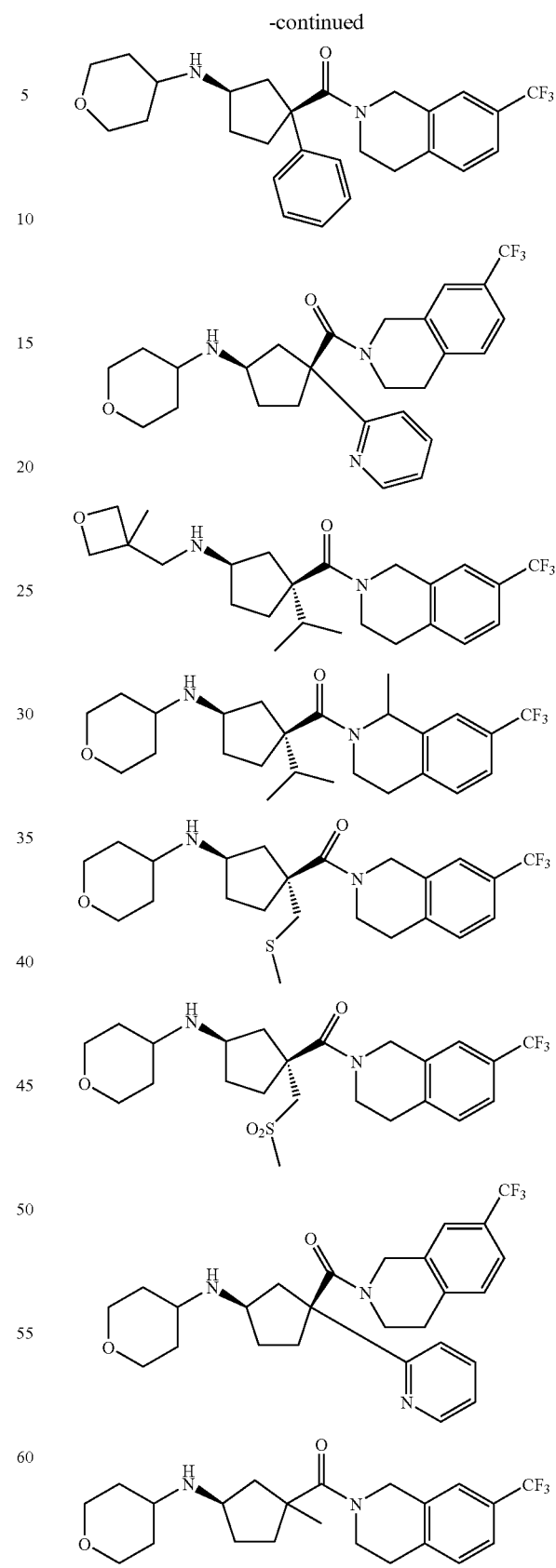

225
-continued
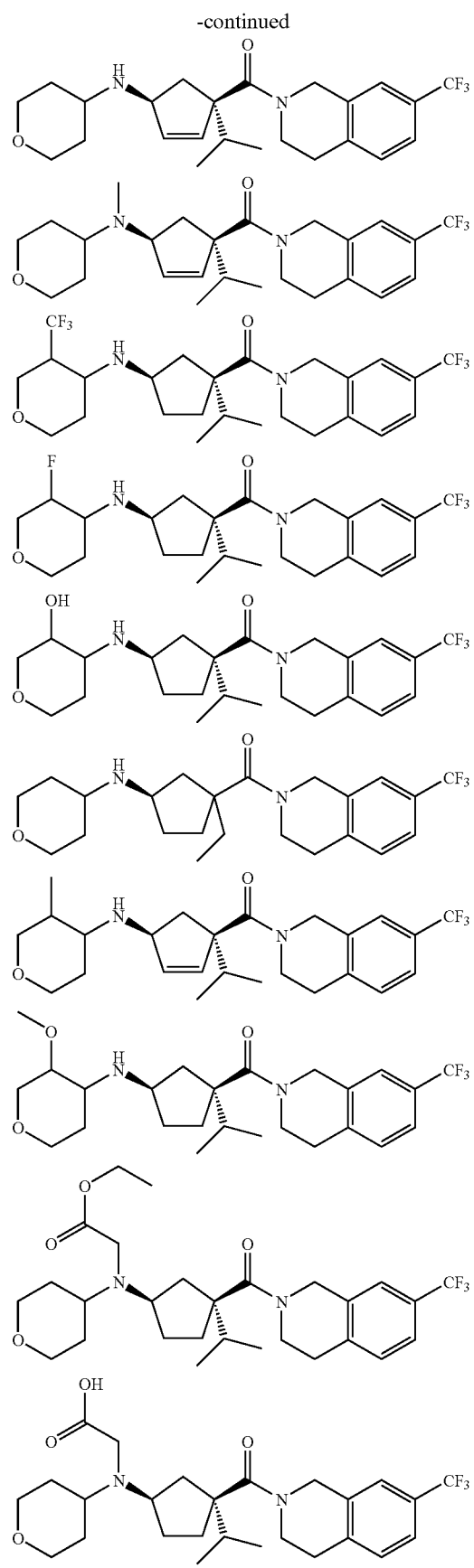
226
-continued
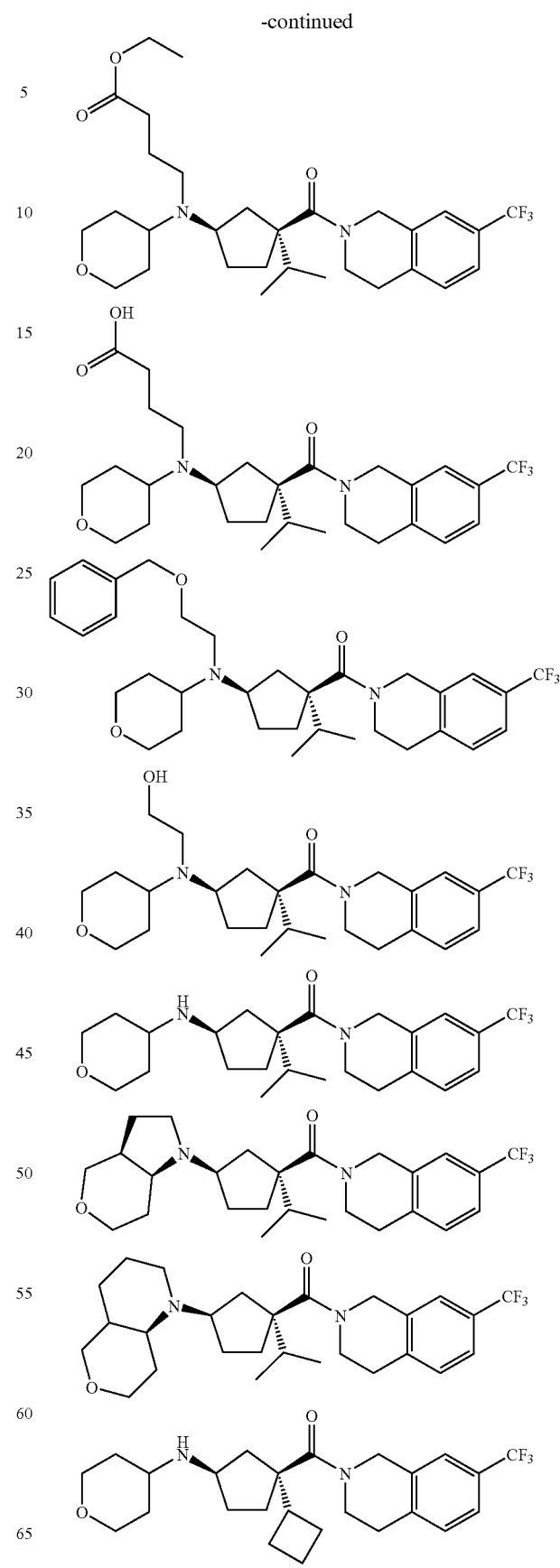

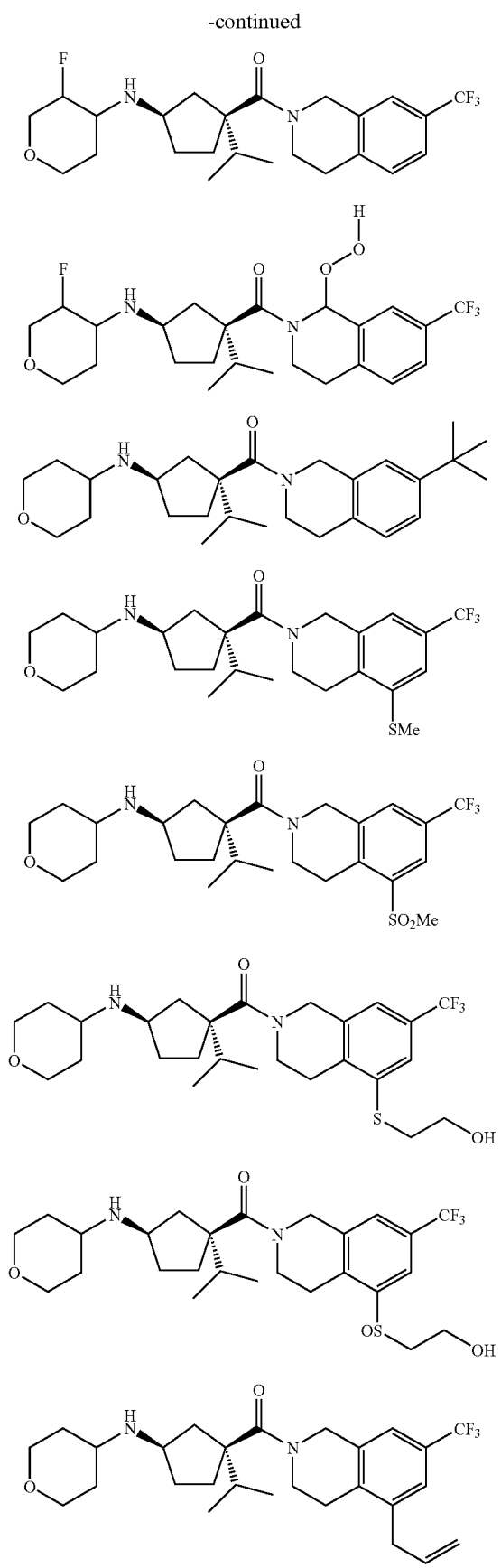
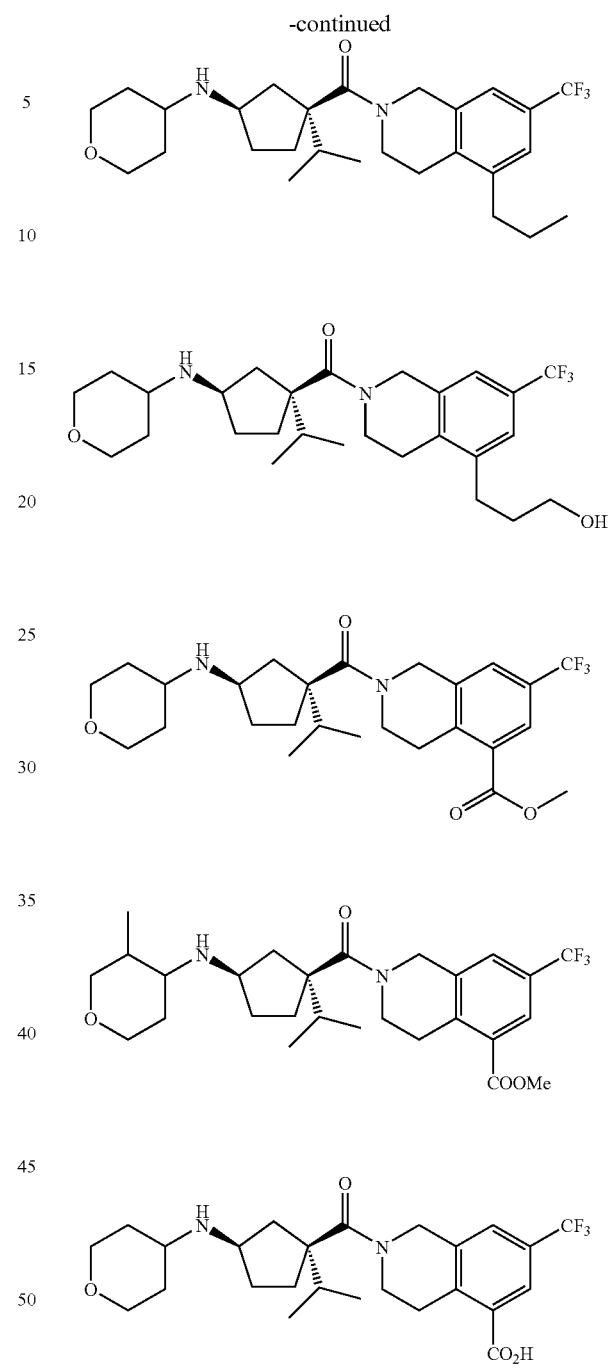

and pharmaceutically acceptable salts and individual diastereomers thereof.

25. A pharmaceutical composition which comprises an inert carrier and a compound of claim 1.

26. A method for the treatment of an inflammatory and immunoregulatory disorder or disease which comprises the administration to a patient of an effective amount of the compound of claim 1.

27. A method for the prevention or treatment of rheumatoid arthritis which comprises the administration to a patient of an effective amount of the compound of claim 1.

* * * * *